(12) United States Patent
Lerner et al.

(10) Patent No.: US 12,258,391 B2
(45) Date of Patent: *Mar. 25, 2025

(54) ANTI-GDF-15 ANTIBODIES

(71) Applicant: AVEO Pharmaceuticals, Inc., Cambridge, MA (US)

(72) Inventors: Lorena Lerner, Newton Centre, MA (US); Sandra Abbott, Boston, MA (US); Ailin Bai, Newton, MA (US); Ting Chen, Acton, MA (US); Maria Isabel Chiu, Newton Centre, MA (US); Qing Liu, Acton, MA (US); Laura Poling, Boston, MA (US); Nianjun Tao, Brighton, MA (US); Solly Weiler, Newton, MA (US); Zhigang Weng, Brookline, MA (US); William M. Winston, Jr., Marlborough, MA (US); Jeno Gyuris, Lincoln, MA (US)

(73) Assignee: AVEO Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/336,713

(22) Filed: Jun. 16, 2023

(65) Prior Publication Data

US 2024/0166734 A1 May 23, 2024

Related U.S. Application Data

(60) Continuation of application No. 16/824,034, filed on Mar. 19, 2020, now Pat. No. 11,725,047, which is a continuation of application No. 15/655,263, filed on Jul. 20, 2017, now Pat. No. 10,597,444, which is a continuation of application No. 14/863,870, filed on Sep. 24, 2015, now Pat. No. 9,725,505, which is a division of application No. 14/137,415, filed on Dec. 20, 2013, now Pat. No. 9,175,076.

(60) Provisional application No. 61/827,325, filed on May 24, 2013, provisional application No. 61/745,508, filed on Dec. 21, 2012.

(51) Int. Cl.
| | |
|---|---|
| *A61K 39/395* | (2006.01) |
| *A61K 39/00* | (2006.01) |
| *A61K 45/06* | (2006.01) |
| *A61P 3/02* | (2006.01) |
| *C07K 16/22* | (2006.01) |
| *C12N 5/10* | (2006.01) |
| *C12N 15/10* | (2006.01) |
| *C12N 15/63* | (2006.01) |

(52) U.S. Cl.
CPC .......... *C07K 16/22* (2013.01); *A61K 39/3955* (2013.01); *A61K 45/06* (2013.01); *A61P 3/02* (2018.01); *A61K 2039/505* (2013.01); *C07K 2317/24* (2013.01); *C07K 2317/76* (2013.01); *C07K 2317/92* (2013.01); *C07K 2319/30* (2013.01); *C12N 5/10* (2013.01); *C12N 15/10* (2013.01); *C12N 15/63* (2013.01)

(58) Field of Classification Search
None
See application file for complete search history.

(56) References Cited

U.S. PATENT DOCUMENTS

| | | | |
|---|---|---|---|
| 5,994,102 | A | 11/1999 | Hudson et al. |
| 6,051,424 | A | 4/2000 | Kato et al. |
| 6,180,602 | B1 | 1/2001 | Kato et al. |
| 6,420,543 | B1 | 7/2002 | Lee et al. |
| 6,465,181 | B2 | 10/2002 | Billing-Medel et al. |
| 6,500,638 | B2 | 12/2002 | Hudson et al. |
| 6,521,227 | B1 | 2/2003 | Hudson et al. |
| 7,157,235 | B2 | 1/2007 | Breit et al. |
| 7,282,351 | B2 | 10/2007 | Hudson et al. |
| 7,514,221 | B2 | 4/2009 | Breit et al. |
| 7,741,055 | B2 | 6/2010 | Hudson et al. |
| 7,919,084 | B2 | 4/2011 | Breit et al. |
| 7,968,303 | B2 | 6/2011 | Breit et al. |
| 8,173,434 | B2 | 5/2012 | Fan et al. |
| 8,192,735 | B2 | 6/2012 | Breit et al. |
| 9,175,076 | B2 | 11/2015 | Lerner et al. |
| 9,334,331 | B2 * | 5/2016 | Igawa ................. A61P 7/04 |
| 9,725,505 | B2 * | 8/2017 | Lerner ................. A61P 3/02 |
| 10,421,807 | B2 * | 9/2019 | Gonzales ............ A61P 17/08 |
| 10,597,444 | B2 | 3/2020 | Lerner et al. |
| 11,725,047 | B2 | 8/2023 | Lerner et al. |
| 2007/0207462 | A1 | 9/2007 | Ichinose et al. |
| 2009/0004181 | A1 | 1/2009 | Breit |
| 2009/0021293 | A1 | 1/2009 | Hebert et al. |
| 2011/0033886 | A1 | 2/2011 | Hess et al. |
| 2011/0065204 | A1 | 3/2011 | Wollert et al. |

(Continued)

FOREIGN PATENT DOCUMENTS

| | | |
|---|---|---|
| CA | 2534871 A1 | 8/2007 |
| EP | 1884777 A1 | 2/2008 |

(Continued)

OTHER PUBLICATIONS

Paul, Fundamental Immunology, (textbook), 1993, Raven Press, New York, pp. 292-295.*

(Continued)

*Primary Examiner* — Elizabeth C. Kemmerer

(74) *Attorney, Agent, or Firm* — Dechert LLP

(57) ABSTRACT

Monoclonal antibodies that bind and inhibit the activity of human GDF15 are disclosed. The antibodies can be used to treat body weight loss, including cachexia, associated with the over-expression of human GDF15.

18 Claims, 36 Drawing Sheets

Specification includes a Sequence Listing.

(56) References Cited

U.S. PATENT DOCUMENTS

| | | |
|---|---|---|
| 2011/0262444 A1 | 10/2011 | Kim |
| 2011/0300548 A1 | 12/2011 | Lambrecht et al. |
| 2012/0083420 A1 | 4/2012 | Clark et al. |
| 2017/0137505 A1 | 5/2017 | Gyuris et al. |
| 2017/0137506 A1 | 5/2017 | Gyuris et al. |
| 2019/0292251 A1 | 9/2019 | Gyuris et al. |
| 2019/0292252 A1 | 9/2019 | Gyuris et al. |
| 2022/0403015 A1 | 12/2022 | Gyuris et al. |

FOREIGN PATENT DOCUMENTS

| | | |
|---|---|---|
| EP | 2047275 A2 | 4/2009 |
| EP | 2103943 A1 | 9/2009 |
| WO | WO-1994003599 A1 | 2/1994 |
| WO | WO-1996018730 A1 | 6/1996 |
| WO | WO-1997000958 A1 | 1/1997 |
| WO | WO-1999006445 A1 | 2/1999 |
| WO | WO-2000020449 A2 | 4/2000 |
| WO | WO-2000056352 A2 | 9/2000 |
| WO | WO-2000070051 A1 | 11/2000 |
| WO | WO-2002020759 A2 | 3/2002 |
| WO | WO-2004041170 A2 | 5/2004 |
| WO | WO-2004043385 A2 | 5/2004 |
| WO | WO-2005044990 A2 | 5/2005 |
| WO | WO-2005099746 A1 | 10/2005 |
| WO | WO-2009021293 A1 | 2/2009 |
| WO | WO-2009046495 A1 | 4/2009 |
| WO | WO-2011117254 A1 | 9/2011 |
| WO | WO-2012113103 A1 | 8/2012 |

OTHER PUBLICATIONS

Casset et al. (Biochem Biophys Res Comm. 2003; 307:198-205).*
Maccallum et al. (J Mol Biol. 1996; 262:732-745).*
Vajdos et al. (J Mol Biol. 2002; 320(2):415-428).*
Holm et al. (Mol Immunol. 2007; 44(6): 1075-1084).*
Chen et al. (J Mol Biol. 1999; 293:865-881).*
Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331 -1342).*
Rabia, et al. (2018, Biochemical Engineering Journal 137:365-374).*
Allan et al., "A selective androgen receptor modulator that reduces prostate tumor size and prevents orchidectomy-induced bone loss in rats." J Steroid Biochem Mol Biol. Jan. 2007;103(1):76-83.
Argiles et al., "Anti-inflammatory therapies in cancer cachexia." Eur J Pharmacol. Sep. 2011;668 Suppl1:S81-6.
Bauerlein et al., "Efficacy of REGN1033, a fully human anti-myostatin antagonist antibody, in rodent muscle function." J. Cachexia Sarcopenia Muscle 2013;4:295-343 Abstract 4-06 from 7th Cachexia Conference, Kobe/Osaka, Japan, Dec. 9-11, 2013.
Baumgartner et al., "Epidemiology of sarcopenia among the elderly in New Mexico." Am J Epidemiol. Apr. 15, 1998;147(8):755-63.
Bauskin et al., "Role of macrophage inhibitory cytokine-1 in tumorigenesis and diagnosis of cancer." Cancer Res. May 15, 2006;66(10):4983-6.
Bialek et al., "A myostatin and activin decoy receptor enhances bone formation in mice." Bone. Mar. 2014; 60:162-171.
Bovee et al., "SERMs and SARMs: detection of their activities with yeast based bioassays." J. Steroid Biochem. Mol. Biol. 2010;118:85-92.
Breit et al. "The TGF- ß superfamily cytokine, MIC-1/GDF15: a pleotrophic cytokine with roles in inflammation, cancer and metabolism" <i>Growth Factors</i>. Oct. 2011;29(5):187-95.
Gasset et al., "A peptide mimetic of an anti-CD4 monoclonal antibody by rational design", Biochem Biophys Res Commun. Jul. 18, 2003;307(1):198-205.

Chen et al., "Discovery and Therpeutic Promise of Selective Androgen Receptor Modulators." Mol. Interv. Jun. 2005; 5(3):173-188.
Chen et al., "Selection and analysis of an optimized anti-VEGF antibody: crystal structure of an affinity-matured Fab in complex with antigen", J Mol Biol. Nov. 5, 1999;293(4): 865-81.
Dalton et al., "The selective androgen receptor modulator GTx-024 (enobosarm) improves lean body mass and physical function in healthy elderly men and postmenopausal women: results of a double-blind, placebo-controlled phase II trial." J Cachexia Sarcopenia Muscle. Sep. 2011;2(3):153-161.
Davenport and Wright, "Treating Obesity: is it all in the gut?" Drug Discov Today (2013), <http://dx.doi.org/10.1016/i.drudis.2013.10.025>.
DeBoer and Marks, "Cachexia: lessons from melanocortin antagonism." Trends Endocrinol Metab. Jul. 2006; 17(5):199-204.
Enomoto et al., "Suppression of cancer cachexia by 20S,21-epoxy-resibufogenin-3-acetate-a novel nonpeptide IL-6, receptor antagonist." Biochem Biophys Res Commun. Oct. 22, 2004;323(3):1096-102.
Evans et al., "Cachexia: a new definition." Clin Nutr. Dec. 2008;27(6):793-9.
Fairlie et al., "Expression of a TGF-beta superfamily protein, macrophage inhibitory cytokine-1, in the yeast Pichia pastoris." Gene. Aug. 22, 2000;254(1 -2):67-76.
Fearon et al., "Cancer cachexia: mediators, signaling, and metabolic pathways." Cell Metab. Aug. 8, 2012; 16(2): 153-66.
Fearon et al., "Definition and classification of cancer cachexia: an international consensus." Lancet Oncol. May 2011;12(5):489-95.
Fong et al. "Cachectin/TNF or IL-1 alpha induces cachexia with redistribution of body proteins." Am J Physiol. Mar. 1989;256(3 Pt 2): R659-65.
Foote et al., (1992), "Antibody Framework residues affecting the conformation of the hypervariableloops," J. Mol. Biol., 224:487-499.
Glass, "Signaling pathways perturbing muscle mass." Curr Opin Clin Nutr Metab Care. May 2010;13(3):225-9.
Guillory et al., "Chapter 3: The Role of Ghrelin in Anorexia-Cachexia Syndromes." Vitamins and Hormones. 2013; 92:61-106.
Hinoi et al. "Positive regulation of osteoclastic differentiation by growth differentiation factor 15 upregulated in osteocytic cells under hypoxia" <i>J Bone Miner Res</i>. Apr. 2012;27(4):938-49.
Holm et al., "Functional mapping and single chain construction of the anti-cytokeratin 8 monoclonal antibody TS1", Mol Immunol. Feb. 2007;44(6):1075-84.
Hryniewicz et al., Partial reversal of cachexia by beta-adrenergic receptor blocker therapy in patients with chronic heart failure. J Card Fail. Dec. 2003;9(6):464-8.
International Search Report and Written Opinion for International Application No. PCT/US2013/077139, dated May 22, 2014, 20 pages.
Inui, "Cancer anorexia-cachexia syndrome: current issues in research and management." Cancer J Clin. Mar.-Apr. 2000;52(2):72-91.
Johnen et al., "Tumor-induced anorexia and weight loss are mediated by the TGF-beta superfamily cytokine MIC-1." Nat Med. Nov. 2007;13(11):1333-40.
Joppa et al., "Central infusion of the melanocortin receptor antagonist agouti-related peptide (AgRP(83-132)) prevents cachexia-related symptoms induced by radiation and colon-26 tumors in mice." Peptides. Mar. 2007;28(3):636-42.
Kalinkovich and Livshits, (2015), "Sarcopenia—The search for emerging biomarkers", Aging Research Reviews, 22:58-71.
Lokireddy et al., "Myostatin is a novel tumoral factor that induces cancer cachexia." Biochem J. Aug. 15, 2012;446(1):23-36.
MacCallum et al., "Antibody-antigen interactions: contact analysis and binding site topography", J Mol Biol. Oct. 11, 1996;262(5):732-45.
Marino et al., "The therapeutic potential of blocking the activin signalling pathway." Cytokine Growth Factor Rev. Oct. 2013;24(5): 477-84.
Matthys and Billiau, "Cytokines and cachexia." Nutrition. Sep. 1997;13(9):763-70.

(56) References Cited

OTHER PUBLICATIONS

Mohler et al., "Nonsteroidal Selective Androgen Receptor Modulators (SARMs): Dissociating the Anabolic and Androgenic Activities of the Androgen Receptor for Therapeutic Benfit." J. Med. Chem. 2008;52(12):3597-3617.

Muscaritoli et al., "Consensus definition of sarcopenia, cachexia and pre-cachexia: joint document elaborated by Special Interest Groups (SIG) 'cachexia-anorexia in chronic wasting diseases' and 'nutrition in geriatrics.'" Clin Nutr. Apr. 2010;29(2):154-9.

Nagata et al., "Design and synthesis of tricyclic tetrahydroquinolines as a new series of nonsteroidal selective androgen receptor modulators (SARMs)." Bioorg. Med. Chem. Lett. 2011;21:1744-1747.

Ng et al., "Synthesis of potent and tissue-selective androgen receptor modulators (SARMs): 2-(2,2,2)-Trifluoroethyl-benzimidazole scaffold", Bioorg Med Chem Lett. Mar. 15, 2007;17(6):1784-7.

Paul, Fundamental Immunology, Raven Press, NY, 1993, pp. 292-295.

Prado et al., "Skeletal muscle anabolism is a side effect of therapy with the MEK inhibitor: selumetinib in patients with cholangiocarcinoma." Br J Cancer. May 8, 2012;106(10):1583-6.

Roth el al. "GDF-15 contributes to proliferation and immune escape of malignant gliomas" <i>Clin Cancer Res</i>. Aug. 1, 2010;16(15):3851-9.

Rüegg and Glass, "Molecular mechanisms and treatment options for muscle wasting diseases." Annu Rev Pharmacol Toxicol. 2011;51:373-95.

Sharma et al., "Molecular targets of cancer cachexia: opportunities for pharmanutritional approaches." PharmaNutrition. 2013, <http://dx.doi.org/10.1016/j.phanu.2013.07.002>.

Steinman and DeBoer, "Chapter 8: Treatment of Cachexia: Melanocortin and Ghrelin Interventions." Vitamins and Hormones. 2013; 92:197-240.

Stewart-Coats et al., "The ACT-ONE trial, a multicentre, randomised, double-blind, placebo- controlled, dose-finding study of the anabolic/catabolic transforming agent, MT-102 in subjects with cachexia related to stage III and IV non-small cell lung cancer and colorectal cancer:study design." J Cachexia Sarcopenia Muscle. Dec. 2011;2(4):201-207.

Strassmann et al., Mechanisms of experimental cancer cachexia. Local involvement of IL-1 in colon-26 tumor. J Immunol. Mar. 15, 1993; 150(6):2341-5.

Temel et al., "Efficacy and safety results from a phase II study of anamorelin HCI, a ghrelin receptor agonist, in NSCLC patients." J. Cachexia Sarcopenia Muscle 2013;4:295-343 Abstract 5-01 from 7th Cachexia Conference, Kobe/Osaka, Japan, Dec. 9-11, 2013.

Thomas, "Loss of skeletal muscle mass in aging: examining the relationship of starvation, sarcopenia and cachexia." Clin Nutr. Aug. 2007;26(4):389-99.

Tisdale, "Cachexia in cancer patients." Nat Rev Cancer. Nov. 2002;2(11):862-71.

Tsai et al., "Anorexia/cachexia of chronic diseases: a role for the TGF-a 3 family cytokine MIC-1/GDF15." J Cachexia Sarcopenia Muscle. Dec. 2012;3(4):239-43.

Tuca et al., "Clinical evaluation and optimal management of cancer cachexia." Crit Rev Oncol Hematol. Dec. 2013;88(3):625-36.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Winter et al., (1993), "Humanized antibodies," Trends Pharmacol Sci., 14:139-43.

Zhang et al., "Serendipitous discovery of novel imidazolopyrazole scaffold as selective androgen receptor modulators." Bioorg Med Chem Lett. Jan. 15, 2007;17(2):439-43.

Zhang et al., "Synthesis and SAR of novel hydantoin derivatives as selective androgen receptor modulators." Bioorg Med Chem Lett. Nov. 15, 2006;16(22):5763-6.

Zhou et al., "Reversal of cancer cachexia and muscle wasting by ActRIIB antagonism leads to prolonged survival." Cell. Aug. 20, 2010;142(4):531-43.

* cited by examiner

Complete Mouse Heavy Chain Variable Region Amino Acid Alignments

```
Heavy Variable           CDR1                                              CDR2
                 1       2        3      333    4       5 55    6                                       7
                 0       0        0      555    0       0 22    0                                       0
                                         AB                     A
01G06  EVLLQQSGPELVKPGASVKIPCKASGYTFT DYNMD- WVKQSHGKSLEWIG QINPNNGGIFFNQKFKG KATLT
03G05  QVQLQQPGAELVKPGASVKLSCKASGYTFT SYWIH- WVNQRPGQGLEWIG DINPSNGRSKYNEKFKN KATMT
04F08  QVTLKESGPGILQPSQTLSLTCSFSGFSLS TYGMGVT WIRQPSGKGLEWLA HIY-WDDDKRYNPSLKS RLTIS
06C11  QVTLKESGPGILQPSQTLSLTCSFSGFSLN TYGMGVS WIRQPSGKGLEWLA HIY-WDDDKRYNPSLKS RLTIS
08G01  EVLLQQSGPEVVKPGASVKIPCKASGYTFT DYNMD- WVKQSHGKSLEWIG EINPNNGGTFYNQKFKG KATLT
14F11  QVTLKESGPGILQPSQTLSLTCSFSGFSLS TYGMGVG WIRQPSGKGLEWLA DIW-WDDDKYYNPSLKS RLTIS
17B11  QVTLKESGPGILQPSQTLSLTCSFSGFSLS TSGMGVS WIRQPSGKGLEWLA HND-WDDDKRYKSSLKS RLTIS CDR3
       7   8    888      1111     1
       1   0    222      0000     1
              ABC        ABC      0
01G06  VDKSSNTAFMEVRSLTSEDTAVYYC AREAITTVGAMDY     WGQGTSVTVSS   (SEQ ID NO:40)
03G05  ADKSSNTAYMQLSSLTSEDSAVYYC AREVLDGAM--DY     WGQGTSVTVSS   (SEQ ID NO:42)
04F08  KDTSNNQVFLKITSVDTADTATYYC AQTGYSNLF--AY     WGQGTLVTVSA   (SEQ ID NO:44)
06C11  KDASNNRVFLKITSVDTADTATYYC AQRGYDDYW--GY     WGQGTLVTISA   (SEQ ID NO:46)
08G01  VDKSSSTAYMELRSLTSEDTAVYYC AREAITTVGAMDY     WGQGTSVTVSS   (SEQ ID NO:48)
14F11  KDTSSNEVFLKIAIVDTADTATYYC ARRGHYSAM--DY     WGQGTSVTVSS   (SEQ ID NO:50)
17B11  KDTSRNQVFLKITSVDTADTATYYC ARRVGGLEGYFDY     WGQGTTLTVSS   (SEQ ID NO:52)
```

FIG. 10

Mouse Heavy Chain CDR Amino Acid Alignments

| Heavy Variable | CDR1 | | CDR2 | |
|---|---|---|---|---|
| 01G06 | DYNMD-- | (SEQ ID NO:1) | QINPNNGGIFFNQKFKG | (SEQ ID NO:7) |
| 03G05 | SYWIH-- | (SEQ ID NO:2) | DINPSNGRSKYNEKFKN | (SEQ ID NO:8) |
| 04F08 | TYGMGVT | (SEQ ID NO:3) | HIY-WDDDKRYNPSLKS | (SEQ ID NO:9) |
| 06C11 | TYGMGVS | (SEQ ID NO:4) | HIY-WDDDKRYNPSLKS | (SEQ ID NO:9) |
| 08G01 | DYNMD-- | (SEQ ID NO:1) | EINPNNGGTFYNQKFKG | (SEQ ID NO:10) |
| 14F11 | TYGMGVG | (SEQ ID NO:5) | DIW-WDDDKYNPSLKS | (SEQ ID NO:11) |
| 17B11 | TSGMGVS | (SEQ ID NO:6) | HND-WDDDKRYKSSLKS | (SEQ ID NO:12) |

| Heavy Variable | CDR3 | |
|---|---|---|
| 01G06 | EAITTVGAMDY | (SEQ ID NO:15) |
| 03G05 | EVLDGAM--DY | (SEQ ID NO:16) |
| 04F08 | TGYSNLF--AY | (SEQ ID NO:17) |
| 06C11 | RGYDDYW--GY | (SEQ ID NO:18) |
| 08G01 | EAITTVGAMDY | (SEQ ID NO:15) |
| 14F11 | RGHYSAM--DY | (SEQ ID NO:19) |
| 17B11 | RVGGLEGYFDY | (SEQ ID NO:20) |

FIG. 11

Complete Mouse Light (Kappa) Chain Variable Region Amino Acid Alignments

```
Light (Kappa) Variable
                                   CDR1                                        CDR2
           1         2         3            4         5         6         7
           0         0         0            0         0         0         0
                     22222     3                      5                   7
                     77777     0                      0                   0
                               ABCD
01G06   DIQMTQSPASLSASVGETVTITCRTSE----NLHNYLAWYQQKQGKSPQLLVYDAKTLADGVPSRFSGSGSGTQ
03G05   DIVLTQSPASLAVSLGQRATISCRASESVDNYGISFMNWFQQKPGQPPKLLIYAASNQGSGVPARFSGSGSGTD
04F08   DIVMTQSQKFMSTSVGDRVSVTCKASQ----NVGTNVAWYQQKLGQSPKTLIYSASYRYSGVPDRFTGSGSGTD
06C11   DIVMTQSQKFMSTSVGDRVSVTCKASQ----NVGTNVAWFQQKPGQSPKALIYSASYRYSGVPDRFTGSGSGTD
08G01   DIQMTQSPASLSASVGETVTITCRASG----NIHNYLAWYQQKQGKSPQLLVYNAKTLADGVPSRFSGSGSGTQ
14F11   DIVMTQSQKFMSTSVGDRVSVTCKASQ----NVGTNVAWYQQKPGQSPKALIYSPSYRYSGVPDRFTGSGSGTD
17B11   DIVLTQSPASLAVSLGQRATISCRASQSVSTSRFSYMHWFQQKPGQAPKLLIKYASNLESGVPARFSGSGSGTD CDR3
           7        8        9           1
           0        0        0           0
01G06   YSLKINSLQPEDFGSYYCQHFWSSPYTFGGGTKLEIK     (SEQ ID NO:76)
03G05   FSLNIHPMEEDTAMYFCQQSKEVPWTFGGGSKLEIK      (SEQ ID NO:78)
04F08   FTLTISNVQSEDLAEYFCQQYNSYPYTFGGGTKLEIK     (SEQ ID NO:80)
06C11   FILTISNVQSEDLAEYFCQQYNNYPLTFGAGTKLELK     (SEQ ID NO:82)
08G01   YSLKINSLQPEDFGSYYCQHFWSSPYTFGGGTKLEIK     (SEQ ID NO:84)
14F11   FTLTISNVQSEDLAEYFCQQYNSYPHTFGGGTKLEMK     (SEQ ID NO:86)
17B11   FTLNIHPVEGEDTATYYCQHSWEIPYTFGGGTKLEIK     (SEQ ID NO:88)
```

FIG. 12

Mouse Light (Kappa) Chain CDR Amino Acid Alignments

Light (Kappa) Variable

| | CDR1 | | CDR2 | |
|---|---|---|---|---|
| 01G06 | RTSE---NLHNYLA | (SEQ ID NO:21) | DAKTLAD | (SEQ ID NO:26) |
| 03G05 | RASESVDNYGISFMN | (SEQ ID NO:22) | AASNQGS | (SEQ ID NO:27) |
| 04F08 | KASQ----NVGTNVA | (SEQ ID NO:23) | SASYRYS | (SEQ ID NO:28) |
| 06C11 | KASQ----NVGTNVA | (SEQ ID NO:23) | SASYRYS | (SEQ ID NO:28) |
| 08G01 | RASG----NIHNYLA | (SEQ ID NO:24) | NAKTLAD | (SEQ ID NO:29) |
| 14F11 | KASQ----NVGTNVA | (SEQ ID NO:23) | SPSYRYS | (SEQ ID NO:30) |
| 17B11 | RASQSVSTSRFSYMH | (SEQ ID NO:25) | YASNLES | (SEQ ID NO:31) |

Light (Kappa) Variable

| | CDR3 | |
|---|---|---|
| 01G06 | QHFWSSPYT | (SEQ ID NO:32) |
| 03G05 | QQSKEVPWT | (SEQ ID NO:33) |
| 04F08 | QQYNSYPYT | (SEQ ID NO:34) |
| 06C11 | QQYNNYPLT | (SEQ ID NO:35) |
| 08G01 | QHFWSSPYT | (SEQ ID NO:32) |
| 14F11 | QQYNSYPHT | (SEQ ID NO:36) |
| 17B11 | QHSWEIPYT | (SEQ ID NO:37) |

FIG. 13

Complete Humanized Heavy Chain Variable Region Amino Acid Alignments

| Heavy Variable | | | | CDR1 | | | CDR2 | |
|---|---|---|---|---|---|---|---|---|
| | 1 | 2 | 3 | 333 | 4 | 5 55 | | 6 7 |
| | 1 | 0 | 0 | 555 | 0 | 0 22 | | 0 0 |
| | | | | AB | | A | | A |
| Ch01G06 Chimeric | EVLLQQSGPELVKPGASVKIPCKASGYTFT | DYNMD-- | WVKQSHGKSLEWIG | QINPNNGGIFFNQKFKG | KATLT |
| Hu01G06 IGHV1-18 | QVQLVQSGAEVKKPGASVKVSCKASGYTFT | DYNMD-- | WVRQAPGKSLEWIG | QINPNNGGIFFNQKFKG | RATLT |
| Hu01G06 IGHV1-69 | QVQLVQSGAEVKKKPGSSVKVSCKASGYTFT | DYNMD-- | WVRQAPGKSLEWIG | QINPNNGGIFFNQKFKG | RATLT |
| Sh01G06 IGHV1-18 M69L | QVQLVQSGAEVKKPGASVKVSCKASGYTFT | DYNMD-- | WVRQAPGQGLEWMG | QINPNNGGIFFNQKFKG | RVTLT |
| Sh01G06 IGHV1-18 M69L K64Q G44S | QVQLVQSGAEVKKPGASVKVSCKASGYTFT | DYNMD-- | WVRQAPGQSLEWMG | QINPNNGGIFFNQKFQG | RVTLT |
| Sh01G06 IGHV1-18 M69L K64Q | QVQLVQSGAEVKKPGASVKVSCKASGYTFT | DYNMD-- | WVRQAPGQGLEWMG | QINPNNGGIFFNQKFQG | RVTLT |
| Sh01G06 IGHV1-69 T30S I69L | QVQLVQSGAEVKKKPGSSVKVSCKASGYTFS | DYNMD-- | WVRQAPGQGLEWMG | QINPNNGGIFFNQKFKG | RVTLT |
| Sh01G06 IGHV1-69 T30S K64Q I69L | QVQLVQSGAEVKKKPGSSVKVSCKASGYTFS | DYNMD-- | WVRQAPGQGLEWMG | QINPNNGGIFFNQKFQG | RVTLT |
| Hu01G06 IGHV1-18 F1 | QVQLVQSGAEVKKPGASVKVSCKASGYTFT | DYNMD-- | WVRQAPGQSLEWMG | QINPNNGGIFFNQKFQG | RVTLT |
| Hu01G06 IGHV1-18 F2 | QVQLVQSGAEVKKPGASVKVSCKASGYTFT | DYNMD-- | WVRQAPGQSLEWMG | QINPYNHLIFFNQKFQG | RVTLT |
| Hu01G06 IGHV1-69 F1 | QVQLVQSGAEVKKKPGSSVKVSCKASGYTFS | DYNMD-- | WVRQAPGQGLEWMG | QINPNNGLIFFNQKFQG | RVTLT |
| Hu01G06 IGHV1-69 F2 | QVQLVQSGAEVKKKPGSSVKVSCKASGYTFS | DYNMD-- | WVRQAPGQGLEWMG | QINPYNHLIFFNQKFKG | RVTLT |
| Ch06C11 Chimeric | QVTLKESGPGILQPSQTLSLTCSFSGFSLN | TYGMGVS | WIRQPSGKGLEWLA | HIY-WDDDKRYNPSLKS | RLTIS |
| HE LM 06C11 IGHV2-70 | QVTLKESGPALVKPTQTLTLTCTFSGFSLN | TYGMGVS | WIRQPPGKALEWLA | HIY-WDDDKRYNPSLKS | RLTIS |
| Hu06C11 IGHV2-5 | QVTLKESGPTLVKPTQTLTLTCTFSGFSLS | TYGMGVG | WIRQPPGKGLEWLA | HIY-WDDDKRYNPSLES | RLTIS |
| Ch14F11 Chimeric | QVTLKESGPGILQPSQTLSLTCTFSGFSLS | TYGMGVG | WIRQPSGKGLEWLA | DIW-WDDDKYYNPSLKS | RLTIS |
| Sh14F11 IGHV2-5 | QITLKESGPTLVKPTQTLTLTCTFSGFSLS | TYGMGVG | WIRQPPGKALEWLA | DIW-WDDDKYYNPSLKS | RLTIT |
| Sh14F11 IGHV2-70 | QVTLKESGPALVKPTQTLTLTCTFSGFSLS | TYGMGVG | WIRQPPGKALEWLA | DIW-WDDDKYYNPSLKS | RLTIS |

FIG. 19

Complete Humanized Heavy Chain Variable Region Amino Acid Alignments

Heavy Variable

```
                                      7         8    8 9      1111    1
                                      1         0    2 0      0000    1
                                                     2        0000    0
                                                ABC            ABC  ABC
                                                                    CDR3
Ch01G06 Chimeric           VDKSSNTAFMEVRSLTSEDTAVYYCAR EAITTVGAMDY WGQGTSVTVSS  (SEQ ID NO:40)
Hu01G06 IGHV1-18           VDTSTNTAYMELRSLRSDDTAVYYCAR EAITTVGAMDY WGQGTLVTVSS  (SEQ ID NO:54)
Hu01G06 IGHV1-69           VDKSTNTAYMELSSLRSEDTAVYYCAR EAITTVGAMDY WGQGTLVTVSS  (SEQ ID NO:56)
Sh01G06 IGHV1-18 M69L      TDTSTSTAYMELRSLRSDDTAVYYCAR EAITTVGAMDY WGQGTLVTVSS  (SEQ ID NO:58)
Sh01G06 IGHV1-18 M69L K64Q G44S TDTSTSTAYMELRSLRSDDTAVYYCAR EAITTVGAMDY WGQGTLVTVSS  (SEQ ID NO:60)
Sh01G06 IGHV1-18 M69L K64Q TDTSTSTAYMELRSLRSDDTAVYYCAR EAITTVGAMDY WGQGTLVTVSS  (SEQ ID NO:62)
Sh01G06 IGHV1-69 T30S I69L ADKSTSTAYMELSSLRSEDTAVYYCAR EAITTVGAMDY WGQGTLVTVSS  (SEQ ID NO:64)
Sh01G06 IGHV1-69 T30S K64Q I69L ADKSTSTAYMELSSLRSEDTAVYYCAR EAITTVGAMDY WGQGTLVTVSS  (SEQ ID NO:66)
Hu01G06 IGHV1-18 F1        TDTSTSTAYMELRSLRSDDTAVYYCAR EAITTVGAMDY WGQGTLVTVSS  (SEQ ID NO:246)
Hu01G06 IGHV1-18 F2        TDTSTSTAYMELRSLRSDDTAVYYCAR EAITTVGAMDY WGQGTLVTVSS  (SEQ ID NO:248)
Hu01G06 IGHV1-69 F1        ADKSTSTAYMELSSLRSEDTAVYYCAR EAITTVGAMDY WGQGTLVTVSS  (SEQ ID NO:250)
Hu01G06 IGHV1-69 F2        ADKSTSTAYMELSSLRSEDTAVYYCAR EAITTVGAMDY WGQGTLVTVSS  (SEQ ID NO:252)
Ch06C11 Chimeric           KDASNNRVFLKITSVDTADTATYYCAQ RGYDDYW--GY WGQGTLVTISA  (SEQ ID NO:46)
HE LM 06C11 IGHV2-70       KDTSKNQVVLTITNVDPVDTAVYYCAQ RGYDDYW--GY WGQGTLVTISS  (SEQ ID NO:68)
Hu06C11 IGHV2-5            KDTSKNQVVLTITNMDPVDTATYYCAQ RGYDDYW--GY WGQGTLVTVSS  (SEQ ID NO:70)
Ch14F11 Chimeric           KDTSSNEVFLKIAIVDTADTATYYCAR RGHYSAM--DY WGQGTSVTVSS  (SEQ ID NO:50)
Sh14F11 IGHV2-5            KDTSKNQVVLTMTNMDPVDTATYYCAR RGHYSAM--DY WGQGTLVTVSS  (SEQ ID NO:72)
Sh14F11 IGHV2-70           KDTSKNQVVLTMTNMDPVDTAVYYCAR RGHYSAM--DY WGQGTLVTVSS  (SEQ ID NO:74)
```

FIG. 19 Continued

Humanized Heavy Chain CDR Amino Acid Alignments

| Heavy Variable | | | | CDR1 | | CDR2 | |
|---|---|---|---|---|---|---|---|
| Ch01G06 Chimeric | | | | DYNMD-- | (SEQ ID NO:1) | QINPNNGGIFFNQKFKG | (SEQ ID NO:7) |
| Hu01G06 IGHV1-18 | | | | DYNMD-- | (SEQ ID NO:1) | QINPNNGGIFFNQKFKG | (SEQ ID NO:7) |
| Hu01G06 IGHV1-69 | | | | DYNMD-- | (SEQ ID NO:1) | QINPNNGGIFFNQKFKG | (SEQ ID NO:7) |
| Sh01G06 IGHV1-18 M69L | | | | DYNMD-- | (SEQ ID NO:1) | QINPNNGGIFFNQKFKG | (SEQ ID NO:7) |
| Sh01G06 IGHV1-18 M69L K64Q G44S | | | | DYNMD-- | (SEQ ID NO:1) | QINPNNGGIFFNQKFQG | (SEQ ID NO:13) |
| Sh01G06 IGHV1-18 M69L K64Q | | | | DYNMD-- | (SEQ ID NO:1) | QINPNNGGIFFNQKFQG | (SEQ ID NO:13) |
| Sh01G06 IGHV1-69 I69L | | | | DYNMD-- | (SEQ ID NO:1) | QINPNNGGIFFNQKFKG | (SEQ ID NO:7) |
| Sh01G06 IGHV1-69 T30S K64Q I69L | | | | DYNMD-- | (SEQ ID NO:1) | QINPNNGGIFFNQKFQG | (SEQ ID NO:13) |
| Hu01G06 IGHV1-18 F1 | | | | DYNMD-- | (SEQ ID NO:1) | QINPYNHLIFFNQKFQG | (SEQ ID NO:236) |
| Hu01G06 IGHV1-18 F2 | | | | DYNMD-- | (SEQ ID NO:1) | QINPNNGLIFFNQKFQG | (SEQ ID NO:237) |
| Hu01G06 IGHV1-69 F1 | | | | DYNMD-- | (SEQ ID NO:1) | QINPYNHLIFFNQKFKG | (SEQ ID NO:238) |
| Hu01G06 IGHV1-69 F2 | | | | DYNMD-- | (SEQ ID NO:1) | QINPNNGLIFFNQKFKG | (SEQ ID NO:239) |
| Ch06C11 Chimeric | | | | TYGMGVS | (SEQ ID NO:4) | HIY-WDDDKRYNPSLKS | (SEQ ID NO:9) |
| HE LM 06C11 IGHV2-70 | | | | TYGMGVS | (SEQ ID NO:4) | HIY-WDDDKRYNPSLKT | (SEQ ID NO:14) |
| Hu06C11 IGHV2-5 | | | | TYGMGVS | (SEQ ID NO:4) | HIY-WDDDKRYNPSLKS | (SEQ ID NO:9) |
| Ch14F11 Chimeric | | | | TYGMGVG | (SEQ ID NO:5) | DIW-WDDDKYYNPSLKS | (SEQ ID NO:11) |
| Sh14F11 IGHV2-5 | | | | TYGMGVG | (SEQ ID NO:5) | DIW-WDDDKYYNPSLKS | (SEQ ID NO:11) |
| Sh14F11 IGHV2-70 | | | | TYGMGVG | (SEQ ID NO:5) | DIW-WDDDKYYNPSLKS | (SEQ ID NO:11) |

FIG. 20

Humanized Heavy Chain CDR Amino Acid Alignments

| Heavy Variable | | | | | CDR3 | |
|---|---|---|---|---|---|---|
| Ch01G06 | Chimeric | | | | EAITTVGAMDY | (SEQ ID NO:15) |
| Hu01G06 | IGHV1-18 | | | | EAITTVGAMDY | (SEQ ID NO:15) |
| Hu01G06 | IGHV1-69 | | | | EAITTVGAMDY | (SEQ ID NO:15) |
| Sh01G06 | IGHV1-18 | M69L | | | EAITTVGAMDY | (SEQ ID NO:15) |
| Sh01G06 | IGHV1-18 | M69L | K64Q | G44S | EAITTVGAMDY | (SEQ ID NO:15) |
| Sh01G06 | IGHV1-18 | M69L | K64Q | | EAITTVGAMDY | (SEQ ID NO:15) |
| Sh01G06 | IGHV1-69 | T30S | I69L | | EAITTVGAMDY | (SEQ ID NO:15) |
| Sh01G06 | IGHV1-69 | T30S | K64Q | I69L | EAITTVGAMDY | (SEQ ID NO:15) |
| Hu01G06 | IGHV1-18 | F1 | | | EAITTVGAMDY | (SEQ ID NO:15) |
| Hu01G06 | IGHV1-18 | F2 | | | EAITTVGAMDY | (SEQ ID NO:15) |
| Hu01G06 | IGHV1-69 | F1 | | | EAITTVGAMDY | (SEQ ID NO:15) |
| Hu01G06 | IGHV1-69 | F2 | | | EAITTVGAMDY | (SEQ ID NO:15) |
| Ch06C11 | Chimeric | | | | RGYDDYW--GY | (SEQ ID NO:18) |
| HE LM 06C11 | IGHV2-70 | | | | RGYDDYW--GY | (SEQ ID NO:18) |
| Hu06C11 | IGHV2-5 | | | | RGYDDYW--GY | (SEQ ID NO:18) |
| Ch14F11 | Chimeric | | | | RGHYSAM--DY | (SEQ ID NO:19) |
| Sh14F11 | IGHV2-5 | | | | RGHYSAM--DY | (SEQ ID NO:19) |
| Sh14F11 | IGHV2-70 | | | | RGHYSAM--DY | (SEQ ID NO:19) |

FIG. 20 Continued

Complete Humanized Light (Kappa) Chain Variable Region Amino Acid Alignments

Light (Kappa) Variable

```
                               1          2          3          4          5          6          7
                               0          0          0          0          0          0          0
                                                        CDR1                   CDR2
      Ch01G06 Chimeric    DIQMTQSPASLSASVGETVTITCRTSENLHNYLAWYQQKQGKSPQLLVYDAKTLADGVPSRFSGSGSGTQ
      Hu01G06 IGKV1-39    DIQMTQSPSSLSASVGDRVTITCRTSENLHNYLAWYQQKPGKSPKLLIYDAKTLADGVPSRFSGSGSGTD
Hu01G06 IGKV1-39 S43A V48I  DIQMTQSPSSLSASVGDRVTITCRTSENLHNYLAWYQQKPGKAPKLLIYDAKTLADGVPSRFSGSGSGTD
Hu01G06 IGKV1-39 V48I   DIQMTQSPSSLSASVGDRVTITCRTSENLHNYLAWYQQKPGKSPKLLIYDAKTLADGVPSRFSGSGSGTD
      Hu01G06 IGKV1-39 F1    DIQMTQSPSSLSASVGDRVTITCRTSENLHNYLAWYQQKPGKAPKLLIYDAKTLADGVPSRFSGSGSGTD
      Hu01G06 IGKV1-39 F2    DIQMTQSPSSLSASVGDRVTITCRTSENLHNYLAWYQQKPGKSPKLLIYDAKTLADGVPSRFSGSGSGTD
      Ch06C11 Chimeric    DIVMTQSQKFMSTSVGDRVSVTCKASQNVGTNVAWFQQKPGQSPKALIYSASYRYSGVPDRFTGSGSGTD
      Sh06C11 IGKV1-16    DIQMTQSPSSLSASVGDRVTITCKASQNVGTNVAWFQQKPGKAPKSLIYSASYRYSGVPSRFSGSGSGTD
      Ch14F11 Chimeric    DIVMTQSQKFMSTSVGDRVSVTCKASQNVGTNVAWYQQKPGQSPKALIYSPSYRYSGVPDRFTGSGSGTD
      Hu14F11 IGKV1-16    DIQMTQSPSSLSASVGDRVTITCKASQNVGTNVAWFQQKPGKSPKALIYSPSYRYSGVPSRFSGSGSGTD
```

Light (Kappa) Variable

```
                               7          8          9
                               1          0          0
                                                                    CDR3
      Ch01G06 Chimeric    YSLKINSLQPEDFGSYYCQHFWSSPYTFGGGTKLEIK   (SEQ ID NO:76)
      Hu01G06 IGKV1-39    YTLTISSLQPEDFATYYCQHFWSSPYTFGQGTKLEIK   (SEQ ID NO:90)
Hu01G06 IGKV1-39 S43A V48I  YTLTISSLQPEDFATYYCQHFWSSPYTFGQGTKLEIK   (SEQ ID NO:92)
Hu01G06 IGKV1-39 V48I   YTLTISSLQPEDFATYYCQHFWSSPYTFGQGTKLEIK   (SEQ ID NO:94)
      Hu01G06 IGKV1-39 F1    YTLTISSLQPEDFATYYCQHFWSSPYTFGQGTKLEIK   (SEQ ID NO:92)
      Hu01G06 IGKV1-39 F2    YTLTISSLQPEDLAEYFCQHFWSDPYTFGAGTKLELK   (SEQ ID NO:254)
      Ch06C11 Chimeric    FILTISNVQSEDLAEYFCQQYNNYPLTFGQGTKLELK   (SEQ ID NO:82)
      Sh06C11 IGKV1-16    FTLTISSLQPEDFATYYCQQYNNYPLTFGQGTKLELK   (SEQ ID NO:96)
      Ch14F11 Chimeric    FTLTISNVQSEDLAEYFCQQYNSYPHTFGGGTKLEMK   (SEQ ID NO:86)
      Hu14F11 IGKV1-16    FTLTISSLQPEDFATYFCQQYNSYPHTFGQGTKLEIK   (SEQ ID NO:98)
```

FIG. 21

Humanized Light (Kappa) Chain CDR Amino Acid Alignments

| Light (Kappa) Variable | | | CDR1 | CDR2 |
|---|---|---|---|---|
| Ch01G06 | Chimeric | | RTSENLHNYLA (SEQ ID NO:21) | DAKTLAD (SEQ ID NO:26) |
| Hu01G06 | IGKV1-39 | | RTSENLHNYLA (SEQ ID NO:21) | DAKTLAD (SEQ ID NO:26) |
| Hu01G06 | IGKV1-39 | S43A V48I | RTSENLHNYLA (SEQ ID NO:21) | DAKTLAD (SEQ ID NO:26) |
| Hu01G06 | IGKV1-39 | V48I | RTSENLHNYLA (SEQ ID NO:21) | DAKTLAD (SEQ ID NO:26) |
| Hu01G06 | IGKV1-39 | F1 | RTSENLHNYLA (SEQ ID NO:21) | DAKTLAD (SEQ ID NO:26) |
| Hu01G06 | IGKV1-39 | F2 | RTSENLHNYLA (SEQ ID NO:21) | DAKTLAD (SEQ ID NO:26) |
| Ch06C11 | Chimeric | | KASQNVGTNVA (SEQ ID NO:23) | SASYRYS (SEQ ID NO:28) |
| Sh06C11 | IGKV1-16 | | KASQNVGTNVA (SEQ ID NO:23) | SASYRYS (SEQ ID NO:28) |
| Ch14F11 | Chimeric | | KASQNVGTNVA (SEQ ID NO:23) | SPSYRYS (SEQ ID NO:30) |
| Hu14F11 | IGKV1-16 | | KASQNVGTNVA (SEQ ID NO:23) | SPSYRYS (SEQ ID NO:30) |

| Light (Kappa) Variable | | | CDR3 |
|---|---|---|---|
| Ch01G06 | Chimeric | | QHFWSSPYT (SEQ ID NO:32) |
| Hu01G06 | IGKV1-39 | | QHFWSSPYT (SEQ ID NO:32) |
| Hu01G06 | IGKV1-39 | S43A V48I | QHFWSSPYT (SEQ ID NO:32) |
| Hu01G06 | IGKV1-39 | V48I | QHFWSSPYT (SEQ ID NO:32) |
| Hu01G06 | IGKV1-39 | F1 | QHFWSSPYT (SEQ ID NO:32) |
| Hu01G06 | IGKV1-39 | F2 | QHFWSDPYT (SEQ ID NO:244) |
| Ch06C11 | Chimeric | | QQYNNYPLT (SEQ ID NO:35) |
| Sh06C11 | IGKV1-16 | | QQYNNYPLT (SEQ ID NO:35) |
| Ch14F11 | Chimeric | | QQYNSYPHT (SEQ ID NO:36) |
| Hu14F11 | IGKV1-16 | | QQYNSYPHT (SEQ ID NO:36) |

FIG. 22

ANTI-GDF-15 ANTIBODIES

CROSS-REFERENCE TO RELATED APPLICATIONS

This application is a continuation of U.S. patent application Ser. No. 16/824,034, filed Mar. 19, 2020, issued as U.S. Pat. No. 11,725,047, which is a continuation of U.S. patent application Ser. No. 15/655,263, filed Jul. 20, 2017, issued as U.S. Pat. No. 10,597,444 on Mar. 24, 2020, which is a continuation of U.S. patent application Ser. No. 14/863,870, filed Sep. 24, 2015, issued as U.S. Pat. No. 9,725,505 on Aug. 8, 2017, which is a divisional of U.S. patent application Ser. No. 14/137,415, filed Dec. 20, 2013, issued as U.S. Pat. No. 9,175,076 on Nov. 3, 2015, which claims the benefit of and priority to U.S. Provisional Patent Application No. 61/827,325, filed May 24, 2013, and U.S. Provisional Patent Application No. 61/745,508, filed Dec. 21, 2012, the entire disclosures of each of which are incorporated by reference herein in their entireties.

SEQUENCE LISTING

The instant application contains a Sequence Listing which has been submitted electronically in ST.26 XML format and is hereby incorporated by reference in its entirety. Said ST.26 XML copy, created on Jun. 16, 2023, is named 406767_029USD1C3_SEQUENCE_LISTING_ST.26.XML and is 425,984 bytes in size.

FIELD OF THE INVENTION

The field of the invention is molecular biology, immunology, cachexia and cachexia-like disorders, and oncology. More particularly, the field is therapeutic antibodies.

BACKGROUND

Involuntary weight loss can be categorized into three primary etiologies that include, cachexia, sarcopenia and starvation. Cachexia is a debilitating metabolic syndrome associated with numerous diseases, including cancer, AIDS, chronic heart failure (also known as congestive heart failure), chronic obstructive pulmonary disease (COPD), chronic kidney disease, tuberculosis, sepsis and other forms of systemic inflammation. Cachexia varies in its manifestations, but generally involves involuntary loss of skeletal muscle mass and some form of underlying illness (Evans et al. (2008) CLIN. NUTR. 27:793-799). Cachexia is a wasting disorder involving involuntary weight loss and may be associated with systemic inflammation and/or an acute inflammatory response. Thomas (2007) CLIN. NUTRITION 26:389-399. Loss of fat mass as well as fat-free mass, such as muscle mass, often is a prominent clinical feature of cachexia. In many but not all cases, cachexia progresses through stages that have been designated precachexia, cachexia and refractory cachexia (Fearon et al. (2011) LANCET ONC. 12:489-495). Two different, but sometimes overlapping, processes appear to drive the development and progression of cachexia: (a) metabolic processes that act directly on muscle, reducing its mass and function; and (b) reduced food intake, which leads to loss of both fat and muscle (Tsai et al. (2012) J. CACHEXIA SARCOPENIA MUSCLE 3:239-243).

Although cachexia is a complex and incompletely understood syndrome, it is clear that GDF15 (also known as MIC-1, PLAB, PDF and NAG-1), a member of the TGF-β superfamily, is an important mediator of cachexia in various diseases (Tsai et al., supra). At least some tumors overexpress and secrete GDF15, and elevated serum GDF15 levels have been associated with various cancers (Johnen et al. (2007) NAT. MED. 13:1333-1340; Bauskin et al. (2006) CANCER RES. 66:4983-4986). Monoclonal antibodies against GDF15 have been recognized as potential anti-cachexia therapeutic agents. See, e.g., U.S. Pat. No. 8,192,735.

Weight loss resulting from cachexia is associated with poor prognosis in various diseases (Evans et al., supra), and cachexia and its consequences are considered to be the direct cause of death in about 20% of cancer deaths (Tisdale (2002) NAT. REV. CANCER 2:862-871). Cachexia is infrequently reversed by nutritional intervention, and currently this syndrome is seldom treated with drug therapy (Evans et al., supra).

Sarcopenia is a clinical condition related to cachexia that is characterized by loss of skeletal muscle mass and muscle strength. The decrease in muscle mass can lead to functional impairment, with loss of strength, increased likelihood of falls, and loss of autonomy. Respiratory function may also be impaired with a reduced vital capacity. During metabolic stress, muscle protein is rapidly mobilized in order to provide the immune system, liver and gut with amino acids, particularly glutamine. Sarcopenia often is a disease of the elderly; however, its development may also be associated with muscle disuse and malnutrition, and may coincide with cachexia. Sarcopenia can be diagnosed based upon functional observations such as low muscle weight and low gait speed. See, e.g., Muscaritoli et al. (2010) CLIN. NUTRITION 29:154-159.

Starvation typically results in a loss of body fat and non-fat mass due to inadequate diet and/or nutritional uptake (Thomas (2007) supra). The effects of starvation often are reversed by improving diet and nutritional, for example, protein, uptake.

Naturally occurring antibodies are multimeric proteins that contain four polypeptide chains (FIG. 1). Two of the polypeptide chains are called heavy chains (H chains), and two of the polypeptide chains are called light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region (CL in FIG. 1). The heavy chain consists of one variable region ($V_H$ in FIG. 1) and at least three constant regions ($C_{H1}$, $C_{H2}$ and $C_{H3}$ in FIG. 1). The variable regions determine the specificity of the antibody. Each variable region comprises three hypervariable regions also known as complementarity determining regions (CDRs) flanked by four relatively conserved framework regions (FRs). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies.

There is a significant unmet need for effective therapeutic agents for treating cachexia and sarcopenia, including monoclonal antibodies targeting GDF15. Such therapeutic agents have the potential to play an important role in the treatment of various cancers and other life-threatening diseases.

SUMMARY

The invention is based, in part, upon the discovery of a family of antibodies that specifically bind human GDF15

(hGDF15). The antibodies contain hGDF15 binding sites based on the CDRs of the antibodies. The antibodies can be used as therapeutic agents. When used as therapeutic agents, the antibodies are engineered, e.g., humanized, to reduce or eliminate an immune response when administered to a human patient.

The disclosed antibodies prevent or inhibit the activity of (i.e., neutralize) hGDF15. When administered to a mammal, the antibodies can inhibit the loss of muscle mass, for example, the loss of muscle mass associated with an underlying disease. The underlying disease may be selected from the group consisting of cancer, chronic heart failure, chronic kidney disease, COPD, AIDS, multiple sclerosis, rheumatoid arthritis, sepsis, and tuberculosis. In some embodiments, the loss of muscle mass may be accompanied by a loss of fat mass. The disclosed antibodies can also be used to inhibit involuntary weight loss in a mammal. In some embodiments, the disclosed antibodies may also be used to inhibit the loss of organ mass. Further, a method of treating cachexia and/or sarcopenia in a mammal comprising administering an effective amount of one of at least one of the disclosed antibodies to a mammal in need thereof is disclosed.

Also disclosed is a method for establishing a steady-state level of mature recombinant human GDF15 (rhGDF15) in plasma or serum in a mammal comprising administering a rhGDF15-immunoglobulin Fc (Fc-rhGDF15) fusion protein to the mammal. The Fc-rhGDF15 can be a mouse Fc mature recombinant human GDF15 (mFc-rhGDF15). In some embodiments, the mammal is a rodent, e.g., a mouse.

In another aspect, a method of treating obesity in a mammal, for example, a human, comprising administering a therapeutically effective amount of Fc-rhGDF15, e.g., a human Fc mature recombinant human GDF15 (hFc-rhGDF15), to the mammal in need thereof, is disclosed. Pharmaceutical compositions comprising an Fc-rhGDF15 fusion protein and a pharmaceutically acceptable carrier are also disclosed.

These and other aspects and advantages of the invention will become apparent upon consideration of the following figures, detailed description, and claims. As used herein, "including" means without limitation, and examples cited are non-limiting. As used herein, "antibody 01G06, 03G05, 04F08, 06C11, 08G01, 14F11, or 17B11" means antibody 01G06, 03G05, 04F08, 06C11, 08G01, 14F11, or 17B11, or humanized variants thereof.

DESCRIPTION OF THE DRAWINGS

The invention can be more completely understood with reference to the following drawings.

FIG. 10 is a sequence alignment showing the amino acid sequence of the complete immunoglobulin heavy chain variable region of antibodies 01G06, 03G05, 04F08, 06C11, 08G01, 14F11, and 17B11. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 11 is a sequence alignment showing the $CDR_1$, $CDR_2$, and $CDR_3$ sequences for each of the immunoglobulin heavy chain variable region sequences in FIG. 10.

FIG. 12 is a sequence alignment showing the amino acid sequence of the complete immunoglobulin light chain variable region of antibodies 01G06, 03G05, 04F08, 06C11, 08G01, 14F11, and 17B11. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 13 is a sequence alignment showing the CDR$_1$, CDR$_2$, and CDR$_3$ sequences for each of the immunoglobulin light chain variable region sequences in FIG. 12.

In FIG. 16A, the arrow indicates intra-peritoneal injection of antibody.

FIG. 19 is a sequence alignment showing the amino acid sequence of the complete immunoglobulin heavy chain variable region of chimeric 01G06 variable region denoted as Ch01G06 Chimeric; humanized 01G06 heavy chain variable regions denoted as Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, and Hu01G06 IGHV1-69 F2; chimeric 06C11 denoted as Ch06C11 Chimeric; humanized 06C11 heavy chain variable regions denoted as HE LM 06C11 IGHV2-70, and Hu06C11 IGHV2-5; chimeric 14F11 denoted as Ch14F11 Chimeric; and humanized 14F11 heavy chain variable regions denoted as Sh14F11 IGHV2-5 and Sh14F11 IGHV2-70. The amino acid sequences for each antibody are aligned against one another, and CDR$_1$, CDR$_2$, and CDR$_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 20 is a sequence alignment showing the CDR$_1$, CDR$_2$, and CDR$_3$ sequences for each of the immunoglobulin heavy chain variable region sequences in FIG. 19.

FIG. 21 is a sequence alignment showing the amino acid sequence of the complete immunoglobulin light chain variable region of chimeric 01G06 denoted as Ch01G06 Chimeric; humanized 01G06 light chain variable regions denoted as Hu01G06 IGKV1-39, Hu01G06 IGKV1-39 S43A V48I, Hu01G06 IGKV1-39 V48I, Hu01G06 IGKV1-39 F1, and Hu01G06 IGKV1-39 F2; chimeric 06C11 denoted as Ch06C11 Chimeric; humanized 06C11 light chain variable region denoted as Sh06C11 IGKV1-16; chimeric 14F11 denoted as Ch14F11 Chimeric; and humanized 14F11 light chain variable region denoted as Hu14F11 IGKV1-16. The amino acid sequences for each antibody are aligned against one another, and CDR$_1$, CDR$_2$, and CDR$_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 22 is a sequence alignment showing the CDR$_1$, CDR$_2$, and CDR$_3$ sequences for each of the immunoglobulin light chain variable region sequences in FIG. 21.

FIG. 29A) similar to levels found in non tumor bearing mice (SHAM (▲); FIG. 29A). The arrows in FIG. 29A indicate intra-peritoneal injection of antibody.

DETAILED DESCRIPTION

Figure 1:
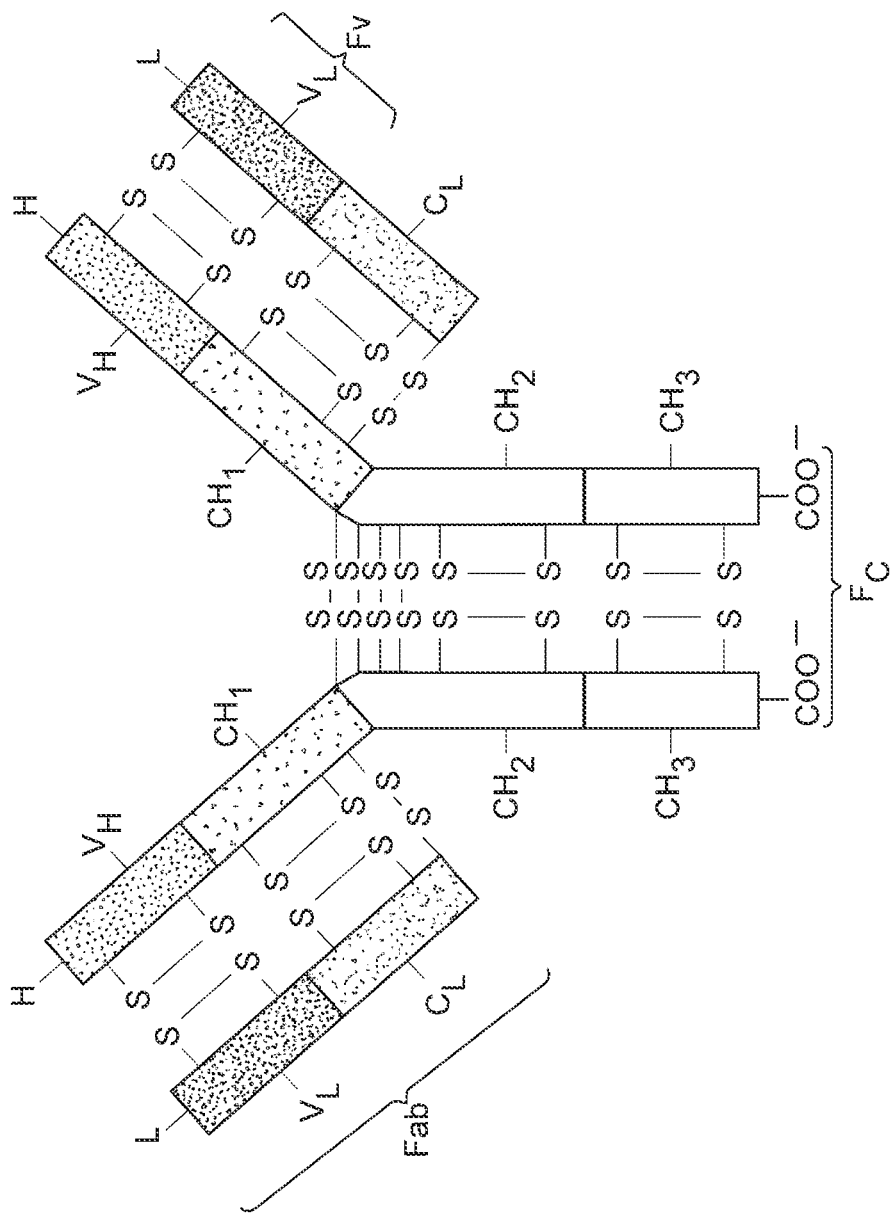
FIG. 1 (prior art) is a schematic representation of a typical naturally-occurring antibody.

The anti-GDF15 antibodies disclosed herein are based on the antigen binding sites of certain monoclonal antibodies that have been selected on the basis of binding and neutralization of human GDF15 (hGDF15). The antibodies contain immunoglobulin variable region CDR sequences that define a binding site for hGDF15.

By virtue of the neutralizing activity of these antibodies, they are useful for treating cachexia and/or sarcopenia. For use as therapeutic agents, the antibodies can be engineered to minimize or eliminate an immune response when administered to a human patient. Various features and aspects of the invention are discussed in more detail below.

As used herein, "cachexia" means a metabolic syndrome associated with underlying disease and characterized by involuntary loss of muscle mass. Cachexia is often accompanied by involuntary weight loss, loss of fat mass, anorexia, inflammation, insulin resistance, fatigue, weakness, significant loss of appetite, and/or increased muscle protein breakdown. Cachexia is distinct from starvation, age-related loss of muscle mass, malabsorption, and hyperthyroidism. Underlying diseases associated with cachexia include cancer, chronic heart failure, chronic kidney disease, COPD, AIDS, multiple sclerosis, rheumatoid arthritis, sepsis, and tuberculosis.

As used herein, "sarcopenia" is understood to be a condition characterized primarily by loss of skeletal muscle mass and muscle strength. Sarcopenia is frequently associated with aging. See, Ruegg and Glass (2011) ANNUAL REV. PHARMACOL. TOXICOL. 51:373-395. In one approach, sarcopenia can be identified in a subject if a value of the appendicular skeletal muscle mass of a subject divided by the height of the subject in meters is more than two standard deviations below the young normal mean. (Thomas (2007) supra; see also Baumgartner et al. (1999) MECH. AGEING DEV. 147:755-763).

As used herein, unless otherwise indicated, "antibody" means an intact antibody (e.g., an intact monoclonal antibody) or antigen-binding fragment of an antibody, including an intact antibody or antigen-binding fragment that has been modified or engineered, or that is a human antibody. Examples of antibodies that have been modified or engineered are chimeric antibodies, humanized antibodies, and multispecific antibodies (e.g., bispecific antibodies). Examples of antigen-binding fragments include Fab, Fab', F(ab')$_2$, Fv, single chain antibodies (e.g., scFv), minibodies and diabodies.

I. Antibodies That Bind GDF15

The antibodies disclosed herein comprise: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding hGDF15 protein.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding hGDF15. A $CDR_{H1}$ comprises an amino acid sequence selected from the group consisting of SEQ ID NO:1 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:2 (03G05), SEQ ID NO:3 (04F08), SEQ ID NO:4 (06C11, Ch06C11 Chimeric, HE LM 06C11 IGHV2-70, Hu06C11 IGHV2-5), SEQ ID NO:5 (14F11, Ch14F11 Chimeric, Sh14F11 IGHV2-5, Sh14F11 IGHV2-70), and SEQ ID NO:6 (17B11); a $CDR_{H2}$ comprises an amino acid sequence selected from the group consisting of SEQ ID NO:7 (01G06, Ch01G06 Chimeric, Hu01G06 IGHV1-18, Hu01G06 IGHV1-69, Sh01G06 IGHV1-18 M69L, Sh01G06 IGHV1-69 T30S I69L), SEQ ID NO:8 (03G05), SEQ ID NO:9 (04F08, 06C11, Ch06C11 Chimeric, Hu06C11 IGHV2-5), SEQ ID NO:10 (08G01), SEQ ID NO:11 (14F11, Ch14F11 Chimeric, Sh14F11 IGHV2-5, Sh14F11 IGHV2-70), SEQ ID NO:12 (17B11), SEQ ID NO: 13 (Sh01G06 IGHV1-18 M69L K64Q G44S, Sh01G06 IGHV1-18 M69L K64Q, Sh01G06 IGHV1-69 T30S K64Q I69L), SEQ ID NO:236 (Hu01G06 IGHV1-18 F1), SEQ ID NO:237 (Hu01G06 IGHV1-18 F2), SEQ ID NO:238 (Hu01G06 IGHV1-69 F1), SEQ ID NO:239 (Hu01G06 IGHV1-69 F2), and SEQ ID NO: 14 (HE LM 06C11 IGHV2-70); and a $CDR_{H3}$ comprises an amino acid sequence selected from the group consisting of SEQ ID NO: 15 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:16 (03G05), SEQ ID NO:17 (04F08), SEQ ID NO: 18 (06C11, Ch06C11 Chimeric, HE LM 06C11 IGHV2-70, Hu06C11 IGHV2-5), SEQ ID NO: 19 (14F11, Ch14F11 Chimeric, Sh14F11 IGHV2-5, Sh14F11 IGHV2-70), and SEQ ID NO:20 (17B11). Throughout this specification, a particular SEQ ID NO. is followed in parentheses by the antibody that was the origin of that sequence. For example, "SEQ ID NO:2 (03G05)" means that SEQ ID NO:2 comes from antibody 03G05.

In some embodiments, the antibody comprises an immunoglobulin heavy chain variable region comprising a $CDR_{H1}$ comprising the amino acid sequence of SEQ ID NO:1 (01G06, Ch01G06 Chimeric, Hu01G06 IGHV1-18, Hu01G06 IGHV1-69, Sh01G06 IGHV1-69 T30S I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:7 (01G06, Ch01G06 Chimeric, Hu01G06 IGHV1-18, Hu01G06 IGHV1-69, Sh01G06 IGHV1-69 T30S I69L), and a CDR$_{H3}$ comprising the amino acid sequence of SEQ ID NO: 15 (01G06, Ch01G06 Chimeric, Hu01G06 IGHV1-18, Hu01G06 IGHV1-69, Sh01G06 IGHV1-69 T30S I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:2 (03G05), a CDR$_{H2}$ comprising the amino acid sequence of SEQ ID NO:8 (03G05), and a CDR$_{H3}$ comprising the amino acid sequence of SEQ ID NO: 16 (03G05).

In some embodiments, the antibody comprises an immunoglobulin heavy chain variable region comprising a CDR$_{H1}$ comprising the amino acid sequence of SEQ ID NO:3 (04F08), a CDR$_{H2}$ comprising the amino acid sequence of SEQ ID NO:9 (04F08), and a CDR$_{H3}$ comprising the amino acid sequence of SEQ ID NO: 17 (04F08).

In some embodiments, the antibody comprises an immunoglobulin heavy chain variable region comprising a CDR$_{H1}$ comprising the amino acid sequence of SEQ ID NO:4 (06C11, Ch06C11 Chimeric, Hu06C11 IGHV2-5), a CDR$_{H2}$ comprising the amino acid sequence of SEQ ID NO:9 (06C11, Ch06C11 Chimeric, Hu06C11 IGHV2-5), and a CDR$_{H3}$ comprising the amino acid sequence of SEQ ID NO:18 (06C11, Ch06C11 Chimeric, Hu06C11 IGHV2-5).

In some embodiments, the antibody comprises an immunoglobulin heavy chain variable region comprising a CDR$_{H1}$ comprising the amino acid sequence of SEQ ID NO:1 (08G01), a CDR$_{H2}$ comprising the amino acid sequence of SEQ ID NO: 10 (08G01), and a CDR$_{H3}$ comprising the amino acid sequence of SEQ ID NO:15 (08G01).

In some embodiments, the antibody comprises an immunoglobulin heavy chain variable region comprising a CDR$_{H1}$ comprising the amino acid sequence of SEQ ID NO:5 (14F11, Ch14F11 Chimeric, Sh14F11 IGHV2-5, Sh14F11 IGHV2-70), a CDR$_{H2}$ comprising the amino acid sequence of SEQ ID NO: 11 (14F11, Ch14F11 Chimeric, Sh14F11 IGHV2-5, Sh14F11 IGHV2-70), and a CDR$_{H3}$ comprising the amino acid sequence of SEQ ID NO:19 (14F11, Ch14F11 Chimeric, Sh14F11 IGHV2-5, Sh14F11 IGHV2-70).

In some embodiments, the antibody comprises an immunoglobulin heavy chain variable region comprising a CDR$_{H1}$ comprising the amino acid sequence of SEQ ID NO:6 (17B11), a CDR$_{H2}$ comprising the amino acid sequence of SEQ ID NO:12 (17B11), and a CDR$_{H3}$ comprising the amino acid sequence of SEQ ID NO:20 (17B11).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO: 13 (Sh01G06 IGHV1-18 M69L K64Q G44S, Sh01G06 IGHV1-18 M69L K64Q, Sh01G06 IGHV1-69 T30S K64Q I69L), and a CDR$_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:236 (Hu01G06 IGHV1-18 F1), and a CDR$_{H3}$ comprising the amino acid sequence of SEQ ID NO: 15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:237 (Hu01G06 IGHV1-18 F2), and a CDR$_{H3}$ comprising the amino acid sequence of SEQ ID NO: 15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:238 (Hu01G06 IGHV1-69 F1), and a CDR$_{H3}$ comprising the amino acid sequence of SEQ ID NO: 15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a CDR$_{H2}$ comprising the amino acid sequence of SEQ ID NO:239 (Hu01G06 IGHV1-69 F2), and a CDR$_{H3}$ comprising the amino acid sequence of SEQ ID NO: 15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a CDR$_{H1}$ comprising the amino acid sequence of SEQ ID NO:4 (HE LM 06C11 IGHV2-70), a CDR$_{H2}$ comprising the amino acid sequence of SEQ ID NO: 14 (HE LM 06C11 IGHV2-70), and a CDR$_{H3}$ comprising the amino acid sequence of SEQ ID NO:18 (HE LM 06C11 IGHV2-70).

Preferably, the CDR$_{H1}$, CDR$_{H2}$, and CDR$_{H3}$ sequences are interposed between fully human or humanized immunoglobulin FR sequences.

In some embodiments, the antibody comprises (a) an immunoglobulin light chain variable region comprising the structure CDR$_{L1}$-CDR$_{L2}$-CDR$_{L3}$, and (b) an immunoglobulin heavy chain variable region, wherein the immunoglobulin light chain variable region and the immunoglobulin heavy chain variable region together define a single binding site for binding hGDF15. A CDR$_{L1}$ comprises an amino acid sequence selected from the group consisting of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:22 (03G05), SEQ ID NO:23 (04F08, 06C11, Ch06C11 Chimeric, Sh06C11 IGKV1-16, 14F11, Ch14F11 Chimeric, Hu14F11 IGKV1-16), SEQ ID NO:24 (08G01), and SEQ ID NO:25 (17B11); a CDR$_{L2}$ comprises an amino acid sequence selected from the group consisting of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:27 (03G05), SEQ ID NO:28 (04F08, 06C11, Ch06C11 Chimeric, Sh06C11 IGKV1-16), SEQ ID NO:29 (08G01), SEQ ID NO:30 (14F11, Ch14F11 Chimeric, Hu14F11 IGKV1-16), and SEQ ID NO:31 (17B11); and a CDR$_{L3}$ comprises an amino acid sequence selected from the group consisting of SEQ ID NO:32 (01G06, Ch01G06 Chimeric, Hu01G06 IGKV1-39, Hu01G06 IGKV1-39 S43A V48I, Hu01G06 IGKV1-39 V48I, 08G01, Hu01G06 IGKV1-39 F1), SEQ ID NO:244 (Hu01G06 IGKV1-39 F2), SEQ ID NO:33 (03G05), SEQ ID NO:34 (04F08), SEQ ID NO:35 (06C11, Ch06C11 Chimeric, Sh06C11 IGKV1-16), SEQ ID NO:36 (14F11, Ch14F11 Chimeric, Hu14F11 IGKV1-16), and SEQ ID NO:37 (17B11).

In some embodiments, the antibody comprises an immunoglobulin light chain variable region comprising a CDR$_{L1}$ comprising the amino acid sequence of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), a CDR$_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), and a CDR$_{L3}$ comprising the amino acid sequence of SEQ ID NO:32 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1).

In some embodiments, the antibody comprises an immunoglobulin light chain variable region comprising a CDR$_{L1}$ comprising the amino acid sequence of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), a CDR$_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), and a CDR$_{L3}$ comprising the amino acid sequence of SEQ ID NO:244 (Hu01G06 IGKV1-39 F2).

In some embodiments, the antibody comprises an immunoglobulin light chain variable region comprising a CDR$_{L1}$ comprising the amino acid sequence of SEQ ID NO:22 (03G05), a CDR$_{L2}$ comprising the amino acid sequence of SEQ ID NO:27 (03G05), and a CDR$_{L3}$ comprising the amino acid sequence of SEQ ID NO:33 (03G05).

In some embodiments, the antibody comprises an immunoglobulin light chain variable region comprising a CDR$_{L1}$ comprising the amino acid sequence of SEQ ID NO:23 (04F08), a CDR$_{L2}$ comprising the amino acid sequence of SEQ ID NO:28 (04F08), and a CDR$_{L3}$ comprising the amino acid sequence of SEQ ID NO:34 (04F08).

In some embodiments, the antibody comprises an immunoglobulin light chain variable region comprising a CDR$_{L1}$ comprising the amino acid sequence of SEQ ID NO:23 (06C11, Ch06C11 Chimeric, Sh06C11 IGKV1-16), a CDR$_{L2}$ comprising the amino acid sequence of SEQ ID NO:28 (06C11, Ch06C11 Chimeric, Sh06C11 IGKV1-16), and a CDR$_{L3}$ comprising the amino acid sequence of SEQ ID NO:35 (06C11, Ch06C11 Chimeric, Sh06C11 IGKV1-16).

In some embodiments, the antibody comprises an immunoglobulin light chain variable region comprising a CDR$_{L1}$ comprising the amino acid sequence of SEQ ID NO:24 (08G01), a CDR$_{L2}$ comprising the amino acid sequence of SEQ ID NO:29 (08G01), and a CDR$_{L3}$ comprising the amino acid sequence of SEQ ID NO:32 (08G01).

In some embodiments, the antibody comprises an immunoglobulin light chain variable region comprising a CDR$_{L1}$ comprising the amino acid sequence of SEQ ID NO:23 (14F11, Ch14F11 Chimeric, Hu14F11 IGKV1-16), a CDR$_{L2}$ comprising the amino acid sequence of SEQ ID NO:30 (14F11, Ch14F11 Chimeric, Hu14F11 IGKV1-16), and a CDR$_{L3}$ comprising the amino acid sequence of SEQ ID NO:36 (14F11, Ch14F11 Chimeric, Hu14F11 IGKV1-16).

In some embodiments, the antibody comprises an immunoglobulin light chain variable region comprising a CDR$_{L1}$ comprising the amino acid sequence of SEQ ID NO:25 (17B11), a CDR$_{L2}$ comprising the amino acid sequence of SEQ ID NO:31 (17B11), and a CDR$_{L3}$ comprising the amino acid sequence of SEQ ID NO:37 (17B11).

Preferably, the CDR$_{L1}$, CDR$_{L2}$, and CDR$_{L3}$ sequences are interposed between fully human or humanized immunoglobulin FR sequences.

In some embodiments, the antibody comprises: (a) an immunoglobulin heavy chain variable region comprising the structure CDR$_{H1}$-CDR$_{H2}$-CDR$_{H3}$ and (b) an immunoglobulin light chain variable region comprising the structure CDR$_{L1}$-CDR$_{L2}$-CDR$_{L3}$, wherein the heavy chain variable region and the light chain variable region together define a single binding site for binding hGDF15. The CDR$_{H1}$ is an amino acid sequence selected from the group consisting of SEQ ID NO:1 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:2 (03G05), SEQ ID NO:3 (04F08), SEQ ID NO:4 (06C11, Ch06C11 Chimeric, HE LM 06C11 IGHV2-70, Hu06C11 IGHV2-5), SEQ ID NO:5 (14F11, Ch14F11 Chimeric, Sh14F11 IGHV2-5, Sh14F11 IGHV2-70), and SEQ ID NO:6 (17B11); the CDR$_{H2}$ is an amino acid sequence selected from the group consisting of SEQ ID NO:7 (01G06, Ch01G06 Chimeric, Hu01G06 IGHV1-18, Hu01G06 IGHV1-69, Sh01G06 IGHV1-18 M69L, Sh01G06 IGHV1-69 T30S I69L), SEQ ID NO:8 (03G05), SEQ ID NO:9 (04F08, 06C11, Ch06C11 Chimeric, Hu06C11 IGHV2-5), SEQ ID NO:10 (08G01), SEQ ID NO:11 (14F11, Ch14F11 Chimeric, Sh14F11 IGHV2-5, Sh14F11 IGHV2-70), SEQ ID NO: 12 (17B11), SEQ ID NO: 13 (Sh01G06 IGHV1-18 M69L K64Q G44S, Sh01G06 IGHV1-18 M69L K64Q, Sh01G06 IGHV1-69 T30S K64Q I69L), SEQ ID NO:236 (Hu01G06 IGHV1-18 F1), SEQ ID NO:237 (Hu01G06 IGHV1-18 F2), SEQ ID NO:238 (Hu01G06 IGHV1-69 F1), SEQ ID NO:239 (Hu01G06 IGHV1-69 F2), and SEQ ID NO: 14 (HE LM 06C11 IGHV2-70); and the $CDR_{H}3$ is an amino acid sequence selected from the group consisting of SEQ ID NO: 15 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:16 (03G05), SEQ ID NO:17 (04F08), SEQ ID NO: 18 (06C11, Ch06C11 Chimeric, HE LM 06C11 IGHV2-70, Hu06C11 IGHV2-5), SEQ ID NO: 19 (14F11, Ch14F11 Chimeric, Sh14F11 IGHV2-5, Sh14F11 IGHV2-70), and SEQ ID NO:20 (17B11). The $CDR_{L1}$ is an amino acid sequence selected from the group consisting of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:22 (03G05), SEQ ID NO:23 (04F08, 06C11, Ch06C11 Chimeric, Sh06C11 IGKV1-16, 14F11, Ch14F11 Chimeric, Hu14F11 IGKV1-16), SEQ ID NO:24 (08G01), and SEQ ID NO:25 (17B11); the $CDR_{L2}$ is an amino acid sequence selected from the group consisting of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:27 (03G05), SEQ ID NO:28 (04F08, 06C11, Ch06C11 Chimeric, Sh06C11 IGKV1-16), SEQ ID NO:29 (08G01), SEQ ID NO:30 (14F11, Ch14F11 Chimeric, Hu14F11 IGKV1-16), and SEQ ID NO:31 (17B11); and the $CDR_{L3}$ is an amino acid sequence selected from the group consisting of SEQ ID NO:32 (01G06, Ch01G06 Chimeric, Hu01G06 IGKV1-39, Hu01G06 IGKV1-39 S43A V48I, Hu01G06 IGKV1-39 V48I, 08G01, Hu01G06 IGKV1-39 F1), SEQ ID NO:244 (Hu01G06 IGKV1-39 F2), SEQ ID NO:33 (03G05), SEQ ID NO:34 (04F08), SEQ ID NO:35 (06C11, Ch06C11 Chimeric, Sh06C11 IGKV1-16), SEQ ID NO:36 (14F11, Ch14F11 Chimeric, Hu14F11 IGKV1-16), and SEQ ID NO:37 (17B11).

In some embodiments, the antibody comprises an immunoglobulin heavy chain variable region comprising a $CDR_{H1}$ comprising an amino acid sequence selected from the group consisting of SEQ ID NO:1 and SEQ ID NO:38 (Hu01G06 IGHV1-18 F1), a $CDR_{H2}$ comprising an amino acid sequence selected from the group consisting of SEQ ID NO:236 and SEQ ID NO:240 (Hu01G06 IGHV1-18 F1), and a $CDR_{H3}$ comprising the amino acid sequence of SEQ ID NO:15 (Hu01G06 IGHV1-18 F1); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1)

In some embodiments, the antibody comprises an immunoglobulin heavy chain variable region comprising a $CDR_{H1}$ comprising an amino acid sequence selected from the group consisting of SEQ ID NO:1 and SEQ ID NO:38 (Hu01G06 IGHV1-18 F2), a $CDR_{H2}$ comprising an amino acid sequence selected from the group consisting of SEQ ID NO:237 and SEQ ID NO:241 (Hu01G06 IGHV1-18 F2), and a $CDR_{H3}$ comprising the amino acid sequence of SEQ ID NO:15 (Hu01G06 IGHV1-18 F2); and an immunoglobulin light chain variable region comprising a $CDR_{L1}$ comprising the amino acid sequence of SEQ ID NO:21 (Hu01G06 IGKV1-39 F2), a $CDR_{L2}$ comprising the amino acid sequence of SEQ ID NO:26 (Hu01G06 IGKV1-39 F2), and a $CDR_{L3}$ comprising the amino acid sequence of SEQ ID NO:244 (Hu01G06 IGKV1-39 F2).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F1), a $CDR_{H2}$ comprising an amino acid sequence selected from the group consisting of SEQ ID NO:238 and SEQ ID NO:241 (Hu01G06 IGHV1-69 F1), and a $CDR_{H3}$ comprising the amino acid sequence of SEQ ID NO:15 (Hu01G06 IGHV1-69 F1); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F2), a $CDR_{H2}$ comprising an amino acid sequence selected from the group consisting of SEQ ID NO:239 and SEQ ID NO:240 (Hu01G06 IGHV1-69 F2), and a $CDR_{H3}$ comprising the amino acid sequence of SEQ ID NO:15 (Hu01G06 IGHV1-69 F2); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F2), a $CDR_{H2}$ comprising an amino acid sequence selected from the group consisting of SEQ ID NO:239 and SEQ ID NO:240 (Hu01G06 IGHV1-69 F2), and a $CDR_{H3}$ comprising the amino acid sequence of SEQ ID NO:15 (Hu01G06 IGHV1-69 F2); and an immunoglobulin light chain variable region comprising a $CDR_{L1}$ comprising the amino acid sequence of SEQ ID NO:21 (Hu01G06 IGKV1-39 F2), a $CDR_{L2}$ comprising the amino acid sequence of SEQ ID NO:26 (Hu01G06 IGKV1-39 F2), and a $CDR_{L3}$ comprising the amino acid sequence of SEQ ID NO:244 (Hu01G06 IGKV1-39 F2).

The antibodies disclosed herein comprise an immunoglobulin heavy chain variable region and an immunoglobulin light chain variable region. In some embodiments, the antibody comprises an immunoglobulin heavy chain variable region selected from the group consisting of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70); and an immunoglobulin light chain variable region.

In other embodiments, the antibody comprises an immunoglobulin light chain variable region selected from the group consisting of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:96 (Sh06C11 IGKV1-16), SEQ ID NO:254 (Hu01G06 IGKV1-39 F2), and SEQ ID NO:98 (Hu14F11 IGKV1-16), and an immunoglobulin heavy chain variable region.

In some embodiments, the antibody comprises an immunoglobulin heavy chain variable region selected from the group consisting of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70), and an immunoglobulin light chain variable region selected from the group consisting of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:96 (Sh06C11 IGKV1-16), SEQ ID NO:254 (Hu01G06 IGKV1-39 F2), and SEQ ID NO:98 (Hu14F11 IGKV1-16).

In some embodiments, the antibody comprises an immunoglobulin heavy chain variable region comprising the amino acid sequence of SEQ ID NO:40 (01G06, Ch01G06 Chimeric), and an immunoglobulin light chain variable region comprising the amino acid sequence of SEQ ID NO:76 (01G06, Ch01G06 Chimeric).

In some embodiments, the antibody comprises an immunoglobulin heavy chain variable region comprising the amino acid sequence of SEQ ID NO:42 (03G05), and an immunoglobulin light chain variable region comprising the amino acid sequence of SEQ ID NO:78 (03G05).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:46 (06C11), and an immunoglobulin light chain variable region comprising the amino acid sequence of SEQ ID NO:82 (06C11).

In some embodiments, the antibody comprises an immunoglobulin heavy chain variable region comprising the amino acid sequence of SEQ ID NO:48 (08G01), and an immunoglobulin light chain variable region comprising the amino acid sequence of SEQ ID NO:84 (08G01).

In some embodiments, the antibody comprises an immunoglobulin heavy chain variable region comprising the amino acid sequence of SEQ ID NO:50 (14F11), and an immunoglobulin light chain variable region comprising the amino acid sequence of SEQ ID NO:86 (14F11).

In some embodiments, the antibody comprises an immunoglobulin heavy chain variable region comprising the amino acid sequence of SEQ ID NO:52 (17B11), and an immunoglobulin light chain variable region comprising the amino acid sequence of SEQ ID NO:88 (17B11).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:90 (Hu01G06 IGKV1-39).

In some embodiments, the antibody comprises an immuoglobulin heavy chain variable region comprising the amino acid sequence of SEQ ID NO:40 (Ch01G06 Chimeric), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:246 (Hu01G06 IGHV1-18 F1), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:248 (Hu01G06 IGHV1-18 F2), and an immunoglobulin light chain variable region comprising the amino acid sequence of SEQ ID NO:254 (Hu01G06 IGKV1-39 F2).

In some embodiments, the antibody comprises an immunoglobulin heavy chain variable region comprising the amino acid sequence of SEQ ID NO:250 (Hu01G06 IGHV1-69 F1), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:254 (Hu01G06 IGKV1-39 F2).

In some embodiments, the antibody comprises an immunoglobulin heavy chain variable region comprising the amino acid sequence of SEQ ID NO:68 (HE LM 06C11 IGHV2-70), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:68 (HE LM 06C11 IGHV2-70), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:48 (08G01), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:84 (08G01).

In certain embodiments, the antibodies disclosed herein comprise an immunoglobulin heavy chain and an immunoglobulin light chain. In some embodiments, the antibody comprises an immunoglobulin heavy chain selected from the group consisting of SEQ ID NO:100 (01G06), SEQ ID NO:104 (03G05), SEQ ID NO:108 (04F08), SEQ ID NO:112 (06C11), SEQ ID NO:116 (08G01), SEQ ID NO:120 (14F11), SEQ ID NO:124 (17B11), SEQ ID NO:176 (Ch01G06 Chimeric), SEQ ID NO:178 (Hu01G06 IGHV1-18), SEQ ID NO:180 (Hu01G06 IGHV1-69), SEQ ID NO:182 (Sh01G06 IGHV1-18 M69L), SEQ ID NO:184 (Sh01G06 IGHV1-18 M69L K64Q G44S), SEQ ID NO:186 (Sh01G06 IGHV1-18 M69L K64Q), SEQ ID NO:188 (Sh01G06 IGHV1-69 T30S I69L), SEQ ID NO:190 (Sh01G06 IGHV1-69 T30S K64Q I69L), SEQ ID NO:256 (Hu01G06 IGHV1-18 F1), SEQ ID NO:258 (Hu01G06 IGHV1-18 F2), SEQ ID NO:260 (Hu01G06 IGHV1-69 F1), SEQ ID NO:262 (Hu01G06 IGHV1-69 F2), SEQ ID NO:192 (Ch06C11 Chimeric), SEQ ID NO:194 (HE LM 06C11 IGHV2-70), SEQ ID NO:196 (Hu06C11 IGHV2-5), SEQ ID NO:198 (Ch14F11 Chimeric), SEQ ID NO:200 (Sh14F11 IGHV2-5), and SEQ ID NO:202 (Sh14F11 IGHV2-70); and an immunoglobulin light chain.

In other embodiments, the antibody comprises an immunoglobulin light chain selected from the group consisting of SEQ ID NO: 102 (01G06), SEQ ID NO:106 (03G05), SEQ ID NO:110 (04F08), SEQ ID NO:114 (06C11), SEQ ID NO:118 (08G01), SEQ ID NO:122 (14F11), SEQ ID NO:126 (17B11), SEQ ID NO:204 (Ch01G06 Chimeric), SEQ ID NO:206 (Hu01G06 IGKV1-39), SEQ ID NO:208 (Hu01G06 IGKV1-39 S43A V48I or Hu01G06 IGKV1-39 F1), SEQ ID NO:210 (Hu01G06 IGKV1-39 V48I), SEQ ID NO:264 (Hu01G06 IGKV1-39 F2), SEQ ID NO:212 (Ch06C11 Chimeric), SEQ ID NO:214 (Sh06C11 IGKV1-16), SEQ ID NO:216 (Ch14F11 Chimeric), and SEQ ID NO:218 (Hu14F11 IGKV1-16), and an immunoglobulin heavy chain.

In some embodiments, the antibody comprises (i) an immunoglobulin heavy chain selected from the group consisting of SEQ ID NO: 100 (01G06), SEQ ID NO:104 (03G05), SEQ ID NO:108 (04F08), SEQ ID NO:112 (06C11), SEQ ID NO:116 (08G01), SEQ ID NO:120 (14F11), SEQ ID NO:124 (17B11), SEQ ID NO: 176 (Ch01G06 Chimeric), SEQ ID NO:178 (Hu01G06 IGHV1-18), SEQ ID NO:180 (Hu01G06 IGHV1-69), SEQ ID NO:182 (Sh01G06 IGHV1-18 M69L), SEQ ID NO:184 (Sh01G06 IGHV1-18 M69L K64Q G44S), SEQ ID NO:186 (Sh01G06 IGHV1-18 M69L K64Q), SEQ ID NO:188 (Sh01G06 IGHV1-69 T30S I69L), SEQ ID NO:190 (Sh01G06 IGHV1-69 T30S K64Q I69L), SEQ ID NO:256 (Hu01G06 IGHV1-18 F1), SEQ ID NO:258 (Hu01G06 IGHV1-18 F2), SEQ ID NO:260 (Hu01G06 IGHV1-69 F1), SEQ ID NO:262 (Hu01G06 IGHV1-69 F2), SEQ ID NO:192 (Ch06C11 Chimeric), SEQ ID NO:194 (HE LM 06C11 IGHV2-70), SEQ ID NO:196 (Hu06C11 IGHV2-5), SEQ ID NO:198 (Ch14F11 Chimeric), SEQ ID NO:200 (Sh14F11 IGHV2-5), and SEQ ID NO:202 (Sh14F11 IGHV2-70), and (ii) an immunoglobulin light chain selected from the group consisting of SEQ ID NO:102 (01G06), SEQ ID NO:106 (03G05), SEQ ID NO:110 (04F08), SEQ ID NO:114 (06C11), SEQ ID NO:118 (08G01), SEQ ID NO:122 (14F11), SEQ ID NO:126 (17B11), SEQ ID NO:204 (Ch01G06 Chimeric), SEQ ID NO:206 (Hu01G06 IGKV1-39), SEQ ID NO:208 (Hu01G06 IGKV1-39 S43A V48I or Hu01G06 IGKV1-39 F1), SEQ ID NO:210 (Hu01G06 IGKV1-39 V48I), SEQ ID NO:264 (Hu01G06 IGKV1-39 F2), SEQ ID NO:212 (Ch06C11 Chimeric), SEQ ID NO:214 (Sh06C11 IGKV1-16), SEQ ID NO:216 (Ch14F11 Chimeric), and SEQ ID NO:218 (Hu14F11 IGKV1-16).

In some embodiments, the antibody comprises an immunoglobulin heavy chain comprising the amino acid sequence of SEQ ID NO:176 (Ch01G06 Chimeric), and an immunoglobulin light chain comprising the amino acid sequence of SEQ ID NO:204 (Ch01G06 Chimeric).

In some embodiments, the antibody comprises an immunoglobulin heavy chain comprising the amino acid sequence of SEQ ID NO:192 (Ch06C11 Chimeric), and an immunoglobulin light chain comprising the amino acid sequence of SEQ ID NO:212 (Ch06C11 Chimeric).

In some embodiments, the antibody comprises an immunoglobulin heavy chain comprising the amino acid sequence of SEQ ID NO:198 (Ch14F11 Chimeric), and an immunoglobulin light chain comprising the amino acid sequence of SEQ ID NO:216 (Ch14F11 Chimeric).

In some embodiments, the antibody comprises an immunoglobulin heavy chain comprising the amino acid sequence of SEQ ID NO:178 (Hu01G06 IGHV1-18), and an immunoglobulin light chain comprising the amino acid sequence of SEQ ID NO:206 (Hu01G06 IGKV1-39).

In some embodiments, the antibody comprises an immunoglobulin heavy chain comprising the amino acid sequence of SEQ ID NO:180 (Hu01G06 IGHV1-69), and an immunoglobulin light chain comprising the amino acid sequence of SEQ ID NO:206 (Hu01G06 IGKV1-39).

In some embodiments, the antibody comprises an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:210 (Hu01G06 IGKV1-39 V48I).

In some embodiments, the antibody comprises an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:210 (Hu01G06 IGKV1-39 V48I).

In some embodiments, the antibody comprises an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:208 (Hu01G06 IGKV1-39 S43A V48I).

In some embodiments, the antibody comprises an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:208 (Hu01G06 IGKV1-39 S43A V48I).

In some embodiments, the antibody comprises an immunoglobulin heavy chain comprising the amino acid sequence of SEQ ID NO:256 (Hu01G06 IGHV1-18 F1), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:258 (Hu01G06 IGHV1-18 F2), and an immunoglobulin light chain comprising the amino acid sequence of SEQ ID NO:264 (Hu01G06 IGKV1-39 F2).

In some embodiments, the antibody comprises an immunoglobulin heavy chain comprising the amino acid sequence of SEQ ID NO:260 (Hu01G06 IGHV1-69 F1), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:262 (Hu01G06 IGHV1-69 F2), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:262 (Hu01G06 IGHV1-69 F2), and an immunoglobulin light chain comprising the amino acid sequence of SEQ ID NO:264 (Hu01G06 IGKV1-39 F2).

In some embodiments, the antibody comprises an immunoglobulin heavy chain comprising the amino acid sequence of SEQ ID NO:194 (HE LM 06C11 IGHV2-70), and an immunoglobulin light chain comprising the amino acid sequence of SEQ ID NO:214 (Sh06C11 IGKV1-16).

In some embodiments, the antibody comprises an immunoglobulin heavy chain comprising the amino acid sequence of SEQ ID NO:196 (Hu06C11 IGHV2-5), and an immunoglobulin light chain comprising the amino acid sequence of SEQ ID NO:214 (Sh06C11 IGKV1-16).

In some embodiments, the antibody comprises an immunoglobulin heavy chain comprising the amino acid sequence of SEQ ID NO:200 (Sh14F11 IGHV2-5), and an immunoglobulin light chain comprising the amino acid sequence of SEQ ID NO:218 (Hu14F11 IGKV1-16)

In some embodiments, the antibody comprises an immunoglobulin heavy chain comprising the amino acid sequence of SEQ ID NO:202 (Sh14F11 IGHV2-70), and an immunoglobulin light chain comprising the amino acid sequence of SEQ ID NO:218 (Hu14F11 IGKV1-16).

In certain embodiments, an isolated antibody that binds hGDF15 comprises an immunoglobulin heavy chain variable region comprising an amino acid sequence that is at least 70%, 75%, 80%, 85%, 90%, 95%, 98%, or 99% identical to the entire variable region or the FR sequence of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70).

In certain embodiments, an isolated antibody that binds hGDF15 comprises an immunoglobulin light chain variable region comprising an amino acid sequence that is at least 70%, 75%, 80%, 85%, 90%, 95%, 98%, or 99% identical to the entire variable region or the FR sequence of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:254 (Hu01G06 IGKV1-39 F2), SEQ ID NO:96 (Sh06C11 IGKV1-16), and SEQ ID NO:98 (Hu14F11 IGKV1-16).

Sequence identity may be determined in various ways that are within the skill of a person skilled in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul, (1993) J. MOL. EVOL. 36:290-300; Altschul et al., (1997) NUCLEIC ACIDS RES. 25:3389-3402, incorporated by reference herein) are tailored for sequence similarity searching. For a discussion of basic issues in searching sequence databases see Altschul et al., (1994) NATURE GENETICS 6:119-129, which is fully incorporated by reference herein). Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference herein). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; −r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty). The equivalent settings in Bestfit protein comparisons are GAP=8 and LEN=2.

In each of the foregoing embodiments, it is contemplated herein that immunoglobulin heavy chain variable region sequences and/or light chain variable region sequences that together bind human GDF15 may contain amino acid alterations (e.g., at least 1, 2, 3, 4, 5, or 10 amino acid substitutions, deletions, or additions) in the framework regions of the heavy and/or light chain variable regions.

In some embodiments, the antibody binds hGDF15 with a $K_D$ of about 300 pM, 250 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, or 10 pM, or lower. Unless otherwise specified, $K_D$ values are determined by surface plasmon resonance methods or biolayer interferometry under the conditions described in Examples 8, 14, and 15.

In some embodiments, a monoclonal antibody binds to the same epitope on hGDF15 (e.g., mature hGDF15 or cleaved rhGDF15) bound by one or more of the antibodies disclosed herein (e.g., antibodies 01G06, 03G05, 04F08, 06C11, 08G01, 14F11, or 17B11). In some embodiments, a monoclonal antibody competes for binding to hGDF15 with one or more of the antibodies disclosed herein (e.g., antibody 01G06, 03G05, 04F08, 06C11, 08G01, 14F11, or 17B11).

Competition assays for determining whether an antibody binds to the same epitope as, or competes for binding with, an anti-GDF15 antibody disclosed herein are known in the art. Exemplary competition assays include immunoassays (e.g., ELISA assays, RIA assays), surface plasmon resonance analysis (e.g., using a BIAcore™ instrument), biolayer interferometry and flow cytometry.

Typically, a competition assay involves the use of an antigen (e.g., a hGDF15 protein or fragment thereof) bound to a solid surface or expressed on a cell surface, a test anti-GDF15-binding antibody and a reference antibody (e.g., antibody 01G06, 03G05, 04F08, 06C11, 08G01, 14F11, or 17B11). The reference antibody is labeled and the test antibody is unlabeled. Competitive inhibition is measured by determining the amount of labeled reference antibody bound to the solid surface or cells in the presence of the test antibody. Usually the test antibody is present in excess (e.g., 1×, 5×, 10×, 20× or 100×). Antibodies identified by competition assay (i.e., competing antibodies) include antibodies binding to the same epitope, or similar (e.g., overlapping) epitopes, as the reference antibody, and antibodies binding to an adjacent epitope sufficiently proximal to the epitope bound by the reference antibody for steric hindrance to occur.

In an exemplary competition assay, a reference anti-GDF15 antibody (e.g., antibody 01G06, 03G05, 04F08, 06C11, 08G01, 14F11, or 17B11) is biotinylated using commercially available reagents. The biotinylated reference antibody is mixed with serial dilutions of the test antibody or unlabeled reference antibody (self-competition control) resulting in a mixture of various molar ratios (e.g., 1×, 5×, 10×, 20× or 100×) of test antibody (or unlabeled reference antibody) to labeled reference antibody. The antibody mixture is added to a hGDF15 polypeptide coated-ELISA plate. The plate is then washed, and horseradish peroxidase (HRP)-strepavidin is added to the plate as the detection reagent. The amount of labeled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are measured using a SpectraMax® M2 spectrometer (Molecular Devices). OD units corresponding to zero percent inhibition are determined from wells without any competing antibody. OD units corresponding to 100% inhibition, i.e., the assay background are determined from wells without any labeled reference antibody or test antibody. Percent inhibition of labeled reference antibody to GDF15 by the test antibody (or the unlabeled reference antibody) at each concentration is calculated as follows: % inhibition=(1−(OD units−100% inhibition)/(0% inhibition−100% inhibition))*100. Persons skilled in the art will appreciate that the competition assay can be performed using various detection systems known in the art.

A competition assay may be conducted in both directions to ensure that the presence of the label does not interfere or otherwise inhibit binding. For example, in the first direction the reference antibody is labeled and the test antibody is unlabeled, and in the second direction, the test antibody is labeled and the reference antibody is unlabeled.

A test antibody competes with the reference antibody for specific binding to the antigen if an excess of one antibody (e.g., 1×, 5×, 10×, 20× or 100×) inhibits binding of the other antibody, e.g., by at least 50%, 75%, 90%, 95% or 99%, as measured in a competitive binding assay.

Two antibodies bind to the same epitope if essentially all amino acid mutations in the antigen that reduce or eliminate binding of one antibody reduce or eliminate binding of the other. Two antibodies bind to overlapping epitopes if only a subset of the amino acid mutations that reduce or eliminate binding of one antibody reduce or eliminate binding of the other.

II. Production of Antibodies

Methods for producing antibodies, such as those disclosed herein, are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukayotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In some embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as glutathione-S-transferase (GST) or histidine tags.

A monoclonal antibody that binds hGDF15, or an antigen-binding fragment of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

III. Antibody Modifications

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-GDF15 antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL. 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and 6,872, 518 (Zauderer).

Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Fully human mAbs can also be prepared and optimized from phage display libraries by techniques referenced in, e.g., Knappik et al., J. MOL. BIOL. 296:57-86, 2000; and Krebs et al., J. Immunol. Meth. 254:67-84 2001).

IV. Therapeutic Uses

The antibodies disclosed herein can be used to treat a variety of disorders, for example, cachexia and/or sarcopenia. In some embodiments, the antibodies disclosed herein (e.g., 01G06, 03G05, 04F08, 06C11, 08G01, 14F11, or 17B11) are used to inhibit the loss of muscle mass, for example, the loss of muscle mass associated with an underlying disease. Underlying diseases associated with cachexia include, but are not limited to, cancer, chronic heart failure, chronic kidney disease, COPD, AIDS, multiple sclerosis, rheumatoid arthritis, sepsis, and tuberculosis. In some embodiments, the disclosed antibodies inhibit loss of muscle mass by at least 40%, 50%, 60%, 70%, 80%, 90%, 95%, 98%, 99%, or 100%.

In some embodiments, a loss of muscle mass is accompanied by a loss of fat mass. The antibodies disclosed herein (e.g., 01G06, 03G05, 04F08, 06C11, 08G01, 14F11, or 17B11) may inhibit loss of fat mass by at least 40%, 50%, 60%, 70%, 80%, 90%, 95%, 98%, 99%, or 100%.

In other embodiments, the antibodies disclosed herein (e.g., 01G06, 03G05, 04F08, 06C11, 08G01, 14F11, or 17B11) are used to treat one or more features accompanying cachexia and/or sarcopenia, e.g., involuntary body weight loss. In some embodiments, the antibodies revert involuntary body weight loss by at least 2%, 5%, 10%, 15%, 20%, 25%, 30% or 35%.

In another embodiment, the antibodies disclosed herein (e.g., 01G06, 03G05, 04F08, 06C11, 08G01, 14F11, or 17B11) are used to inhibit loss of organ mass, for example, loss of organ mass associated with an underlying disease. Underlying diseases associated with cachexia include, but are not limited to, cancer, chronic heart failure, chronic kidney disease, COPD, AIDS, multiple sclerosis, rheumatoid arthritis, sepsis, and tuberculosis. In some embodiments, the disclosed antibodies inhibit loss of organ mass by at least 40%, 50%, 60%, 70%, 80%, 90%, 95%, 98%, 99%, or 100%. In some embodiments, loss of organ mass is observed in heart, liver, kidney, and/or spleen. In some embodiments, the loss of organ mass in accompanied by a loss of muscle mass, a loss of fat mass and/or involuntary weight loss.

Antibody 01G06, 03G05, 04F08, 06C11, 08G01, 14F11, or 17B11 can be used in therapy. For example, antibody 01G06, 03G05, 04F08, 06C11, 08G01, 14F11, or 17B11 can be used to treat cachexia and/or sarcopenia. Use of antibody 01G06, 03G05, 04F08, 06C11, 08G01, 14F11, or 17B11 to treat cachexia and/or sarcopenia in a mammal comprises administering to the mammal a therapeutically effective amount of the antibody.

Sarcopenia, muscle wasting disorders and significant muscle weight loss may occur in the absence of cachexia, decreased appetite or body weight loss. In certain embodiments, therefore, one or more of the anti-GDF antibodies of the invention (for example, antibody 01G06, 03G05, 04F08, 06C11, 08G01, 14F11, or 17B11) can be used to treat a subject suffering from, or who has been diagnosed with, sarcopenia, a muscle wasting disorder and/or significant muscle weight loss, whether or not the subject has, or has been diagnosed with, cachexia or decreased appetite. Such a method comprises administering a therapeutically effective amount of one or more antibodies of the invention to the subject in need thereof.

The Fc-rhGDF15 fusion proteins disclosed herein can be used to treat obesity. In some embodiments, the hFc-rhGDF15 fusion proteins disclosed herein are used to inhibit weight gain or to reduce body weight by at least 5%, 10%, 15%, 20%, 25%, 30%, 35%, 40%, 45% or 50%. Use of an hFc-hGDF15 fusion protein to treat obesity in a mammal comprises administering to the mammal a therapeutically effective amount of the fusion protein.

As used herein, "treat," "treating" and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of an active component (e.g., an antibody or a fusion protein) is in the range of 0.1 mg/kg to 100 mg/kg, e.g., 1 mg/kg to 100 mg/kg, e.g., 1 mg/kg to 10 mg/kg, e.g., 2.0 mg/kg to 10 mg/kg. The amount administered will depend on variables such as the type and extent of disease or indication to be treated, the overall health of the patient, the in vivo potency of the antibody or fusion protein, the pharmaceutical formulation, the serum half-life of the antibody or fusion protein, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody or fusion protein, and the disease being treated. Exemplary dosing frequencies are once per day, once per week and once every two weeks. In some embodiments, dosing is once every two weeks. A preferred route of administration is parenteral, e.g., intravenous infusion. Formulation of monoclonal antibody-based drugs and fusion protein-based drugs are within ordinary skill in the art. In some embodiments, the antibody or fusion protein is lyophilized, and then reconstituted in buffered saline, at the time of administration. The effective amount of a second active agent, for example, an anti-cancer agent or the other agents discussed below, will also follow the principles discussed hereinabove and will be chosen so as to elicit the required therapeutic benefit in the patient.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies or fusion proteins, such as those disclosed herein, can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

In addition to the GDF15 (i.e., MIC-1/PLAB/PDF/NAG-1) pathway, other cytokines implicated in cachexia include Activin A and IL-6. Increased activin levels have been associated with cancer-associated cachexia and gonadal tumors. See, e.g., Marino et al. (2013) CYTOKINE & GROWTH FACTOR REV. 24:477-484. Activin A is a member of the TGF-beta family, and is a ligand of the activin type 2 receptor, ActRIIB. See, e.g., Zhou et al. (2010) CELL 142: 531-543. Circulating levels of IL-6 have been shown to correlate with weight loss in cancer patients, as well as with reduced survival. See, e.g., Fearon et al. (2012) CELL METABOLISM 16:153-166.

Accordingly, in certain embodiments of the present invention, one or more inhibitors of Activin-A or the Activin-A receptor, ActRIIB, IL-6 or the IL-6 receptor (IL-6R), may be administered in combination with (for example, administered at the same time as, administered before, or administered after) an antibody of the present invention that inhibits GDF-15 activity. Exemplary inhibitors of Activin A or ActRIIB, include, for example, an anti-Activin-A antibody or an antigen binding fragment thereof, an anti-ActRIIB antibody or an antigen binding fragment thereof, a small molecule inhibitor of Activin-A, a small molecule inhibitor of ActRIIB, and a 'decoy' receptor of ActRIIB, such as a soluble ActRIIB receptor and a fusion of the soluble ActRIIB receptor with an Fc molecule (ActRIIB-Fc). See, for example, Zhou et al. (2010), supra. Suitable inhibitors of IL-6 or IL-6R, include an anti-IL-6 antibody or an antigen binding fragment thereof, an anti-IL-6R antibody or an antigen binding fragment thereof, a small molecule inhibitor of IL-6, a small molecule inhibitor of IL-6R, and a 'decoy' receptor of IL-6R, such as a soluble IL-6 receptor and a fusion of the soluble IL-6 receptor with an Fc molecule (IL6R-Fc). See, e.g., Enomoto et al. (2004) BIOCHEM. AND BIOPHYS. RES. COMM. 323:1096-1102; Argiles et al. (2011) EUR. J. PHARMACOL. 668:S81-S86; Tuca et al. (2013) ONCOLOGY/HEMATOLOGY 88:625-636. Suitable inhibitors of IL-6 or IL-6R may include, for example, Tocilizumab (Actemra®, Hoffmann-LaRoche), a humanized anti-IL-6R monoclonal antibody approved for treatment of rheumatoid arthritis, and Sarilumab/REGN88 (Regeneron), a humanized anti-IL6R antibody in clinical development for treatment of rheumatoid arthritis; and Selumetinib/AZD6244 (AstraZeneca), an allosteric inhibitor of MEK, which has been shown to inhibit IL-6 production. Prado et al. (2012) BRITISH J. CANCER 106:1583-1586.

TNFα and IL-1 are cytokines known to be involved in mediation of the proinflammatory response, which are also implicated in muscle depletion, anorexia and cachexia. Increased circulating levels of TNFα appear to inhibit myogenesis. TNFα, also known as "cachectin," stimulates interleukin-1 secretion and is implicated in the induction of cachexia. IL-1 is a potent trigger of the acute-phase inflammatory response, and it has been shown that infusion of IL-1 can lead to marked weight loss and appetite loss. IL-1 has been shown to contribute to the initiation of cancer cachexia in mice bearing a murine colon-26 adenocarcinoma (Strassmann et al. (1993) J. IMMUNOL. 150:2341). See also, Mathys and Billiau (1997) NUTRITION 13:763-770; Fong et al. (1989) AM. J. PHYSIOL.-REGULATORY, INTEGRATIVE AND COMPARATIVE PHYSIOL., 256:R659-R665. Thus, TNFα inhibitors and IL-1 inhibitors that are used in the treatment of rheumatoid arthritis may also be useful in the treatment of cachexia.

Accordingly, in certain embodiments of the present invention, one or more inhibitors of TNFα or IL-1 may be administered in combination with (for example, administered at the same time as, administered before, or administered after) an antibody of the present invention that inhibits GDF-15 activity. Suitable inhibitors of TNFα or IL-1 include an anti-TNFα antibody or an antigen binding fragment thereof, an anti-IL-1 antibody or an antigen binding fragment thereof, a small molecule inhibitor of TNFα or IL-1, and a 'decoy' receptor of TNFα or IL-1, such as a soluble TNFα or IL-1 receptor and a fusion of the soluble form of TNFα or IL-1 with an Fc molecule. Suitable inhibitors of TNFα include for example, etanercept (Enbrel®, Pfizer/Amgen), infliximab (Remicade®, Janssen Biotech), adalimumab (Humira®, Abbvie), golimumab (Simponi®, Johnson and Johnson/Merck), and certolizumab pegol (Cimzia®, UCB). Suitable IL-1 inhibitors include, for example, Xilonix® antibody that targets IL-1α (XBiotech), anikinra (Kinaret®, Amgen), canakinumab (Ilaris®, Novartis), and rilonacept (Arcalyst®, Regeneron). In certain embodiments, the TNFα inhibitor or IL-1 inhibitor, which is typically administered systemically for the treatment of rheumatoid arthritis may be administered locally and directly to the tumor site.

Myostatin, also known as GDF-8, is a member of the TGF-β family of peptides that is a negative regulator of muscle mass, as shown by increased muscle mass in myostatin deficient mammals. Myostatin is a ligand of the activin type 2 receptor, ActRIIB. Accordingly, in certain embodiments of the present invention, one or more inhibitors of myostatin or its receptor may be administered in combination with (for example, administered at the same time as, administered before, or administered after) an antibody of the invention that inhibits GDF-15 activity. Suitable inhibitors of myostatin or ActRIIB, include an anti-myostatin antibody or an antigen binding fragment thereof, an anti-ActRIIB antibody or an antigen binding fragment thereof, a small molecule inhibitor of myostatin, a small molecule inhibitor of ActRIIB, and a 'decoy' receptor of GDF-8, such as a soluble ActRIIB and a fusion of the soluble form of ActRIIB with an Fc molecule. See, e.g., Lokireddy et al. (2012) BIOCHEM. J. 446(1):23-26. Myostatin inhibitors that may be suitable for the present invention include REGN1033 (Regeneron); see Bauerlein et al. (2013) J. CACHEXIA SARCOPENIA MUSCLE: Abstracts of the 7th Cachexia Conference, Kobe/Osaka, Japan, Dec. 9-11, 2013, Abstract 4-06; LY2495655 (Lilly), a humanized anti-myostatin antibody in clinical development by Eli Lilly; see also "A PHASE 2 STUDY OF LY2495655 IN PARTICIPANTS WITH PANCREATIC CANCER," available on the world wide web at clinicaltrials.gov/ct2/NCT01505530; NML identifier: NCT01505530; ACE-031 (Acceleron Pharma); and stamulumab (Pfizer).

Agents such as Ghrelin or ghrelin mimetics, or other growth hormone secretagogues (GHS) which are able to activate the GHS receptor (GHS-R1a), also known as the ghrelin receptor, may be useful for increasing food intake and body weight in humans. See Guillory et al. (2013) in VITAMINS AND HORMONES vol. 92, chap.3; and Steinman and DeBoer (2013) VITAMINS AND HORMONES vol. 92, chap. 8. Suitable ghrelin mimetics include anamorelin (Helsinn, Lugano, CH); See Temel et al. (2013) J. CACHEXIA SARCOPENIA MUSCLE: Abstracts of the 7th Cachexia Conference, Kobe/Osaka, Japan, Dec. 9-11, 2013, Abstract 5-01. Other suitable GHS molecules can be identified, for example, using the growth hormone secretagogue receptor Ghrelin competition assay described in PCT Publication Nos. WO2011/117254 and WO2012/113103.

Agonists of the androgen receptor, including small molecules and other selective androgen receptor modulators (SARMs) may be useful in treating cachexia and/or sarcopenia. See, e.g., Mohler et al. (2009) J. MED. CHEM. 52:3597-3617; Nagata et al. (2011) BIOORGANIC AND MED. CHEM. LETTERS 21:1744-1747; and Chen et al. (2005) MOL. INTERV. 5:173-188. Ideally, SARMs should act as full agonists, like testosterone, in anabolic target tissues, such as muscle and bone, but should demonstrate only partial or pure androgen receptor antagonistic activities on prostate tissue. See, e.g., Bovee et al. (2010) J. STEROID BIOCHEM. & MOL. BIOL. 118:85-92. Suitable SARMs can be identified, for example, by use of the methods and assays described in Zhang et al. (2006) BIOORG. MED. CHEM. LETT. 16:5763-5766; and Zhang et al. (2007) BIOORG. MED. CHEM. LETT. 17:439-443. Suitable SARMs include, for example, GTx-024 (enobosarm, Ostarine®, GTx, Inc.), a SARM in phase II clinical development by GTx, Inc. See also, Dalton et al. (2011) J. CACHEXIA SARCOPENIA MUSCLE 2:153-161. Other suitable SARMs include 2-(2,2,2)-trifluoroethyl-benzimidazoles (Ng et al. (2007) BIOORG. MED. CHEM. LETT. 17:1784-1787) and JNJ-26146900 (Allan et al. (2007) J. STEROID BIOCHEM. & MOL. BIOL. 103:76-83).

β-adrenergic receptor blockers, or beta-blockers, have been studied for their effect on body weight in cachexic subjects, and have been associated with partial reversal of cachexia in patients with congestive heart failure. See, e.g., Hryniewicz et al. (2003) J. CARDIAC FAILURE 9:464-468. Beta-blocker MT-102 (PsiOxus Therapeutics, Ltd.) has been evaluated in a phase 2 clinical trial for subjects with cancer cachexia. See Coats et al. (2011) J. CACHEXIA SARCOPENIA MUSCLE 2:201-207.

Melanocortin receptor-knockout mice with a genetic defect in melanocortin signaling exhibit a phenotype opposite that of cachexia: increased appetite, increased lean body mass, and decreased metabolism. Thus, melanocortin antagonism has emerged as a potential treatment for cachexia associated with chronic disease (DeBoer and Marks (2006) TRENDS IN ENDOCRINOLOGY AND METABOLISM 17:199-204). Accordingly, in certain embodiments of the present invention, one or more inhibitors of a melanocortin peptide or a melanocortin receptor may be administered in combination (for example, administered at the same time as, administered before, or administered after) with an antibody of the invention that inhibits GDF-15 activity. Suitable inhibitors of melanocortins or melanocortin receptors include an anti-melanocortin peptide antibody or an antigen binding fragment thereof, an anti-melanocortin receptor antibody or an antigen binding fragment thereof, a small molecule inhibitor of a melanocortin peptide, a small molecule inhibitor of a melanocortin receptor, and a 'decoy' receptor of a melanocortin receptor, such as soluble melanocortin receptor and a fusion of a soluble melanocortin receptor with an Fc molecule. Suitable melacortin receptor inhibitors include, for example, the melanocortin receptor antagonist agouri-related peptide (AgRP(83-132)), which has been demonstrated to prevent cachexia-related symptoms in a mouse model of cancer-related cachexia (Joppa et al. (2007) PEPTIDES 28:636-642).

Anti-cancer agents, especially those that can cause cachexia and elevate GDF-15 levels, such as cisplatin, may be used in methods of the present invention in combination with (for example, administered at the same time as, administered before, or administered after) an anti-GDF-15 antibody of the invention. Many cancer patients are weakened by harsh courses of radio- and/or chemotherapy, which can limit the ability of the patient to tolerate such therapies, and hence restrict the dosage regimen. Certain cancer agents themselves, such as fluorouracil, Adriamycin, methotrexate and cisplatin, may contribute to cachexia, for example by inducing severe gastrointestinal complications. See, e.g., Inui (2002) CANCER J. FOR CLINICIANS 52:72-91. By the methods of the present invention, in which an anti-cancer agent is administered in combination with an anti-GDF-15 antibody of the invention, it is possible to decrease the incidence and/or severity of cachexia, and ultimately increase the maximum tolerated dose of such an anti-cancer agent. Accordingly, efficacy of treatment with anti-cancer agents that may cause cachexia can be improved by reducing the incidence of cachexia as a dose-limiting adverse effect, and by allowing administration of higher doses of a given anti-cancer agent.

Thus, the present invention includes pharmaceutical compositions comprising an anti-GDF-15 antibody of the present invention in combination with an agent selected from the group consisting of an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, an IL-1α inhibitor, a myostatin inhibitor, a beta-blocker, a melanocortin peptide inhibitor, a melanocortin receptor inhibitor, and an anti-cancer agent. The present invention also includes methods of treating, preventing or minimizing cachexia and/or sarcopenia in a mammal comprising administering to a mammal in need thereof a pharmaceutical composition or compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, an IL-1α inhibitor, a myostatin inhibitor, a beta-blocker, a melanocortin peptide inhibitor, or a melanocortin receptor inhibitor.

In another embodiment, the invention comprises a method of inhibiting loss of muscle mass associated with an underlying disease comprising administering to a mammal in need thereof a pharmaceutical composition or compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, an IL-1α inhibitor, a myostatin inhibitor, a beta-blocker, a melanocortin peptide inhibitor, or a melanocortin receptor inhibitor to prevent or reduce loss of muscle mass. The underlying disease may be selected from the group consisting of cancer, chronic heart failure, chronic kidney disease, COPD, AIDS, multiple sclerosis, rheumatoid arthritis, sepsis, and tuberculosis. Additionally, in certain embodiments, the loss of muscle mass is accompanied by a loss of fat mass.

In yet further embodiments, the present invention comprises a method of inhibiting or reducing involuntary weight loss in a mammal comprising administering to a mammal in need thereof a pharmaceutical composition or pharmaceutical compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, a IL-1α inhibitor, a myostatin inhibitor, a beta-blocker, a melanocortin peptide inhibitor, or a melanocortin receptor inhibitor.

Certain anti-cancer agents, such as cisplatin, have one or more undesirable adverse effects that involve causing or increasing one or more syndromes such as cachexia, sarcopenia, muscle wasting, bone wasting or involuntary body weight loss. Accordingly, in certain embodiments, the present invention comprises a method of treating cancer, while preventing, minimizing or reducing the occurrence, frequency or severity of cachexia, sarcopenia, or muscle wasting, bone wasting or involuntary loss of body weight in a mammal, comprising administering to a mammal in need thereof a pharmaceutical composition comprising an effective amount of an anti-GDF-15 antibody of the present invention in combination with one or more anti-cancer agents. In particular embodiments, the invention comprises a method of treating cancer, while preventing, minimizing or reducing the occurrence, frequency or severity of cachexia, sarcopenia or muscle wasting, bone wasting or involuntary loss of body weight in a mammal, comprising administering to a mammal in need thereof a pharmaceutical composition comprising an effective amount of an anti-GDF-15 antibody of the invention in combination with one or more anti-cancer agents known to cause or increase the occurrence, frequency or severity of cachexia, sarcopenia, or muscle wasting, bone wasting or involuntary loss of body weight in a mammal.

EXAMPLES

The following Examples are merely illustrative and are not intended to limit the scope or content of the invention in any way.

Example 1: Human GDF15 Serum Levels in Mouse Xenograft Tumor Models

Figure 2:
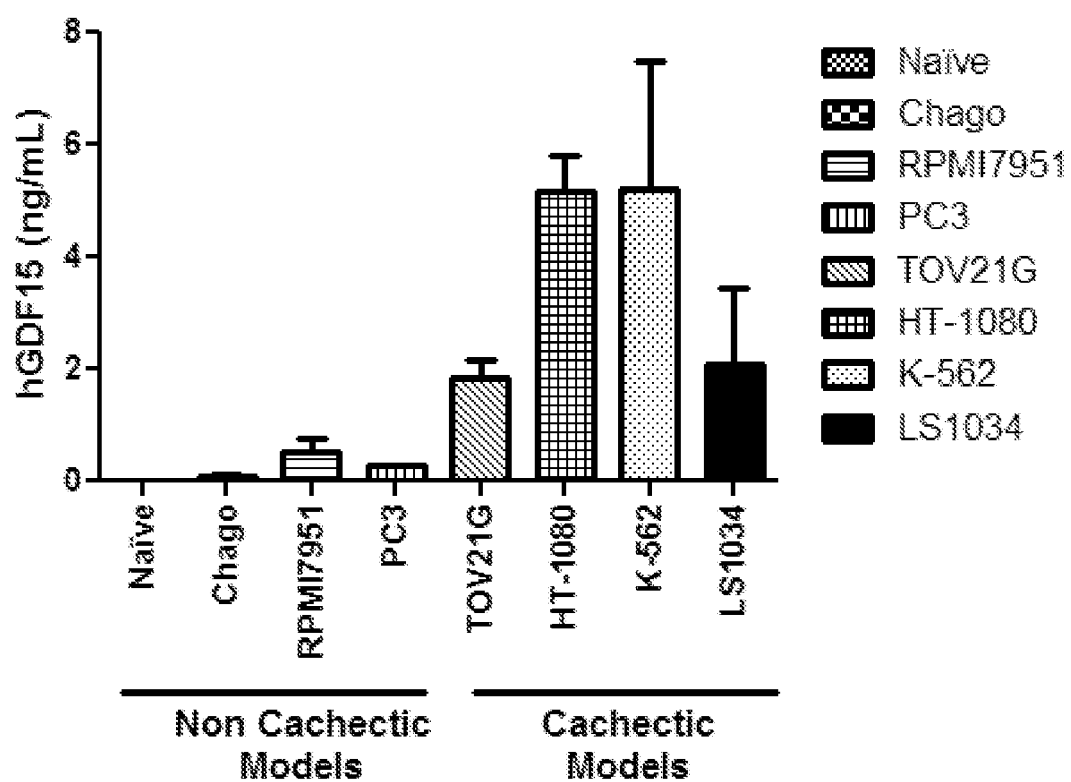
FIG. 2 is a graph representing results from an experiment to measure hGDF15 serum levels in naïve mice or mice bearing human xenograft tumors (Chago, RPMI7951, PC3, TOV21G, HT-1080, K-562, LS1034), as determined by ELISA.

In this example, the amount of hGDF15 in the serum of mice bearing various xenograft tumors was measured. Serum was collected from three mice for each of the following tumor xenograft models: Chago, RPMI7951, PC3, TOV21G, HT-1080, K-562, and LS1034. Serum was also collected from three naïve mice as a control. Human GDF15 serum levels were determined by ELISA (R&D Systems, Cat. No. DY957E). Mice bearing human xenograft tumors that induce cachexia had serum levels of hGDF15 above 2 ng/mL, while mice bearing human xenograft tumors that do not induce cachexia had serum levels of hGDF15 below 1 ng/mL (FIG. 2). Naïve mice had no detectable hGDF15 (control). These results indicate that a serum level of approximately 2 ng/mL GDF15 is a threshold for inducing cachexia in this mouse model. Similar levels of hGDF15 were also observed in plasma when determined by ELISA.

Example 2: Non-Tumor Bearing Mouse Model of Cachexia

Figure 3:
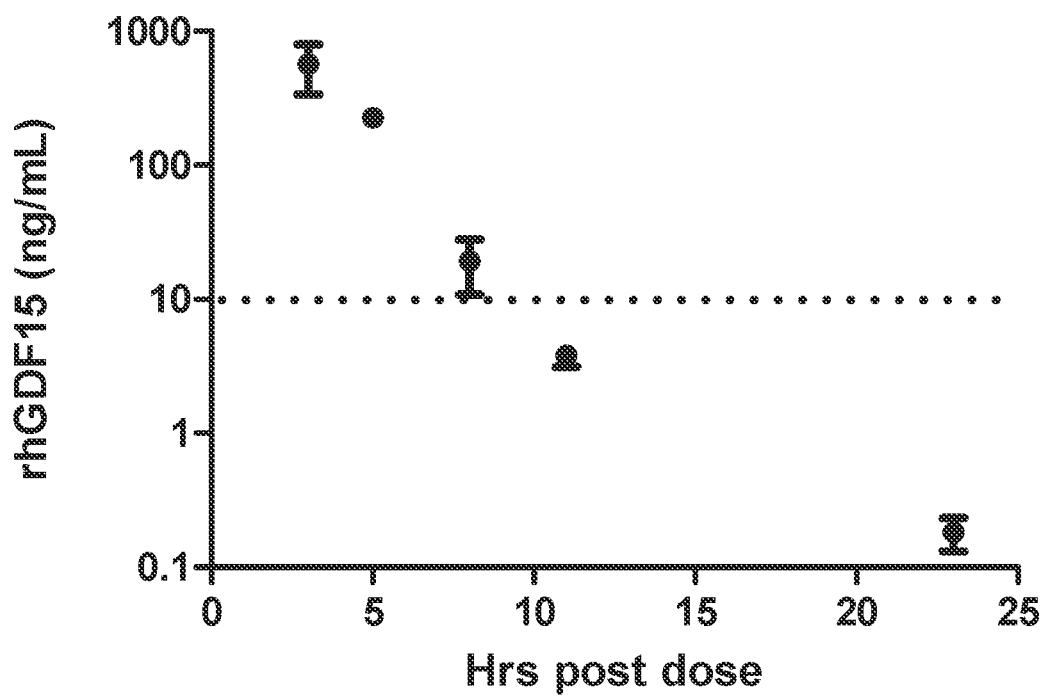
FIG. 3 is a plot representing results from an experiment to determine the plasma pharmacokinetics (PK) of cleaved rhGDF15 administered by subcutaneous injection (1 µg/g) in naïve ICR-SCID mice, as determined by ELISA.
Figure 4:
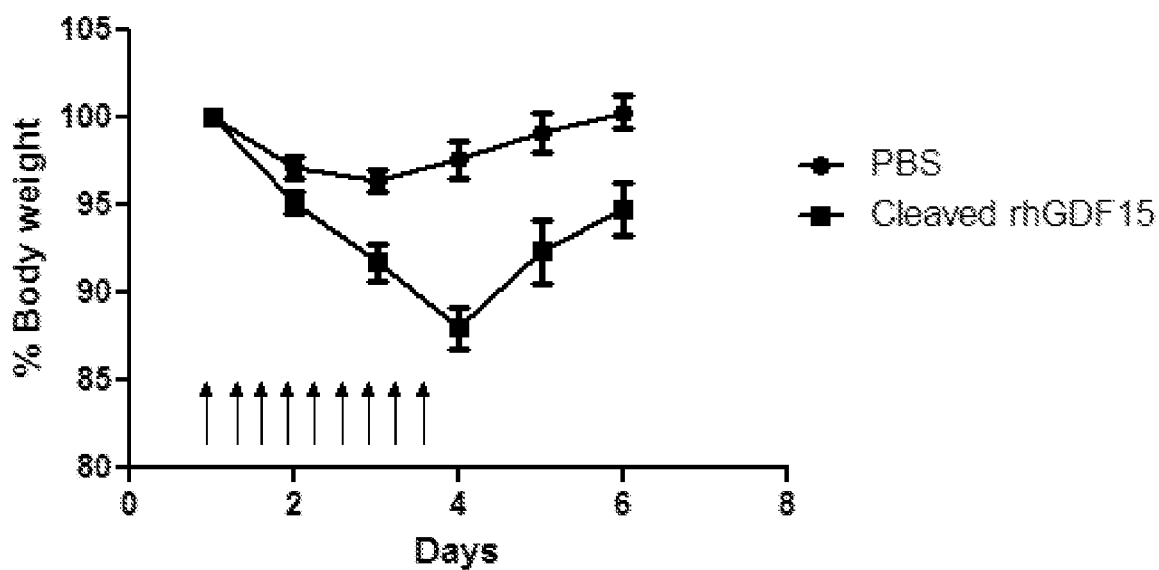
FIG. 4 is a graph summarizing results from an experiment to measure cachectic activity of cleaved rhGDF15 protein (■) and negative control (PBS (●)) to induce body weight loss in immune-incompetent mice, ICR-SCID. Arrows indicate subcutaneous doses of 1 µg/g of rhGDF15.

An existing non-tumor bearing mouse model of cachexia is based on the injection of mature rhGDF15 into a mouse (Johnen et al. (1997) NAT. MED. 13:1333-1340). Mature rhGDF15 corresponds to amino acids 197 to 308 of hGDF15 protein. Mature rhGDF15 can be produced in the yeast *Pichia pastoris* as described in Fairlie et al. (2000) GENE 254:67-76). Cleaved-rhGDF15 corresponds to amino acids 197 to 308 of hGDF15 protein released from an Fc-rhGDF15 fusion protein. In FIGS. 3-4 described below, cleaved-rhGDF15 was produced by enzymatic digestion of mFc-rhGDF15 fusion protein with Factor Xa, and subsequent purification, prior to injection in mice.

To investigate the half-life of cleaved-rhGDF15, plasma was collected from a group of three mice after single dose of cleaved-rhGDF15 (1 μg/g) at different time points (2, 5, 8, 11, and 23 hours). Human GDF15 plasma levels were determined by ELISA (R&D Systems, Cat. No. DY957E). As shown in FIG. 3, cleaved-rhGDF15 was rapidly cleared from the plasma following injection. Eleven hours post-injection, the amount of cleaved-rhGDF15 in the plasma was below 10 ng/mL, and, within 23-hours, cleaved-rhGDF15 was almost completely cleared from the plasma.

The rapid clearance of cleaved-rhGDF15 in non-tumor bearing mice was further investigated. Eight-week old female ICR-SCID mice were randomized into two groups of ten mice each. Mice were dosed subcutaneously into the flank every eight hours for three days (a total of nine doses) with one of the following treatments: PBS (control) or cleaved-rhGDF15 at 1 μg/g. Body weight was measured daily. Statistical analyses were performed using a two-way ANOVA.

As shown in FIG. 4, cleaved-rhGDF15 induced body weight loss. After nine doses over a three day period, percent body weight dropped to 88% at day 4 (p<0.001), but approximately 24 hours after the last dose the mice began to gain weight. On day 6, the last day of the experiment, percent body weight increased to 94.8 percent (p<0.001). These results indicate that weight loss induced by cleaved-rhGDF15 is not sustained over long periods of time. The activity observed with cleaved-rhGDF15 described herein was similar to that observed with mature rhGDF15 in the existing mouse model (Johnen et al., supra).

The existing non-tumor bearing mouse model for cachexia relies on the injection of large amounts of mature rhGDF15 delivered in multiple doses per day to induce muscle loss and body weight loss (Johnen et al., supra). It appears that if mature rhGDF15 or cleaved-rhGDF15 is used, the mice do not sustain muscle weight loss or body weight loss for long periods of time without continuous dosing. This limits the usefulness of such models. Moreover, repeated dosing requires frequent handling of these mice which introduces stress that can compromise the reliability of body weight loss measurements. For example, as shown in FIG. 4, mice treated with multiple doses of PBS demonstrated a body weight drop due to the stress of repeated dosing and handling.

Example 3: GDF15 Fusion Proteins

In view of the large amounts of mature rhGDF15 (or cleaved-rhGDF15) and the labor intensity required to induce non-tumor bearing cachexia mouse models (as well as the resulting limitations of these models), we investigated alternate forms of rhGDF15 to induce a cachetic phenotype in mice. This Example describes the construction and production of two fusion proteins consisting of GDF15 and an immunoglobulin Fc fragment, designated mFc-rhGDF15 (mouse IgG1 Fc fused to the amino terminus of mature human GDF15) and rFc-rmGDF15 (rabbit IgG1 Fc fused to the amino terminus of mature mouse GDF15). The GDF15 fusion proteins were designed using methods known in the art. The mFc-rhGDF15 DNA sequences were constructed from fragments using overlap extension PCR to include (in the following order): 5' HindIII restriction site, Kozak consensus sequence, amino terminal signal sequence, mouse IgG1 Fc, Factor Xa cleavage site, a polypeptide linker (GGGGS) (SEQ ID NO: 139), mature hGDF15, stop codon, and a 3' EcoRI restriction site. The rFc-rmGDF15 amino acid sequences were converted to codon-optimized DNA sequences and synthesized to include (in the following order): 5' HindIII restriction site, Kozak consensus sequence, amino terminal signal sequence, rabbit IgG1 Fc, a polypeptide linker (GGGG) (SEQ ID NO: 265), mature mouse GDF15, stop codon, and a 3' EcoRI restriction site.

The GDF15 fusion proteins were subcloned into the mammalian expression vector pEE14.4 (Lonza, Basel, Switzerland) via HindIII and EcoRI sites using In-Fusion™ PCR cloning (Clontech, Mountain View, CA). GDF15 fusion proteins were stably expressed in CHOK1SV cells using the GS System™ (Lonza Biologics) in order to produce large quantities of purified protein. Each expression vector was linearized and transfected into CHOK1SV cells. Stable clones were selected in the presence of methionine sulfoximine. Secreted proteins produced by CHOK1SV stably transfected cell lines were purified by Protein A and size exclusion chromatography.

The nucleic acid sequence and the encoded protein sequence defining the mouse IgG1 Fc-mature human GDF15 fusion protein (mFc-rhGDF15) are shown below. mFc-rhGDF15 contains mouse IgG1 Fc from amino acids 1-222, Factor Xa cleavage site from amino acids 223-228, an artificial linker sequence from amino acids 229-233, and mature hGDF15 from amino acids 234-345.

Nucleic Acid Sequence Encoding the Mouse IgG1 Fc—Mature Human GDF15 Fusion Protein (mFc-rhGDF15) (SEQ ID NO:219)

```
   1 gggtgtaaac cctgcatctg cacggtgccg gaggtgtcct ccgtctttat cttccctccc 61 aaacccaagg atgtgctgac aatcactttg actccaaaag tcacatgcgt agtcgtggac 121 atctcgaaag acgacccgga agtgcagttc tcgtggtttg ttgatgatgt agaagtgcat 181 accgctcaaa cccagccgag ggaagaacag tttaacagca cgtttaggag tgtgtcggaa 241 ctgcccatta tgcaccagga ttggcttaat gggaaggagt tcaaatgtcg cgtgaatagt 301 gcggcgttcc cagcccctat tgaaaagact atttccaaaa cgaagggtcg gcccaaagct 361 ccccaagtat acacaatccc tccgccgaaa gaacaaatgg caaaagacaa agtgagtttg 421 acgtgcatga tcacggactt ttttccggag gatatcaccg tcgaatggca atggaatggg 481 caacctgccg aaaactacaa gaatacacaa cccattatgg ataccgatgg atcgtatttc 541 gtctactcaa agttgaacgt acagaagtca aattgggagg cagggaatac gttcacttgc 601 agtgttttgc acgaaggcct ccataaccac catacggaaa agtcactgtc gcactcccg 661 ggaaaaatcg agggcagaat ggatggtgga ggagggtcgg cgcgcaacgg ggaccactgt 721 ccgctcgggc cggggcgttg ctgccgtctg cacacggtcc gcgcgtcgct ggaagacctg 781 ggctgggccg attgggtgct gtcgccacgg gaggtgcaag tgaccatgtg catcgcgcg 841 tgcccgagcc agttccgggc ggcaaacatg cacgcgcaga tcaagacgag cctgcaccgc 901 ctgaagcccg acacggtgcc agcgccctgc tgcgtgcccg ccagctacaa tcccatggtg 961 ctcattcaaa agaccgacac cggggtgtcg ctccagacct atgatgactt gttagccaaa 1021 gactgccact gcata
```

Protein Sequence Defining the Mouse IgG1 Fc—Mature Human GDF15 Fusion Protein (mFc-rhGDF15) (SEQ ID NO:220)

```
  1 gckpcictvp evssvfifpp kpkdvltitl tpkvtcvvvd iskddpevqf swfvddvevh 61 taqtqpreeq fnstfrsvse lpimhqdwln gkefkcrvns aafpapiekt isktkgrpka 121 pqvytippppk eqmakdkvsl tcmitdffpe ditvewqwng qpaenykntq pimdtdgsyf 181 vysklnvqks nweagntftc svlheglhnh htekslshsp gkiegrmdgg ggsarngdhc 241 plgpgrccrl htvrasledl gwadwvlspr evqvtmciga cpsqfraanm haqiktslhr 301 lkpdtvpapc cvpasynpmv liqktdtgvs lqtyddllak dchci
```

The nucleic acid sequence and the encoded protein sequence defining the rabbit IgG1 Fc-mature mouse GDF15 fusion protein (rFc-rmGDF15) are shown below. rFc-rmGDF15 contains rabbit IgG1 Fc from amino acids 1-223, an artificial linker sequence from amino acids 224-227, and mature mouse GDF15 from amino acids 228-342.

Nucleic Acid Sequence Encoding the Rabbit IgG1 Fc—Mature Mouse GDF15 Fusion Protein (rFc-rmGDF15) (SEQ ID NO:221)

```
   1 tcgaaaccca cttgccctcc tccggagctg ttgggcggac cctccgtgtt tatctttccc 61 ccgaagccga aagataccct tatgatctca cggacgccgg aggtcacttg cgtagtagtg 121 gatgtgtcgg aggatgaccc cgaagtccag ttcacctggt atatcaataa cgagcaagtg 181 aggacagcga ggccccccact tagggagcag cagttcaact ccacaattcg ggtcgtcagc 241 actttgccca tcgctcatga ggactggctc cgcggaaaag agttcaagtg taaggtgcat 301 aacaaggcat tgccagcgcc tattgaaaag acaatctcga aggcgcgagg gcagccgctc 361 gagcccaaag tgtatacgat gggacccccg agggaagaat tgtcgtcgcg ctcagtaagc 421 cttacgtgca tgattaacgg tttctaccct agcgacatca gcgtagagtg ggaaaagaat 481 ggaaaggcgg aggataacta caagacgact cccgcggtgc tggattcgga tgggtcgtac 541 tttctgtata gcaaattgtc agtcccgacc tcagaatggc agagggtga cgtgttcacg 601 tgctccgtga tgcacgaagc acttcacaat cactacaccc agaaatcaat ctcgcggtcc 661 ccaggcaaag gtggaggagg gtcggctcac gcccaccctc gcgattcgtg tccgctgggg 721 cctggtagat gctgtcatct cgagacagtc caggccacgc tggaggacct cggggtggtca 781 gactgggtcc tgtccccacg acaactgcag ctttcgatgt gcgtggggga atgtccgcac 841 ttgtacagat cggcgaatac ccacgctcag attaaggcac gactccatgg tttgcagcca 901 gataaagtcc ccgcaccttg ctgtgtcccc agctcatata ctcctgtcgt actcatgcat 961 cggacagaca gcggcgtgtc gcttcaaacg tatgacgacc tcgtagcgag aggatgtcat 1021 tgcgcc
```

Protein Sequence Defining the Rabbit IgG1 Fc—Mature Mouse GDF15 Fusion Protein (rFc-rmGDF15) (SEQ ID NO:222)

```
  1 skptcpppel lggpsvfifp pkpkdtlmis rtpevtcvvv dseddpevq ftwyinneqv 61 rtarpplreq qfnstirvvs tlpiahedwl rgkefkckvh nkalpapiek tiskargqpl 121 epkvytmgpp reelssrsvs ltcmingfyp sdisvewekn gkaednyktt pavldsdgsy 181 flysklsvpt sewqrgdvft csvmhealhn hytqksisrs pgkggggsah ahprdscplg
```

-continued

```
241 pgrcchletv qatledlgws dwvlsprqlq lsmcvgecph lyrsanthaq ikarlhglqp 301 dkvpapccvp ssytpvvlmh rtdsgvslqt yddlvargch ca
```

The following sequences represent exemplary protein sequences for human IgG1 Fc-mature human GDF15 fusion proteins (hFc-rhGDF15). hFc-rhGDF15 Xa consists of human IgG1 Fc from amino acids 1-227, Factor Xa cleavage site from amino acids 228-233, an artificial linker sequence from amino acids 234-238, and mature hGDF15 from amino acids 239-350. hFc-rhGDF15 consists of human IgG1 Fc from amino acids 1-227, an artificial linker sequence from amino acids 228-232, and mature hGDF15 from amino acids 233-344.

Protein Sequence Defining the Human IgG1 Fc—Mature Human GDF15 Fusion Protein with Xa Cleavage Site (hFc-hGDF15 Xa) (SEQ ID NO:223)

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsreemtk nqvsltclvk gfypsdiave wesngqpenn ykttppvlds
181 dgsfflyskl tvdksrwqqg nvfscsvmhe alhnhytqks lslspgkieg rmdggggsar
241 ngdhcplgpg rccrlhtvra sledlgwadw vlsprevqvt mcigacpsqf raanmhaqik
301 tslhrlkpdt vpapccvpas ynpmvliqkt dtgvslqtyd dllakdchci
```

Protein Sequence Defining the Human IgG1 Fc—Mature Human GDF15 Fusion Protein with (hFc-hGDF15) (SEQ ID NO:224)

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsreemtk nqvsltclvk gfypsdiave wesngqpenn ykttppvlds
181 dgsfflyskl tvdksrwqqg nvfscsvmhe alhnhytqks lslspgkggg gsarngdhcp
241 lgpgrccrlh tvrasledlg wadwvlspre vqvtmcigac psqfraanmh aqiktslhrl
301 kpdtvpapcc vpasynpmvl iqktdtgvsl qtyddllakd chci
```

Example 4: Fc-rhGDF15 Induced Cachexia Model

This Example describes the generation of an Fc-GDF15-induced cachexia model in mice. Immune-competent (Balb/C) and immune-incompetent (CB17-Scid) mice were randomized into three groups of ten mice each. Each group received one of the following treatments: PBS (control), mFc-rhGDF15 (as described in Example 3), or rFc-rmGDF15 (as described in Example 3) at 1p g/g. Eight-week old female mice were dosed subcutaneously into the flank for three days (Balb/C) or once (CB17-Scid). Body weight was measured daily.

Figure 5A:
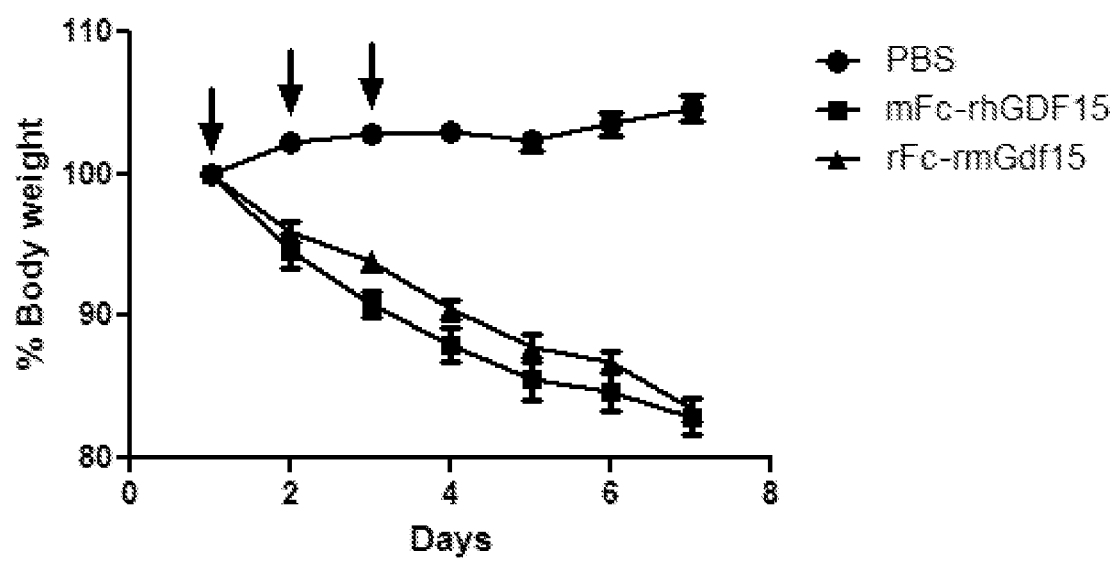
FIGS. 5A and 5B are graphs summarizing results from an experiment to measure cachectic activity of mFc-rhGDF15 (a mouse Fc fused to the amino terminus of a mature recombinant human GDF15; ■), rFc-rmGDF15 (a rabbit Fc fused to the amino terminus of a mature recombinant mouse GDF15; ▲), and negative control (PBS; ●) to induce body weight loss in immune-competent Balb/C mice (FIG. 5A) and immune-incompetent CB17-SCID mice (FIG. 5B). Arrows indicate subcutaneous doses of 1 µg/g of recombinant protein.
Figure 5B:
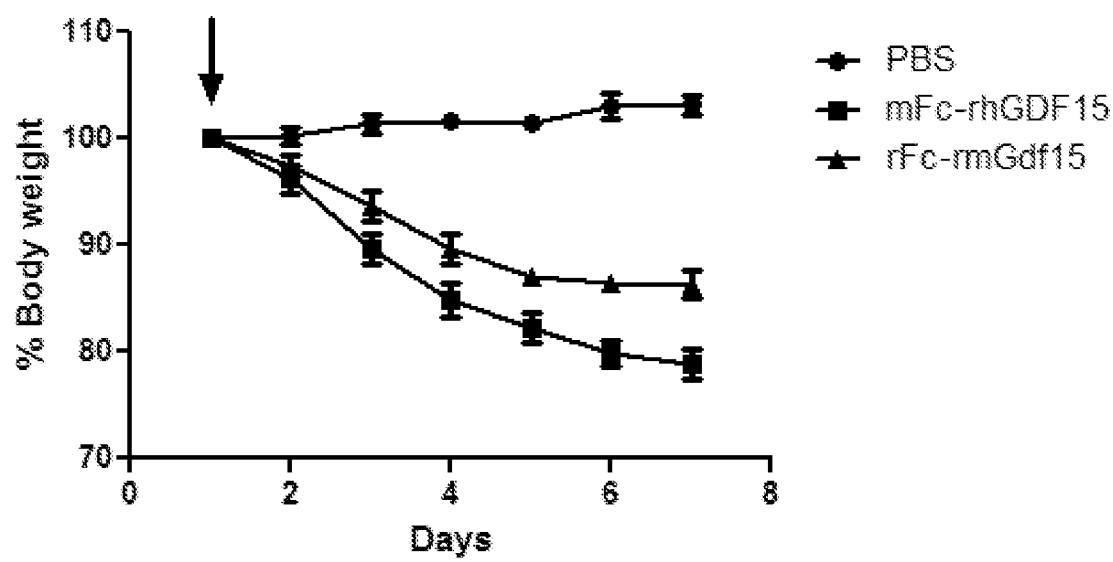

As shown in FIG. 5A and FIG. 5B, administration of mFc-rhGDF15 or rFc-rmGDF15 induced body weight loss in immune-competent mice (FIG. 5A) and immune-incompetent mice (FIG. 5B). These results indicate that a steady-state level of active rhGDF15 was achieved, because regardless of dose (one vs. three doses), both mFc-rhGDF15 and rFc-rmGDF15 induced sustained weight loss over the measured time course (7 days).

The fusion proteins, mFc-rhGDF15 and rFc-rmGDF15, were further tested in additional immune-competent (C57BL6, Swiss Webster) and immune-incompetent (ICR-SCID) mouse strains. In each tested mouse strain, the administration of mFc-rhGDF15 or rFc-rmGDF15 induced cachexia, as measured by body weight loss. Similar results were obtained regardless of whether mFc-rhGDF15 was dosed subcutaneously or intraperitoneally.

It was also investigated whether mFc-rhGDF15 induced weight loss regardless of the age of the mice treated with fusion protein. Swiss Webster (immune-competent) female mice of different ages (7, 13 and 25 weeks old) were divided into two groups of ten and treated with three doses per day of mFc-rhGDF15 or PBS (0.8 µg/g, 7 week old mice; 0.6 µg/g, 13 week old mice; or 0.4 µg/g, 25 week old mice).

mFc-rhGDF15-induced weight loss was observed in all three mice age populations. In each age population, the mice lost approximately 10% of their body weight following treatment with mFc-rhGDF15 measured at ten days post treatment.

In another experiment, mFc-rhGDF15 induction of cachexia was investigated by measuring the loss of body weight, the loss of muscle mass, the loss of fat mass, and the expression levels of two molecular markers indicative of muscle degradation (i.e., mMuRF1 and mAtrogin). MuRF1 and Atrogin are E3-ubiquitin ligases that are upregulated in multiple models of muscle atrophy and cachexia (Glass, D. (2010) Curr. Opin. Clin. Nutr. Met. Care 13:225-229).

Eight-week old female ICR-SCID mice were randomly divided into ten groups of ten mice each. Five groups (ten mice each) were dosed subcutaneously in the flank with PBS (control) and five groups (ten mice each) were dosed subcutaneously in the flank with mFc-rhGDF15 at 1.6 µg/g on day one. Body weight was measured daily for up to 17 days. One control group and one treatment group were sacrificed at different time points (0, 1, 3, 7 and 16 days post dose). Gonadal fat and gastrocnemius muscles were removed surgically from each group of mice at the indicated sacrifice time, and weighed. Tissues were snap frozen in liquid nitrogen, and RNA was isolated from the gastrocnemius muscle samples. Levels of mMuRF1 and mAtrogin mRNA were measured by qRT-PCR in samples corresponding to groups collected after 1, 7, and 16 days post dose. Statistical analyses were performed using a two-way ANOVA.

Figure 6A:
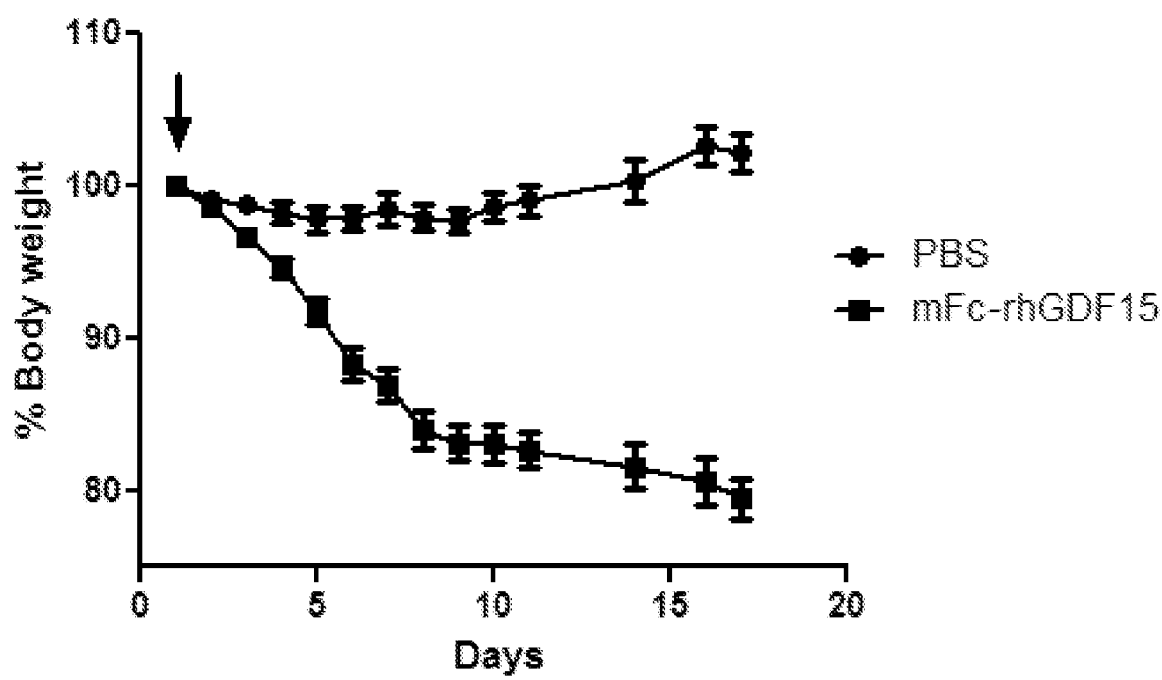
FIGS. 6A-6E are graphs summarizing results from an experiment to demonstrate cachectic activity of mFc-rhGDF15 (■) and negative control (PBS; ●) to induce body weight loss in immune-incompetent ICR-SCID mice (FIG. 6A; arrows indicate subcutaneous doses of 1 µg/g of mFc-rhGDF15); to induce loss of adipose tissue or gonadal fat mass (FIG. 6B); to induce loss of muscle mass of gastrocnemius muscle (FIG. 6C; Gastroc Mass); and to increase mRNA expression of muscle degradation molecular markers (mMuRF1 (FIG. 6D) and mAtrogin (FIG. 6E)).
Figure 6B:
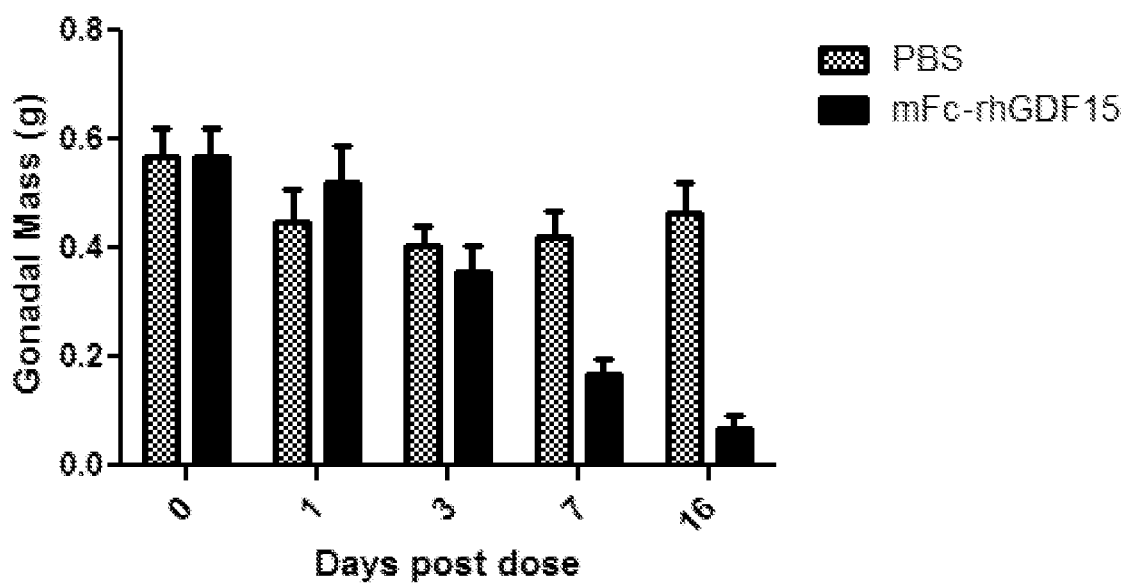
Figure 6C:
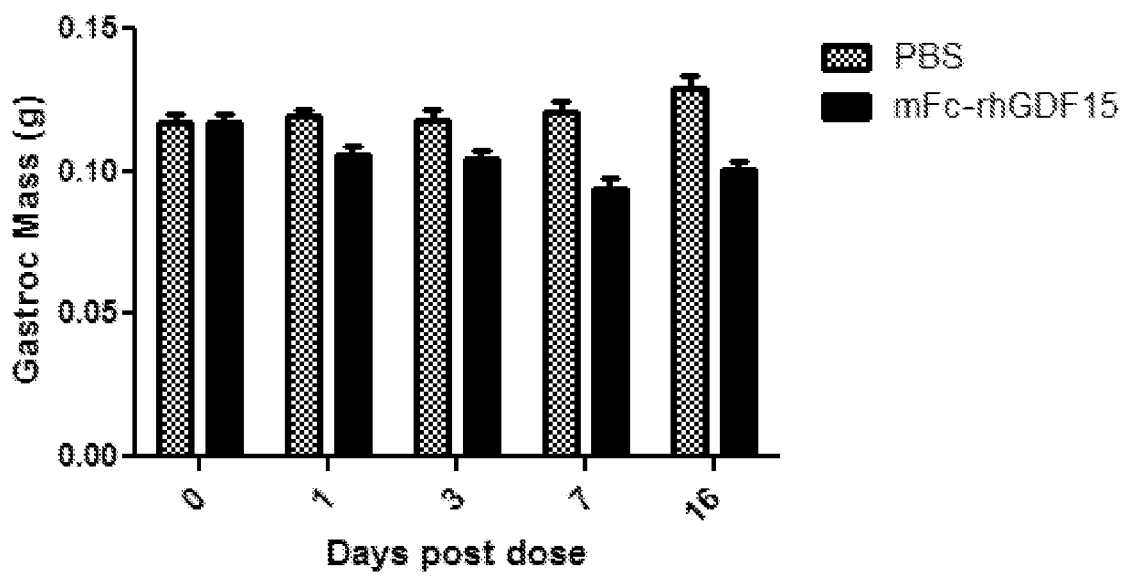
Figure 6D:
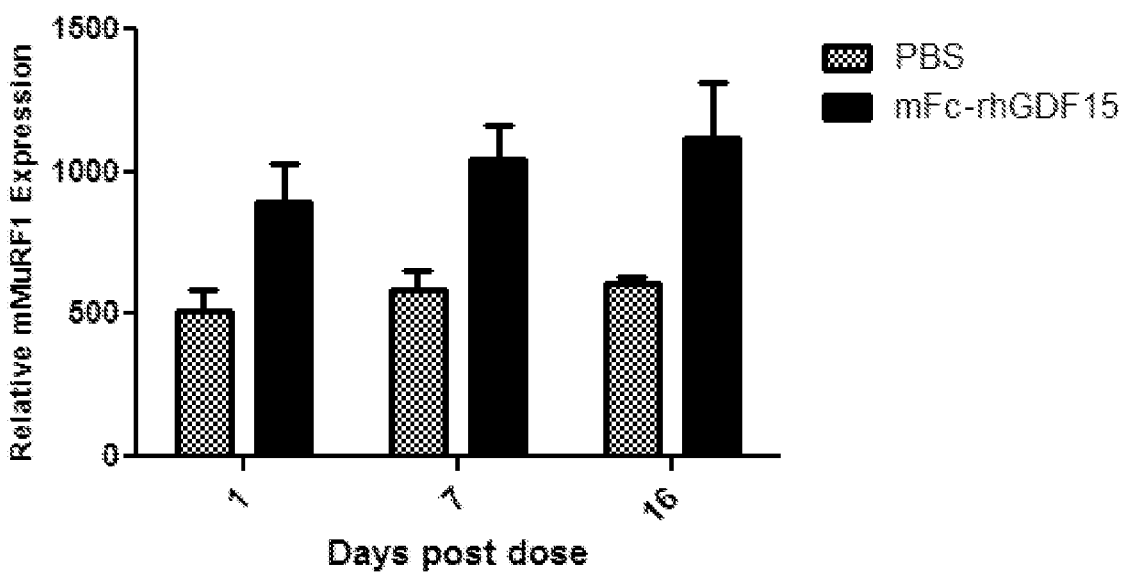
Figure 6E:
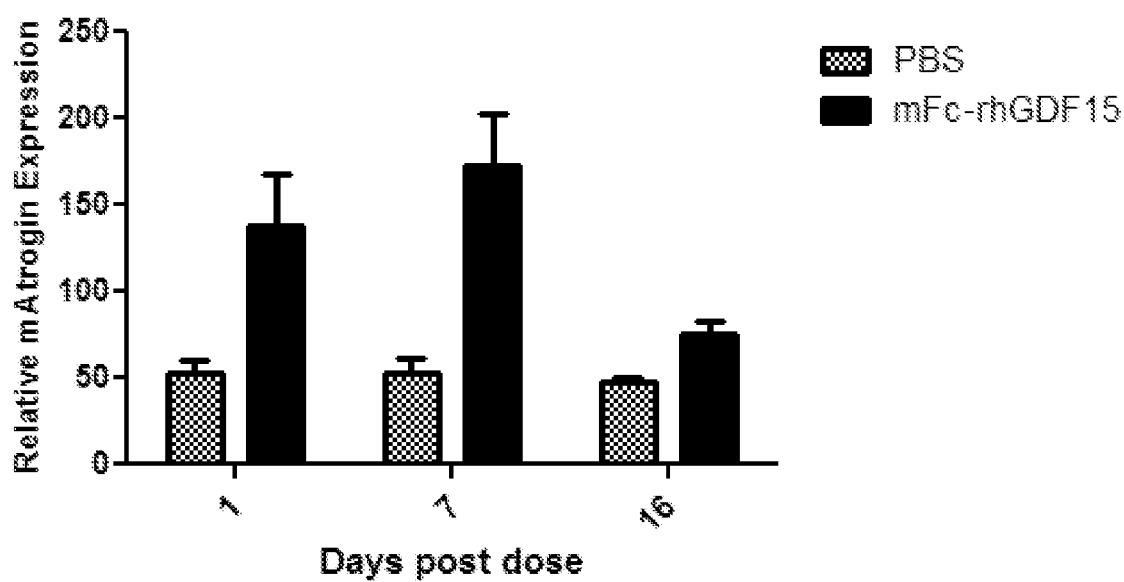

As shown in FIG. 6A, mFc-rhGDF15 induced body weight loss in ICR-SCID mice. Percent body weight was 79.4 percent when measured after 16 days following one dose of mFc-rhGDF15 (p<0.001). mFc-rhGDF15 also induced loss of fat (adipose tissue), as observed by the loss of gonadal fat (FIG. 6B; p<0.01 at day 7 and p<0.001 at day 16) and loss of muscle, as observed by the loss of gastrocnemius muscle (FIG. 6C; p<0.05 at days 1 and 3, and p<0.0001 at days 7 and 16). Administration of mFc-rhGDF15 also elevated gene expression of two enzymes associated with muscle degradation and cachexia, mMuRF1 (FIG. 6D; 6<0.001 at days 1, 7, and 16) and mAtrogin (FIG. 6E; p<0.001 at days 1 and 7, and p<0.01 at day 16).

These results indicated that mFc-rhGDF15 induces cachexia in mice.

Example 5: mFc-rhGDF15 Induces Cachexia with a Longer GDF15 Half-Life in Serum

Figure 7:
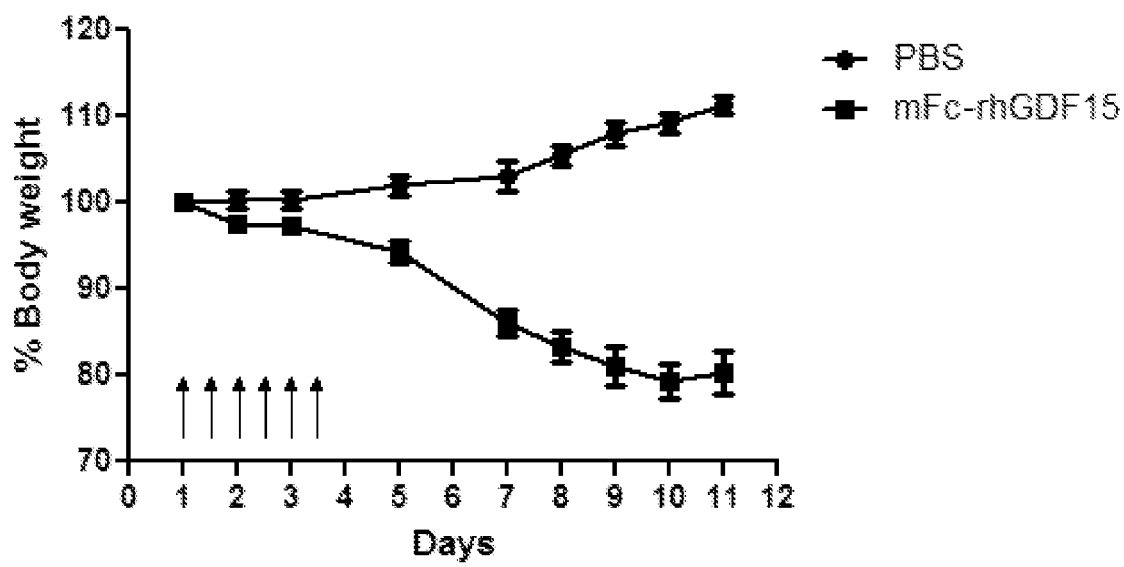
FIG. 7 is a graph summarizing results from an experiment to measure cachectic activity of mFc-rhGDF15 (■) and negative control (PBS; ●) to induce body weight loss in immune-incompetent Balb/C nude mice. Arrows indicate subcutaneous doses of 1.33 µg/g of mFc-rhGDF15.

In this Example, the serum hGDF15 levels were measured following administration of mFc-rhGDF15, to determine the half-life of rhGDF15 in this model. Eight-week old female Balb/C nude mice were randomly divided into two groups of twelve mice each. Mice were dosed subcutaneously in the flank every twelve hours for three days (a total of six doses) with one of the following treatments: PBS (control) or mFc-rhGDF15 at 1.33 µg/g. Body weight was measured daily. As shown in FIG. 7, mFc-rhGDF15 induced sustained body weight loss for at least one week after the final injection.

In this experiment, hGDF15 serum levels were measured 0.2, 5, and 8 days after the last dose of mFc-rhGDF15. Mice were sacrificed at the indicated time, and sera were collected. Human GDF15 serum levels were determined by ELISA (R&D Systems, Cat. No. DY957E). Table 1 provides the serum levels (pg/mL) for each mouse in the study.

TABLE 1

| Days post last dose | Mouse # | Treatment Agent | µg/g | Serum GDF15 (µg/mL); ELISA |
|---|---|---|---|---|
| 0.2 | 1 | mFc-rhGDF15 | 1.33 | 10.02 |
| 0.2 | 2 | mFc-rhGDF15 | 1.33 | 9.54 |
| 0.2 | 3 | mFc-rhGDF15 | 1.33 | 9.36 |
| 5 | 4 | mFc-rhGDF15 | 1.33 | 8.24 |
| 5 | 5 | mFc-rhGDF15 | 1.33 | 8.01 |
| 5 | 6 | mFc-rhGDF15 | 1.33 | 6.59 |
| 8 | 7 | mFc-rhGDF15 | 1.33 | 5.60 |
| 8 | 8 | mFc-rhGDF15 | 1.33 | 5.52 |
| 8 | 9 | mFc-rhGDF15 | 1.33 | 5.57 |

The results in Table 1 reveal that strong, sustained levels of hGDF15 are present in the serum at least eight days after the last dose of mFc-rhGDF15.

Figure 8:
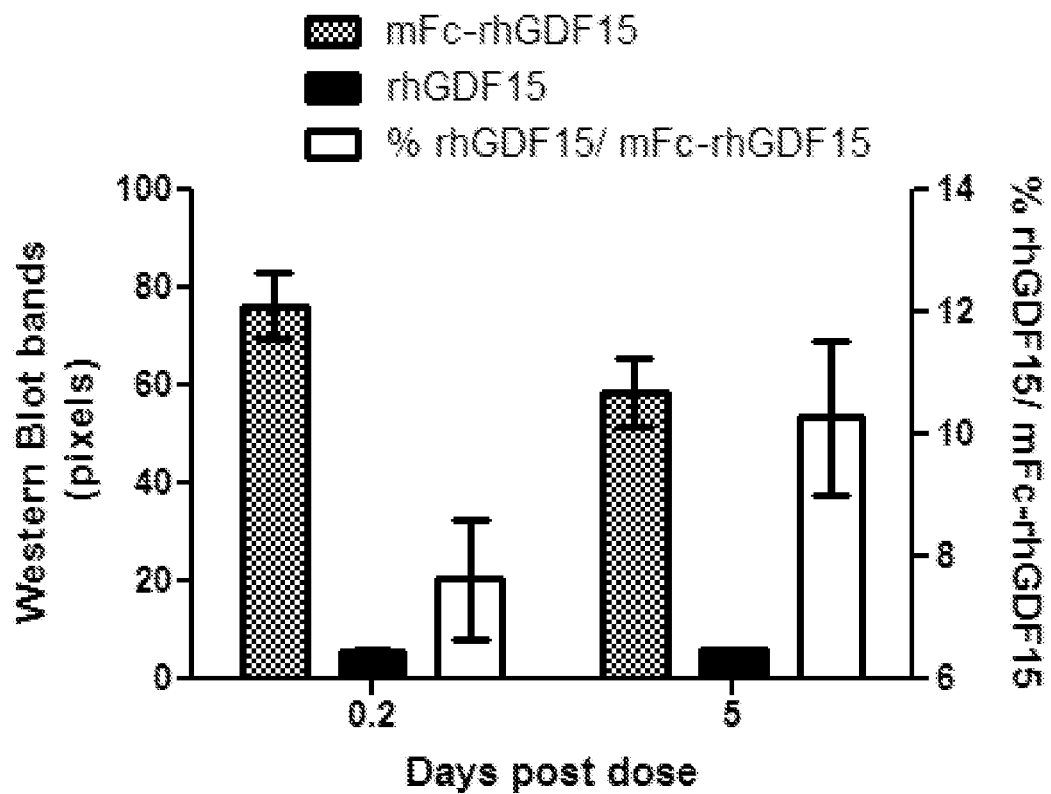
FIG. 8 is a graph summarizing results from an experiment to measure serum levels of mFc-rhGDF15 in mice dosed with the recombinant protein. The presence of mFc-rhGDF15 was determined by Western Blot. Two positive bands corresponding to mFc-rhGDF15 and rhGDF15 (according to the appropriate molecular size) were quantified by Licor. The percentage of released-rhGDF15 versus mFc-rhGDF15 was calculated.

Serum samples from day 0.2 and day 5 after the last dose were also analyzed by Western blot (reducing gel; blot with an antibody against hGDF15 (R&D Systems, Cat. No AF957)) and quantified by Licor to determine the stability of mFc-rhGDF15 in the serum. Unexpectedly, two bands were observed. The upper band was approximately 40 kDa, and appeared to be mFc-rhGDF15. The lower band was approximately 15 kDa, and appeared to be cleaved mature rhGDF15. This indicated that mature rhGDF15 was released from mFc-rhGDF15 in the serum. Quantification of the two bands showed that about 90% of the rhGDF15 present in the serum was in the form of mFc-rhGDF15, with about 10% of the total rhGDF15 in the serum being present as the cleaved mature form (FIG. 8). Quantification showed a slight decrease in mFc-rhGDF15 in the serum samples collected five days after the last dose, but, surprisingly, a constant level of mature rhGDF15 remained in the serum. The ratio of mature rhGDF15 to mFc-rhGDF15 slightly increased over time, as a result of a decrease in mFc-rhGDF15 in the serum. Similar results were observed when rFc-rmGDF15 was injected into mice.

The results presented in FIGS. 7-8 and Table 1 were unexpected. The expectation was that very little, if any, mature rhGDF15 would be cleaved (released) from the mFc-rhGDF15 by day 0.2, and that any cleaved rhGDF15 would be rapidly cleared from the serum, as had been previously observed. For example, in FIG. 4, a series of nine doses at 1 µg/g per dose (for a total of 9 µg/g) of cleaved-rhGDF15 was required to induce significant body weight loss in mice. These mice gained weight, almost immediately when dosing stopped. In contrast, a single dose of mFc-rhGDF15 at 0.1 µg/g was sufficient to induce significant body weight loss for at least eight days (FIG. 9A; ten ICR-SCID mice dosed intrapertioneally with 0.1 µg/g on day 1). The data in Table 1 revealed that rhGDF15 serum levels were stable for at least eight days, when rhGDF15 was administered as an mFc-rhGDF15 fusion protein.

Figure 9A:
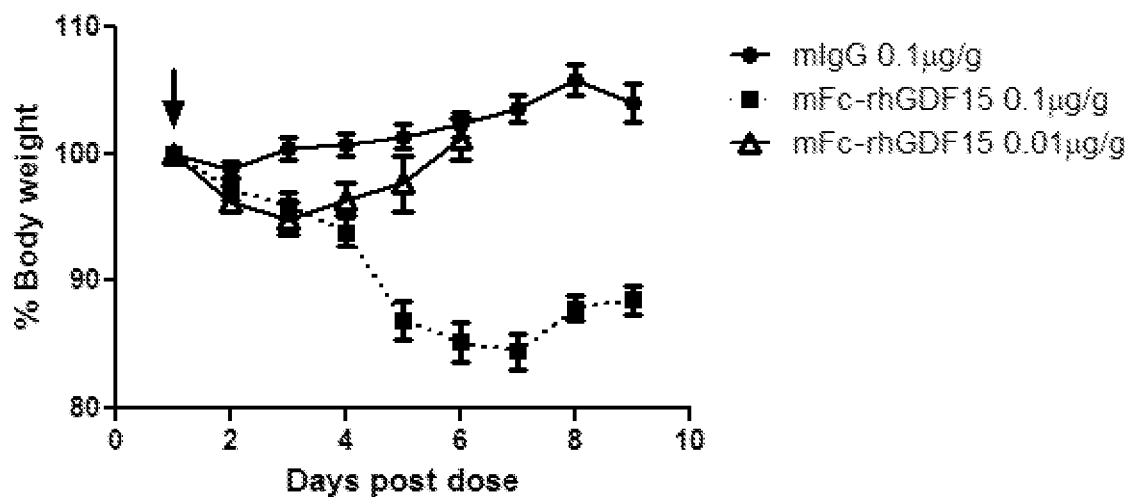
FIG. 9A is a graph summarizing results from an experiment to measure cachectic activity of mFc-rhGDF15 (0.1 µg/g (■), 0.01 µg/g (Δ)) and negative control (mIgG 0.1 µg/g (●)) to induce body weight loss in immune-incompetent ICR-SCID mice. Arrows indicate the intraperitoneal dose of the recombinant protein.

To determine the source of activity resulting in sustained body weight loss, we investigated whether the observed rhGDF15 activity was attributable to the mFc-rhGDF15 fusion protein, the released mature rhGDF15 form, or both. As shown in FIG. 9A, a low dose of mFc-rhGDF15 (0.1 µg/g) resulted in body weight loss continuing for at least eight days. A lower dose of mFc-rhGDF15 (0.01 µg/g) also induced body weight loss, but the effect was not sustained for longer than 3 days post dose.

Figure 9B:
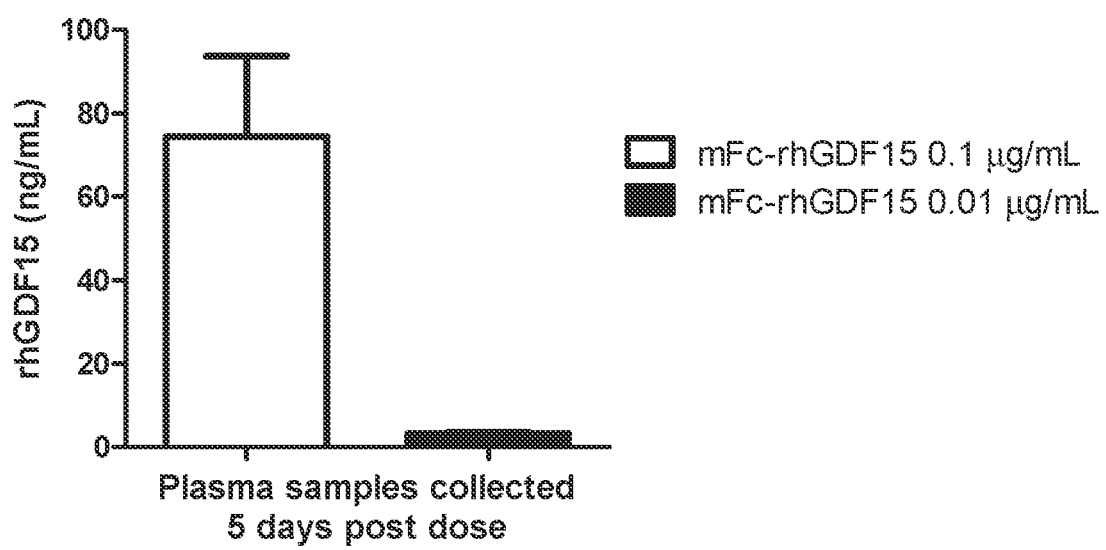
FIG. 9B is a graph representing the total level of rhGDF15 in the plasma of mice dosed with mFc-rhGDF15 (0.1 µg/g (□), 0.01 µg/g (■)) five days post dose, as determined by ELISA.

In this experiment, plasma was collected from three mice each dosed with 0.1 µg/g or 0.01 µg/g at 5 days post dose. Total rhGDF15 was measured by ELISA as described above. Total rhGDF15 plasma levels in the mice dosed with 0.1 µg/g were above 70 ng/mL, consistent with the observation that these mice had significant weight loss (FIG. 9B). Total rhGDF15 plasma levels in mice dosed with 0.01 µg/g were approximately 3.3 ng/mL, but it was observed that these mice were gaining weight (FIG. 9A and FIG. 9B). As described in FIG. 2, the threshold for hGDF15 to induce cachexia in tumor bearing mice is approximately 2 ng/mL. Thus, if both forms of rhGDF15 were active (i.e., mFc-rhGDF15 and released mature rhGDF15), then these mice should be losing weight, not gaining weight (i.e., 3.3 ng/mL total rhGDF15 is above the threshold of approximately 2 ng/mL hGDF15).

To determine which form was the active form (i.e., either mFc-rhGDF15 or released mature rhGDF15), we considered the data from FIG. 8 which showed that approximately 90% of the total rhGDF15 in serum was in the mFc-rhGDF15 form, and the remaining 10% was the released mature form. Based on this extrapolation, approximately 3.0 ng/mL of rhGDF15 in the plasma was in the mFc-rhGDF15 form (i.e., 90% of 3.3 ng/mL). Once again, if mFc-rhGDF15 were active, these mice would be losing weight, not gaining weight because 3.3 ng/mL mFc-rhGDF15 is above the threshold of approximately 2 ng/mL hGDF15. The mice dosed with 0.1 µg/g mFc-rhGDF15 served as an internal control, because these mice had sustained body weight loss indicating that at least one of the two forms must be active. A calculation of 10% of 70 ng/mL total rhGDF15 in these mice is 7 ng/mL released mature rhGDF15. This amount is consistent with inducing the observed body weight loss and the threshold observed in FIG. 2. Thus, the data indicate that the mFc-rhGDF15 is not an active form of the protein, and only the mature rhGDF15 is active. These results were unexpected, because: (a) there was no reason to predict that the Fc fusion protein (mFc-rhGDF15) would be inactive; and (b) there was no reason to predict that the Fc fusion protein would release mature rhGDF15 at the observed rate.

These results indicate that mFc-rhGDF15 sustains a cachetic phenotype by slowly releasing mature rhGDF15 into the serum. These results further indicate that a steady state level of mature rhGDF15 in the plasma or serum can be achieved in a non-tumor bearing mouse by administering mFc-rhGDF15 to the mouse. Therefore, administration of mFc-rhGDF15 to non-tumor bearing mice is particularly useful as a mouse model of cachexia with a robust and sustained loss of muscle mass, loss of fat mass, and body weight loss (see FIGS. 6A-C).

Example 6: Anti-GDF15 Antibodies

This Example describes the production of anti-GDF15 monoclonal antibodies. Immunizations, fusions, and primary screens were conducted using conventional methods following the Repetitive Immunization Multiple Sites (RIMMS) protocol. Five AJ mice and five Balb/c mice were immunized with 6×His (SEQ ID NO: 266) tagged recombinant human GDF15 (His-rhGDF15) (R&D Systems, Inc., Minneapolis, MN). Two Balb/c mice with sera displaying the highest anti-GDF15 activity by Enzyme Linked Immunosorbent Assay (ELISA) were chosen for subsequent fusion. Spleens and lymph nodes from the appropriate mice were harvested. B-cells were harvested and fused with a myeloma line. Fusion products were serially diluted onto forty 96-well plates to near clonality. Two AJ mice with sera displaying the highest anti-GDF15 activity by ELISA were chosen for subsequent fusion. Spleens and lymph nodes from the appropriate mice were harvested. B-cells were harvested and fused with a myeloma line. Fusion products were serially diluted onto forty 96-well plates to near clonality.

Approximately 3,840 supernatants from the cell fusions were screened by ELISA for binding to rhGDF15. A total of 172 supernatants containing antibodies against GDF15 were further characterized in vitro. A panel of hybridomas was selected, subcloned and expanded. Antibodies were expressed and subsequently purified by affinity chromatography on Protein G resin, under standard conditions.

Example 7: Antibody Sequence Analysis

The light chain isotype and heavy chain isotype of each monoclonal antibody in Example 6 was determined using the IsoStrip™ Mouse Monoclonal Antibody Isotyping Kit according the kit vendor's instructions (Roche Applied Science, Indianapolis, IN). All antibodies were found to be kappa light chain, and IgG1 or IgG2b heavy chain.

The heavy and light chain variable regions of the mouse monoclonal antibodies were sequenced using 5' RACE (Rapid Amplification of cDNA Ends). Total RNA was extracted from each monoclonal hybridoma cell line using the RNeasy® Miniprep kit according to the kit vendor's instructions (Qiagen, Valencia, CA). Full-length first strand cDNA containing 5' ends was generated using the SMARTer™ RACE cDNA Amplification Kit (Clontech, Mountain View, CA) according to the kit vendor's instructions for 5' RACE.

The variable regions of the light (kappa) and heavy (IgG10r IgG2b) chains were amplified by PCR using KOD Hot Start Polymerase (EMD Chemicals, Gibbstown, NJ) according to the kit vendor's instructions. For amplification of 5' cDNA ends in conjunction with the SMARTer™ RACE cDNA Amplification Kit, the Universal Primer Mix A primer (Clontech), a mix of: 5' CTAATACGACTCAC-TATAGGGCAAGCAGTGGTATCAACGCAGAGT 3' (SEQ ID NO:233) and 5' CTAATACGACTCAC-TATAGGGC 3' (SEQ ID NO:225), was used as a 5' primer. Heavy chain variable regions were amplified using the above 5' primers and a 3' IgG1 constant region specific primer, 5' TATGCAAGGCTTACAACCACA 3' (SEQ ID NO:226), or a 3' IgG2b constant region specific primer, 5' AGGACAGGGGTTGATTGTTGA 3' (SEQ ID NO:227). Kappa chain variable regions were first amplified with the above 5' primers and a 3' kappa constant region specific primer, 5' CTCATTCCTGTTGAAGCTCTTGACAAT 3' (SEQ ID NO:228). The light chains were subjected to a second, nested, round of PCR using the Nested Universal Primer A (Clontech) 5' primer, 5' AAGCAGTGGTAT-CAACGCAGAGT 3' (SEQ ID NO:229) and a nested 3' kappa constant region specific primer, 5' CGACT-GAGGGCACCTCCAGATGTT 3' (SEQ ID NO:230). Individual PCR products were either purified using the Qiaquick® PCR Purification kit or isolated by agarose gel electrophoresis and purified using the Qiaquick® Gel Purification kit according to the kit vendor's instructions (Qiagen). The PCR products were subsequently cloned into the pCR®4Blunt plasmid using the Zero Blunt® TOPO® PCR Cloning according to the kit vendor's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGCCAGT 3') (SEQ ID NO:231) and M13 Reverse primers (5' CAGGAAACAGCTATGACC 3') (SEQ ID NO:232) by Beckman Genomics (Danvers, MA), using standard dideoxy DNA sequencing methods to identify the sequence of the variable region sequences. The sequences were analyzed using Vector NTI software (Invitrogen) and the IMGT/V-Quest web server (imgt.cines.fr) to identify and confirm variable region sequences.

The nucleic acid sequences encoding and the protein sequences defining variable regions of the murine monoclonal antibodies are shown below (amino terminal signal peptide sequences are not shown). CDR sequences (Kabat definition) are indicated by bold font and underlining in the amino acid sequences.

Nucleic Acid Sequence Encoding the Heavy Chain Variable Region of the 01G06 Antibody (SEQ ID NO:39)

```
  1 gaggtcctgc tgcaacagtc tggacctgag ctggtgaagc ctggggcttc agtgaagata
 61 ccctgcaagg cttctggata cacattcact gactacaaca tggactgggt gaagcagagc
121 catggaaaga gccttgagtg gattggacaa attaatccta acaatggtgg tatttcttc
```

-continued

```
181 aaccagaagt tcaagggcaa ggccacattg actgtagaca agtcctccaa tacagccttc
241 atggaggtcc gcagcctgac atctgaggac actgcagtct attactgtgc aagagaggca
301 attactacgg taggcgctat ggactactgg ggtcaaggaa cctcagtcac cgtctcctca
```

Protein Sequence Defining the Heavy Chain Variable
Region of the 01G06 Antibody (SEQ ID NO:40)

```
 1 evllqqsgpe lvkpgasvki pckasgytft dynmdwvkqs hgkslewigq inpnnggiff
61 nqkfkgkatl tvdkssntaf mevrsltsed tavyycarea ittvgamdyw gqgtsvtvss
```

Nucleic Acid Sequence Encoding the Kappa Chain Variable
Region of the 01G06 Antibody (SEQ ID NO:75)

```
  1 gacatccaga tgactcagtc tccagcctcc ctatctgcat ctgtgggaga aactgtcacc
 61 atcacatgtc gaacaagtga gaatcttcac aattatttag catggtatca gcagaaacag
121 ggaaaatctc ctcagctcct ggtctatgat gcaaaaacct tagcagatgg tgtgccatca
181 aggttcagtg gcagtggatc aggaacacaa tattctctca gatcaacag cctgcagcct
241 gaagatttg ggagttatta ctgtcaacat ttttggagta gtccttacac gttcggaggg
301 gggaccaagc tggaaataaa a
```

Protein Sequence Defining the Kappa Chain Variable
Region of the 01G06 Antibody (SEQ ID NO:76)

```
 1 diqmtqspas lsasvgetvt itcrtsenlh nylawyqqkq gkspqllvyd aktladgvps
61 rfsgsgsgtq yslkinslqp edfgsyycqh fwsspytfgg gtkleik
```

Nucleic Acid Sequence Encoding the Heavy Chain Variable
Region of the 03G05 Antibody (SEQ ID NO:41)

```
  1 caggtccaac tgcagcagcc tggggctgaa ctggtgaagc ctggggcttc agtgaagctg
 61 tcctgcaagg cttctggcta caccttcacc agctactgga ttcactggg gaaccagagg
121 cctggacaag gccttgagtg gattggagac attaatccta gcaacggccg tagtaagtat
181 aatgagaagt tcaagaacaa ggccacaatg actgcagaca atcctccaa cacagcctac
241 atgcaactca gcagcctgac atctgaggac tctgcggtct attactgtgc aagagaggtt
301 ctggatggtg ctatggacta ctggggtcaa ggaaccctcag tcaccgtctc ctca
```

Protein Sequence Defining the Heavy Chain Variable
Region of the 03G05 Antibody (SEQ ID NO:42)

```
 1 qvqlqqpgae lvkpgasvkl sckasgytft sywihwvnqr pgqglewigd inpsngrsky
61 nekfknkatm tadkssntay mqlssltsed savyycarev ldgamdywgq gtsvtvss
```

Nucleic Acid Sequence Encoding the Kappa Chain Variable
Region of the 03G05 Antibody (SEQ ID NO:77)

```
  1 gacattgtgt tgacccaatc tccagcttct ttggctgtgt ctctagggca gagggccacc
 61 atctcctgca gagccagcga aagtgttgat aattatgca ttagtttat gaactggttc
121 caacagaaac caggacagcc acccaaactc ctcatctatg ctgcatccaa ccaaggctcc
```

-continued

```
181 ggggtccctg ccaggtttag tggcagtggg tctgggacag acttcagcct caacatccat 241 cctatggagg aggatgatac tgcaatgtat ttctgtcagc aaagtaagga ggttccgtgg 301 acgttcggtg gaggctccaa gctggaaatc aaa
```

Protein Sequence Defining the Kappa Chain Variable
Region of the 03G05 Antibody (SEQ ID NO:78)

```
  1 divltqspas lavslgqrat isc rasesvd nygisfmn wf qqkpgqppkl liy aasnqgs 61 gvparfsgsg sgtdfslnih pmeeddtamy fc qqskevpw t fgggsklei k
```

Nucleic Acid Sequence Encoding the Heavy Chain Variable
Region of the 04F08 Antibody (SEQ ID NO:43)

```
  1 caggttactc tgaaagagtc tggccctggg atattgcagc cctcccagac cctcagtctg 61 acttgttctt tctctgggtt ttcactgagc acttatggta tgggtgtgac ctggattcgt 121 cagccttcag gaaagggtct ggagtggctg gcacacattt actgggatga tgacaagcgc 181 tataacccat ccctgaagag ccggctcaca atctccaagg atacctccaa caaccaggta 241 ttcctcaaga tcaccagtgt ggacactgca gatactgcca catactactg tgctcaaacg 301 gggtatagta acttgtttgc ttactgggc caagggactc tggtcactgt ctctgca
```

Protein Sequence Defining the Heavy Chain Variable
Region of the 04F08 Antibody (SEQ ID NO:44)

```
  1 qvtlkesgpg ilqpsqtlsl tcsfsgfsls tygmgvt wir qpsgkglewl ahiywdddkr 61 ynpslks rlt iskdtsnnqv flkitsvdta dtatyycaqt gysnlfay wg qgtlvtvsa
```

Nucleic Acid Sequence Encoding the Kappa Chain Variable
Region of the 04F08 Antibody (SEQ ID NO:79)

```
  1 gacattgtga tgacccagtc tcaaaaattc atgtccacat cagtaggaga cagggtcagc 61 gtcacctgca aggccagtca gaatgtgggt actaatgtag cctggtatca acagaaatta 121 ggacaatctc ctaaaacact gatttactcg gcatcctacc ggtacagtgg agtccctgat 181 cgcttcacag gcagtggatc tgggacagat ttcactctca ccatcagcaa tgtgcagtct 241 gaagacttgg cagagtattt ctgtcagcaa tataacagct atccgtacac gttcggaggg 301 gggaccaagc tggaaataaa a
```

Protein Sequence Defining the Kappa Chain Variable
Region of the 04F08 Antibody (SEQ ID NO:80)

```
  1 divmtqsqkf mstsvgdrvs vtc kasqnvg tnva wyqqkl gqspktliys asyrys gvpd 61 rftgsgsgtd ftltisnvqs edlaeyfcqq ynsypyt fgg gtkleik
```

Nucleic Acid Sequence Encoding the Heavy Chain Variable
Region of the 06C11 Antibody (SEQ ID NO:45)

```
  1 caggttactc tgaaagagtc tggccctggg atattgcagc cctcccagac cctcagtctg 61 acttgttctt tctctgggtt ttcactgaac acttatggta tgggtgtgag ctggattcgt 121 cagccttcag gaaagggtct ggagtggctg gcacacattt actgggatga tgacaagcgc 181 tataacccat ccctgaagag ccggctcaca atctccaagg atgcctccaa caaccgggtc
```

-continued

```
241 ttcctcaaga tcaccagtgt ggacactgca gatactgcca catactactg tgctcaaaga
301 ggttatgatg attactgggg ttactggggc caagggactc tggtcactat ctctgca
```

Protein Sequence Defining the Heavy Chain Variable Region of the 06C11 Antibody (SEQ ID NO:46)

```
  1 qvtlkesgpg ilqpsqtlsl tcsfsgfsln tygmgvswir qpsgkglewl ahiywdddkr
 61 ynpslksrlt iskdasnnrv flkitsvdta dtatyycaqr gyddywgywg qgtlvtisa
```

Nucleic Acid Sequence Encoding the Kappa Chain Variable Region of the 06C11 Antibody (SEQ ID NO:81)

```
  1 gacattgtga tgacccagtc tcaaaaattc atgtccacat cagtaggaga cagggtcagc
 61 gtcacctgca aggccagtca gaatgtgggt actaatgtag cctggtttca acagaaacca
121 ggtcaatctc ctaaagcact gatttactcg gcatcttacc ggtacagtgg agtccctgat
181 cgcttcacag gcagtggatc tgggacagat ttcattctca ccatcagcaa tgtgcagtct
241 gaagacctgg cagagtattt ctgtcagcaa tataacaact atcctctcac gttcggtgct
301 gggaccaagc tggagctgaa a
```

Protein Sequence Defining the Kappa Chain Variable Region of the 06C11 Antibody (SEQ ID NO:82)

```
  1 divmtqsqkf mstsvgdrvs vtckasqnvg tnvawfqqkp gqspkaliys asyrysgvpd
 61 rftgsgsgtd filtisnvqs edlaeyfcqq ynnypltfga gtklelk
```

Nucleic Acid Sequence Encoding the Heavy Chain Variable Region of the 08G01 Antibody (SEQ ID NO:47)

```
  1 gaggtcctgc tgcaacagtc tggacctgag gtggtgaagc ctggggcttc agtgaagata
 61 ccctgcaagg cttctggata cacattcact gactacaaca tggactgggt gaagcagagc
121 catggaaaga gccttgagtg gattggagag attaatccta acaatggtgg tactttctac
181 aaccagaagt tcaagggcaa ggccacattg actgtagaca gtcctccag cacagcctac
241 atggagctcc gcagcctgac atctgaggac actgcagtct attactgtgc aagagaggca
301 attactacgg taggcgctat ggactactgg ggtcaaggaa cctcagtcac cgtctcctca
```

Protein Sequence Defining the Heavy Chain Variable Region of the 08G01 Antibody (SEQ ID NO:48)

```
  1 evllqqsgpe vvkpgasvki pckasgytft dynmdwvkqs hgkslewige inpnnggtfy
 61 nqkfkgkatl tvdkssstay melrsltsed tavyycarea ittvgamdyw gqgtsvtvss
```

Nucleic Acid Sequence Encoding the Kappa Chain Variable Region of the 08G01 Antibody (SEQ ID NO:83)

```
  1 gacatccaga tgactcagtc tccagcctcc ctatctgcat ctgtgggaga aactgtcacc
 61 atcacatgtc gagcaagtgg gaatattcac aattatttag catggtatca gcagaaacag
121 ggaaaatctc ctcagctcct ggtctataat gcaaaaacct tagcagatgg tgtgccatca
181 aggttcagtg gcagtggatc aggaacacaa tattctctca gatcaacag cctgcagcct
```

```
                          -continued
241  gaagatttg ggagttatta ctgtcaacat ttttggagtt ctccttacac gttcggaggg 301  gggaccaagc tggaaataaa a
```

Protein Sequence Defining the Kappa Chain Variable
Region of the 08G01 Antibody (SEQ ID NO:84)

```
  1  diqmtqspas lsasvgetvt itcrasgnih nylawyqqkq gkspqllvyn aktladgvps 61  rfsgsgsgtq yslkinslqp edfgsyycqh fwsspytfgg gtkleik
```

Nucleic Acid Sequence Encoding the Heavy Chain Variable
Region of the 14F11 Antibody (SEQ ID NO:49)

```
  1  caggttactc tgaaagagtc tggccctgga atattgcagc cctcccagac cctcagtctg 61  acttgttctt tctctgggtt ttcactgagc acttatggta tgggtgtagg ctggattcgt 121  cagccttcag gaaagggtct agagtggctg gcagacattt ggtgggatga cgataagtac 181  tataacccat ccctgaagag ccggctcaca atctccaagg atacctccag caatgaggta 241  ttcctcaaga tcgccattgt ggacactgca gatactgcca cttactactg tgctcgaaga 301  ggtcactact ctgctatgga ctactggggt caaggaacct cagtcaccgt ctcctca
```

Protein Sequence Defining the Heavy Chain Variable
Region of the 14F11 Antibody (SEQ ID NO:50)

```
  1  qvtlkesgpg ilqpsqtlsl tcsfsgfsls tygmgvgwir qpsgkglewl adiwwdddky 61  ynpslksrlt iskdtssnev flkiaivdta dtatyycarr ghysamdywg qgtsvtvss
```

Nucleic Acid Sequence Encoding the Kappa Chain Variable
Region of the 14F11 Antibody (SEQ ID NO:85)

```
  1  gacattgtaa tgacccagtc tcaaaaattc atgtccacat cagtaggaga cagggtcagc 61  gtcacctgca aggccagtca gaatgtgggt actaatgtag cctggtatca acagaaacca 121  gggcaatctc ctaaagcact gatttactcg ccatcctacc ggtacagtgg agtccctgat 181  cgcttcacag gcagtggatc tgggacagat ttcactctca ccatcagcaa tgtgcagtct 241  gaagacttgg cagaatattt ctgtcagcaa tataacagct atcctcacac gttcggaggg 301  gggaccaagc tggaaatgaa a
```

Protein Sequence Defining the Kappa Chain Variable
Region of the 14F11 Antibody (SEQ ID NO:86)

```
  1  divmtqsqkf mstsvgdrvs vtckasqnvg tnvawyqqkp gqspkaliys psyrysgvpd 61  rftgsgsgtd ftltisnvqs edlaeyfcqq ynsyphtfgg gtklemk
```

Nucleic Acid Sequence Encoding the Heavy Chain Variable
Region of the 17B11 Antibody (SEQ ID NO:51)

```
  1  caggttactc tgaaagagtc tggccctggg atattgcagc cctcccagac cctcagtctg 61  acttgttctt tctctgggtt ttcactgagc acttctggta tgggtgtgag ttggattcgt 121  cagccttcag gaaagggtct ggagtggctg gcacacaatg actgggatga tgacaagcgc 181  tataagtcat ccctgaagag ccggctcaca atatccaagg atacctccag aaaccaggta 241  ttcctcaaga tcaccagtgt ggacactgca gatactgcca catactactg tgctcgaaga
```

```
301 gttgggggat tagagggcta ttttgattac tggggccaag gcaccactct cacagtctcc 361 tca
```

Protein Sequence Defining the Heavy Chain Variable Region of the 17B11 Antibody (SEQ ID NO:52)

```
  1  qvtlkesgpg ilqpsqtlsl tcsfsgfsls tsgmgvswir qpsgkglewl ahndwdddkr 61  yksslksrlt iskdtsrnqv flkitsvdta dtatyycarr vgglegyfdy wgqgttltvs 121  s
```

Nucleic Acid Sequence Encoding the Kappa Chain Variable Region of the 17B11 Antibody (SEQ ID NO:87)

```
  1  gacattgtgc tgacacagtc tcctgcttcc ttagctgtat ctctggggca gagggccacc 61  atctcatgca gggccagcca aagtgtcagt acatctaggt ttagttatat gcactggttc 121  caacagaaac caggacaggc acccaaactc ctcatcaagt atgcatccaa cctagaatct 181  ggggtccctg ccaggttcag tggcagtggg tctgggacag acttcaccct caacatccat 241  cctgtggagg gggaggatac tgcaacatat tactgtcagc acagttggga gattccgtac 301  acgttcggag gggggaccaa gctggaaata aaa
```

Protein Sequence Defining the Kappa Chain Variable Region of the 17B11 Antibody (SEQ ID NO:88)

```
  1  divltqspas layslgqrat iscrasqsvs tsrfsymhwf qqkpgqapkl likyasnles 61  gvparfsgsg sgtdftlnih pvegedtaty ycqhsweipy tfgggtklei k
```

The amino acid sequences defining the immunoglobulin heavy chain variable regions for the antibodies produced in Example 6 are aligned in FIG. 10. Amino terminal signal peptide sequences (for expression/secretion) are not shown. $CDR_1$, $CDR_2$, and $CDR_3$ (Kabat definition) are identified by boxes. FIG. 11 shows an alignment of the separate $CDR_1$, $CDR_2$, and $CDR_3$ sequences for each antibody.

The amino acid sequences defining the immunoglobulin light chain variable regions of the antibodies in Example 6 are aligned in FIG. 12. Amino terminal signal peptide sequences (for expression/secretion) are not shown. $CDR_1$, $CDR_2$ and $CDR_3$ are identified by boxes. FIG. 13 shows an alignment of the separate $CDR_1$, $CDR_2$, and $CDR_3$ sequences for each antibody.

Table 2 shows the SEQ ID NO. of each sequence discussed in this Example.

TABLE 2

| SEQ. ID NO. | Nucleic Acid or Protein |
| --- | --- |
| 39 | 01G06 Heavy Chain Variable Region - nucleic acid |
| 40 | 01G06 Heavy Chain Variable Region - protein |
| 75 | 01G06 Light (kappa) Chain Variable Region - nucleic acid |
| 76 | 01G06 Light (kappa) Chain Variable Region - protein |
| 1 | 01G06 Heavy Chain $CDR_1$ |
| 7 | 01G06 Heavy Chain $CDR_2$ |
| 15 | 01G06 Heavy Chain $CDR_3$ |
| 21 | 01G06 Light (kappa) Chain $CDR_1$ |
| 26 | 01G06 Light (kappa) Chain $CDR_2$ |
| 32 | 01G06 Light (kappa) Chain $CDR_3$ |
| 41 | 03G05 Heavy Chain Variable Region - nucleic acid |

TABLE 2-continued

| SEQ. ID NO. | Nucleic Acid or Protein |
| --- | --- |
| 42 | 03G05 Heavy Chain Variable Region - protein |
| 77 | 03G05 Light (kappa) Chain Variable Region - nucleic acid |
| 78 | 03G05 Light (kappa) Chain Variable Region - protein |
| 2 | 03G05 Heavy Chain $CDR_1$ |
| 8 | 03G05 Heavy Chain $CDR_2$ |
| 16 | 03G05 Heavy Chain $CDR_3$ |
| 22 | 03G05 Light (kappa) Chain $CDR_1$ |
| 27 | 03G05 Light (kappa) Chain $CDR_2$ |
| 33 | 03G05 Light (kappa) Chain $CDR_3$ |
| 43 | 04F08 Heavy Chain Variable Region - nucleic acid |
| 44 | 04F08 Heavy Chain Variable Region - protein |
| 79 | 04F08 Light (kappa) Chain Variable Region - nucleic acid |
| 80 | 04F08 Light (kappa) Chain Variable Region - protein |
| 3 | 04F08 Heavy Chain $CDR_1$ |
| 9 | 04F08 Heavy Chain $CDR_2$ |
| 17 | 04F08 Heavy Chain $CDR_3$ |
| 23 | 04F08 Light (kappa) Chain $CDR_1$ |
| 28 | 04F08 Light (kappa) Chain $CDR_2$ |
| 34 | 04F08 Light (kappa) Chain $CDR_3$ |
| 45 | 06C11 Heavy Chain Variable Region - nucleic acid |
| 46 | 06C11 Heavy Chain Variable Region - protein |
| 81 | 06C11 Light (kappa) Chain Variable Region - nucleic acid |
| 82 | 06C11 Light (kappa) Chain Variable Region - protein |
| 4 | 06C11 Heavy Chain $CDR_1$ |
| 9 | 06C11 Heavy Chain $CDR_2$ |
| 18 | 06C11 Heavy Chain $CDR_3$ |
| 23 | 06C11 Light (kappa) Chain $CDR_1$ |
| 28 | 06C11 Light (kappa) Chain $CDR_2$ |
| 35 | 06C11 Light (kappa) Chain $CDR_3$ |
| 47 | 08G01 Heavy Chain Variable Region - nucleic acid |
| 48 | 08G01 Heavy Chain Variable Region - protein |

TABLE 2-continued

| SEQ. ID NO. | Nucleic Acid or Protein |
|---|---|
| 83 | 08G01 Light (kappa) Chain Variable Region - nucleic acid |
| 84 | 08G01 Light (kappa) Chain Variable Region - protein |
| 1 | 08G01 Heavy Chain CDR$_1$ |
| 10 | 08G01 Heavy Chain CDR$_2$ |
| 15 | 08G01 Heavy Chain CDR$_3$ |
| 24 | 08G01 Light (kappa) Chain CDR$_1$ |
| 29 | 08G01 Light (kappa) Chain CDR$_2$ |
| 32 | 08G01 Light (kappa) Chain CDR$_3$ |
| 49 | 14F11 Heavy Chain Variable Region - nucleic acid |
| 50 | 14F11 Heavy Chain Variable Region - protein |
| 85 | 14F11 Light (kappa) Chain Variable Region - nucleic acid |
| 86 | 14F11 Light (kappa) Chain Variable Region - protein |
| 5 | 14F11 Heavy Chain CDR$_1$ |
| 11 | 14F11 Heavy Chain CDR$_2$ |
| 19 | 14F11 Heavy Chain CDR$_3$ |
| 23 | 14F11 Light (kappa) Chain CDR$_1$ |

TABLE 2-continued

| SEQ. ID NO. | Nucleic Acid or Protein |
|---|---|
| 30 | 14F11 Light (kappa) Chain CDR$_2$ |
| 36 | 14F11 Light (kappa) Chain CDR$_3$ |
| 51 | 17B11 Heavy Chain Variable Region - nucleic acid |
| 52 | 17B11 Heavy Chain Variable Region - protein |
| 87 | 17B11 Light (kappa) Chain Variable Region - nucleic acid |
| 88 | 17B11 Light (kappa) Chain Variable Region - protein |
| 6 | 17B11 Heavy Chain CDR$_1$ |
| 12 | 17B11 Heavy Chain CDR$_2$ |
| 20 | 17B11 Heavy Chain CDR$_3$ |
| 25 | 17B11 Light (kappa) Chain CDR$_1$ |
| 31 | 17B11 Light (kappa) Chain CDR$_2$ |
| 37 | 17B11 Light (kappa) Chain CDR$_3$ |

Mouse monoclonal antibody heavy chain CDR sequences (Kabat. Chothia. and IMGT definitions) are shown in Table 3.

TABLE 3

Kabat

| | CDR1 | CDR2 | CDR3 | Variable Region SEQ ID NO |
|---|---|---|---|---|
| 01G06 | DYNMD (SEQ ID NO: 1) | QINPNNGGIFFNQKFKG (SEQ ID NO: 7) | EAITTVGAMDY (SEQ ID NO: 15) | 40 |
| 03G05 | SYWIH (SEQ ID NO: 2) | DINPSNGRSKYNEKFKN (SEQ ID NO: 8) | EVLDGAMDY (SEQ ID NO: 16) | 42 |
| 04F08 | TYGMGVT (SEQ ID NO: 3) | HIYWDDDKRYNPSLKS (SEQ ID NO: 9) | TGYSNLFAY (SEQ ID NO: 17) | 44 |
| 06C11 | TYGMGVS (SEQ ID NO: 4) | HIYWDDDKRYNPSLKS (SEQ ID NO: 9) | RGYDDYWGY (SEQ ID NO: 18) | 46 |
| 08G01 | DYNMD (SEQ ID NO: 1) | EINPNNGGTFYNQKFKG (SEQ ID NO: 10) | EAITTVGAMDY (SEQ ID NO: 15) | 48 |
| 14F11 | TYGMGVG (SEQ ID NO: 5) | DIWWDDDKYYNPSLKS (SEQ ID NO: 11) | RGHYSAMDY (SEQ ID NO: 19) | 50 |
| 17B11 | TSGMGVS (SEQ ID NO: 6) | HNDWDDDKRYKSSLKS (SEQ ID NO: 12) | RVGGLEGYFDY (SEQ ID NO: 20) | 52 |

Chothia

| | CDR1 | CDR2 | CDR3 | Variable Region SEQ ID NO |
|---|---|---|---|---|
| 01G06 | GYTFTDY (SEQ ID NO: 38) | NPNNGG (SEQ ID NO: 143) | EAITTVGAMDY (SEQ ID NO: 15) | 40 |
| 03G05 | GYTFTSY (SEQ ID NO: 128) | NPSNGR (SEQ ID NO: 144) | EVLDGAMDY (SEQ ID NO: 16) | 42 |
| 04F08 | GFSLSTYGM (SEQ ID NO: 130) | YWDDD (SEQ ID NO: 145) | TGYSNLFAY (SEQ ID NO: 17) | 44 |
| 06C11 | GFSLNTYGM (SEQ ID NO: 132) | YWDDD (SEQ ID NO: 145) | RGYDDYWGY (SEQ ID NO: 18) | 46 |
| 08G01 | GYTFTDY (SEQ ID NO: 38) | NPNNGG (SEQ ID NO: 143) | EAITTVGAMDY (SEQ ID NO: 15) | 48 |
| 14F11 | GFSLSTYGM (SEQ ID NO: 130) | WWDDD (SEQ ID NO: 146) | RGHYSAMDY (SEQ ID NO: 19) | 50 |
| 17B11 | GFSLSTSGM (SEQ ID NO: 134) | DWDDD (SEQ ID NO: 147) | RVGGLEGYFDY (SEQ ID NO: 20) | 52 |

TABLE 3-continued

| | IMGT | | | |
|---|---|---|---|---|
| | CDR1 | CDR2 | CDR3 | Variable Region SEQ ID NO |
| 01G06 | GYTFTDYN (SEQ ID NO: 136) | INPNNGGI (SEQ ID NO: 148) | AREAITTVGAMDY (SEQ ID NO: 154) | 40 |
| 03G05 | GYTFTSYW (SEQ ID NO: 138) | INPSNGRS (SEQ ID NO: 149) | AREVLDGAMDY (SEQ ID NO: 155) | 42 |
| 04F08 | GFSLSTYGMG (SEQ ID NO: 140) | IYWDDDK (SEQ ID NO: 150) | AQTGYSNLFAY (SEQ ID NO: 156) | 44 |
| 06C11 | GFSLNTYGMG (SEQ ID NO: 141) | IYWDDDK (SEQ ID NO: 150) | AQRGYDDYWGY (SEQ ID NO: 157) | 46 |
| 08G01 | GYTFTDYN (SEQ ID NO: 136) | INPNNGGT (SEQ ID NO: 151) | AREAITTVGAMDY (SEQ ID NO: 154) | 48 |
| 14F11 | GFSLSTYGMG (SEQ ID NO: 140) | IWWDDDK (SEQ ID NO: 152) | ARRGHYSAMDY (SEQ ID NO: 158) | 50 |
| 17B11 | GFSLSTSGMG (SEQ ID NO: 142) | NDWDDDK (SEQ ID NO: 153) | ARRVGGLEGYFDY (SEQ ID NO: 159) | 52 |

Mouse monoclonal antibody Kappa light chain CDR sequences (Kabat, Chothia, and IMGT definitions) are shown in Table 4.

TABLE 4

| | Kabat/Chothia | | | |
|---|---|---|---|---|
| | CDR1 | CDR2 | CDR3 | Variable Region SEQ ID NO |
| 01G06 | RTSENLHNYLA (SEQ ID NO: 21) | DAKTLAD (SEQ ID NO: 26) | QHFWSSPYT (SEQ ID NO: 32) | 76 |
| 03G05 | RASESVDNYGISFMN (SEQ ID NO: 22) | AASNQGS (SEQ ID NO: 27) | QQSKEVPWT (SEQ ID NO: 33) | 78 |
| 04F08 | KASQNVGTNVA (SEQ ID NO: 23) | SASYRYS (SEQ ID NO: 28) | QQYNSYPYT (SEQ ID NO: 34) | 80 |
| 06C11 | KASQNVGTNVA (SEQ ID NO: 23) | SASYRYS (SEQ ID NO: 28) | QQYNNYPLT (SEQ ID NO: 35) | 82 |
| 08G01 | RASGNIHNYLA (SEQ ID NO: 24) | NAKTLAD (SEQ ID NO: 29) | QHFWSSPYT (SEQ ID NO: 32) | 84 |
| 14F11 | KASQNVGTNVA (SEQ ID NO: 23) | SPSYRYS (SEQ ID NO: 30) | QQYNSYPHT (SEQ ID NO: 36) | 86 |
| 17B11 | RASQSVSTSRFSYMH (SEQ ID NO: 25) | YASNLES (SEQ ID NO: 31) | QHSWEIPYT (SEQ ID NO: 37) | 88 |

| | IMGT | | | |
|---|---|---|---|---|
| | CDR1 | CDR2 | CDR3 | Variable Region SEQ ID NO |
| 01G06 | ENLHNY (SEQ ID NO: 160) | DAK | QHFWSSPYT (SEQ ID NO: 32) | 76 |
| 03G05 | ESVDNYGISF (SEQ ID NO: 161) | AAS | QQSKEVPWT (SEQ ID NO: 33) | 78 |
| 04F08 | QNVGTN (SEQ ID NO: 162) | SAS | QQYNSYPYT (SEQ ID NO: 34) | 80 |
| 06C11 | QNVGTN (SEQ ID NO: 162) | SAS | QQYNNYPLT (SEQ ID NO: 35) | 82 |
| 08G01 | GNIHNY (SEQ ID NO: 163) | NAK | QHFWSSPYT (SEQ ID NO: 32) | 84 |

TABLE 4-continued

| | | | | |
|---|---|---|---|---|
| 14F11 | QNVGTN (SEQ ID NO: 162) | SPS | QQYNSYPHT (SEQ ID NO: 36) | 86 |
| 17B11 | QSVSTSRFSY (SEQ ID NO: 164) | YAS | QHSWEIPYT (SEQ ID NO: 37) | 88 |

To create the complete heavy or kappa chain antibody sequences, each variable sequence above is combined with its respective constant region. For example, a complete heavy chain comprises a heavy variable sequence followed by the murine IgG1 or IgG2b heavy chain constant sequence, and a complete kappa chain comprises a kappa variable sequence followed by the murine kappa light chain constant sequence.

Nucleic Acid Sequence Encoding the Murine IgG1 Heavy Chain Constant Region (SEQ ID NO: 165)

```
  1  gccaaaacga caccccatc tgtctatcca ctggccctg gatctgctgc ccaaactaac
 61  tccatggtga ccctgggatg cctggtcaag ggctatttcc ctgagccagt gacagtgacc
121  tggaactctg gatccctgtc cagcggtgtg cacaccttcc cagctgtcct gcagtctgac
181  ctctacactc tgagcagctc agtgactgtc cctccagca cctggcccag cgagaccgtc
241  acctgcaacg ttgcccaccc ggccagcagc accaaggtgg acaagaaaat tgtgcccagg
301  gattgtggtt gtaagccttg catatgtaca gtcccagaag tatcatctgt cttcatcttc
361  cccccaaagc ccaaggatgt gctcaccatt actctgactc ctaaggtcac gtgtgttgtg
421  gtagacatca gcaaggatga tcccgaggtc cagttcagct ggtttgtaga tgatgtggag
481  gtgcacacag ctcagacgca accccgggag gagcagttca acagcacttt ccgctcagtc
541  agtgaacttc ccatcatgca ccaggactgg ctcaatggca aggagttcaa atgcagggtc
601  aacagtgcag ctttccctgc ccccatcgag aaaaccatct ccaaaaccaa aggcagaccg
661  aaggctccac aggtgtacac cattccacct cccaaggagc agatggccaa ggataaagtc
721  agtctgacct gcatgataac agacttcttc cctgaagaca ttactgtgga gtggcagtgg
781  aatgggcagc cagcggagaa ctacaagaac actcagccca tcatggacac agatggctct
841  tacttcgtct acagcaagct caatgtgcag aagagcaact gggaggcagg aaatactttc
901  acctgctctg tgttacatga gggcctgcac aaccaccata ctgagaagag cctctcccac
961  tctcctggta aa
```

Protein Sequence Defining the Murine IgG1 Heavy Chain Constant Region (SEQ ID NO:166)

```
  1  akttppsvyp lapgsaaqtn smvtlgclvk gyfpepvtvt wnsgslssgv htfpavlqsd
 61  lytlsssvtv psstwpsetv tcnvahpass tkvdkkivpr dcgckpcict vpevssvfif
121  ppkpkdvlti tltpkvtcvv vdiskddpev qfswfvddve vhtaqtqpre eqfnstfrsv
181  selpimhqdw lngkefkcrv nsaafpapie ktisktkgrp kapqvytipp pkeqmakdkv
241  sltcmitdff peditvewqw ngqpaenykn tqpimdtdgs yfvysklnvq ksnweagntf
301  tcsvlheglh nhhtekslsh spgk
```

Nucleic Acid Sequence Encoding the Murine IgG2b Heavy
Chain Constant Region (SEQ ID NO:167)

```
  1  gccaaaacaa cacccccatc agtctatcca ctggcccctg ggtgtggaga tacaactggt
 61  tcctccgtga ctctgggatg cctggtcaag ggctacttcc ctgagtcagt gactgtgact
121  tggaactctg gatccctgtc cagcagtgtg cacaccttcc cagctctcct gcagtctgga
181  ctctacacta tgagcagctc agtgactgtc cctccagca cctggccaag tcagaccgtc
241  acctgcagcg ttgctcaccc agccagcagc accacggtgg acaaaaaact gagcccagc
301  gggcccattt caacaatcaa cccctgtcct ccatgcaagg agtgtcacaa atgcccagct
361  cctaacctcg agggtggacc atccgtcttc atcttccctc caaatatcaa ggatgtactc
421  atgatctccc tgacacccaa ggtcacgtgt gtggtggtgg atgtgagcga ggatgaccca
481  gacgtccaga tcagctggtt tgtgaacaac gtggaagtac acacagctca gacacaaacc
541  catagagagg attacaacag tactatccgg gtggtcagca ccctccccat ccagcaccag
601  gactggatga gtggcaagga gttcaaatgc aaggtcaaca acaaagacct cccatcaccc
661  atcgagagaa ccatctcaaa aattaaaggg ctagtcagag ctccacaagt atacatcttg
721  ccgccaccag cagagcagtt gtccaggaaa gatgtcagtc tcacttgcct ggtcgtgggc
781  ttcaaccctg gagacatcag tgtggagtgg accagcaatg ggcatacaga ggagaactac
841  aaggacaccg caccagtcct agactctgac ggttcttact tcatatatag caagctcaat
901  atgaaaacaa gcaagtggga gaaaacagat tccttctcat gcaacgtgag acacgagggt
961  ctgaaaaatt actacctgaa gaagaccatc tcccggtctc cgggtaaa
```

Protein Sequence Defining the Murine I9G2b Heavy Chain
Constant Region (SEQ ID NO:168)

```
  1  akttppsvyp lapgcgdttg ssvtlgclvk gyfpesvtvt wnsgslsssv htfpallqsg
 61  lytmsssvtv psstwpsqtv tcsvahpass ttvdkkleps gpistinpcp pckechkcpa
121  pnleggpsvf ifppnikdvl misltpkvtc vvvdvseddp dvqiswfvnn vevhtaqtqt
181  hredynstir vvstlpiqhq dwmsgkefkc kvnnkdlpsp iertiskikg lvrapqvyil
241  pppaeqlsrk dvsltclvvg fnpgdisvew tsnghteeny kdtapvldsd gsyfiyskln
301  mktskwektd sfscnvrheg lknyylkkti srspgk
```

Nucleic Acid Sequence Encoding the Murine Kappa Light
Chain Constant Region (SEQ ID NO:169)

```
  1  cgggctgatg ctgcaccaac tgtatccatc ttcccaccat ccagtgagca gttaacatct
 61  ggaggtgcct cagtcgtgtg cttcttgaac aacttctacc ccaaagacat caatgtcaag
121  tggaagattg atggcagtga acgacaaaat ggcgtcctga acagttggac tgatcaggac
181  agcaaagaca gcacctacag catgagcagc accctcacgt tgaccaagga cgagtatgaa
241  cgacataaca gctatacctg tgaggccact cacaagacat caacttcacc cattgtcaag
301  agcttcaaca ggaatgagtg t
```

Protein Sequence Defining the Murine Kappa Light Chain
Constant Region (SEQ ID NO:170)

```
  1  radaaptvsi fppsseqlts ggasvvcfln nfypkdinvk wkidgserqn gvlnswtdqd
 61  skdstysmss tltltkdeye rhnsytceat hktstspivk sfnrnec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length immunoglobulin heavy chain and light chain sequences. It is also contemplated that the variable region sequences can be ligated to other constant region sequences to produce active full length immunoglobulin heavy and light chains.

Nucleic Acid Sequence Encoding the Full Length Heavy Chain Sequence (Heavy Chain Variable Region and IgG1 Constant Region) of 01G06 (SEQ ID NO:99)

```
   1  gaggtcctgc tgcaacagtc tggacctgag ctggtgaagc ctggggcttc agtgaagata
  61  ccctgcaagg cttctggata cacattcact gactacaaca tggactgggt gaagcagagc
 121  catggaaaga gccttgagtg gattggacaa attaatccta acaatggtgg tatttttctc
 181  aaccagaagt tcaagggcaa ggccacattg actgtagaca agtcctccaa tacagccttc
 241  atggaggtcc gcagcctgac atctgaggac actgcagtct attactgtgc aagagaggca
 301  attactacgg taggcgctat ggactactgg ggtcaaggaa cctcagtcac cgtctcctca
 361  gccaaaacga cacccccatc tgtctatcca ctggcccctg gatctgctgc ccaaactaac
 421  tccatggtga ccctgggatg cctggtcaag ggctatttcc ctgagccagt gacagtgacc
 481  tggaactctg gatccctgtc cagcggtgtg cacaccttcc cagctgtcct gcagtctgac
 541  ctctacactc tgagcagctc agtgactgtc ccctccagca cctggcccag cgagaccgtc
 601  acctgcaacg ttgcccaccc ggccagcagc accaaggtgg acaagaaaat tgtgcccagg
 661  gattgtggtt gtaagccttg catatgtaca gtcccagaag tatcatctgt cttcatcttc
 721  cccccaaagc ccaaggatgt gctcaccatt actctgactc ctaaggtcac gtgtgttgtg
 781  gtagacatca gcaaggatga tcccgaggtc cagttcagct ggtttgtaga tgatgtggag
 841  gtgcacacag ctcagacgca accccggagg gagcagttca acagcacttt ccgctcagtc
 901  agtgaacttc ccatcatgca ccaggactgg ctcaatggca aggagttcaa atgcagggtc
 961  aacagtgcag cttttcctgc ccccatcgag aaaaccatct ccaaaaccaa aggcagaccg
1021  aaggctccac aggtgtacac cattccacct cccaaggagc agatggccaa ggataaagtc
1081  agtctgacct gcatgataac agacttcttc cctgaagaca ttactgtgga gtggcagtgg
1141  aatgggcagc cagcggagaa ctacaagaac actcagccca tcatggacac agatggctct
1201  tacttcgtct acagcaagct caatgtgcag aagagcaact gggaggcagg aaatactttc
1261  acctgctctg tgttacatga gggcctgcac aaccaccata ctgagaagag cctctcccac
1321  tctcctggta aa
```

Protein Sequence Defining the Full Length Heavy Chain Sequence (Heavy Chain Variable Region and IgG1 Constant Region) of 01G06 (SEQ ID NO:100)

```
  1  evllqqsgpe lvkpgasvki pckasgytft dynmdwvkqs hgkslewigq inpnnggiff
 61  nqkfkgkatl tvdkssntaf mevrsltsed tavyycarea ittvgamdyw gqgtsvtvss
121  akttppsvyp lapgsaaqtn smvtlgclvk gyfpepvtvt wnsgslssgv htfpavlqsd
181  lytlsssvtv psstwpsetv tcnvahpass tkvdkkivpr dcgckpcict vpevssvfif
241  ppkpkdvlti tltpkvtcvv vdiskddpev qfswfvddve vhtaqtqpre eqfnstfrsv
301  selpimhqdw lngkefkcrv nsaafpapie ktisktkgrp kapqvytipp pkeqmakdkv
361  sltcmitdff peditvewqw ngqpaenykn tqpimdtdgs yfvysklnvq ksnweagntf
421  tcsvlheglh nhhtekslsh spgk
```

Nucleic Acid Sequence Encoding the Full Length Light Chain Sequence (Kappa Chain Variable Region and Constant Region) of 01G06 (SEQ ID NO:101)

```
  1  gacatccaga tgactcagtc tccagcctcc ctatctgcat ctgtgggaga aactgtcacc
 61  atcacatgtc gaacaagtga gaatcttcac aattatttag catggtatca gcagaaacag
121  ggaaaatctc ctcagctcct ggtctatgat gcaaaaacct tagcagatgg tgtgccatca
181  aggttcagtg gcagtggatc aggaacacaa tattctctca agatcaacag cctgcagcct
241  gaagattttg ggagttatta ctgtcaacat ttttggagta gtccttacac gttcggaggg
301  gggaccaagc tggaaataaa acgggctgat gctgcaccaa ctgtatccat cttcccacca
361  tccagtgagc agttaacatc tggaggtgcc tcagtcgtgt gcttcttgaa caacttctac
421  cccaaagaca tcaatgtcaa gtggaagatt gatggcagtg aacgacaaaa tggcgtcctg
481  aacagttgga ctgatcagga cagcaaagac agcacctaca gcatgagcag cccctcacg
541  ttgaccaagg acgagtatga acgacataac agctatacct gtgaggccac tcacaagaca
601  tcaacttcac ccattgtcaa gagcttcaac aggaatgagt gt
```

Protein Sequence Defining the Full Length Light Chain Sequence (Kappa Chain Variable Region and Constant Region) of 01G06 (SEQ ID NO:102)

```
  1  diqmtqspas lsasvgetvt itcrtsenlh nylawyqqkq gkspqllvyd aktladgvps
 61  rfsgsgsgtq yslkinslqp edfgsyycqh fwsspytfgg gtkleikrad aaptvsifpp
121  sseqltsgga svvcflnnfy pkdinvkwki dgserqngvl nswtdqdskd stysmsstlt
181  ltkdeyerhn sytceathkt stspivksfn rnec
```

Nucleic Acid Sequence Encoding the Full Length Heavy Chain Sequence (Heavy Chain Variable Region and IgG1 Constant Region) of 03G05 (SEQ ID NO:103)

```
  1  caggtccaac tgcagcagcc tggggctgaa ctggtgaagc ctggggcttc agtgaagctg
 61  tcctgcaagg cttctggcta caccttcacc agctactgga ttcactgggt gaaccagagg
121  cctggacaag gccttgagtg gattggagac attaatccta gcaacggccg tagtaagtat
181  aatgagaagt tcaagaacaa ggccacaatg actgcagaca atcctccaa cacagcctac
241  atgcaactca gcagcctgac atctgaggac tctgcggtct attactgtgc aagagaggtt
301  ctggatggtg ctatggacta ctggggtcaa ggaacctcag tcaccgtctc ctcagccaaa
361  acgacacccc catctgtcta tccactggcc cctggatctg ctgcccaaac taactccatg
421  gtgaccctgg gatgcctggt caagggctat ttccctgagc cagtgacagt gacctggaac
481  tctggatccc tgtccagcgg tgtgcacacc ttcccagctg tcctgcagtc tgacctctac
541  actctgagca gctcagtgac tgtcccctcc agcacctggc ccagcgagac cgtcacctgc
601  aacgttgccc acccggccag cagcaccaag gtggacaaga aaattgtgcc cagggattgt
661  ggttgtaagc cttgcatatg tacagtccca gaagtatcat ctgtcttcat cttccccca
721  aagcccaagg atgtgctcac cattactctg actcctaagg tcacgtgtgt tgtggtagac
781  atcagcaagg atgatcccga ggtccagttc agctggtttg tagatgatgt ggaggtgcac
841  acagctcaga cgcaaccccg ggaggagcag ttcaacagca ctttccgctc agtcagtgaa
901  cttcccatca tgcaccagga ctggctcaat ggcaaggagt tcaaatgcag ggtcaacagt
961  gcagctttcc ctgcccccat cgagaaaacc atctccaaaa ccaaaggcag accgaaggct
```

-continued

```
1021  ccacaggtgt  acaccattcc  acctcccaag  gagcagatgg  ccaaggataa  agtcagtctg 1081  acctgcatga  taacagactt  cttccctgaa  gacattactg  tggagtggca  gtggaatggg 1141  cagccagcgg  agaactacaa  gaacactcag  cccatcatgg  acacagatgg  ctcttacttc 1201  gtctacagca  agctcaatgt  gcagaagagc  aactgggagg  caggaaatac  tttcacctgc 1261  tctgtgttac  atgagggcct  gcacaaccac  catactgaga  agagcctctc  ccactctcct 1321  ggtaaa
```

Protein Sequence Defining the Full Length Heavy Chain Sequence (Heavy Chain Variable Region and IgG1 Constant Region) of 03G05 (SEQ ID NO:104)

```
  1  qvqlqqpgae  lvkpgasvkl  sckasgytft  sywihwvnqr  pgqglewigd  inpsngrsky 61  nekfknkatm  tadkssntay  mqlssltsed  savyycarev  ldgamdywgq  gtsvtvssak 121  ttppsvypla  pgsaaqtnsm  vtlgclvkgy  fpepvtvtwn  sgslssgvht  fpavlqsdly 181  tlsssvtvps  stwpsetvtc  nvahpasstk  vdkkivprdc  gckpcictvp  evssvfifpp 241  kpkdvltitl  tpkvtcvvvd  iskddpevqf  swfvddvevh  taqtqpreeq  fnstfrsvse 301  lpimhqdwln  gkefkcrvns  aafpapiekt  isktkgrpka  pqvytipppk  eqmakdkvsl 361  tcmitdffpe  ditvewqwng  qpaenykntq  pimdtdgsyf  vysklnvqks  nweagntftc 421  svlheglhnh  htekslshsp  gk
```

Nucleic Acid Sequence Encoding the Full Length Light Chain Sequence (Kappa Chain Variable Region and Constant Region) of 03G05 (SEQ ID NO:105)

```
  1  gacattgtgt  tgacccaatc  tccagcttct  ttggctgtgt  ctctagggca  gagggccacc 61  atctcctgca  gagccagcga  aagtgttgat  aattatggca  ttagtttat   gaactggttc 121  caacagaaac  caggacagcc  acccaaactc  ctcatctatg  ctgcatccaa  ccaaggctcc 181  ggggtccctg  ccaggtttag  tggcagtggg  tctgggacag  acttcagcct  caacatccat 241  cctatggagg  aggatgatac  tgcaatgtat  ttctgtcagc  aaagtaagga  ggttccgtgg 301  acgttcggtg  gaggctccaa  gctggaaatc  aaacgggctg  atgctgcacc  aactgtatcc 361  atcttcccac  catccagtga  gcagttaaca  tctggaggtg  cctcagtcgt  gtgcttcttg 421  aacaacttct  accccaaaga  catcaatgtc  aagtggaaga  ttgatggcag  tgaacgacaa 481  aatggcgtcc  tgaacagttg  gactgatcag  gacagcaaag  acagcaccta  cagcatgagc 541  agcaccctca  cgttgaccaa  ggacgagtat  gaacgacata  acagctatac  ctgtgaggcc 601  actcacaaga  catcaacttc  acccattgtc  aagagcttca  acaggaatga  gtgt
```

Protein Sequence Defining the Full Length Light Chain Sequence (Kappa Chain Variable Region and Constant Region) of 03G05 (SEQ ID NO:106)

```
  1  divltqspas  lavslgqrat  iscrasesvd  nygisfmnwf  qqkpgqppkl  liyaasnqgs 61  gvparfsgsg  sgtdfslnih  pmeeddtamy  fcqqskevpw  tfgggsklei  kradaaptvs 121  ifppsseqlt  sggasvvcfl  nnfypkdinv  kwkidgserq  ngvlnswtdq  dskdstysms 181  stltltkdey  erhnsytcea  thktstspiv  ksfnrnec
```

Nucleic Acid Sequence Encoding the Full Length Heavy
Chain Sequence (Heavy Chain Variable Region and IgG1
Constant Region) of 04F08 (SEQ ID NO:107)

```
   1    caggttactc tgaaagagtc tggccctggg atattgcagc cctcccagac cctcagtctg
  61    acttgttctt tctctgggtt ttcactgagc acttatggta tgggtgtgac ctggattcgt
 121    cagccttcag gaaagggtct ggagtggctg gcacacattt actgggatga tgacaagcgc
 181    tataacccat ccctgaagag ccggctcaca atctccaagg atacctccaa caaccaggta
 241    ttcctcaaga tcaccagtgt ggacactgca gatactgcca catactactg tgctcaaacg
 301    gggtatagta acttgtttgc ttactggggc caagggactc tggtcactgt ctctgcagcc
 361    aaaacgacac ccccatctgt ctatccactg gcccctggat ctgctgccca aactaactcc
 421    atggtgaccc tgggatgcct ggtcaagggc tatttccctg agccagtgac agtgacctgg
 481    aactctggat ccctgtccag cggtgtgcac accttccag ctgtcctgca gtctgacctc
 541    tacactctga gcagctcagt gactgtcccc tccagcacct ggcccagcga gaccgtcacc
 601    tgcaacgttg cccacccggc cagcagcacc aaggtggaca gaaaaattgt gcccagggat
 661    tgtggttgta agccttgcat atgtacagtc cagaagtat catctgtctt catcttcccc
 721    ccaaagccca aggatgtgct caccattact ctgactccta aggtcacgtg tgttgtggta
 781    gacatcagca aggatgatcc cgaggtccag ttcagctggt ttgtagatga tgtggaggtg
 841    cacacagctc agacgcaacc ccgggaggag cagttcaaca gcactttccg ctcagtcagt
 901    gaacttccca tcatgcacca ggactggctc aatggcaagg agttcaaatg cagggtcaac
 961    agtgcagctt ccctgcccc catcgagaaa accatctcca aaccaaagg cagaccgaag
1021    gctccacagg tgtacaccat tccacctccc aaggagcaga tggccaagga taaagtcagt
1081    ctgacctgca tgataacaga cttcttccct gaagacatta ctgtggagtg cagtggaat
1141    gggcagccag cggagaacta caagaacact cagcccatca tggacacaga tggctcttac
1201    ttcgtctaca gcaagctcaa tgtgcagaag agcaactggg aggcaggaaa tactttcacc
1261    tgctctgtgt tacatgaggg cctgcacaac caccatactg agaagagcct ctcccactct
1321    cctggtaaa
```

Protein Sequence Defining the Full Length Heavy Chain
Sequence (Heavy Chain Variable Region and IgG1 Constant
Region) of 04F08 (SEQ ID NO:108)

```
  1    qvtlkesgpg ilqpsqtlsl tcsfsgfsls tygmgvtwir qpsgkglewl ahiywdddkr
 61    ynpslksrlt iskdtsnnqv flkitsvdta dtatyycaqt gysnlfaywg qgtlvtvsaa
121    kttppsvypl apgsaaqtns mvtlgclvkg yfpepvtvtw nsgslssgvh tfpavlqsdl
181    ytlsssvtvp sstwpsetvt cnvahpasst kvdkkivprd cgckpcictv pevssvfifp
241    pkpkdvltit ltpkvtcvvv diskddpevq fswfvddvev htaqtqpree qfnstfrsvs
301    elpimhqdwl ngkefkcrvn saafpapiek tisktkgrpk apqvytippp keqmakdkvs
361    ltcmitdffp editvewqwn gqpaenyknt qpimdtdgsy fvysklnvqk snweagntft
421    csvlheglhn hhtekslshs pgk
```

Nucleic Acid Sequence Encoding the Full Length Light Chain Sequence (Kappa Chain Variable Region and Constant Region) of 04F08 (SEQ ID NO: 109)

```
  1  gacattgtga tgacccagtc tcaaaaattc atgtccacat cagtaggaga cagggtcagc
 61  gtcacctgca aggccagtca gaatgtgggt actaatgtag cctggtatca acagaaatta
121  ggacaatctc ctaaaacact gatttactcg gcatcctacc ggtacagtgg agtccctgat
181  cgcttcacag gcagtggatc tgggacagat ttcactctca ccatcagcaa tgtgcagtct
241  gaagacttgg cagagtattt ctgtcagcaa tataacagct atccgtacac gttcggaggg
301  gggaccaagc tggaaataaa acgggctgat gctgcaccaa ctgtatccat cttcccacca
361  tccagtgagc agttaacatc tggaggtgcc tcagtcgtgt gcttcttgaa caacttctac
421  cccaaagaca tcaatgtcaa gtggaagatt gatggcagtg aacgacaaaa tggcgtcctg
481  aacagttgga ctgatcagga cagcaaagac agcacctaca gcatgagcag caccctcacg
541  ttgaccaagg acgagtatga acgacataac agctatacct gtgaggccac tcacaagaca
601  tcaacttcac ccattgtcaa gagcttcaac aggaatgagt gt
```

Protein Sequence Defining the Full Length Light Chain Sequence (Kappa Chain Variable Region and Constant Region) of 04F08 (SEQ ID NO:110)

```
  1  divmtqsqkf mstsvgdrvs vtckasqnvg tnvawyqqkl gqspktliys asyrysgvpd
 61  rftgsgsgtd ftltisnvqs edlaeyfcqq ynsypytfgg gtkleikrad aaptvsifpp
121  sseqltsgga svvcflnnfy pkdinvkwki dgserqngvl nswtdqdskd stysmsstlt
181  ltkdeyerhn sytceathkt stspivksfn rnec
```

Nucleic Acid Sequence Encoding the Full Length Heavy Chain Sequence (Heavy Chain Variable Region and IgG1 Constant Region) of 06C11 (SEQ ID NO:111)

```
  1  caggttactc tgaaagagtc tggccctggg atattgcagc cctcccagac cctcagtctg
 61  acttgttctt tctctgggtt ttcactgaac acttatggta tgggtgtgag ctggattcgt
121  cagccttcag gaaagggtct ggagtggctg gcacacattt actgggatga tgacaagcgc
181  tataacccat ccctgaagag ccggctcaca atctccaagg atgcctccaa caaccgggtc
241  ttcctcaaga tcaccagtgt ggacactgca gatactgcca catactactg tgctcaaaga
301  ggttatgatg attactgggg ttactggggc caagggactc tggtcactgt ctctgcagcc
361  aaaacgacac ccccatctgt ctatccactg gcccctggat ctgctgccca aactaactcc
421  atggtgaccc tgggatgcct ggtcaagggc tatttccctg agccagtgac agtgacctgg
481  aactctggat ccctgtccag cggtgtgcac accttcccag ctgtcctgca gtctgacctc
541  tacactctga gcagctcagt gactgtcccc tccagcacct ggcccagcga gaccgtcacc
601  tgcaacgttg cccacccggc cagcagcacc aaggtggaca agaaaattgt gcccagggat
661  tgtggttgta agccttgcat atgtacagtc ccagaagtat catctgtctt catcttcccc
721  ccaaagccca aggatgtgct caccattact ctgactccta aggtcacgtg tgttgtggta
781  gacatcagca aggatgatcc cgaggtccag ttcagctggt ttgtagatga tgtggaggtg
841  cacacagctc agacgcaacc ccgggaggag cagttcaaca gcactttccg ctcagtcagt
901  gaacttccca tcatgcacca ggactggctc aatggcaagg agttcaaatg cagggtcaac
961  agtgcagctt tccctgcccc catcgagaaa accatctcca aaaccaaagg cagaccgaag
```

-continued

```
1021    gctccacagg tgtacaccat tccacctccc aaggagcaga tggccaagga taaagtcagt 1081    ctgacctgca tgataacaga cttcttccct gaagacatta ctgtggagtg gcagtggaat 1141    gggcagccag cggagaacta caagaacact cagcccatca tggacacaga tggctcttac 1201    ttcgtctaca gcaagctcaa tgtgcagaag agcaactggg aggcaggaaa tactttcacc 1261    tgctctgtgt tacatgaggg cctgcacaac caccatactg agaagagcct ctcccactct 1321    cctggtaaa
```

Protein Sequence Defining the Full Length Heavy Chain Sequence (Heavy Chain Variable Region and IgG1 Constant Region) of 06C11 (SEQ ID NO:112)

```
  1    qvtlkesgpg ilqpsqtlsl tcsfsgfsln tygmgvswir qpsgkglewl ahiywdddkr 61    ynpslksrlt iskdasnnrv flkitsvdta dtatyycaqr gyddywgywg qgtlvtisaa 121    kttppsvypl apgsaaqtns mvtlgclvkg yfpepvtvtw nsgslssgvh tfpavlqsdl 181    ytlsssvtvp sstwpsetvt cnvahpasst kvdkkivprd cgckpcictv pevssvfifp 241    pkpkdvltit ltpkvtcvvv diskddpevq fswfvddvev htaqtqpree qfnstfrsvs 301    elpimhqdwl ngkefkcrvn saafpapiek tisktkgrpk apqvytippp keqmakdkvs 361    ltcmitdffp editvewqwn gqpaenyknt qpimdtdgsy fvysklnvqk snweagntft 421    csvlheglhn hhtekslshs pgk
```

Nucleic Acid Sequence Encoding the Full Length Light Chain Sequence (Kappa Chain Variable Region and Constant Region) of 06C11 (SEQ ID NO:113)

```
  1    gacattgtga tgacccagtc tcaaaaattc atgtccacat cagtaggaga cagggtcagc 61    gtcacctgca aggccagtca aaatgtgggt actaatgtag cctggtttca acagaaacca 121    ggtcaatctc ctaaagcact gatttactcg gcatcttacc ggtacagtgg agtccctgat 181    cgcttcacag gcagtggatc tgggacagat ttcattctca ccatcagcaa tgtgcagtct 241    gaagacctgg cagagtattt ctgtcagcaa tataacaact atcctctcac gttcggtgct 301    gggaccaagc tggagctgaa acgggctgat gctgcaccaa ctgtatccat cttcccacca 361    tccagtgagc agttaacatc tggaggtgcc tcagtcgtgt gcttcttgaa caacttctac 421    cccaaagaca tcaatgtcaa gtggaagatt gatggcagtg aacgacaaaa tggcgtcctg 481    aacagttgga ctgatcagga cagcaaagac agcacctaca gcatgagcag caccctcacg 541    ttgaccaagg acgagtatga acgacataac agctatacct gtgaggccac tcacaagaca 601    tcaacttcac ccattgtcaa gagcttcaac aggaatgagt gt
```

Protein Sequence Defining the Full Length Light Chain Sequence (Kappa Chain Variable Region and Constant Region) of 06C11 (SEQ ID NO: 114)

```
  1    divmtqsqkf mstsvgdrvs vtckasqnvg tnvawfqqkp gqspkaliys asyrysgvpd 61    rftgsgsgtd filtisnvqs edlaeyfcqq ynnypltfga gtklelkrad aaptvsifpp 121    sseqltsgga svvcflnnfy pkdinvkwki dgserqngvl nswtdqdskd stysmsstlt 181    ltkdeyerhn sytceathkt stspivksfn rnec
```

Nucleic Acid Sequence Encoding the Full Length Heavy Chain Sequence (Heavy Chain Variable Region and IgG2b Constant Region) of 08G01 (SEQ ID NO:115)

```
   1  gaggtcctgc tgcaacagtc tggacctgag gtggtgaagc ctggggcttc agtgaagata
  61  ccctgcaagg cttctggata cacattcact gactacaaca tggactgggt gaagcagagc
 121  catggaaaga gccttgagtg gattggagag attaatccta acaatggtgg tactttctac
 181  aaccagaagt tcaagggcaa ggccacattg actgtagaca agtcctccag cacagcctac
 241  atggagctcc gcagcctgac atctgaggac actgcagtct attactgtgc aagagaggca
 301  attactacgg taggcgctat ggactactgg ggtcaaggaa cctcagtcac cgtctcctca
 361  gccaaaacaa cccccatc agtctatcca ctggcccctg ggtgtggaga tacaactggt
 421  tcctccgtga ctctgggatg cctggtcaag ggctacttcc ctgagtcagt gactgtgact
 481  tggaactctg gatccctgtc cagcagtgtg cacaccttcc cagctctcct gcagtctgga
 541  ctctacacta tgagcagctc agtgactgtc cctccagca cctggccaag tcagaccgtc
 601  acctgcagcg ttgctcaccc agccagcagc accacggtgg acaaaaaact gagcccagc
 661  gggcccattt caacaatcaa ccctgtcct ccatgcaagg agtgtcacaa atgcccagct
 721  cctaacctcg agggtggacc atccgtcttc atcttccctc caaatatcaa ggatgtactc
 781  atgatctccc tgacacccaa ggtcacgtgt gtggtggtgg atgtgagcga ggatgaccca
 841  gacgtccaga tcagctggtt tgtgaacaac gtggaagtac acacagctca gacacaaacc
 901  catagagagg attacaacag tactatccgg gtggtcagca ccctccccat ccagcaccag
 961  gactggatga gtggcaagga gttcaaatgc aaggtcaaca acaaagacct cccatcaccc
1021  atcgagagaa ccatctcaaa aattaaaggg ctagtcagag ctccacaagt atacatcttg
1081  ccgccaccag cagagcagtt gtccaggaaa gatgtcagtc tcacttgcct ggtcgtgggc
1141  ttcaaccctg gagacatcag tgtggagtgg accagcaatg gcatacaga ggagaactac
1201  aaggacaccg caccagtcct agactctgac ggttcttact tcatatatag caagctcaat
1261  atgaaaacaa gcaagtggga gaaaacagat tccttctcat gcaacgtgag cacgagggt
1321  ctgaaaaatt actacctgaa gaagaccatc tcccggtctc cgggtaaa
```

Protein Sequence Defining the Full Length Heavy Chain Sequence (Heavy Chain Variable Region and IgG2b Constant Region) of 08G01 (SEQ ID NO:116)

```
   1  evllqqsgpe vvkpgasvki pckasgytft dynmdwvkqs hgkslewige inpnnggtfy
  61  nqkfkgkatl tvdkssstay melrsltsed tavyycarea ittvgamdyw gqgtsvtvss
 121  akttppsvyp lapgcgdttg ssvtlgclvk gyfpesvtvt wnsgslsssv htfpallqsg
 181  lytmsssvtv psstwpsqtv tcsvahpass ttvdkkleps gpistinpcp pckechkcpa
 241  pnleggpsvf ifppnikdvl misltpkvtc vvvdvseddp dvqiswfvnn vevhtaqtqt
 301  hredynstir vvstlpiqhq dwmsgkefkc kvnnkdlpsp iertiskikg lvrapqvyil
 361  pppaeqlsrk dvsltclvvg fnpgdisvew tsnghteeny kdtapvldsd gsyfiyskln
 421  mktskwektd sfscnvrheg lknyylkkti srspgk
```

Nucleic Acid Sequence Encoding the Full Length Light Chain Sequence (Kappa Chain Variable Region and Constant Region) of 08G01 (SEQ ID NO:117)

```
  1  gacatccaga tgactcagtc tccagcctcc ctatctgcat ctgtgggaga aactgtcacc
 61  atcacatgtc gagcaagtgg gaatattcac aattatttag catggtatca gcagaaacag
121  ggaaaatctc ctcagctcct ggtctataat gcaaaaacct tagcagatgg tgtgccatca
181  aggttcagtg gcagtggatc aggaacacaa tattctctca agatcaacag cctgcagcct
241  gaagattttg ggagttatta ctgtcaacat ttttggagtt ctccttacac gttcggaggg
301  gggaccaagc tggaaataaa acgggctgat gctgcaccaa ctgtatccat cttcccacca
361  tccagtgagc agttaacatc tggaggtgcc tcagtcgtgt gcttcttgaa caacttctac
421  cccaaagaca tcaatgtcaa gtggaagatt gatggcagtg aacgacaaaa tggcgtcctg
481  aacagttgga ctgatcagga cagcaaagac agcacctaca gcatgagcag caccctcacg
541  ttgaccaagg acgagtatga acgacataac agctatacct gtgaggccac tcacaagaca
601  tcaacttcac ccattgtcaa gagcttcaac aggaatgagt gt
```

Protein Sequence Defining the Full Length Light Chain Sequence (Kappa Chain Variable Region and Constant Region) of 08G01 (SEQ ID NO:118)

```
  1  diqmtqspas lsasvgetvt itcrasgnih nylawyqqkq gkspqllvyn aktladgvps
 61  rfsgsgsgtq yslkinslqp edfgsyycqh fwsspytfgg gtkleikrad aaptvsifpp
121  sseqltsgga svvcflnnfy pkdinvkwki dgserqngvl nswtdqdskd stysmsstlt
181  ltkdeyerhn sytceathkt stspivksfn rnec
```

Nucleic Acid Sequence Encoding the Full Length Heavy Chain Sequence (Heavy Chain Variable Region and IgG1 Constant Region) of 14F11 (SEQ ID NO:119)

```
  1  caggttactc tgaaagagtc tggccctgga atattgcagc cctcccagac cctcagtctg
 61  acttgttctt tctctgggtt ttcactgagc acttatggta tgggtgtagg ctggattcgt
121  cagccttcag gaaagggtct agagtggctg cagacatttg gtgggatga cgataagtac
181  tataacccat ccctgaagag ccggctcaca atctccaagg atacctccag caatgaggta
241  ttcctcaaga tcgccattgt ggacactgca gatactgcca cttactactg tgctcgaaga
301  ggtcactact ctgctatgga ctactggggt caaggaacct cagtcaccgt ctcctcagcc
361  aaaacgacac cccatctgt ctatccactg cccctggat ctgctgccca aactaactcc
421  atggtgaccc tgggatgcct ggtcaagggc tatttccctg agccagtgac agtgacctgg
481  aactctggat ccctgtccag cggtgtgcac accttcccag ctgtcctgca gtctgacctc
541  tacactctga gcagctcagt gactgtcccc tccagcacct ggcccagcga gaccgtcacc
601  tgcaacgttg cccacccggc cagcagcacc aaggtggaca agaaaattgt gcccaggat
661  tgtggttgta agccttgcat atgtacagtc ccagaagtat catctgtctt catcttcccc
721  ccaaagccca aggatgtgct caccattact ctgactccta aggtcacgtg tgttgtggta
781  gacatcagca aggatgatcc cgaggtccag ttcagctggt ttgtagatga tgtggaggtg
841  cacacagctc agacgcaacc ccgggaggag cagttcaaca gcactttccg ctcagtcagt
901  gaacttccca tcatgcacca ggactggctc aatggcaagg agttcaaatg cagggtcaac
961  agtgcagctt ccctgcccc catcgagaaa accatctcca aaaccaaagg cagaccgaag
```

-continued

```
1021    gctccacagg tgtacaccat tccacctccc aaggagcaga tggccaagga taaagtcagt 1081    ctgacctgca tgataacaga cttcttccct gaagacatta ctgtggagtg gcagtggaat 1141    gggcagccag cggagaacta caagaacact cagcccatca tggacacaga tggctcttac 1201    ttcgtctaca gcaagctcaa tgtgcagaag agcaactggg aggcaggaaa tactttcacc 1261    tgctctgtgt tacatgaggg cctgcacaac caccatactg agaagagcct ctcccactct 1321    cctaataaa
```

Protein Sequence Defining the Full Length Heavy Chain Sequence (Heavy Chain Variable Region and IgG1 Constant Region) of 14F11 (SEQ ID NO:120)

```
  1   qvtlkesgpg ilqpsqtlsl tcsfsgfsls tygmgvgwir qpsgkglewl adiwwdddky 61   ynpslksrlt iskdtssnev flkiaivdta dtatyycarr ghysamdywg qgtsvtvssa 121   kttppsvypl apgsaaqtns mvtlgclvkg yfpepvtvtw nsgslssgvh tfpavlqsdl 181   ytlsssvtvp sstwpsetvt cnvahpasst kvdkkivprd cgckpcictv pevssvfifp 241   pkpkdvltit ltpkvtcvvv diskddpevq fswfvddvev htaqtqpree qfnstfrsvs 301   elpimhqdwl ngkefkcrvn saafpapiek tisktkgrpk apqvytippp keqmakdkvs 361   ltcmitdffp editvewqwn gqpaenyknt qpimdtdgsy fvysklnvqk snweagntft 421   csvlheglhn hhtekslshs pgk
```

Nucleic Acid Sequence Encoding the Full Length Light Chain Sequence (Kappa Chain Variable Region and Constant Region) of 14F11 (SEQ ID NO: 121)

```
  1     gacattgtaa tgacccagtc tcaaaaattc atgtccacat cagtaggaga cagggtcagc 61     gtcacctgca aggccagtca gaatgtgggt actaatgtag cctggtatca acagaaacca 121     gggcaatctc ctaaagcact gatttactcg ccatcctacc ggtacagtgg agtccctgat 181     cgcttcacag gcagtggatc tgggacagat ttcactctca ccatcagcaa tgtgcagtct 241     gaagacttgg cagaatattt ctgtcagcaa tataacagct atcctcacac gttcggaggg 301     gggaccaagc tggaaatgaa acgggctgat gctgcaccaa ctgtatccat cttcccacca 361     tccagtgagc agttaacatc tggaggtgcc tcagtcgtgt gcttcttgaa caacttctac 421     cccaaagaca tcaatgtcaa gtggaagatt gatggcagtg aacgacaaaa tggcgtcctg 481     aacagttgga ctgatcagga cagcaaagac agcacctaca gcatgagcag caccctcacg 541     ttgaccaagg acgagtatga acgacataac agctatacct gtgaggccac tcacaagaca 601     tcaacttcac ccattgtcaa gagcttcaac aggaatgagt gt
```

Protein Sequence Defining the Full Length Light Chain Sequence (Kappa Chain Variable Region and Constant Region) of 14F11 (SEQ ID NO:122)

```
  1    divmtqsqkf mstsvgdrvs vtckasqnvg tnvawyqqkp gqspkaliys psyrysgvpd 61    rftgsgsgtd ftltisnvqs edlaeyfcqq ynsyphtfgg gtklemkrad aaptvsifpp 121    sseqltsgga svvcflnnfy pkdinvkwki dgserqngvl nswtdqdskd stysmsstlt 181    ltkdeyerhn sytceathkt stspivksfn rnec
```

Nucleic Acid Sequence Encoding the Full Length Heavy Chain Sequence (Heavy Chain Variable Region and IgG1 Constant Region) of 17B11 (SEQ ID NO:123)

```
   1   caggttactc tgaaagagtc tggccctggg atattgcagc cctcccagac cctcagtctg
  61   acttgttctt tctctgggtt tcactgagc  acttctggta tgggtgtgag ttggattcgt
 121   cagccttcag gaaagggtct ggagtggctg gcacacaatg actgggatga tgacaagcgc
 181   tataagtcat ccctgaagag ccggctcaca atatccaagg atacctccag aaaccaggta
 241   ttcctcaaga tcaccagtgt ggacactgca gatactgcca catactactg tgctcgaaga
 301   gttgggggat tagagggcta ttttgattac tggggccaag gcaccactct cacagtctcc
 361   tcagccaaaa cgacaccccc atctgtctat ccactggccc ctggatctgc tgcccaaact
 421   aactccatgg tgaccctggg atgcctggtc aagggctatt tccctgagcc agtgacagtg
 481   acctggaact ctggatccct gtccagcggt gtgcacacct cccagctgt  cctgcagtct
 541   gacctctaca ctctgagcag ctcagtgact gtcccctcca gcacctggcc cagcgagacc
 601   gtcacctgca acgttgccca cccggccagc agcaccaagg tggacaagaa aattgtgccc
 661   agggattgtg gttgtaagcc ttgcatatgt acagtcccag aagtatcatc tgtcttcatc
 721   ttccccccaa agcccaagga tgtgctcacc attactctga ctcctaaggt cacgtgtgtt
 781   gtggtagaca tcagcaagga tgatcccgag gtccagttca gctggtttgt agatgatgtg
 841   gaggtgcaca cagctcagac gcaacccgg  gaggagcagt tcaacagcac tttccgctca
 901   gtcagtgaac ttcccatcat gcaccaggac tggctcaatg caaggagtt  caaatgcagg
 961   gtcaacagtg cagctttccc tgccccatc  gagaaaacca ctccaaaac  caaaggcaga
1021   ccgaaggctc cacaggtgta caccattcca cctcccaagg agcagatggc caaggataaa
1081   gtcagtctga cctgcatgat aacagacttc ttccctgaag acattactgt ggagtggcag
1141   tggaatgggc agccagcgga gaactacaag aacactcagc ccatcatgga cacagatggc
1201   tcttacttcg tctacagcaa gctcaatgtg cagaagagca ctgggaggc  aggaaatact
1261   ttcacctgct ctgtgttaca tgagggcctg cacaaccacc atactgagaa gagcctctcc
1321   cactctcctg gtaaa
```

Protein Sequence Defining the Full Length Heavy Chain Sequence (Heavy Chain Variable Region and IgG1 Constant Region) of 17B11 (SEQ ID NO:124)

```
  1   qvtlkesgpg ilqpsqtlsl tcsfsgfsls tsgmgvswir qpsgkglewl ahndwdddkr
 61   yksslksrlt iskdtsrnqv flkitsvdta dtatyycarr vgglegyfdy wgqgttltvs
121   sakttppsvy plapgsaaqt nsmvtlgclv kgyfpepvtv twnsgslssg vhtfpavlqs
181   dlytlsssvt vpsstwpset vtcnvahpas stkvdkkivp rdcgckpcic tvpevssvfi
241   fppkpkdvlt itltpkvtcv vvdiskddpe vqfswfvddv evhtaqtqpr eeqfnstfrs
301   vselpimhqd wlngkefkcr vnsaafpapi ektisktkgr pkapqvytip ppkeqmakdk
361   vsltcmitdf fpeditvewq wngqpaenyk ntqpimdtdg syfvysklnv qksnweagnt
421   ftcsvlhegl hnhhteksls hspgk
```

Nucleic Acid Sequence Encoding the Full Length Light Chain Sequence (Kappa Chain Variable Region and Constant Region) of 17B11 (SEQ ID NO:125)

```
  1  gacattgtgc tgacacagtc tcctgcttcc ttagctgtat ctctggggca gagggccacc
 61  atctcatgca gggccagcca aagtgtcagt acatctaggt ttagttatat gcactggttc
121  caacagaaac caggacaggc acccaaactc ctcatcaagt atgcatccaa cctagaatct
181  ggggtccctg ccaggttcag tggcagtggg tctgggacag acttcaccct caacatccat
241  cctgtggagg gggaggatac tgcaacatat tactgtcagc acagttggga gattccgtac
301  acgttcggag ggggaccaa gctggaaata aaacgggctg atgctgcacc aactgtatcc
361  atcttcccac catccagtga gcagttaaca tctggaggtg cctcagtcgt gtgcttcttg
421  aacaacttct accccaaaga catcaatgtc aagtggaaga ttgatggcag tgaacgacaa
481  aatggcgtcc tgaacagttg gactgatcag gacagcaaag acagcaccta cagcatgagc
541  agcaccctca cgttgaccaa ggacgagtat gaacgacata cagctatac ctgtgaggcc
601  actcacaaga tcaacttc acccattgtc aagagcttca acaggaatga gtgt
```

Protein Sequence Defining the Full Length Light Chain Sequence (Kappa Chain Variable Region and Constant Region) of 17B11 (SEQ ID NO: 126)

```
  1  divltqspas lavslgqrat iscrasqsvs tsrfsymhwf qqkpgqapkl likyasnles
 61  gvparfsgsg sgtdftlnih pvegedtaty ycqhsweipy tfgggtklei kradaaptvs
121  ifppsseqlt sggasvvcfl nnfypkdinv kwkidgserq ngvlnswtdq dskdstysms
181  stltltkdey erhnsytcea thktstspiv ksfnrnec
```

Table 5 shows the correspondence between the full-length sequences of the antibodies discussed in this Example with those presented in the Sequence Listing.

TABLE 5

| SEQ ID NO. | Nucleic Acid or Protein |
|---|---|
| 99 | 01G06_Heavy Variable + IgG1 Constant - nucleic acid |
| 100 | 01G06_Heavy Variable + IgG1 Constant - protein |
| 101 | 01G06_Kappa Variable + Constant - nucleic acid |
| 102 | 01G06_Kappa Variable + Constant - protein |
| 103 | 03G05 Heavy Variable + IgG1 Constant - nucleic acid |
| 104 | 03G05 Heavy Variable + IgG1 Constant - protein |
| 105 | 03G05 Kappa Variable + Constant - nucleic acid |
| 106 | 03G05 Kappa Variable + Constant - protein |
| 107 | 04F08 Heavy Variable + IgG1 Constant - nucleic acid |
| 108 | 04F08 Heavy Variable + IgG1 Constant - protein |
| 109 | 04F08 Kappa Variable + Constant - nucleic acid |
| 110 | 04F08 Kappa Variable + Constant - protein |
| 111 | 06C11 Heavy Variable + IgG1 Constant - nucleic acid |
| 112 | 06C11 Heavy Variable + IgG1 Constant - protein |
| 113 | 06C11 Kappa Variable + Constant - nucleic acid |
| 114 | 06C11 Kappa Variable + Constant - protein |
| 115 | 08G01 Heavy Variable + IgG2b Constant - nucleic acid |
| 116 | 08G01 Heavy Variable + IgG2b Constant - protein |
| 117 | 08G01 Kappa Variable + Constant - nucleic acid |
| 118 | 08G01 Kappa Variable + Constant - protein |
| 119 | 14F11 Heavy Variable + IgG1 Constant - nucleic acid |
| 120 | 14F11 Heavy Variable + IgG1 Constant - protein |
| 121 | 14F11 Kappa Variable + Constant - nucleic acid |
| 122 | 14F11 Kappa Variable + Constant - protein |
| 123 | 17B11 Heavy Variable + IgG1 Constant - nucleic acid |
| 124 | 17B11 Heavy Variable + IgG1 Constant - protein |
| 125 | 17B11 Kappa Variable + Constant - nucleic acid |
| 126 | 17B11 Kappa Variable + Constant - protein |

Example 8: Binding Affinities

The binding affinities and kinetics of binding of antibodies to 6×His tagged (SEQ ID NO: 266) recombinant human GDF15 (His-rhGDF15 (R&D Systems, Inc.)), untagged recombinant human GDF15 (rhGDF15 (Peprotech, Rocky Hill, NJ), and recombinant human GDF15 produced as either mouse Fc fused to human GDF15 (mFc-rhGDF15) or a version in which the Fc was enzymatically removed (cleaved-rhGDF15) were measured by surface plasmon resonance, using a Biacore® T100 instrument (GE Healthcare, Piscataway, NJ).

Rabbit anti-mouse IgGs (GE Healthcare) were immobilized on carboxymethylated dextran CM4 sensor chips (GE Healthcare) by amine coupling, according to a standard protocol. Analyses were performed at 37° C. using PBS containing 0.05% surfactant P20 as running buffer. The antibodies were captured in individual flow cells at a flow rate of 10 µL/minute. Injection time was varied for each antibody to yield an Rmax between 30 and 60 RU. 250 µg/mL mouse Fc (Jackson ImmunoResearch, West Grove, PA) was injected at 30 µL/minute for 120 seconds to block non-specific binding of capture antibodies to mouse Fc portion of the recombinant GDF15 protein when needed. Buffer, mFc-rhGDF15, cleaved-rhGDF15, His-rhGDF15, or rhGDF15 diluted in running buffer was injected sequentially over a reference surface (no antibody captured) and the active surface (antibody to be tested) for 240 seconds at 60 µL/minute. The dissociation phase was monitored for up to 1500 seconds. The surface was then regenerated with two 60-second injections of 10 mM Glycine-HCl, pH 1.7, at a flow rate of 30 μL/minute. The GDF15 concentration range tested was 30 nM to 0.625 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined. Kinetic values of the monoclonal antibodies on mFc-rhGDF15, cleaved rhGDF15, His-rhGDF15, or rhGDF15 are summarized in Tables 6, 7, 8, and 9, respectively.

TABLE 6

Antibody Binding to mFc-rhGDF15

| Antibody | $k_a$ (1/Ms) | $k_d$ (1/s) | $K_D$ (M) | n |
|---|---|---|---|---|
| 01G06 | 5.6E+06 | 7.0E−04 | 2.1E−10 | 7 |
| 03G05 | 1.0E+07 | 6.4E−04 | 6.9E−11 | 3 |
| 04F08 | 3.6E+06 | 6.4E−04 | 1.9E−10 | 3 |
| 06C11 | 4.5E+06 | 6.8E−04 | 1.7E−10 | 5 |
| 08G01 | 6.0E+06 | 1.1E−03 | 1.9E−10 | 4 |
| 14F11 | 1.7E+06 | 3.3E−04 | 2.2E−10 | 4 |
| 17B11 | 3.7E+06 | 5.1E−04 | 1.4E−10 | 3 |

The data in Table 6 demonstrate that antibodies bind mFc-rhGDF15 with a $K_D$ of about 250 pM or less, 200 pM or less, 150 pM or less, 100 pM or less, 75 pM or less, or 50 pM or less.

Kinetic values of the monoclonal antibodies on cleaved-rhGDF15 are summarized in Table 7.

TABLE 7

Antibody Binding to Cleaved-rhGDF15

| Antibody | $k_a$ (1/Ms) | $k_d$ (1/s) | $K_D$ (M) | n |
|---|---|---|---|---|
| 01G06 | 7.5E+06 | 8.6E−04 | 1.1E−10 | 1 |
| 06C11 | 1.2E+07 | 2.0E−03 | 1.7E−10 | 2 |
| 14F11 | 5.7E+06 | 6.0E−04 | 1.1E−10 | 1 |

The data in Table 7 demonstrate that antibodies 01G06, 06C11 and 14F11 bind cleaved-rhGDF15 with a $K_D$ of about 200 pM or less, 150 pM or less, or 100 pM or less.

Kinetic values of the monoclonal antibodies on His-rhGDF15 are summarized in Table 8.

TABLE 8

Antibody Binding to His-rhGDF15

| Antibody | $k_a$ (1/Ms) | $k_d$ (1/s) | $K_D$ (M) | n |
|---|---|---|---|---|
| 01G06 | 1.4E+07 | 1.1E−03 | 8.1E−11 | 2 |
| 06C11 | 2.9E+07 | 1.5E−03 | 5.1E−11 | 2 |
| 14F11 | 4.4E+06 | 4.2E−04 | 9.6E−11 | 1 |

The data in Table 8 demonstrate that antibodies 01G06, 06C11 and 14F11 bind His-rhGDF15 with a $K_D$ of about 150 pM or less, 100 pM or less, 75 pM or less, or 50 pM or less.

Kinetic values of the monoclonal antibodies on rhGDF15 are summarized in Table 9.

TABLE 9

Antibody Binding to rhGDF15

| Antibody | $k_a$ (1/Ms) | $k_d$ (1/s) | $K_D$ (M) | n |
|---|---|---|---|---|
| 01G06 | 2.1E+07 | 1.9E−03 | 9.3E−11 | 1 |
| 06C11 | 2.2E+07 | 4.6E−03 | 2.1E−10 | 1 |
| 14F11 | 3.1E+07 | 2.2E−03 | 7.1E−11 | 1 |

The data in Table 9 demonstrate that antibodies 01G06, 06C11 and 14F11 bind rhGDF15 with a $K_D$ of about 250 pM or less, 200 pM or less, 150 pM or less, 100 pM or less, 75 pM or less, or 50 pM or less.

Example 9: Reversal of Cachexia in an mFc-rhGDF15-Induced Model

This Example demonstrates the reversal of cachexia (as indicated by body weight loss) by antibody 01G06, 03G05, 04F08, 06C11, 14F11, or 17B11 in an mFc-rhGDF15-induced cachexia model. mFc-rhGDF15 (2 μg/g) was administered subcutaneously into the flank of 8-week old female ICR-SCID mice. Body weight was measured daily. When body weight reached 93%, the mice were randomized into seven groups of ten mice each. Each group received one of the following treatments: murine IgG control, 01G06, 03G05, 04F08, 06C11, 14F11, or 17B11 at 10 mg/kg. Treatment was administered once by intra-peritoneal injection. Treatment with antibody 01G06, 03G05, 04F08, 06C11, 14F11, or 17B11 resulted in body weight increase relative to initial weight or about 100% (p<0.001) (FIG. 14 and Table 10).

TABLE 10

| Gr. | Treatment Agent | mg/kg | % Body Weight | ANOVA Analysis (compared to mIgG) |
|---|---|---|---|---|
| 1 | mIgG | 10 | 77.1 | NA |
| 2 | 01G06 | 10 | 94.1 | p < 0.001 |
| 3 | 03G05 | 10 | 95.1 | p < 0.001 |
| 4 | 04F08 | 10 | 95.8 | p < 0.001 |
| 5 | 06C11 | 10 | 93.8 | p < 0.001 |
| 7 | 14F11 | 10 | 95.4 | p < 0.001 |
| 8 | 17B11 | 10 | 92.8 | p < 0.001 |

Figure 14:
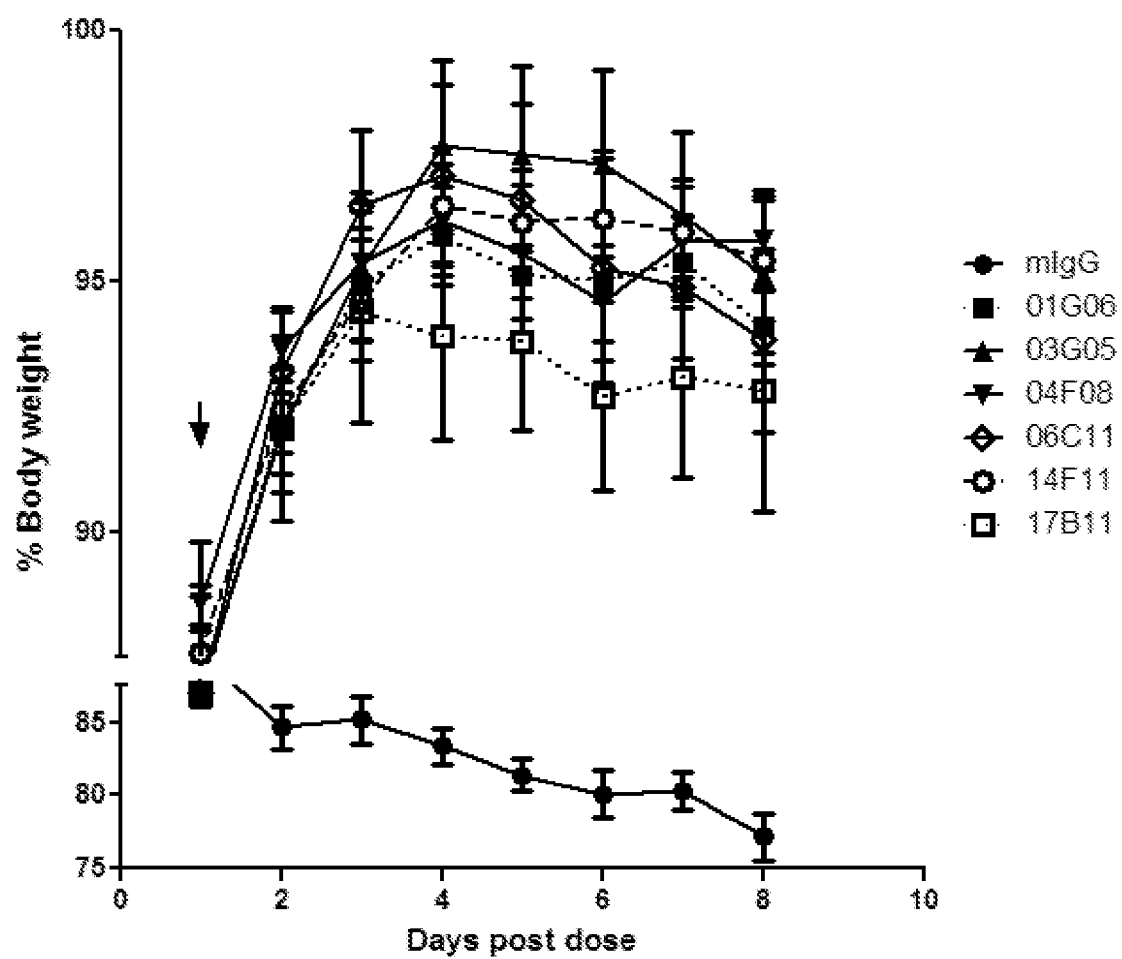
FIG. 14 is a graph summarizing results from an experiment to measure cachectic inhibitory activity of anti-GDF15 antibodies 01G06 (■), 03G05 (▲), 04F08 (▼), 06C11 (◇), 14F11 (¤), and 17B11 (□), and a murine IgG control (●; mIgG) dosed at 10 mg/kg in an mFc-rhGDF15 cachectic model in ICR-SCID mice. The arrow indicates intra-peritoneal injection of antibody.

The data in FIG. 14 and Table 10 indicate that the disclosed anti-GDF15 antibodies can reverse cachexia in an mFc-rhGDF15-induced mouse model (i.e., a non-tumor bearing mouse model).

Example 10: Reversal of Cachexia in an HT-1080 Xenograft Tumor Model

This Example demonstrates the reversal of cachexia (as indicated by body weight loss) by antibody 01G06, 03G05, 04F08, 06C11, 08G01, 14F11 or 17B11 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5 \times 10^6$ cells per mouse in 50% matrigel. Body weight was measured daily. When body weight reached 93%, the mice were randomized into eight groups of ten mice each. Each group received one of the following treatments: murine IgG control, 01G06, 03G05, 04F08, 06C11, 08G01, 14F11 or 17B11 at 10 mg/kg. Treatment was administered every three days by intra-peritoneal injection. Treatment with antibody 01G06, 03G05, 04F08, 06C11, 08G01, 14F11 or 17B11 resulted in body weight increase relative to initial weight or about 100% (p<0.001) (FIG. 15 and Table 11).

TABLE 11

| GR. | TREATMENT AGENT | MG/KG | % BODY WEIGHT | ANOVA ANALYSIS (COMPARED TO MIGG) |
|---|---|---|---|---|
| 1 | MIGG | 10 | 81.4 | NA |
| 2 | 01G06 | 10 | 103.3 | P < 0.001 |
| 3 | 03G05 | 10 | 106.1 | p < 0.001 |
| 4 | 04F08 | 10 | 104.3 | p < 0.001 |
| 5 | 06C11 | 10 | 106.6 | p < 0.001 |
| 6 | 08G01 | 10 | 105.3 | p < 0.001 |
| 7 | 14F11 | 10 | 99.6 | p < 0.001 |
| 8 | 17B11 | 10 | 103.7 | p < 0.001 |

Figure 15:
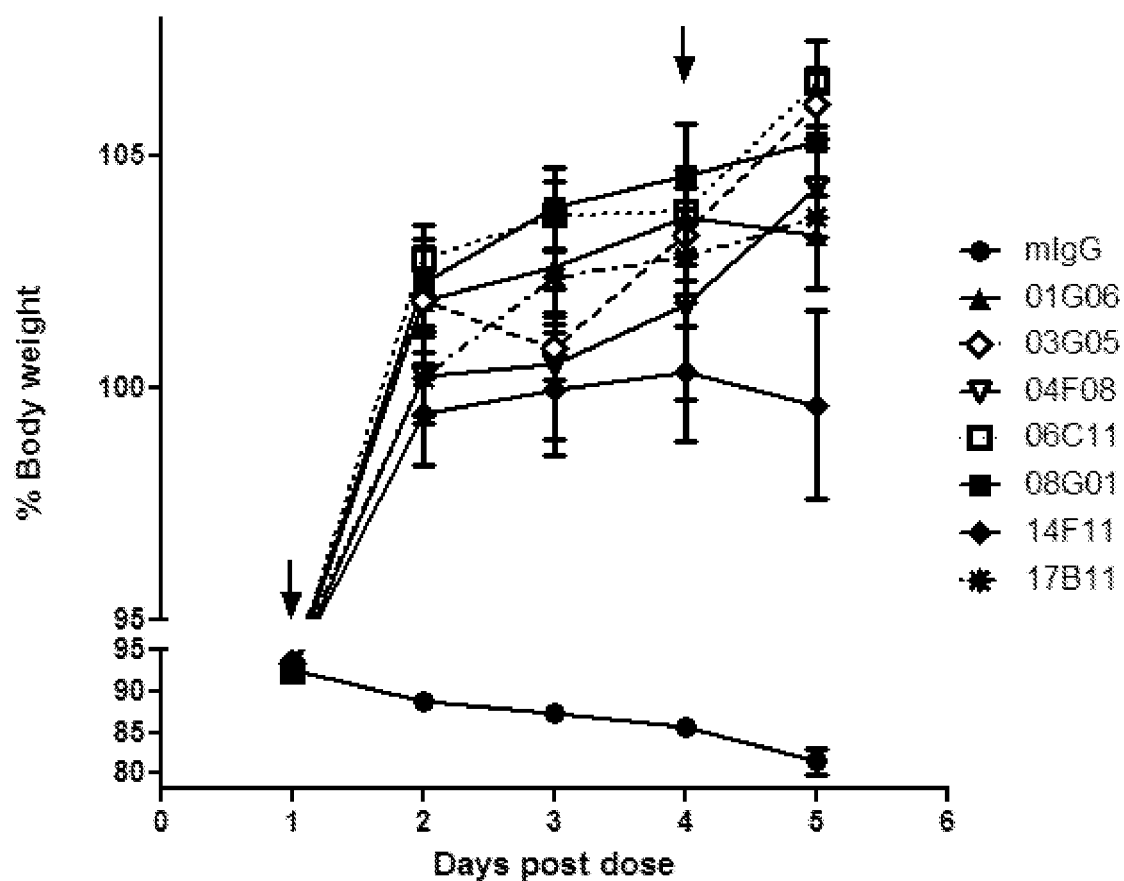
FIG. 15 is a graph summarizing results from an experiment to measure cachectic inhibitory activity of anti-GDF15 antibodies 01G06 (▲), 03G05 (◇), 04F08 (▽), 06C11(□), 08G01 (■), 14F11 (♦), and 17B11 (*), and a murine IgG control (●; mIgG), dosed at 10 mg/kg in an HT-1080 fibrosarcoma tumor xenograft model in ICR-SCID mice. The arrows indicate intra-peritoneal injection of antibody every three days.

The data in FIG. 15 and Table 11 indicate that the disclosed anti-GDF15 anti bodies can reverse cachexia in an HT-1080 fibrosarcoma xenograft model.

Figure 16A:
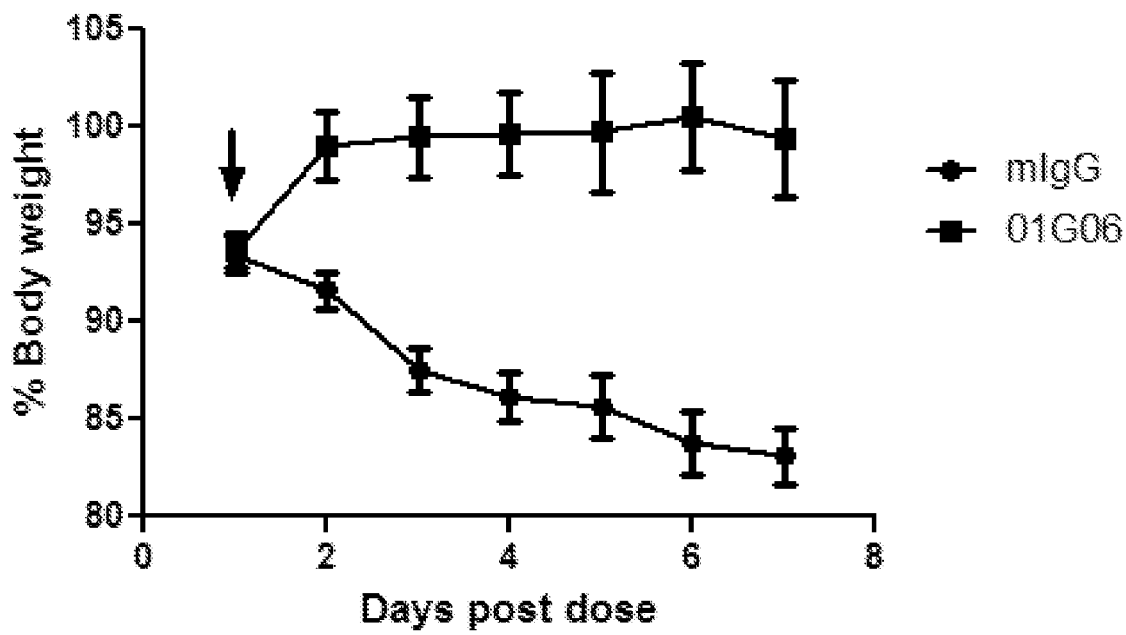
FIGS. 16A-16E are graphs summarizing results from an experiment to demonstrate anti-cachectic activity of anti-GDF15 antibody 01G06 (■), dosed at 10 mg/kg, in immune-incompetent mice (ICR-SCID) bearing an HT-1080 fibrosarcoma tumor xenograft model. Treatment with antibody 01G06 reversed body weight loss (FIG. 16A); induced a significant increase in food consumption for up to three days post dose (FIG. 16B); induced a gain of gonadal fat mass (FIG. 16C); induced a gain of muscle mass of gastrocnemius muscle (FIG. 16D); and decreased mRNA expression of muscle degradation molecular markers (mMuRF1 and mAtrogin (FIG. 16E)) compared to negative control (murine IgG (●)).

Additional studies were conducted with antibody 01G06 to demonstrate the reversal of cachexia in this mouse model. HT-1080 cells were grown and inoculated subcutaneously into the flank of 8-week old female ICR SCID mice as described above. When body weight reached 93%, the mice were randomized into two groups of ten mice each. Each group received one of the following treatments: murine IgG control or 01G06 at 10 mg/kg. Treatment was administered once by intra-peritoneal injection. As shown in FIG. 16A, treatment with antibody 01G06 resulted in body weight increase to initial weight or 100% (p<0.001) (FIG. 16A).

Figure 16B:
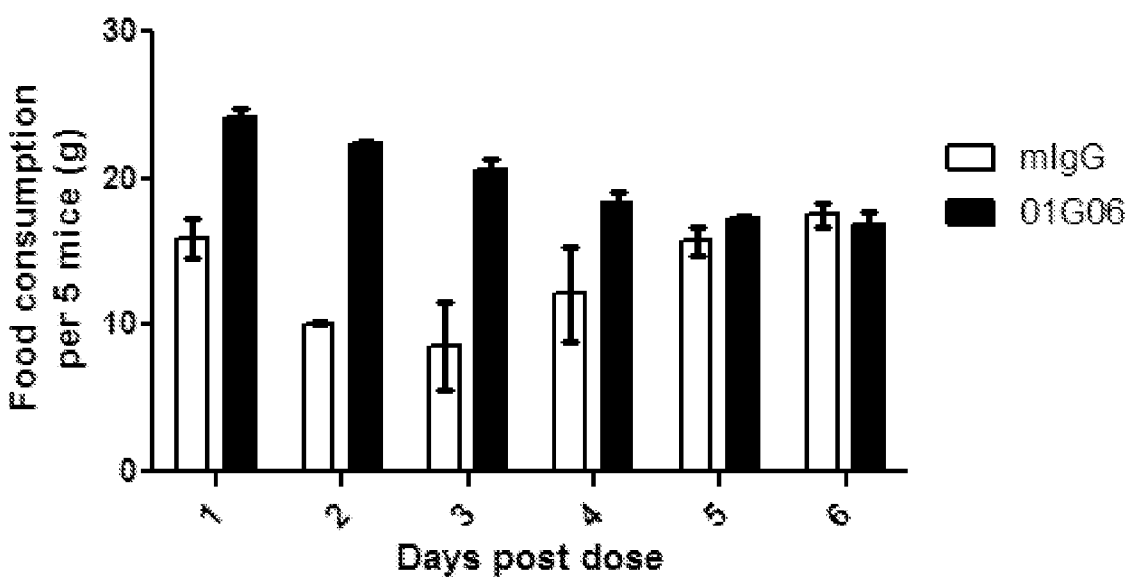

Food consumption was determined by weighing the food supply given to the mice daily (FIG. 16B). A significant increase in food consumption was observed in the 01G06 treated group for the first three days post treatment. After that time, no significant change was observed compared to the control group (mIgG).

Water consumption was determined by weighing the water supply given to the mice daily. No significant change in water consumption was observed between groups.

In this experiment, a group of ten mice were sacrificed at the time of the dose (baseline or 93% body weight, without treatment) and at the end of study (seven days post dose, either mIgG or 01G06). Gonadal fat and the gastrocnemius muscles were removed surgically and weighed as described above in Example 4 and tissues were snap frozen in liquid nitrogen. RNA was isolated from the gastrocnemius muscle samples to determine the levels of mMuRF1 and mAtrogin mRNA by RT-PCR, as described in Example 4.

Figure 16C:
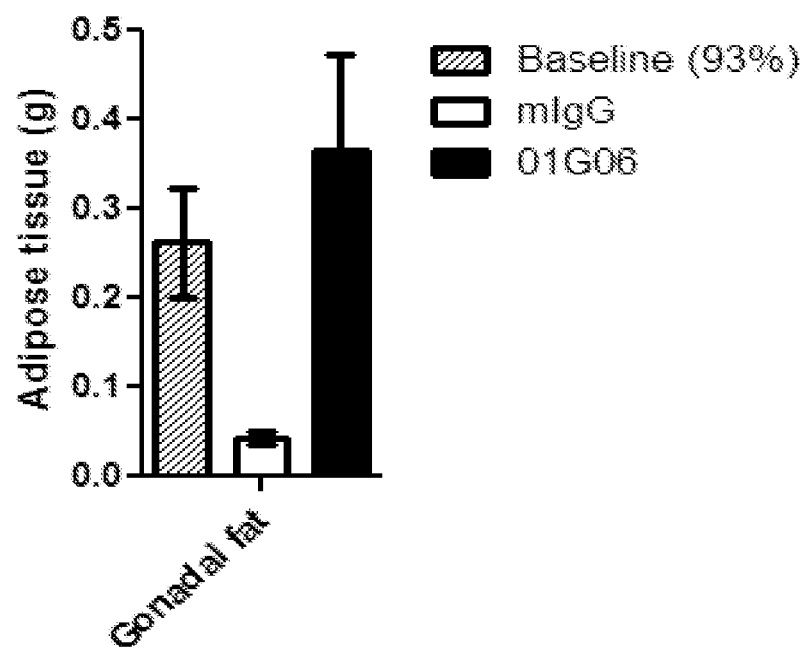
Figure 16D:
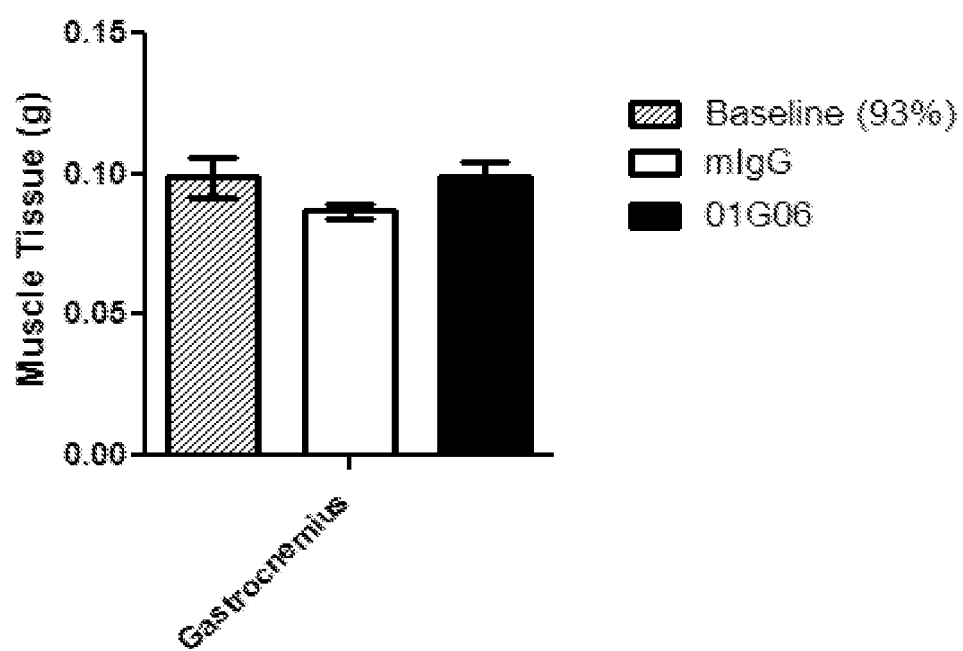
Figure 16E:
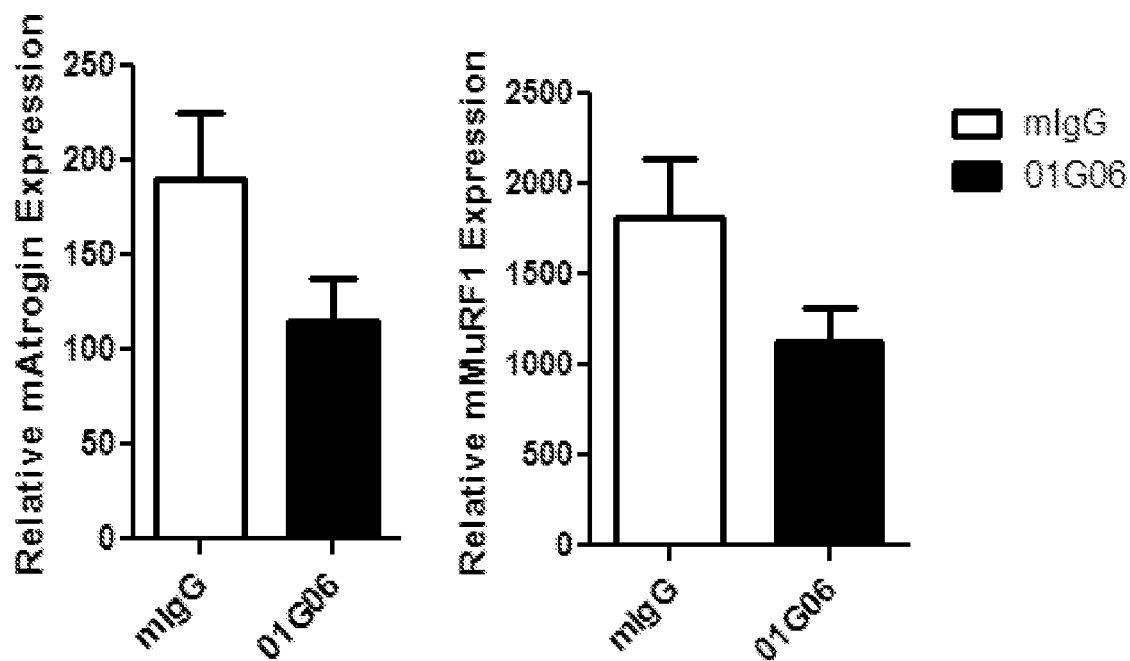

As shown in FIG. 16C, a significant reduction in gonadal fat mass was observed seven days post dose with mIgG, but not in the group treated with antibody 01G06. In addition, mice treated with mIgG displayed significant gastrocnemius muscle loss compared to the baseline group, while the group of mice treated with antibody 01G06 did not (FIG. 16D). Further, the levels of muscular degradation markers, mMuRF1 and mAtrogin, were significantly higher in the mIgG group compared to the 01G06 group (FIG. 16E).

These results indicate that the disclosed anti-GDF15 antibodies can reverse cachexia measured by the loss of muscle mass, the loss of fat and involuntary weight loss in an HT-1080 xenograft tumor model.

Example 11: Reversal of Cachexia in an HT-1080 Xenograft Tumor Model

This Example demonstrates the reversal of cachexia (as indicated by body weight loss) by antibody 01G06 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5 \times 10^6$ cells per mouse in 50% matrigel. Body weight was measured daily. When body weight reached 80%, the mice were randomized into two groups of five mice each. Each group received one of the following treatments: murine IgG control, 01G06 dosed at 2 mg/kg on day 1 and day 7. Treatment was administered by intra-peritoneal injection. Treatment with antibody 01G06 resulted in body weight increase relative to initial weight or about 100% (p<0.001) (FIG. 17A and Table 12).

TABLE 12

| Gr. | Treatment Agent | mg/kg | % Body Weight | ANOVA Analysis (compared to mIgG) |
|---|---|---|---|---|
| 1 | mIgG | 2 | 66.4 | NA |
| 2 | 01G06 | 2 | 97.16 | p < 0.001 |

Figure 17A:
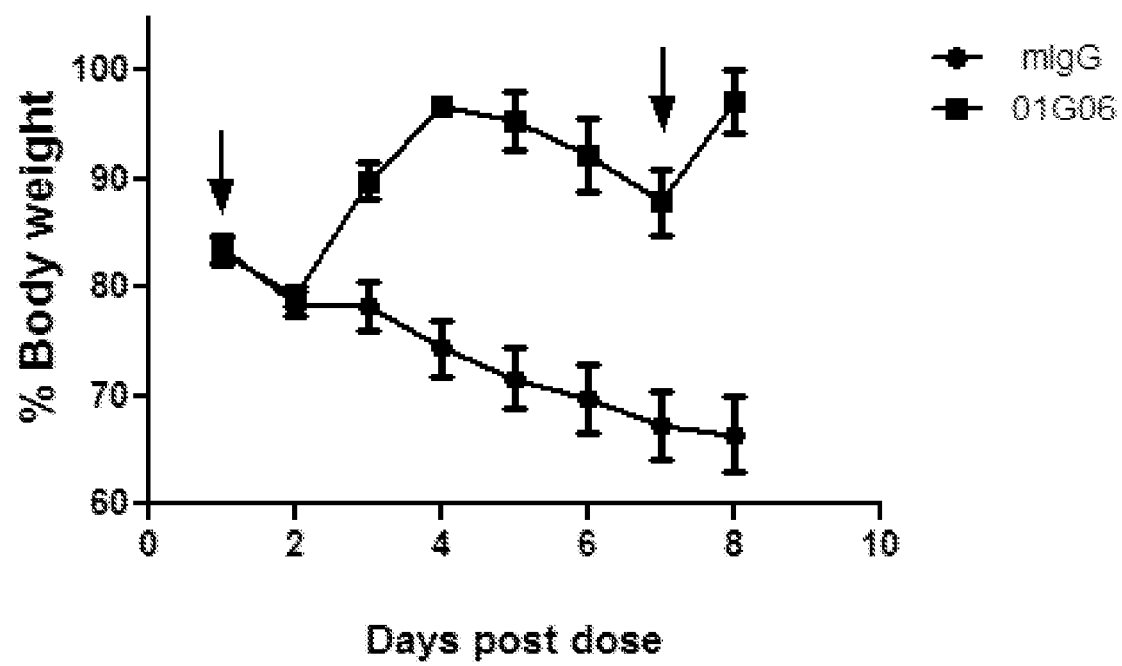
FIGS. 17A-17B are graphs summarizing results from an experiment to demonstrate anti-cachectic activity of anti-GDF15 antibody 01G06 (■), dosed at 2 mg/kg, in immune-incompetent mice (ICR-SCID) bearing an HT-1080 fibrosarcoma tumor xenograft model. Treatment with antibody 01G06 reversed body weight loss compared to murine IgG (●) (FIG. 17A); and induced a gain of organ mass (liver, heart, spleen, kidney) and induced a gain of tissue mass (gonadal and gastrocnemius) (FIG. 17B) compared to negative control (murine IgG) and baseline (day 1). The arrows in FIG. 17A indicate intra-peritoneal injection of antibody.
Figure 17B:
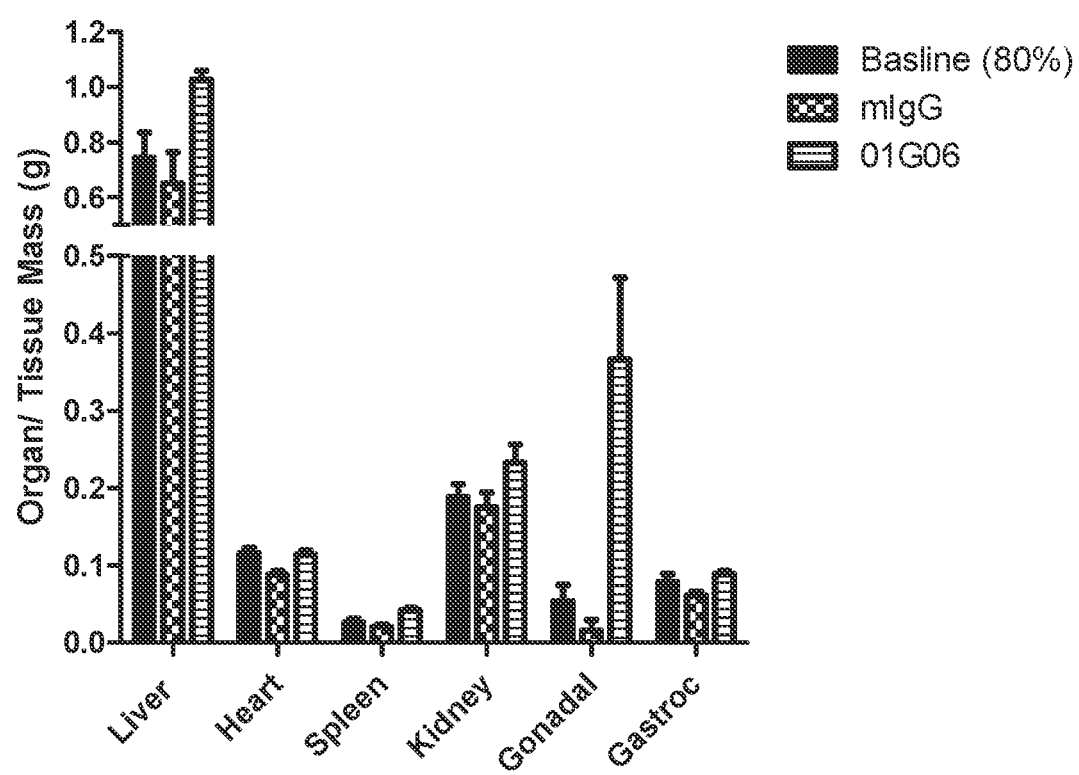

The data in FIGS. 17A-B and Table 12 indicate that the disclosed anti-GDF15 antibodies can reverse cachexia in an HT-1080 fibrosarcoma xenograft model.

In this experiment, a group of five mice were sacrificed at the time of dosing (baseline or 80% body weight loss, without treatment) and at the end of study (seven days post dose, either mIgG or 01G06). Liver, heart, slpeen, kidney, gonadal fat and the gastrocnemius muscles were removed surgically and weighed. As shown in FIG. 17B, a significant loss in liver, heart, spleen, kidney, gonadal fat and gastrocnemius muscle mass was observed seven days post dose with mIgG, but not in the group treated with antibody 01G06. In addition, mice treated with antibody 01G06 displayed significant liver and gonadal muscle gain compared to the baseline group (FIG. 17B).

These results indicate that the disclosed anti-GDF15 antibodies can reverse cachexia measured by the loss of key organ mass, loss of muscle mass, loss of fat and involuntary weight loss in an HT-1080 xenograft tumor model.

Example 12: Reversal of Cachexia in a K-562 Xenograft Tumor Model

This Example demonstrates the reversal of cachexia (as indicated by body weight loss) by antibody 01G06, 03G05, 04F08, 06C11, 08G01, 14F11 or 17B11 in a K-562 leukemia xenograft model. K-562 cells were grown in culture at 37° C. in an atmosphere containing 5% $CO_2$, using Iscove's Modified Dulbecco's Medium (ATCC Catalog No. 30-2005) containing 10% FBS. Cells were inoculated subcutaneously into the flank of 8-week old female CB17SCRFMF mice with $2.5 \times 10^6$ cells per mouse in 50% matrigel. Body weight was measured daily. When body weight reached 93%, the mice were randomly distributed into eight groups of ten mice each. Each group received one of the following treatments: murine IgG control, 01G06, 03G05, 04F08, 06C11, 08G01, 14F11 or 17B11 at 10 mg/kg. Treatment was administered every three days by intra-peritoneal injection. Treatment with antibody 01G06, 03G05, 04F08, 06C11, 08G01, 14F11 or 17B11 resulted in body weight increase relative to initial weight or about 100% (p<0.001) (FIG. 18 and Table 13).

TABLE 13

| Gr. | Treatment | | % Body Weight | ANOVA Analysis (compared to mIgG) |
|---|---|---|---|---|
| | Agent | mg/kg | | |
| 1 | mIgG | 10 | 90.4 | NA |
| 2 | 01G06 | 10 | 106.5 | p < 0.001 |
| 3 | 03G05 | 10 | 109.8 | p < 0.001 |
| 4 | 04F08 | 10 | 108.9 | p < 0.001 |
| 5 | 06C11 | 10 | 109.5 | p < 0.001 |
| 6 | 08G01 | 10 | 107.2 | p < 0.001 |
| 7 | 14F11 | 10 | 107.0 | p < 0.001 |
| 8 | 17B11 | 10 | 105.3 | p < 0.001 |

Figure 18:
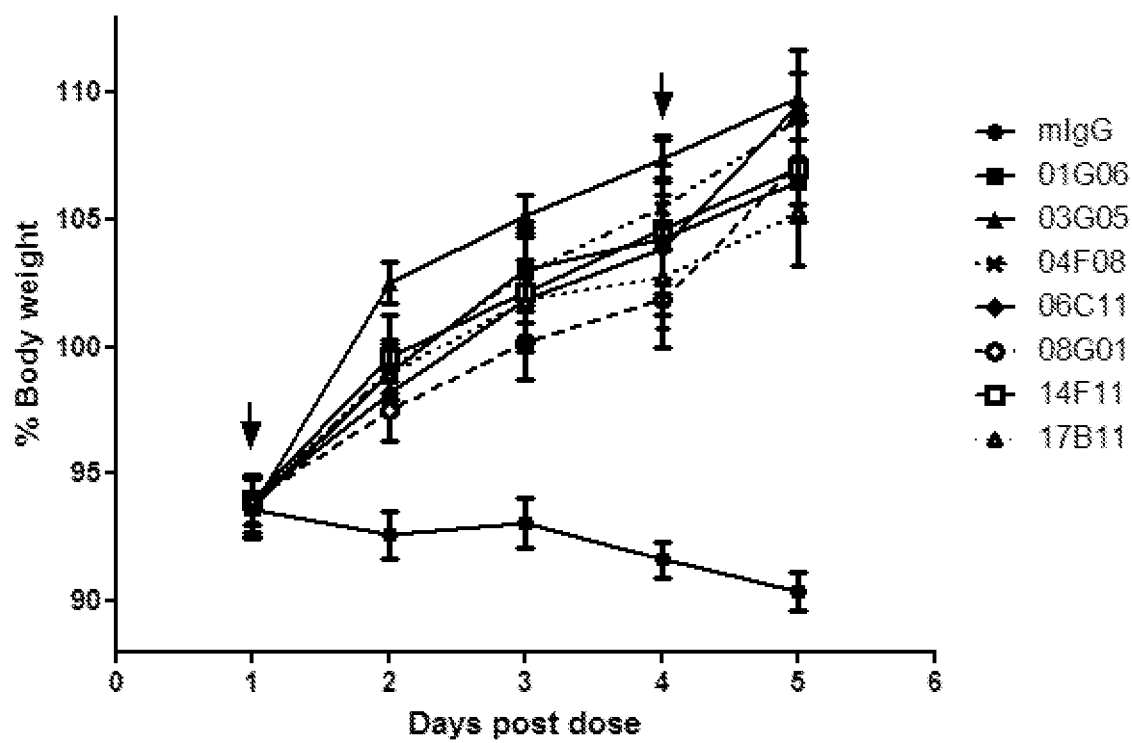
FIG. 18 is a graph summarizing results from an experiment to measure cachectic inhibitory activity of anti-GDF15 antibodies 01G06 (■), 03G05 (▲), 04F08 (X), 06C11(♦), 08G01 (○), 14F11 (□), and 17B11 (Δ), and a murine IgG control (●) dosed at 10 mg/kg in a K-562 leukemia tumor xenograft model in immune-incompetent (CB17SCRFMF) mice. The arrows indicate intra-peritoneal injection of antibody.

The data in FIG. 18 and Table 13 indicate that the disclosed anti-GDF15 antibodies can reverse cachexia in a K-562 xenograft tumor model.

Example 13: Additional Xenograft Tumor Models

Antibody 01G06 was tested in additional tumor xenograft models including the TOV-21G ovarian xenograft model and the LS1034 colon xenograft model. In each model, antibody 01G06 reversed body weight loss compared to a PBS control (p<0.001 for the TOV-21G model and p<0.01 for the LS1034 model).

Example 14: Humanization of Anti-GDF15 Antibodies

This Example describes the humanization and chimerization of three murine antibodies, designated 01G06, 06C11, and 14F11, and the characterization of the resulting humanized antibodies. The humanized anti-GDF15 antibodies were designed, affinity matured by targeted CDR mutagenesis, and optimized using methods known in the art. The amino acid sequences were converted to codon-optimized DNA sequences and synthesized to include (in the following order): 5' HindIII restriction site, Kozak consensus sequence, amino terminal signal sequence, humanized variable region, human IgG1 or Kappa constant region, stop codon, and a 3' EcoRI restriction site.

Chimeric (murine variable region and human constant region) 01G06, 06C11, and 14F11 heavy (human IgG1) and light (human Kappa) chains were also constructed. To generate chimeric antibodies, the murine variable regions were fused to the human constant region, and codon-optimized DNA sequences were synthesized, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza, Basel, Switzerland) via HindIII and EcoRI sites using In-Fusion™ PCR cloning (Clontech, Mountain View, CA). The humanized and chimeric Kappa light chains were subcloned into pEE14.4 (Lonza) via HindIII and EcoRI sites using In-Fusion™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to human GDF15 was measured as described below. The results are summarized in Tables 24-27.

Each of the possible combinations of the chimeric or humanized 01G06 immunoglobulin heavy chain and immunoglobulin light chain variable regions is set forth below in Table 14.

TABLE 14

| Antibody Name | Light Chain Variable Region | Heavy Chain Variable Region |
|---|---|---|
| Hu01G06-1 | Ch01G06 Chimeric Kappa (SEQ ID NO: 76) | Ch01G06 Chimeric Heavy (SEQ ID NO: 40) |
| Hu01G06-14 | Ch01G06 Chimeric Kappa (SEQ ID NO: 76) | Hu01G06 IGHV1-18 Heavy (SEQ ID NO: 54) |
| Hu01G06-15 | Ch01G06 Chimeric Kappa (SEQ ID NO: 76) | Hu01G06 IGHV1-69 Heavy (SEQ ID NO: 56) |
| Hu01G06-147 | Ch01G06 Chimeric Kappa (SEQ ID NO: 76) | Sh01G06 IGHV1-18 M69L Heavy (SEQ ID NO: 58) |
| Hu01G06-148 | Ch01G06 Chimeric Kappa (SEQ ID NO: 76) | Sh01G06 IGHV1-18 M69L K64Q G44S Heavy (SEQ ID NO: 60) |
| Hu01G06-149 | Ch01G06 Chimeric Kappa (SEQ ID NO: 76) | Sh01G06 IGHV1-18 M69L K64Q Heavy (SEQ ID NO: 62) |
| Hu01G06-150 | Ch01G06 Chimeric Kappa (SEQ ID NO: 76) | Sh01G06 IGHV1-69 T30S I69L Heavy (SEQ ID NO: 64) |
| Hu01G06-151 | Ch01G06 Chimeric Kappa (SEQ ID NO: 76) | Sh01G06 IGHV1-69 T30S K64Q I69L Heavy (SEQ ID NO: 66) |
| Hu01G06-4 | Hu01G06 IGKV1-39 Kappa (SEQ ID NO: 90) | Ch01G06 Chimeric Heavy (SEQ ID NO: 40) |
| Hu01G06-46 | Hu01G06 IGKV1-39 Kappa (SEQ ID NO: 90) | Hu01G06 IGHV1-18 Heavy (SEQ ID NO: 54) |
| Hu01G06-52 | Hu01G06 IGKV1-39 Kappa (SEQ ID NO: 90) | Hu01G06 IGHV1-69 Heavy (SEQ ID NO: 56) |
| Hu01G06-100 | Hu01G06 IGKV1-39 Kappa (SEQ ID NO: 90) | Sh01G06 IGHV1-18 M69L Heavy (SEQ ID NO: 58) |
| Hu01G06-102 | Hu01G06 IGKV1-39 Kappa (SEQ ID NO: 90) | Sh01G06 IGHV1-18 M69L K64Q G44S Heavy (SEQ ID NO: 60) |
| Hu01G06-101 | Hu01G06 IGKV1-39 Kappa (SEQ ID NO: 90) | Sh01G06 IGHV1-18 M69L K64Q Heavy (SEQ ID NO: 62) |

TABLE 14-continued

| Antibody Name | Light Chain Variable Region | Heavy Chain Variable Region |
|---|---|---|
| Hu01G06-103 | Hu01G06 IGKV1-39 Kappa (SEQ ID NO: 90) | Sh01G06 IGHV1-69 T30S I69L Heavy (SEQ ID NO: 64) |
| Hu01G06-104 | Hu01G06 IGKV1-39 Kappa (SEQ ID NO: 90) | Sh01G06 IGHV1-69 T30S K64Q I69L Heavy(SEQ ID NO: 66) |
| Hu01G06-152 | Hu01G06 IGKV1-39 S43A V48I Kappa (SEQ ID NO: 92) | Ch01G06 Chimeric Heavy (SEQ ID NO: 40) |
| Hu01G06-71 | Hu01G06 IGKV1-39 S43A V48I Kappa (SEQ ID NO: 92) | Hu01G06 IGHV1-18 Heavy (SEQ ID NO: 54) |
| Hu01G06-77 | Hu01G06 IGKV1-39 S43A V48I Kappa (SEQ ID NO: 92) | Hu01G06 IGHV1-69 Heavy (SEQ ID NO: 56) |
| Hu01G06-110 | Hu01G06 IGKV1-39 S43A V48I Kappa (SEQ ID NO: 92) | Sh01G06 IGHV1-18 M69L Heavy (SEQ ID NO: 58) |
| Hu01G06-112 | Hu01G06 IGKV1-39 S43A V48I Kappa (SEQ ID NO: 92) | Sh01G06 IGHV1-18 M69L K64Q G44S Heavy (SEQ ID NO: 60) |
| Hu01G06-111 | Hu01G06 IGKV1-39 S43A V48I Kappa (SEQ ID NO: 92) | Sh01G06 IGHV1-18 M69L K64Q Heavy (SEQ ID NO: 62) |
| Hu01G06-113 | Hu01G06 IGKV1-39 S43A V48I Kappa (SEQ ID NO: 92) | Sh01G06 IGHV1-69 T30S I69L Heavy (SEQ ID NO: 64) |
| Hu01G06-114 | Hu01G06 IGKV1-39 S43A V48I Kappa (SEQ ID NO: 92) | Sh01G06 IGHV1-69 T30S K64Q I69L Heavy (SEQ ID NO: 66) |
| Hu01G06-122 | Hu01G06 IGKV1-39 S43A V48I Kappa(SEQ ID NO: 92) | Hu01G06 IGHV1-18 F1 Heavy (SEQ ID NO: 246) |
| Hu01G06-119 | Hu01G06 IGKV1-39 S43A V48I Kappa(SEQ ID NO: 92) | Hu01G06 IGHV1-18 F2 Heavy (SEQ ID NO: 248) |
| Hu01G06-135 | Hu01G06 IGKV1-39 S43A V48I Kappa(SEQ ID NO: 92) | Hu01G06 IGHV1-69 F1 Heavy (SEQ ID NO: 250) |
| Hu01G06-138 | Hu01G06 IGKV1-39 S43A V48I Kappa(SEQ ID NO: 92) | Hu01G06 IGHV1-69 F2 Heavy (SEQ ID NO: 252) |
| Hu01G06-153 | Hu01G06 IGKV1-39 V48I Kappa (SEQ ID NO: 94) | Ch01G06 Chimeric Heavy (SEQ ID NO: 40) |
| Hu01G06-69 | Hu01G06 IGKV1-39 V48I Kappa (SEQ ID NO: 94) | Hu01G06 IGHV1-18 Heavy (SEQ ID NO: 54) |
| Hu01G06-75 | Hu01G06 IGKV1-39 V48I Kappa (SEQ ID NO: 94) | Hu01G06 IGHV1-69 Heavy (SEQ ID NO: 56) |
| HU01G06-105 | Hu01G06 IGKV1-39 V48I Kappa (SEQ ID NO: 94) | Sh01G06 IGHV1-18 M69L Heavy (SEQ ID NO: 58) |
| Hu01G06-107 | Hu01G06 IGKV1-39 V48I Kappa (SEQ ID NO: 94) | Sh01G06 IGHV1-18 M69L K64Q G44S Heavy (SEQ ID NO: 60) |
| Hu01G06-106 | Hu01G06 IGKV1-39 V48I Kappa (SEQ ID NO: 94) | Sh01G06 IGHV1-18 M69L K64Q Heavy (SEQ ID NO: 62) |
| Hu01G06-108 | Hu01G06 IGKV1-39 V48I Kappa (SEQ ID NO: 94) | Sh01G06 IGHV1-69 T30S I69L Heavy (SEQ ID NO: 64) |
| Hu01G06-109 | Hu01G06 IGKV1-39 V48I Kappa (SEQ ID NO: 94) | Sh01G06 IGHV1-69 T30S K64Q I69L Heavy (SEQ ID NO: 66) |
| Hu01G06-154 | Hu01G06 IGKV1-39 F2 Kappa (SEQ ID NO: 254) | Ch01G06 Chimeric Heavy (SEQ ID NO: 40) |
| Hu01G06-155 | Hu01G06 IGKV1-39 F2 Kappa (SEQ ID NO: 254) | Hu01G06 IGHV1-18 Heavy (SEQ ID NO: 54) |
| Hu01G06-156 | Hu01G06 IGKV1-39 F2 Kappa (SEQ ID NO: 254) | Hu01G06 IGHV1-69 Heavy (SEQ ID NO: 56) |
| Hu01G06-157 | Hu01G06 IGKV1-39 F2 Kappa (SEQ ID NO: 254) | Sh01G06 IGHV1-18 M69L Heavy (SEQ ID NO: 58) |
| Hu01G06-158 | Hu01G01 IGKV1-39 F2 Kappa (SEQ ID NO: 254) | Sh01G06 IGHV1-18 M69L K64Q G44S Heavy (SEQ ID NO: 60) |
| Hu01G06-159 | Hu01G06 IGKV1-39 F2 Kappa (SEQ ID NO: 254) | Sh01G06 IGHV1-18 M69L K64Q Heavy (SEQ ID NO: 62) |
| Hu01G06-160 | Hu01G06 IGKV1-39 F2 Kappa (SEQ ID NO: 254) | Sh01G06 IGHV1-69 T30S I69L Heavy (SEQ ID NO: 64) |
| Hu01G06-161 | Hu01G06 IGKV1-39 F2 Kappa (SEQ ID NO: 254) | Su01G06 IGHV1-69 T30S K64Q I69L Heavy (SEQ ID NO: 66) |
| Hu01G06-130 | Hu01G06 IGKV1-39 F2 Kappa (SEQ ID NO: 254) | Hu01G06 IGHV1-18 F1 Heavy (SEQ ID NO: 246) |
| Hu01G06-127 | Hu01G06 IGKV1-39 F2 Kappa (SEQ ID NO: 254) | Hu01G06 IGHV1-18 F2 Heavy (SEQ ID NO: 248) |
| Hu01G06-143 | Hu01G06 IGKV1-39 F2 Kappa (SEQ ID NO: 254) | Hu01G06 IGHV1-69 F1 Heavy (SEQ ID NO: 250) |
| Hu01G06-146 | Hu01G06 IGKV1-39 F2 Kappa (SEQ ID NO: 254) | Hu01G06 IGHV1-69 F2 Heavy (SEQ ID NO: 252) |

Each of the possible combinations of the chimeric or humanized 06C11 immunoglobulin heavy chain and immunoglobulin light chain variable regions is set forth below in Table 15.

TABLE 15

| Antibody Name | Light Chain Variable Region | Heavy Chain Variable Region |
|---|---|---|
| Hu06C11-1 | Ch06C11 Chimeric Kappa (SEQ ID NO: 82) | Ch06C11 Chimeric Heavy (SEQ ID NO: 46) |
| Hu06C11-7 | Ch06C11 Chimeric Kappa (SEQ ID NO: 82) | HE LM 06C11 IGHV2-70 Heavy (SEQ ID NO: 68) |
| Hu06C11-10 | Ch06C11 Chimeric Kappa (SEQ ID NO: 82) | Hu06C11 IGHV2-5 Heavy (SEQ ID NO: 70) |
| Hu06C11-12 | Sh06C11 IGKV1-16 Kappa (SEQ ID NO: 96) | Ch06C11 Chimeric Heavy (SEQ ID NO: 46) |
| Hu06C11-27 | Sh06C11 IGKV1-16 Kappa (SEQ ID NO: 96) | HE LM 06C11 IGHV2-70 Heavy (SEQ ID NO: 68) |
| Hu06C11-30 | Sh06C11 IGKV1-16 Kappa (SEQ ID NO: 96) | Hu06C11 IGHV2-5 Heavy (SEQ ID NO: 70) |

Each of the possible combinations of the chimeric or humanized 14F11 immunoglobulin heavy chain and immunoglobulin light chain variable regions is set forth below in Table 16.

TABLE 16

| Antibody Name | Light Chain Variable Region | Heavy Chain Variable Region |
|---|---|---|
| Hu14F11-1 | Ch14F11 Chimeric Kappa (SEQ ID NO: 86) | Ch14F11 Chimeric Heavy (SEQ ID NO: 50) |
| Hu14F11-14 | Ch14F11 Chimeric Kappa (SEQ ID NO: 86) | Sh14F11 IGHV2-5 Heavy (SEQ ID NO: 72) |
| Hu14F11-15 | Ch14F11 Chimeric Kappa (SEQ ID NO: 86) | Sh14F11 IGHV2-70 Heavy (SEQ ID NO: 74) |
| Hu14F11-11 | Hu14F11 IGKV1-16 Kappa (SEQ ID NO: 98) | Ch14F11 Chimeric Heavy (SEQ ID NO: 50) |
| Hu14F11-39 | Hu14F11 IGKV1-16 Kappa (SEQ ID NO: 98) | Sh14F11 IGHV2-5 Heavy (SEQ ID NO: 72) |
| Hu14F11-47 | Hu14F11 IGKV1-16 Kappa (SEQ ID NO: 98) | Sh14F11 IGHV2-70 Heavy (SEQ ID NO: 74) |

Each of the possible combinations of the chimeric 04F08, 06C11, and 14F11 immunoglobulin heavy chain and immunoglobulin light chain variable regions is set forth below in Table 17.

TABLE 17

| Light Chain Variable Region | Heavy Chain Variable Region |
|---|---|
| 04F08 Chimeric Kappa (SEQ ID NO: 80) | Ch06C11 Chimeric Heavy (SEQ ID NO: 46) |
| 04F08 Chimeric Kappa (SEQ ID NO: 80) | Ch14F11 Chimeric Heavy (SEQ ID NO: 50) |
| Ch06C11 Chimeric Kappa (SEQ ID NO: 82) | 04F08 Chimeric Heavy (SEQ ID NO: 44) |
| Ch06C11 Chimeric Kappa (SEQ ID NO: 82) | Ch14F11 Chimeric Heavy (SEQ ID NO: 50) |
| Ch14F11 Chimeric Kappa (SEQ ID NO: 86) | 04F08 Chimeric Heavy (SEQ ID NO: 44) |
| Ch14F11 Chimeric Kappa (SEQ ID NO: 86) | Ch06C11 Chimeric Heavy (SEQ ID NO: 46) |
| Light Chain Variable Region (SEQ ID NO: 86) | Heavy Chain Variable Region (SEQ ID NO: 46) |

Each of the possible combinations of the chimeric 01G06 and chimeric 08G01 immunoglobulin heavy chain and immunoglobulin light chain variable regions is set forth below in Table 18.

TABLE 18

| Light Chain Variable Region | Heavy Chain Variable Region |
|---|---|
| Ch01G06 Chimeric Kappa (SEQ ID NO: 76) | 08G01 Chimeric Heavy (SEQ ID NO: 48) |
| 08G01 Chimeric Kappa (SEQ ID NO: 84) | Ch01G06 Chimeric Heavy (SEQ ID NO: 40) |

The nucleic acid sequences and the encoded protein sequences defining variable regions of the chimeric and humanized 01G06, 06C11, and 14F11 antibodies are summarized below (amino terminal signal peptide sequences are not shown). CDR sequences (Kabat definition) are shown in bold and are underlined in the amino acid sequences.

Nucleic Acid Sequence Encoding the Ch01G06 Chimeric Heavy Chain Variable Region (SEQ ID NO: 127)

```
  1  gaagtgttgt tgcagcagtc agggccggag ttggtaaaac cgggagcgtc ggtgaaaatc
 61  ccgtgcaaag cgtcggggta tacgtttacg gactataaca tggattgggt gaaacagtcg
121  catgggaaat cgcttgaatg gattggtcag atcaatccga ataatggagg aatcttcttt
181  aatcagaagt ttaaaggaaa agcgacgctt acagtcgata agtcgtcgaa cacggcgttc
241  atggaagtac ggtcgcttac gtcggaagat acggcggtct attactgtgc gagggaggcg
301  attacgacgg tgggagcgat ggactattgg ggacaaggga cgtcggtcac ggtatcgtcg
```

Protein Sequence Defining the Ch01G06 Chimeric Heavy Chain Variable Region (SEQ ID NO:40)

```
  1  evllqqsgpe lvkpgasvki pckasgytft dynmdwvkqs hgkslewigq inpnnggiff
 61  nqkfkgkatl tvdkssntaf mevrsltsed tavyycarea ittvgamdyw gqgtsvtvss
```

Nucleic Acid Sequence Encoding the Hu01G06 IGHV1-18
Heavy Chain Variable Region (SEQ ID NO:53)

```
  1  caagtgcaac ttgtgcagtc gggtgcggaa gtcaaaaagc cgggagcgtc ggtgaaagta
 61  tcgtgtaaag cgtcgggata tacgtttacg gactataaca tggactgggt acgacaggca
121  ccggggaaat cgttggaatg gatcggacag attaatccga acaatggggg aattttcttt
181  aatcagaaat tcaaaggacg ggcgacgttg acggtcgata catcgacgaa tacggcgtat
241  atggaattga ggtcgcttcg ctcggacgat acggcggtct attactgcgc cagggaggcg
301  atcacgacgg tagggcgat ggattattgg ggacagggga cgcttgtgac ggtatcgtcg
```

Protein Sequence Defining the Hu01G06 IGHV1-18 Heavy
Chain Variable Region (SEQ ID NO:54)

```
  1  qvqlvqsgae vkkpgasvkv sckasgytft dynmdwvrqa pgkslewigq inpnnggiff
 61  nqkfkgratl tvdtstntay melrslrsdd tavyycarea ittvgamdyw gqgtlvtvss
```

Nucleic Acid Sequence Encoding the Hu01G06 IGHV1-69
Heavy Chain Variable Region (SEQ ID NO:55)

```
  1  caagtccagc ttgtccagtc gggagcggaa gtgaagaaac cggggtcgtc ggtcaaagta
 61  tcgtgtaaag cgtcgggata tacgtttacg gactataaca tggattgggt acgacaggct
121  ccgggaaaat cattggaatg gattggacag attaatccga ataatggggg tatcttcttt
181  aatcaaaagt ttaaagggag ggcgacgttg acggtggaca atcgacaaa tacggcgtat
241  atggaattgt cgtcgcttcg gtcggaggac acggcggtgt attactgcgc gagggaggcg
301  atcacgacgg tcggggcgat ggattattgg ggacagggaa cgcttgtgac ggtatcgtcg
```

Protein Sequence Defining the Hu01G06 IGHV1-69 Heavy
Chain Variable Region (SEQ ID NO:56)

```
  1  qvqlvqsgae vkkpgssvkv sckasgytft dynmdwvrqa pgkslewigq inpnnggiff
 61  nqkfkgratl tvdkstntay melsslrsed tavyycarea ittvgamdyw gqgtlvtvss
```

Nucleic Acid Sequence Encoding the Sh01G06 IGHV1-18
M69L Heavy Chain Variable Region (SEQ ID NO:57)

```
  1  caggtccagc ttgtgcaatc gggagcggaa gtgaagaaac cgggagcgtc ggtaaaagtc
 61  tcgtgcaaag cgtcggggta tacgtttacg gactataaca tggactgggt gcgccaagcg
121  cctggacagg gtcttgaatg gatggggcag attaatccga ataatggagg gatcttcttt
181  aatcagaaat tcaaaggaag ggtaacgctg acgacagaca cgtcaacatc gacggcctat
241  atggaattgc ggtcgttgcg atcagatgat acggcggtct actattgtgc gagggaggcg
301  attacgacgg tgggagcgat ggattattgg ggacagggga cgttggtaac ggtatcgtcg
```

Protein Sequence Defining the Sh01G06 IGHV1-18 M69L
Heavy Chain Variable Region (SEQ ID NO:58)

```
  1  qvqlvqsgae vkkpgasvkv sckasgytft dynmdwvrqa pgqglewmgq inpnnggiff
 61  nqkfkgrvtl ttdtststay melrslrsdd tavyycarea ittvgamdyw gqgtlvtvss
```

Nucleic Acid Sequence Encoding the Sh01G06 IGHV1-18 M69L K64Q G44S Heavy Chain Variable Region (SEQ ID NO:59)

```
  1   caggtccagc ttgtgcaatc gggagcggaa gtgaagaaac cgggagcgtc ggtaaaagtc
 61   tcgtgcaaag cgtcggggta tacgtttacg gactataaca tggactgggt gcgccaagcg
121   cctggacaga gccttgaatg gatggggcag attaatccga ataatggagg gatcttcttt
181   aatcagaaat tccagggaag ggtaacgctg acgacagaca cgtcaacatc gacggcctat
241   atggaattgc ggtcgttgcg atcagatgat acggcggtct actattgtgc gagggaggcg
301   attacgacgg tgggagcgat ggattattgg gacagggga cgttggtaac ggtatcgtcg
```

Protein Sequence Defining the Sh01G06 IGHV1-18 M69L K64Q G44S Heavy Chain Variable Region (SEQ ID NO:60)

```
  1   qvqlvqsgae vkkpgasvkv sckasgytft dynmdwvrqa pgqslewmgq inpnnggiff
 61   nqkfqgrvtl ttdtststay melrslrsdd tavyycarea ittvgamdyw gqgtlvtvss
```

Nucleic Acid Sequence Encoding the Sh01G06 IGHV1-18 M69L K64Q Heavy Chain Variable Region (SEQ ID NO:61)

```
  1   caggtccagc ttgtgcaatc gggagcggaa gtgaagaaac cgggagcgtc ggtaaaagtc
 61   tcgtgcaaag cgtcggggta tacgtttacg gactataaca tggactgggt gcgccaagcg
121   cctggacagg gtcttgaatg gatggggcag attaatccga ataatggagg gatcttcttt
181   aatcagaaat tccagggaag ggtaacgctg acgacagaca cgtcaacatc gacggcctat
241   atggaattgc ggtcgttgcg atcagatgat acggcggtct actattgtgc gagggaggcg
301   attacgacgg tgggagcgat ggattattgg gacagggga cgttggtaac ggtatcgtcg
```

Protein Sequence Defining the Sh01G06 IGHV1-18 M69L K64Q Heavy Chain Variable Region (SEQ ID NO:62)

```
  1   qvqlvqsgae vkkpgasvkv sckasgytft dynmdwvrqa pgqglewmgq inpnnggiff
 61   nqkfqgrvtl ttdtststay melrslrsdd tavyycarea ittvgamdyw gqgtlvtvss
```

Nucleic Acid Sequence Encoding the Sh01G06 IGHV1-69 T30S I69L Heavy Chain Variable Region (SEQ ID NO:63)

```
  1   caagtacagc ttgtacagtc gggagcggaa gtcaagaaac cgggatcgtc ggtcaaagtg
 61   tcgtgtaaag cgtcgggata tacgtttagc gactataaca tggattgggt gcgacaagcg
121   cctgggcagg gacttgaatg gatgggtcag atcaatccga ataatggggg aatcttttc
181   aatcagaagt ttaaagggag ggtaacgctg acggcggata aaagcacgtc aacggcgtat
241   atggagttgt cgtcgttgcg gtcggaggac acggcggtct attactgcgc gagggaagcg
301   attacgacgg tgggagcgat ggattattgg ggcagggaa cgcttgtaac ggtgtcatcg
```

Protein Sequence Defining the Sh01G06 IGHV1-69 T30S I69L Heavy Chain Variable Region (SEQ ID NO:64)

```
  1   qvqlvqsgae vkkpgssvkv sckasgytfs dynmdwvrqa pgqglewmgq inpnnggiff
 61   nqkfkgrvtl tadkststay melsslrsed tavyycarea ittvgamdyw gqgtlvtvss
```

Nucleic Acid Sequence Encoding the Sh01G06 IGHV1-69
T30S K64Q I69L Heavy Chain Variable Region (SEQ ID
NO:65)

```
  1  caagtacagc ttgtacagtc gggagcggaa gtcaagaaac cgggatcgtc ggtcaaagtg
 61  tcgtgtaaag cgtcgggata tacgtttagc gactataaca tggattgggt gcgacaagcg
121  cctgggcagg gacttgaatg gatgggtcag atcaatccga ataatggggg aatcttttc
181  aatcagaagt tcaggggag ggtaacgctg acggcggata aaagcacgtc aacggcgtat
241  atggagttgt cgtcgttgcg gtcggaggac acggcggtct attactgcgc gagggaagcg
301  attacgacgg tgggagcgat ggattattgg gggcagggaa cgcttgtaac ggtgtcatcg
```

Protein Sequence Defining the Sh01G06 IGHV1-69 T30S
K64Q I69L Heavy Chain Variable Region (SEQ ID NO:66)

```
  1  qvqlvqsgae vkkpgssvkv sckasgytfs dynmdwvrqa pgqglewmgq inpnnggiff
 61  nqkfqgrvtl tadkststay melsslrsed tavyycarea ittvgamdyw gqgtlvtvss
```

Nucleic Acid Sequence Encoding the Hu01G06 IGHV1-18
F1 Heavy Chain Variable Region (SEQ ID NO:245)

```
  1  caggtccagc ttgtgcaatc gggagcggaa gtgaagaaac cgggagcgtc ggtaaaagtc
 61  tcgtgcaaag cgtcggggta tacgtttacg gactataaca tggactgggt gcgccaagcg
121  cctggacaga gccttgaatg gatggggcag attaatccgt acaatcacct gatcttcttt
181  aatcagaaat tccagggaag ggtaacgctg acgacagaca cgtcaacatc gacggcctat
241  atggaattgc ggtcgttgcg atcagatgat acggcggtct actattgtgc gagggaggcg
301  attacgacgg tgggagcgat ggattattgg gacagggga cgttggtaac ggtatcgtcg
```

Protein Sequence Defining the Hu01G06 IGHV1-18 F1
Heavy Chain Variable Region (SEQ ID NO:246)

```
  1  qvqlvqsgae vkkpgasvkv sckasgytft dynmdwvrqa pgqslewmgq inpynhliff
 61  nqkfqgrvtl ttdtststay melrslrsdd tavyycarea ittvgamdyw gqgtlvtvss
```

Nucleic Acid Sequence Encoding the Hu01G06 IGHV1-18
F2 Heavy Chain Variable Region (SEQ ID NO:247)

```
  1  caggtccagc ttgtgcaatc gggagcggaa gtgaagaaac cgggagcgtc ggtaaaagtc
 61  tcgtgcaaag cgtcggggta tacgtttacg gactataaca tggactgggt gcgccaagcg
121  cctggacaga gccttgaatg gatggggcag attaatccga ataatggact gatcttcttt
181  aatcagaaat tccagggaag ggtaacgctg acgacagaca cgtcaacatc gacggcctat
241  atggaattgc ggtcgttgcg atcagatgat acggcggtct actattgtgc gagggaggcg
301  attacgacgg tgggagcgat ggattattgg gacagggga cgttggtaac ggtatcgtcg
```

Protein Sequence Defining the Hu01G06 IGHV1-18 F2
Heavy Chain Variable Region (SEQ ID NO:248)

```
  1  qvqlvqsgae vkkpgasvkv sckasgytft dynmdwvrqa pgqslewmgq inpnngliff
 61  nqkfqgrvtl ttdtststay melrslrsdd tavyycarea ittvgamdyw gqgtlvtvss
```

Nucleic Acid Sequence Encoding the Hu01G06 IGHV1-69
F1 Heavy Chain Variable Region (SEQ ID NO:249)

```
  1    caagtacagc ttgtacagtc gggagcggaa gtcaagaaac cgggatcgtc ggtcaaagtg
 61    tcgtgtaaag cgtcgggata tacgtttagc gactataaca tggattgggt gcgacaagcg
121    cctgggcagg gacttgaatg gatgggtcag atcaatccga ataatgggct gatcttttc
181    aatcagaagt ttaaagggag ggtaacgctg acggcggata aaagcacgtc aacggcgtat
241    atggagttgt cgtcgttgcg gtcggaggac acggcggtct attactgcgc gagggaagcg
301    attacgacgg tgggagcgat ggattattgg gggcagggaa cgcttgtaac ggtgtcatcg
```

Protein Sequence Defining the Hu01G06 IGHV1-69 F1
Heavy Chain Variable Region (SEQ ID NO:250)

```
  1    qvglvqsgae vkkpgssvkv sckasgytfs dynmdwvrqa pgqglewmgq inpnngliff
 61    nqkfkgrvtl tadkststay melsslrsed tavyycarea ittvgamdyw gqgtlvtvss
```

Protein Sequence Defining the Hu01G06 IGHV1-69 F1
Heavy Chain Variable Region (SEQ ID NO:251)

```
  1    caagtacagc ttgtacagtc gggagcggaa gtcaagaaac cgggatcgtc ggtcaaagtg
 61    tcgtgtaaag cgtcgggata tacgtttagc gactataaca tggattgggt gcgacaagcg
121    cctgggcagg gacttgaatg gatgggtcag atcaatccgt acaatcacct gatcttttc
181    aatcagaagt ttaaagggag ggtaacgctg acggcggata aaagcacgtc aacggcgtat
241    atggagttgt cgtcgttgcg gtcggaggac acggcggtct attactgcgc gagggaagcg
301    attacgacgg tgggagcgat ggattattgg gggcagggaa cgcttgtaac ggtgtcatcg
```

Protein Sequence Defining the Hu01G06 IGHV1-69 F1
Heavy Chain Variable Region (SEQ ID NO:252)

```
  1    qvqlvqsgae vkkpgssvkv sckasgytfs dynmdwvrqa pgqglewmgq inpynhliff
 61    nqkfkgrvtl tadkststay melsslrsed tavyycarea ittvgamdyw gqgtlvtvss
```

Nucleic Acid Sequence Encoding the Ch06C11 Chimeric
Heavy Chain Variable Region (SEQ ID NO: 129)

```
  1    caggtgacac tcaaagaatc aggacccgga atccttcagc ccagccagac cttgtcgctg
 61    acttgttcgt tctccggttt cagcctgaat acttatggga tgggtgtgtc atggatcagg
121    caaccgtccg ggaaaggatt ggagtggctc gcgcacatct actgggacga tgacaaacgc
181    tacaatcctt cgctgaagag ccgattgacg atttccaagg atgcctcgaa caaccgggta
241    tttcttaaga tcacgtcggt cgatacggca gacacggcga cctattactg cgcccaaaga
301    gggtacgatg actattgggg atattggggc caggggacac tcgtcacaat ttcagct
```

Protein Sequence Defining the Ch06C11 Chimeric Heavy
Chain Variable Region (SEQ ID NO:46)

```
  1    qvtlkesgpg ilqpsqtlsl tcsfsgfsln tygmgvswir qpsgkglewl ahiywdddkr
 61    ynpslksrlt iskdasnnrv flkitsvdta dtatyycaqr gyddywgywg qgtlvtisa
```

Nucleic Acid Sequence Encoding the HE LM 06C11
IGHV2-70 Heavy Chain Variable Region (SEQ ID NO:67)

```
  1  caggtgactt tgaaagaatc cggtcccgca ttggtaaagc caacccagac acttacgctc
 61  acatgtacat tttccggatt cagcttgaac acttacggga tgggagtgtc gtggattcgg
121  caacctccgg ggaaggctct ggagtggctg gcgcacatct actgggatga tgacaaaagg
181  tataacccct cacttaaaac gagactgacg atctcgaagg acacaagcaa gaatcaggtc
241  gtcctcacga ttacgaatgt agacccggtg gatactgccg tctattactg cgcgcaacgc
301  gggtatgatg actactgggg atattggggt cagggcaccc tcgtgaccat ctcgtca
```

Protein Sequence Defining the HE LM 06C11 IGHV2-70
Heavy Chain Variable Region (SEQ ID NO:68)

```
  1  qvtlkesgpa lvkptqtltl tctfsgfsln tygmgvswir qppgkalewl ahiywdddkr
 61  ynpslktrlt iskdtsknqv vltitnvdpv dtavyycaqr gyddywgywg qgtlvtiss
```

Nucleic Acid Sequence Encoding the Hu06C11 IGHV2-5
Heavy Chain Variable Region (SEQ ID NO:69)

```
  1  caagtaacgc tcaaggagtc cggacccacc ttggtgaagc cgacgcagac cttgactctt
 61  acgtgcactt tctcggggtt ttcactgaat acgtacggga tgggtgtctc atggatcagg
121  caacctccgg ggaaaggatt ggaatggctg gcgcacatct actgggatga cgataagaga
181  tataacccaa gcctcaagtc gcggctcacc attacaaaag atacatcgaa aaatcaggtc
241  gtacttacta tcacgaacat ggaccccgtg gacacagcaa catattactg tgcccagcgc
301  ggctatgacg attattgggg ttactgggga cagggaacac tggtcacggt gtccagc
```

Protein Sequence Defining the Hu06C11 IGHV2-5 Heavy
Chain Variable Region (SEQ ID NO:70)

```
  1  qvtlkesgpt lvkptqtltl tctfsgfsln tygmgvswir qppgkglewl ahiywdddkr
 61  ynpslksrlt itkdtsknqv vltitnmdpv dtatyycaqr gyddywgywg qgtlvtvss
```

Nucleic Acid Sequence Encoding the Ch14F11 Chimeric
Heavy Chain Variable Region (SEQ ID NO:131)

```
  1  caggtcacgc tgaaagagtc aggtcccgga atccttcaac cttcgcagac attgtcactc
 61  acatgttcct tctccgggtt ctcgctctcg acttatggca tgggtgtagg atggattcgg
121  cagcccagcg ggaaggggct tgagtggttg gcggatatct ggtgggacga cgacaaatac
181  tacaatccga gcctgaagtc ccgcctcacc atttcgaaag atacgtcatc aaacgaagtc
241  tttttgaaga tcgccatcgt ggacacggcg gatacagcga cgtattactg cgccagaagg
301  ggacactaca gcgcaatgga ttattgggga caggggacct cggtgactgt gtcgtcc
```

Protein Sequence Defining the Ch14F11 Chimeric Heavy
Chain Variable Region (SEQ ID NO:50)

```
  1  qvtlkesgpg ilqpsqtlsl tcsfsgfsls tygmgvgwir qpsgkglewl adiwwdddky
 61  ynpslksrlt iskdtssnev flkiaivdta dtatyycarr ghysamdywg qgtsvtvss
```

Nucleic Acid Sequence Encoding the Sh14F11 IGHV2-5
Heavy Chain Variable Region (SEQ ID NO:71)

```
  1  cagatcactt tgaaagaaag cggaccgacc ttggtcaagc ccacacaaac cctcacgctc
 61  acgtgtacat tttcggggtt ctcgctttca acttacggga tgggagtagg gtggattcgc
121  cagccgcctg gtaaagcgtt ggagtggctt gcagacatct ggtgggacga cgataagtac
181  tataatccct cgctcaagtc cagactgacc atcacgaaag atacgagcaa gaaccaggtc
241  gtgctgacaa tgactaacat ggacccagtg gatacggcta catattactg cgccaggcgg
301  ggtcactact cagcgatgga ttattggggc cagggaacac tggtaacggt gtcgtcc
```

Protein Sequence Defining the Sh14F11 IGHV2-5 Heavy
Chain Variable Region (SEQ ID NO:72)

```
  1  qitlkesgpt lvkptqtltl tctfsgfsls tygmgvgwir qppgkalewl adiwwdddky
 61  ynpslksrlt itkdtsknqv vltmtnmdpv dtatyycarr ghysamdywg qgtlvtvss
```

Nucleic Acid Sequence Encoding the Sh14F11 IGHV2-70
Heavy Chain Variable Region (SEQ ID NO:73)

```
  1  caagtgactc tcaaggagtc cggacccgcc ctggtcaaac caacgcagac actgacgctc
 61  acatgcacct tcagcggatt ttcgttgtca acgtacggca tgggtgtggg gtggattcgc
121  cagcctccgg ggaaagccct tgaatggttg gcggacatct ggtgggatga tgacaagtac
181  tataatccct cacttaagtc acggttgacg atctcgaaag acaccagcaa gaaccaggta
241  gtgctgacaa tgactaacat ggacccggtc gatacagcgg tctactattg tgctagaagg
301  ggacactact ccgcaatgga ttattggggt cagggacgc tcgtaaccgt gtcgtcg
```

Protein Sequence Defining the Sh14F11 IGHV2-70 Heavy
Chain Variable Region (SEQ ID NO:74)

```
  1  qvtlkesgpa lvkptqtltl tctfsgfsls tygmgvgwir qppgkalewl adiwwdddky
 61  ynpslksrlt iskdtsknqv vltmtnmdpv dtavyycarr ghysamdywg qgtlvtvss
```

Nucleic Acid Sequence Encoding the Ch01G06 Chimeric
Kappa Chain Variable Region (SEQ ID NO: 133)

```
  1  gacatccaaa tgacccagtc acccgcgagc ctttcggcgt cggtcggaga aacggtcacg
 61  atcacgtgcc ggacatcaga gaatctccat aactacctcg cgtggtatca acagaagcag
121  gggaagtcgc cccagttgct tgtatacgat gcgaaaacgt tggcggatgg ggtgccgtcc
181  agattctcgg gatcgggctc ggggacgcag tactcgctca agatcaattc gctgcagccg
241  gaggactttg gtcgtacta ttgtcagcat ttttggtcat caccgtatac atttggaggt
301  ggaacgaaac ttgagattaa g
```

Protein Sequence Defining the Ch01G06 Chimeric Kappa
Chain Variable Region (SEQ ID NO:76)

```
  1  diqmtqspas lsasvgetvt itcrtsenlh nylawyqqkq gkspqllvyd aktladgvps
 61  rfsgsgsgtq yslkinslqp edfgsyycqh fwsspytfgg gtkleik
```

Nucleic Acid Sequence Encoding the Hu01G06 IGKV1-39
Kappa Chain Variable Region (SEQ ID NO:89)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaagtcac cgaaactcct tgtctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgt cgccctacac atttgggcag
301  gggaccaagt tggaaatcaa g
```

Protein Sequence Defining the Hu01G06 IGKV1-39 Kappa
Chain Variable Region (SEQ ID NO:90)

```
  1  diqmtqspss lsasvgdrvt itcrtsenlh nylawyqqkp gkspkllvyd aktladgvps
 61  rfsgsgsgtd ytltisslqp edfatyycqh fwsspytfgq gtkleik
```

Nucleic Acid Sequence Encoding the Hu01G06 IGKV1-39
S43A V48I Kappa Chain Variable Region (Also Referred to
Herein as Hu01G06 IGKV1-39 F1 Kappa Chain Variable
Region; SEQ ID NO:91)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaaggccc cgaaactcct tatctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgt cgccctacac atttgggcag
301  gggaccaagt tggaaatcaa g
```

Protein Sequence Defining the Hu01G06 IGKV1-39 S43A
V48I Kappa Chain Variable Region (Also Referred to
Herein as Hu01G06 IGKV1-39 F1 Kappa Chain Variable
Region; SEQ ID NO:92)

```
  1  diqmtqspss lsasvgdrvt itcrtsenlh nylawyqqkp gkapklliyd aktladgvps
 61  rfsgsgsgtd ytltisslqp edfatyycqh fwsspytfgq gtkleik
```

Nucleic Acid Sequence Encoding the Hu01G06 IGKV1-39
V48I Kappa Chain Variable Region (SEQ ID NO:93)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaagtcac cgaaactcct tatctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgt cgccctacac atttgggcag
301  gggaccaagt tggaaatcaa g
```

Protein Sequence Defining the Hu01G06 IGKV1-39 V48I
Kappa Chain Variable Region (SEQ ID NO:94)

```
  1  diqmtqspss lsasvgdrvt itcrtsenlh nylawyqqkp gkspklliyd aktladgvps
 61  rfsgsgsgtd ytltisslqp edfatyycqh fwsspytfgq gtkleik
```

Nucleic Acid Sequence Encoding the Hu01G06 IGKV1-39
F1 Kappa Chain Variable Region (Also Referred to Herein
as Hu01G06 IGKV1-39 S43A V48I Kappa Chain Variable
Region; SEQ ID NO:91)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaaggccc cgaaactcct tatctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgt cgccctacac atttgggcag
301  gggaccaagt tggaaatcaa g
```

Protein Sequence Defining the Hu01G06 IGKV1-39 F1
Kappa Chain Variable Region (Also Referred to Herein as
Hu01G06 IGKV1-39 S43A V48I Kappa Chain Variable
Region; SEQ ID NO:92)

```
  1  diqmtqspss lsasvgdrvt itcrtsenlh nylawyqqkp gkapklliyd aktladgvps
 61  rfsgsgsgtd ytltisslqp edfatyycqh fwsspytfgq gtkleik
```

Nucleic Acid Sequence Encoding the Hu01G06 IGKV1-39
F2 Kappa Chain Variable Region (SEQ ID NO:253)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaagtcac cgaaactcct tatctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgg accctacac atttgggcag
301  gggaccaagt tggaaatcaa g
```

Protein Sequence Defining the Hu01G06 IGKV1-39 F2
Kappa Chain Variable Region (SEQ ID NO:254)

```
  1  diqmtqspss lsasvgdrvt itcrtsenlh nylawyqqkp gkspklliyd aktladgvps
 61  rfsgsgsgtd ytltisslqp edfatyycqh fwsdpytfgq gtkleik
```

Nucleic Acid Sequence Encoding the Ch06C11 Chimeric
Kappa Chain Variable Region (SEQ ID NO: 135)

```
  1  gatatcgtca tgacccagtc ccagaagttc atgtcaactt cagtgggaga cagagtgtcc
 61  gtcacatgta agcctcgca aaatgtggga accaacgtag cgtggttcca gcagaaacct
121  ggccaatcac cgaaggcact gatctactcg gccagctata ggtactcggg agtaccagat
```

-continued

```
181 cggtttacgg ggtcggggag cgggacggac tttatcctca ctatttccaa tgtccagtcg 241 gaggaccttg cggaatactt ctgccagcag tataacaact atcccctcac gtttggtgct 301 ggtacaaaat tggagttgaa g
```

Protein Sequence Defining the Ch06C11 Chimeric Kappa
Chain Variable Region (SEQ ID NO:82)

```
  1 divmtqsqkf mstsvgdrvs vtckasqnvg tnvawfqqkp gqspkaliys asyrysgvpd 61 rftgsgsgtd filtisnvqs edlaeyfcqq ynnypltfga gtklelk
```

Nucleic Acid Sequence Encoding the Sh06C11 IGKV1-16[15]
Kappa Chain Variable Region (SEQ ID NO:95)

```
  1 gacatccaaa tgacccaatc gccctcctcc ctctccgcat cagtagggga ccgcgtcaca 61 attacttgca aagcgtcgca gaacgtcgga acgaatgtgg cgtggtttca gcagaagccc 121 ggaaaagctc cgaagagctt gatctactcg gcctcatata ggtattcggg tgtgccgagc 181 cggtttagcg ggtcggggtc aggtactgat ttcacgctca caatttcatc gttgcagcca 241 gaagatttcg ccacatatta ctgtcagcag tacaacaatt accctctgac gttcggccag 301 ggaaccaaac ttgagatcaa g
```

Protein Sequence Defining the Sh06C11 IGKV1-16 Kappa
Chain Variable Region (SEQ ID NO:96)

```
  1 diqmtqspss lsasvgdrvt itckasqnvg tnvawfqqkp gkapksliys asyrysgvps 61 rfsgsgsgtd ftltisslqp edfatyycqq ynnypltfgq gtkleik
```

Nucleic Acid Sequence Encoding the Ch14F11 Chimeric
Kappa Chain Variable Region (SEQ ID NO: 137)

```
  1 gacatcgtga tgacacagtc acagaaattc atgtccacat ccgtcggtga tagagtatcc 61 gtcacgtgta aggcctcgca aaacgtagga actaatgtgg cgtggtatca acagaagcca 121 ggacagtcac ccaaagcact catctacagc ccctcatatc ggtacagcgg ggtgccggac 181 aggttcacgg gatcggggag cgggaccgat tttacactga ccatttcgaa tgtccagtcg 241 gaggaccttg cggaatactt ctgccagcag tataactcgt accctcacac gtttggaggt 301 ggcactaagt tggagatgaa a
```

Protein Sequence Defining the Ch14F11 Chimeric Kappa[50]
Chain Variable Region (SEQ ID NO:86)

```
  1 divmtqsqkf mstsvgdrvs vtckasqnvg tnvawyqqkp gqspkaliys psyrysgvpd 61 rftgsgsgtd ftltisnvqs edlaeyfcqq ynsyphtfgg gtklemk
```

Nucleic Acid Sequence Encoding the Hu14F11 IGKV1-16
Kappa Chain Variable Region (SEQ ID NO:97)

```
  1 gatatccaga tgacacagtc accctcgtcg ctctcagctt ccgtaggcga cagggtcact 61 attacgtgta aagcatcaca gaacgtcgga acgaatgtgg cgtggtttca gcagaagccc 121 gggaagagcc ccaaagcgct tatctactcc ccgtcgtatc ggtattccgg tgtgccaagc
```

```
181  agattttcgg ggtcaggttc gggaactgac tttaccctga ccatctcgtc cctccaaccg 241  gaagatttcg ccacgtactt ctgccagcag tacaacagct atcctcacac attcggacaa 301  gggacaaagt tggagattaa a
```

Protein Sequence Defining the Hu14F11 IGKV1-16 Kappa Chain Variable Region (SEQ ID NO:98)

```
  1  diqmtqspss lsasvgdrvt itckasqnvg tnvawfqqkp gkspkaliys psyrysgvps 61  rfsgsgsgtd ftltisslqp edfatyfcqq ynsyphtfgq gtkleik
```

The amino acid sequences defining the immunoglobulin heavy chain variable regions for the antibodies produced in Example 13 are aligned in FIG. 19. Amino terminal signal peptide sequences (for proper expression/secretion) are not shown. $CDR_1$, $CDR_2$, and $CDR_3$ (Kabat definition) are identified by boxes. FIG. 20 show an alignment of the separate $CDR_1$, $CDR_2$, and $CDR_3$ sequences for each of the variable region sequences shown in FIG. 19.

The amino acid sequences defining the immunoglobulin light chain variable regions for the antibodies in Example 13 are aligned in FIG. 21. Amino terminal signal peptide sequences (for proper expression/secretion) are not shown. $CDR_1$, $CDR_2$ and $CDR_3$ are identified by boxes. FIG. 22 shows an alignment of the separate $CDR_1$, $CDR_2$, and $CDR_3$ sequences for each of the variable region sequences shown in FIG. 21.

Table 19 is a concordance chart showing the SEQ ID NO. of each sequence discussed in this Example.

TABLE 19

| SEQ. ID NO. | Nucleic Acid or Protein |
|---|---|
| 127 | Ch01G06 Chimeric Heavy Chain Variable Region - nucleic acid |
| 40 | Ch01G06 Chimeric Heavy Chain Variable Region - protein |
| 1 | Ch01G06 Chimeric Heavy Chain $CDR_1$ |
| 7 | Ch01G06 Chimeric Heavy Chain $CDR_2$ |
| 15 | Ch01G06 Chimeric Heavy Chain $CDR_3$ |
| 53 | Hu01G06 IGHV1-18 Heavy Chain Variable Region - nucleic acid |
| 54 | Hu01G06 IGHV1-18 Heavy Chain Variable Region - protein |
| 1 | Hu01G06 IGHV1-18 Heavy Chain $CDR_1$ |
| 7 | Hu01G06 IGHV1-18 Heavy Chain $CDR_2$ |
| 15 | Hu01G06 IGHV1-18 Heavy Chain $CDR_3$ |
| 55 | Hu01G06 IGHV1-69 Heavy Chain Variable Region - nucleic acid |
| 56 | Hu01G06 IGHV1-69 Heavy Chain Variable Region - protein |
| 1 | Hu01G06 IGHV1-69 Heavy Chain $CDR_1$ |
| 7 | Hu01G06 IGHV1-69 Heavy Chain $CDR_2$ |
| 15 | Hu01G06 IGHV1-69 Heavy Chain $CDR_3$ |
| 57 | Sh01G06 IGHV1-18 M69L Heavy Chain Variable Region - nucleic acid |
| 58 | Sh01G06 IGHV1-18 M69L Heavy Chain Variable Region - protein |
| 1 | Sh01G06 IGHV1-18 M69L Heavy Chain $CDR_1$ |
| 7 | Sh01G06 IGHV1-18 M69L Heavy Chain $CDR_2$ |
| 15 | Sh01G06 IGHV1-18 M69L Heavy Chain $CDR_3$ |
| 59 | Sh01G06 IGHV1-18 M69L K64Q G44S Heavy Chain Variable Region - nucleic acid |
| 60 | Sh01G06 IGHV1-18 M69L K64Q G44S Heavy Chain Variable Region - protein |
| 1 | Sh01G06 IGHV1-18 M69L K64Q G44S Heavy Chain $CDR_1$ |
| 13 | Sh01G06 IGHV1-18 M69L K64Q G44S Heavy Chain $CDR_2$ |
| 15 | Sh01G06 IGHV1-18 M69L K64Q G44S Heavy Chain $CDR_3$ |
| 61 | Sh01G06 IGHV1-18 M69L K64Q Heavy Chain Variable Region - nucleic acid |
| 62 | Sh01G06 IGHV1-18 M69L K64Q Heavy Chain Variable Region - protein |
| 1 | Sh01G06 IGHV1-18 M69L K64Q Heavy Chain $CDR_1$ |
| 13 | Sh01G06 IGHV1-18 M69L K64Q Heavy Chain $CDR_2$ |
| 15 | Sh01G06 IGHV1-18 M69L K64Q Heavy Chain $CDR_3$ |
| 63 | Sh01G06 IGHV1-69 T30S I69L Heavy Chain Variable Region - nucleic acid |
| 64 | Sh01G06 IGHV1-69 T30S I69L Heavy Chain Variable Region - protein |
| 1 | Sh01G06 IGHV1-69 T30S I69L Heavy Chain $CDR_1$ |
| 7 | Sh01G06 IGHV1-69 T30S I69L Heavy Chain $CDR_2$ |
| 15 | Sh01G06 IGHV1-69 T30S I69L Heavy Chain $CDR_3$ |
| 65 | Sh01G06 IGHV1-69 T30S K64Q I69L Heavy Chain Variable Region - nucleic acid |
| 66 | Sh01G06 IGHV1-69 T30S K64Q I69L Heavy Chain Variable Region - protein |
| 1 | Sh01G06 IGHV1-69 T30S K64Q I69L Heavy Chain $CDR_1$ |
| 13 | Sh01G06 IGHV1-69 T30S K64Q I69L Heavy Chain $CDR_2$ |
| 15 | Sh01G06 IGHV1-69 T30S K64Q I69L Heavy Chain $CDR_3$ |
| 245 | Hu01G06 IGHV1-18 F1 Heavy Chain Variable Region - nucleic acid |
| 246 | Hu01G06 IGHV1-18 F1 Heavy Chain Variable Region - protein |
| 1 | Hu01G06 IGHV1-18 F1 Heavy Chain $CDR_1$ |
| 236 | Hu01G06 IGHV1-18 F1 Heavy Chain $CDR_2$ |
| 15 | Hu01G06 IGHV1-18 F1 Heavy Chain $CDR_3$ |
| 247 | Hu01G06 IGHV1-18 F2 Heavy Chain Variable Region - nucleic acid |
| 248 | Hu01G06 IGHV1-18 F2 Heavy Chain Variable Region - protein |

TABLE 19-continued

| SEQ. ID NO. | Nucleic Acid or Protein |
|---|---|
| 1 | Hu01G06 IGHV1-18 F2 Heavy Chain CDR$_1$ |
| 237 | Hu01G06 IGHV1-18 F2 Heavy Chain CDR$_2$ |
| 15 | Hu01G06 IGHV1-18 F2 Heavy Chain CDR$_3$ |
| 259 | Hu01G06 IGHV1-69 F1 Heavy Chain Variable Region - nucleic acid |
| 250 | Hu01G06 IGHV1-69 F1 Heavy Chain Variable Region - protein |
| 1 | Hu01G06 IGHV1-69 F1 Heavy Chain CDR$_1$ |
| 238 | Hu01G06 IGHV1-69 F1 Heavy Chain CDR$_2$ |
| 15 | Hu01G06 IGHV1-69 F1 Heavy Chain CDR$_3$ |
| 251 | Hu01G06 IGHV1-69 F2 Heavy Chain Variable Region - nucleic acid |
| 252 | Hu01G06 IGHV1-69 F2 Heavy Chain Variable Region - protein |
| 1 | Hu01G06 IGHV1-69 F2 Heavy Chain CDR$_1$ |
| 239 | Hu01G06 IGHV1-69 F2 Heavy Chain CDR$_2$ |
| 15 | Hu01G06 IGHV1-69 F2 Heavy Chain CDR$_3$ |
| 129 | Ch06C11 Chimeric Heavy Chain Variable Region - nucleic acid |
| 46 | Ch06C11 Chimeric Heavy Chain Variable Region - protein |
| 4 | Ch06C11 Chimeric Heavy Chain CDR$_1$ |
| 9 | Ch06C11 Chimeric Heavy Chain CDR$_2$ |
| 18 | Ch06C11 Chimeric Heavy Chain CDR$_3$ |
| 67 | HE LM 06C11 IGHV2-70 Heavy Chain Variable Region - nucleic acid |
| 68 | HE LM 06C11 IGHV2-70 Heavy Chain Variable Region - protein |
| 4 | HE LM 06C11 IGHV2-70 Heavy Chain CDR$_1$ |
| 14 | HE LM 06C11 IGHV2-70 Heavy Chain CDR$_2$ |
| 18 | HE LM 06C11 IGHV2-70 Heavy Chain CDR$_3$ |
| 69 | Hu06C11 IGHV2-5 Heavy Chain Variable Region - nucleic acid |
| 70 | Hu06C11 IGHV2-5 Heavy Chain Variable Region - protein |
| 4 | Hu06C11 IGHV2-5 Heavy Chain CDR$_1$ |
| 9 | Hu06C11 IGHV2-5 Heavy Chain CDR$_2$ |
| 18 | Hu06C11 IGHV2-5 Heavy Chain CDR$_3$ |
| 131 | Ch14F11 Chimeric Heavy Chain Variable Region - nucleic acid |
| 50 | Ch14F11 Chimeric Heavy Chain Variable Region - protein |
| 5 | Ch14F11 Chimeric Heavy Chain CDR$_1$ |
| 11 | Ch14F11 Chimeric Heavy Chain CDR$_2$ |
| 19 | Ch14F11 Chimeric Heavy Chain CDR$_3$ |
| 71 | Sh14F11 IGHV2-5 Heavy Chain Variable Region - nucleic acid |
| 72 | Sh14F11 IGHV2-5 Heavy Chain Variable Region - protein |
| 5 | Sh14F11 IGHV2-5 Heavy Chain CDR$_1$ |
| 11 | Sh14F11 IGHV2-5 Heavy Chain CDR$_2$ |
| 19 | Sh14F11 IGHV2-5 Heavy Chain CDR$_3$ |
| 73 | Sh14F11 IGHV2-70 Heavy Chain Variable Region - nucleic acid |
| 74 | Sh14F11 IGHV2-70 Heavy Chain Variable Region - protein |
| 5 | Sh14F11 IGHV2-70 Heavy Chain CDR$_1$ |
| 11 | Sh14F11 IGHV2-70 Heavy Chain CDR$_2$ |
| 19 | Sh14F11 IGHV2-70 Heavy Chain CDR$_3$ |
| 133 | Ch01G06 Chimeric Light (kappa) Chain Variable Region - nucleic acid |
| 76 | Ch01G06 Chimeric Light (kappa) Chain Variable Region - protein |
| 21 | Ch01G06 Chimeric Light (kappa) Chain CDR$_1$ |
| 26 | Ch01G06 Chimeric Light (kappa) Chain CDR$_2$ |
| 32 | Ch01G06 Chimeric Light (kappa) Chain CDR$_3$ |
| 89 | Hu01G06 IGKV1-39 Light (kappa) Chain Variable Region - nucleic acid |
| 90 | Hu01G06 IGKV1-39 Light (kappa) Chain Variable Region - protein |
| 21 | Hu01G06 IGKV1-39 Light (kappa) Chain CDR$_1$ |
| 26 | Hu01G06 IGKV1-39 Light (kappa) Chain CDR$_2$ |
| 32 | Hu01G06 IGKV1-39 Light (kappa) Chain CDR$_3$ |
| 91 | Hu01G06 IGKV1-39 S43A V48I Light (kappa) Chain Variable Region - nucleic acid |
| 92 | Hu01G06 IGKV1-39 S43A V48I Light (kappa) Chain Variable Region - protein |
| 21 | Hu01G06 IGKV1-39 S43A V48I Light (kappa) Chain CDR$_1$ |
| 26 | Hu01G06 IGKV1-39 S43A V48I Light (kappa) Chain CDR$_2$ |
| 32 | Hu01G06 IGKV1-39 S43A V48I Light (kappa) Chain CDR$_3$ |
| 93 | Hu01G06 IGKV1-39 V48I Light (kappa) Chain Variable Region - nucleic acid |
| 94 | Hu01G06 IGKV1-39 V48I Light (kappa) Chain Variable Region - protein |
| 21 | Hu01G06 IGKV1-39 V48I Light (kappa) Chain CDR$_1$ |
| 26 | Hu01G06 IGKV1-39 V48I Light (kappa) Chain CDR$_2$ |
| 32 | Hu01G06 IGKV1-39 V48I Light (kappa) Chain CDR$_3$ |
| 91 | Hu01G06 IGKV1-39 F1 Light (kappa) Chain Variable Region - nucleic acid |
| 92 | Hu01G06 IGKV1-39 F1 Light (kappa) Chain Variable Region - protein |
| 21 | Hu01G06 IGKV1-39 F1 Light (kappa) Chain CDR$_1$ |
| 26 | Hu01G06 IGKV1-39 F1 Light (kappa) Chain CDR$_2$ |
| 32 | Hu01G06 IGKV1-39 F1 Light (kappa) Chain CDR$_3$ |
| 253 | Hu01G06 IGKV1-39 F2 Light (kappa) Chain Variable Region - nucleic acid |
| 254 | Hu01G06 IGKV1-39 F2 Light (kappa) Chain Variable Region - protein |
| 21 | Hu01G06 IGKV1-39 F2 Light (kappa) Chain CDR$_1$ |
| 26 | Hu01G06 IGKV1-39 F2 Light (kappa) Chain CDR$_2$ |
| 244 | Hu01G06 IGKV1-39 F2 Light (kappa) Chain CDR$_3$ |
| 135 | Ch06C11 Chimeric Light (kappa) Chain Variable Region - nucleic acid |
| 82 | Ch06C11 Chimeric Light (kappa) Chain Variable Region - protein |
| 23 | Ch06C11 Chimeric Light (kappa) Chain CDR$_1$ |
| 28 | Ch06C11 Chimeric Light (kappa) Chain CDR$_2$ |
| 35 | Ch06C11 Chimeric Light (kappa) Chain CDR$_3$ |

TABLE 19-continued

| SEQ. ID NO. | Nucleic Acid or Protein |
|---|---|
| 95 | Sh06C11 IGKV1-16 Light (kappa) Chain Variable Region - nucleic acid |
| 96 | Sh06C11 IGKV1-16 Light (kappa) Chain Variable Region - protein |
| 23 | Sh06C11 IGKV1-16 Light (kappa) Chain CDR$_1$ |
| 28 | Sh06C11 IGKV1-16 Light (kappa) Chain CDR$_2$ |
| 35 | Sh06C11 IGKV1-16 Light (kappa) Chain CDR$_3$ |
| 137 | Ch14F11 Chimeric Light (kappa) Chain Variable Region - nucleic acid |
| 86 | Ch14F11 Chimeric Light (kappa) Chain Variable Region - protein |
| 23 | Ch14F11 Chimeric Light (kappa) Chain CDR$_1$ |
| 30 | Ch14F11 Chimeric Light (kappa) Chain CDR$_2$ |
| 36 | Ch14F11 Chimeric Light (kappa) Chain CDR$_3$ |
| 97 | Hu14F11 IGKV1-16 Light (kappa) Chain Variable Region - nucleic acid |
| 98 | Hu14F11 IGKV1-16 Light (kappa) Chain Variable Region - protein |
| 23 | Hu14F11 IGKV1-16 Light (kappa) Chain CDR$_1$ |
| 30 | Hu14F11 IGKV1-16 Light (kappa) Chain CDR$_2$ |
| 36 | Hu14F11 IGKV1-16 Light (kappa) Chain CDR$_3$ |

Humanized monoclonal antibody heavy chain CDR sequences (Kabat, Chothia, and IMGT definitions) are shown in Table 20.

TABLE 20

| | CDR1 | CDR2 | CDR3 | Variable Region SEQ ID NO: |
|---|---|---|---|---|
| | | Kabat | | |
| Ch01G06 Chimeric | DYNMD (SEQ ID NO: 1) | QINPNNGGIFFNQKFKG (SEQ ID NO: 7) | EAITTVGAMDY (SEQ ID NO: 15) | 40 |
| Hu01G06 IGHV1-18 | DYNMD (SEQ ID NO: 1) | QINPNNGGIFFNQKFKG (SEQ ID NO: 7) | EAITTVGAMDY (SEQ ID NO: 15) | 54 |
| Hu01G06 IGHV1-69 | DYNMD (SEQ ID NO: 1) | QINPNNGGIFFNQKFKG (SEQ ID NO: 7) | EAITTVGAMDY (SEQ ID NO: 15) | 56 |
| Sh01G06 IGHV1-18 M69L | DYNMD (SEQ ID NO: 1) | QINPNNGGIFFNQKFKG (SEQ ID NO: 7) | EAITTVGAMDY (SEQ ID NO: 15) | 58 |
| Sh01G06 IGHV1-18 M69L K64Q G44S | DYNMD (SEQ ID NO: 1) | QINPNNGGIFFNQKFQG (SEQ ID NO: 13) | EAITTVGAMDY (SEQ ID NO: 15) | 60 |
| Sh01G06 IGHV1-18 M69L K64Q | DYNMD (SEQ ID NO: 1) | QINPNNGGIFFNQKFQG (SEQ ID NO: 13) | EAITTVGAMDY (SEQ ID NO: 15) | 62 |
| Sh01G06 IGHV1-69 T30S I69L | DYNMD (SEQ ID NO: 1) | QINPNNGGIFFNQKFKG (SEQ ID NO: 7) | EAITTVGAMDY (SEQ ID NO: 15) | 64 |
| Sh01G06 IGHV1-69 T30S K64Q I69L | DYNMD (SEQ ID NO: 1) | QINPNNGGIFFNQKFQG (SEQ ID NO: 13) | EAITTVGAMDY (SEQ ID NO: 15) | 66 |
| Hu01G06 IGHV1-18F1 | DYNMD (SEQ ID NO: 1) | QINPYNHLIFFNQKFQG (SEQ ID NO: 236) | EAITTVGAMDY (SEQ ID NO: 15) | 246 |
| Hu01G06 IGHV1-18F2 | DYNMD (SEQ ID NO: 1) | QINPNNGLIFFNQKFQG (SEQ ID NO: 237) | EAITTVGAMDY (SEQ ID NO: 15) | 248 |
| Hu01G06 IGHV1-69F1 | DYNMD (SEQ ID NO: 1) | QINPNNGLIFFNQKFKG (SEQ ID NO: 238) | EAITTVGAMDY (SEQ ID NO: 15) | 250 |
| Hu01G06 IGHV1-69F2 | DYNMD (SEQ ID NO: 1) | QINPYNHLIFFNQKFKG (SEQ ID NO: 239) | EAITTVGAMDY (SEQ ID NO: 15) | 252 |
| Ch06C11 Chimeric | TYGMGVS (SEQ ID NO: 4) | HIYWDDDKRYNPSLKS (SEQ ID NO: 9) | RGYDDYWGY (SEQ ID NO: 18) | 46 |
| HE LM 06C11 IGHV2-70 | TYGMGVS (SEQ ID NO: 4) | HIYWDDDKRYNPSLKT (SEQ ID NO: 14) | RGYDDYWGY (SEQ ID NO: 18) | 68 |
| Hu06C11 IGHV2-5 | TYGMGVS (SEQ ID NO: 4) | HIYWDDDKRYNPSLKS (SEQ ID NO: 9) | RGYDDYWGY (SEQ ID NO: 18) | 70 |

TABLE 20-continued

|  | CDR1 | CDR2 | CDR3 | Variable Region SEQ ID NO: |
|---|---|---|---|---|
| Ch14F11 Chimeric | TYGMGVG (SEQ ID NO: 5) | DIWWDDDKYYNPSLKS (SEQ ID NO: 11) | RGHYSAMDY (SEQ ID NO: 19) | 50 |
| Sh14F11 IGHV2-5 | TYGMGVG (SEQ ID NO: 5) | DIWWDDDKYYNPSLKS (SEQ ID NO: 11) | RGHYSAMDY (SEQ ID NO: 19) | 72 |
| Sh14F11 IGHV2-70 | TYGMGVG (SEQ ID NO: 5) | DIWWDDDKYYNPSLKS (SEQ ID NO: 11) | RGHYSAMDY (SEQ ID NO: 19) | 74 |
| Chothia | | | | |
| Ch01G06 Chimeric | GYTFTDY (SEQ ID NO: 38) | NPNNGG (SEQ ID NO: 143) | EAITTVGAMDY (SEQ ID NO: 15) | 40 |
| Hu0106 IGHV1-18 | GYTFTDY (SEQ ID NO: 38) | NPNNGG (SEQ ID NO: 143) | EAITTVGAMDY (SEQ ID NO: 15) | 54 |
| Hu01G06 IGHV1-69 | GYTFTDY (SEQ ID NO: 38) | NPNNGG (SEQ ID NO: 143) | EAITTVGAMDY (SEQ ID NO: 15) | 56 |
| Sh01G06 IGHV1-18 M69L | GYTFTDY (SEQ ID NO: 38) | NPNNGG (SEQ ID NO: 143) | EAITTVGAMDY (SEQ ID NO: 15) | 58 |
| Sh01G06 IGHV1-18 M69L K64Q G44S | GYTFTDY (SEQ ID NO: 38) | NPNNGG (SEQ ID NO: 143) | EAITTVGAMDY (SEQ ID NO: 15) | 60 |
| Sh01G06 IGHV1-18 M69L K64Q | GYTFTDY (SEQ ID NO: 38) | NPNNGG (SEQ ID NO: 143) | EAITTVGAMDY (SEQ ID NO: 15) | 62 |
| Sh01G06 IGHV1-69 T30S I69L | GYTFSDY (SEQ ID NO: 234) | NPNNGG (SEQ ID NO: 143) | EAITTVGAMDY (SEQ ID NO: 15) | 64 |
| Sh01G06 IGHV1-69 T30S K64Q I69L | GYTFSDY (SEQ ID NO: 234) | NPNNGG (SEQ ID NO: 143) | EAITTVGAMDY (SEQ ID NO: 15) | 66 |
| Hu01G06 IGHV1-18 F1 | GYTFTDY (SEQ ID NO: 38) | NPYNHL (SEQ ID NO: 240) | EAITTVGAMDY (SEQ ID NO: 15) | 246 |
| Hu01G06 IGHV1-18 F2 | GYTFTDY (SEQ ID NO: 38) | NPNNGL (SEQ ID NO: 241) | EAITTVGAMDY (SEQ ID NO: 15) | 248 |
| Hu01G06 IGHV1-69 F1 | GYTFSDY (SEQ ID NO: 234) | NPNNGL (SEQ ID NO: 241) | EAITTVGAMDY (SEQ ID NO: 15) | 250 |
| Hu01G06 IGHV1-69 F2 | GYTFSDY (SEQ ID NO: 234) | NPYNHL (SEQ ID NO: 240) | EAITTVGAMDY (SEQ ID NO: 15) | 252 |
| Ch06C11 Chimeric | GFSLNTYGM (SEQ ID NO: 132) | YWDDD (SEQ ID NO: 145) | RGYDDYWGY (SEQ ID NO: 18) | 46 |
| HE LM 06C11 IGHV2-70 | GFSLNTYGM (SEQ ID NO: 132) | YWDDD (SEQ ID NO: 145) | RGYDDYWGY (SEQ ID NO: 18) | 68 |
| Hu06C11 IGHV2-5 | GFSLNTYGM (SEQ ID NO: 132) | YWDDD (SEQ ID NO: 145) | RGYDDYWGY (SEQ ID NO: 18) | 70 |
| Ch14F11 Chimeric | GFSLSTYGM (SEQ ID NO: 130) | WWDDD (SEQ ID NO: 146) | RGHYSAMDY (SEQ ID NO: 19) | 50 |
| Sh14F11 IGHV2-5 | GFSLSTYGM (SEQ ID NO: 130) | WWDDD (SEQ ID NO: 146) | RGHYSAMDY (SEQ ID NO: 19) | 72 |
| Sh14F11 IGHV2-70 | GFSLSTYGM (SEQ ID NO: 130) | WWDDD (SEQ ID NO: 146) | RGHYSAMDY (SEQ ID NO: 19) | 74 |
| IMGT | | | | |
| Ch01G06 Chimeric | GYTFTDYN (SEQ ID NO: 136) | INPNNGGI (SEQ ID NO: 148) | AREAITTVGAMDY (SEQ ID NO: 154) | 40 |
| Hu01G06 IGHV1-18 | GYTFTDYN (SEQ ID NO: 136) | INPNNGGI (SEQ ID NO: 148) | AREAITTVGAMDY (SEQ ID NO: 154) | 54 |

TABLE 20-continued

|  | CDR1 | CDR2 | CDR3 | Variable Region SEQ ID NO: |
|---|---|---|---|---|
| Hu01G06 IGHV1-69 | GYTFTDYN (SEQ ID NO: 136) | INPNNGGI (SEQ ID NO: 148) | AREAITTVGAMDY (SEQ ID NO: 154) | 56 |
| Sh01G06 IGHV1-18 M69L | GYTFTDYN (SEQ ID NO: 136) | INPNNGGI (SEQ ID NO: 148) | AREAITTVGAMDY (SEQ ID NO: 154) | 58 |
| Sh01G06 IGHV1-18 M69L K64Q G44S | GYTFTDYN (SEQ ID NO: 136) | INPNNGGI (SEQ ID NO: 148) | AREAITTVGAMDY (SEQ ID NO: 154) | 60 |
| Sh01G06 IGHV1-18 M69L K64Q | GYTFTDYN (SEQ ID NO: 136) | INPNNGGI (SEQ ID NO: 148) | AREAITTVGAMDY (SEQ ID NO: 154) | 62 |
| Sh01G06 IGHV1-69 T30S I69L | GYTFSDYN (SEQ ID NO: 235) | INPNNGGI (SEQ ID NO: 148) | AREAITTVGAMDY (SEQ ID NO: 154) | 64 |
| Sh01G06 IGHV1-69 T30S K64Q I69L | GYTFSDYN (SEQ ID NO: 235) | INPNNGGI (SEQ ID NO: 148) | AREAITTVGAMDY (SEQ ID NO: 154) | 66 |
| Hu01G06 IGHV1-18 F1 | GYTFTDYN (SEQ ID NO: 136) | INPYNHLI (SEQ ID NO: 242) | AREAITTVGAMDY (SEQ ID NO: 154) | 246 |
| Hu01G06 IGHV1-18 F2 | GYTFTDYN (SEQ ID NO: 136) | INPNNGLI (SEQ ID NO: 243) | AREAITTVGAMDY (SEQ ID NO: 154) | 248 |
| Hu01G06 IGHV1-69 F1 | GYTFSDYN (SEQ ID NO: 235) | INPNNGLI (SEQ ID NO: 243) | AREAITTVGAMDY (SEQ ID NO: 154) | 250 |
| Hu01G06 IGHV1-69 F2 | GYTFSDYN (SEQ ID NO: 235) | INPYNHLI (SEQ ID NO: 242) | AREAITTVGAMDY (SEQ ID NO: 154) | 252 |
| Ch06C11 Chimeric | GFSLNTYGMG (SEQ ID NO: 141) | IYWDDDK (SEQ ID NO: 150) | AQRGYDDYWGY (SEQ ID NO: 157) | 46 |
| HE LM 06C11 IGHV2-70 | GFSLNTYGMG (SEQ ID NO: 141) | IYWDDDK (SEQ ID NO: 150) | AQRGYDDYWGY (SEQ ID NO: 157) | 68 |
| Hu06C11 IGHV2-5 | GFSLNTYGMG (SEQ ID NO: 141) | IYWDDDK (SEQ ID NO: 150) | AQRGYDDYWGY (SEQ ID NO: 157) | 70 |
| Ch14F11 Chimeric | GFSLSTYGMG (SEQ ID NO: 140) | IWWDDDK (SEQ ID NO: 152) | ARRGHYSAMDY (SEQ ID NO: 158) | 50 |
| Sh14F11 IGHV2-5 | GFSLSTYGMG (SEQ ID NO: 140) | IWWDDDK (SEQ ID NO: 152) | ARRGHYSAMDY (SEQ ID NO: 158) | 72 |
| Sh14F11 IGHV2-70 | GFSLSTYGMG (SEQ ID NO: 140) | IWWDDDK (SEQ ID NO: 152) | ARRGHYSAMDY (SEQ ID NO: 158) | 74 |

Humanized monoclonal antibody Kappa light chain CDR sequences (Kabat, Chothia, and IMGT definitions) are shown in Table 21.

TABLE 21

|  | CDR1 | CDR2 | CDR3 | Variable Region SEQ ID NO: |
|---|---|---|---|---|
| Kabat/Chothia | | | | |
| Ch01G06 Chimeric | RTSENLHNYLA (SEQ ID NO: 21) | DAKTLAD (SEQ ID NO: 26) | QHFWSSPYT (SEQ ID NO: 32) | 76 |
| Hu01G06 IGKV1-39 | RTSENLHNYLA (SEQ ID NO: 21) | DAKTLAD (SEQ ID NO: 26) | QHFWSSPYT (SEQ ID NO: 32) | 90 |
| Hu01G06 IGKV1-39 S43A V48I (also known as Hu0106 IGKV1-39 F1) | RTSENLHNYLA (SEQ ID NO: 21) | DAKTLAD (SEQ ID NO: 26) | QHFWSSPYT (SEQ ID NO: 32) | 92 |

TABLE 21-continued

| | CDR1 | CDR2 | CDR3 | Variable Region SEQ ID NO: |
|---|---|---|---|---|
| Hu01G06 IGKV1-39 V48I | RTSENLHNYLA (SEQ ID NO: 21) | DAKTLAD (SEQ ID NO: 26) | QHFWSSPYT (SEQ ID NO: 32) | 94 |
| Hu01G06 IGKV1-39 F1 (also known as Hu01G06 IGKV1-39 S43A V48I) | RTSENLHNYLA (SEQ ID NO: 21) | DAKTLAD (SEQ ID NO: 26) | QHFWSSPYT (SEQ ID NO: 32) | 92 |
| Hu01G06 IGKV1-39 F2 | RTSENLHNYLA (SEQ ID NO: 21) | DAKTLAD (SEQ ID NO: 26) | QHFWSDPYT (SEQ ID NO: 244) | 254 |
| Ch06C11 Chimeric | KASQNVGTNVA (SEQ ID NO: 23) | SASYRYS (SEQ ID NO: 28) | QQYNNYPLT (SEQ ID NO: 35) | 82 |
| Sh06C11 IGKV1-16 | KASQNVGTNVA (SEQ ID NO: 23) | SASYRYS (SEQ ID NO: 28) | QQYNNYPLT (SEQ ID NO: 35) | 96 |
| Ch14F11 Chimeric | KASQNVGTNVA (SEQ ID NO: 23) | SPSYRYS (SEQ ID NO: 30) | QQYNSYPHT (SEQ ID NO: 36) | 86 |
| Hu14F11 IGKV1-16 | KASQNVGTNVA (SEQ ID NO: 23) | SPSYRYS (SEQ ID NO: 30) | QQYNSYPHT (SEQ ID NO: 36) | 98 |
| IMGT | | | | |
| Ch01G06 Chimeric | ENLHNY (SEQ ID NO: 160) | DAK | QHFWSSPYT (SEQ ID NO: 32) | 76 |
| Hu01G06 IGKV1-39 | ENLHNY (SEQ ID NO: 160) | DAK | QHFWSSPYT (SEQ ID NO: 32) | 90 |
| Hu01G06 IGKV1-39 S43A V48I (also known as Hu01G06 IGKV1-39 F1) | ENLHNY (SEQ ID NO: 160) | DAK | QHFWSSPYT (SEQ ID NO: 32) | 92 |
| Hu01G06 IGKV1-39 V48I | ENLHNY (SEQ ID NO: 160) | DAK | QHFWSSPYT (SEQ ID NO: 32) | 94 |
| Hu01G06 IGKV1-39 F1 (also known as Hu01G06 IGKV1-39 S43A V48I) | ENLHNY (SEQ ID NO: 160) | DAK | QHFWSSPYT (SEQ ID NO: 32) | 92 |
| Hu01G06 IGKV1-39 F2 | ENLHNY (SEQ ID NO: 160) | DAK | QHFWSDPYT (SEQ ID NO: 244) | 254 |
| Ch06C11 Chimeric | QNVGTN (SEQ ID NO: 162) | SAS | QQYNNYPLT (SEQ ID NO: 35) | 82 |
| Sh06C11 IGKV1-16 | QNVGTN (SEQ ID NO: 162) | SAS | QQYNNYPLT (SEQ ID NO: 35) | 96 |
| Ch14F11 Chimeric | QNVGTN (SEQ ID NO: 162) | SPS | QQYNSYPHT (SEQ ID NO: 36) | 86 |
| Hu14F11 IGKV1-16 | QNVGTN (SEQ ID NO: 162) | SPS | QQYNSYPHT (SEQ ID NO: 36) | 98 |

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence. A complete kappa chain comprises a kappa variable sequence followed by the human kappa light chain constant sequence.

Nucleic Acid Sequence Encoding the Human IgG1 Heavy Chain Constant Region (SEQ ID NO:171)

```
  1 gcctcaacaa aaggaccaag tgtgttccca ctcgccccta gcagcaagag tacatccggg
 61 ggcactgcag cactcggctg cctcgtcaag gattattttc cagagccagt aaccgtgagc
121 tggaacagtg gagcactcac ttctggtgtc catacttttc ctgctgtcct gcaaagctct
181 ggcctgtact cactcagctc cgtcgtgacc gtgccatctt catctctggg cactcagacc
```

```
241 tacatctgta atgtaaacca caagcctagc aatactaagg tcgataagcg ggtggaaccc 301 aagagctgcg acaagactca cacttgtccc ccatgccctg cccctgaact tctgggcggt 361 cccagcgtct ttttgttccc accaaagcct aaagatactc tgatgataag tagaacaccc 421 gaggtgacat gtgttgttgt agacgtttcc cacgaggacc cagaggttaa gttcaactgg 481 tacgttgatg gagtcgaagt acataatgct aagaccaagc ctagagagga gcagtataat 541 agtacatacc gtgtagtcag tgttctcaca gtgctgcacc aagactggct caacggcaaa 601 gaatacaaat gcaaagtgtc caacaaagca ctcccagccc tatcgagaa gactattagt 661 aaggcaaagg ggcagcctcg tgaaccacag gtgtacactc tgccacccag tagagaggaa 721 atgacaaaga accaagtctc attgacctgc ctggtgaaag gcttctaccc cagcgacatc 781 gccgttgagt gggagagtaa cggtcagcct gagaacaatt acaagacaac cccccagtg 841 ctggatagtg acgggtcttt ctttctgtac agtaagctga ctgtggacaa gtcccgctgg 901 cagcagggta acgtcttcag ctgttccgtg atgcacgagg cattgcacaa ccactacacc 961 cagaagtcac tgagcctgag cccagggaag
```

Protein Sequence Defining the Human IgG1 Heavy Chain
Constant Region (SEQ ID NO:172)

```
  1 astkgpsvfp lapssksts  gtaalgclvk dyfpepvtvs wnsgaltsgv htfpavlqss 61 glyslssvvt vpssslgtqt yicnvnhkps ntkvdkrvep kscdkthtcp pcpapellgg 121 psvflfppkp kdtlmisrtp evtcvvvdvs hedpevkfnw yvdgvevhna ktkpreeqyn 181 styrvvsvlt vlhqdwlngk eykckvsnka lpapiektis kakgqprepq vytlppsree 241 mtknqvsltc lvkgfypsdi avewesngqp ennykttppv ldsdgsffly skltvdksrw 301 qqgnvfscsv mhealhnhyt qkslslspgk
```

Nucleic Acid Sequence Encoding the Human Kappa Light
Chain Constant Region (SEQ ID NO:173)

```
  1 cgcacagttg ctgcccccag cgtgttcatt ttcccaccta gcgatgagca gctgaaaagc 61 ggtactgcct ctgtcgtatg cttgctcaac aactttacc cacgtgaggc taaggtgcag 121 tggaaagtgg ataatgcact tcaatctgga aacagtcaag agtccgtgac agaacaggac 181 agcaaagact caacttattc actctcttcc accctgactc tgtccaaggc agactatgaa 241 aaacacaagg tatacgcctg cgaggttaca caccagggtt tgtctagtcc tgtcaccaag 301 tccttcaata ggggcgaatg t
```

Protein Sequence Defining the Human Kappa Light Chain
Constant Region (SEQ ID NO:174)

```
  1 rtvaapsvfi fppsdeqlks gtasvvclln nfypreakvq wkvdnalqsg nsqesvteqd 61 skdstyslss tltlskadye khkvyacevt hqglsspvtk sfnrgec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length immunoglobulin heavy chain and light chain sequences. It is also contemplated that the variable region sequences can be ligated to other constant region sequences to produce active full length immunoglobulin heavy and light chains.

Nucleic Acid Sequence Encoding the Full Length Ch01G06 Chimeric Heavy Chain (Mouse Heavy Chain Variable Region and Human IgG1 Constant Region) (SEQ ID NO:175)

```
   1 gaagtgttgt tgcagcagtc agggccggag ttggtaaaac cgggagcgtc ggtgaaaatc
  61 ccgtgcaaag cgtcggggta tacgtttacg gactataaca tggattgggt gaaacagtcg
 121 catgggaaat cgcttgaatg gattggtcag atcaatccga ataatggagg aatcttcttt
 181 aatcagaagt ttaaaggaaa agcgacgctt acagtcgata agtcgtcgaa cacggcgttc
 241 atggaagtac ggtcgcttac gtcggaagat acggcggtct attactgtgc gagggaggcg
 301 attacgacgg tgggagcgat ggactattgg ggacaaggga cgtcggtcac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc tatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Ch01G06 Chimeric Heavy Chain (Mouse Heavy Chain Variable Region and Human IgG1 Constant Region) (SEQ ID NO:176)

```
   1 evllqqsgpe lvkpgasvki pckasgytft dynmdwvkqs hgkslewigq inpnnggiff
  61 nqkfkgkatl tvdkssntaf mevrsltsed tavyycarea ittvgamdyw gqgtsvtvss
 121 astkgpsvfp lapsskstsg gtaalgclvk dyfpepvtvs wnsgaltsgv htfpavlqss
 181 glyslssvvt vpssslgtqt yicnvnhkps ntkvdkrvep kscdkthtcp pcpapellgg
 241 psvflfppkp kdtlmisrtp evtcvvvdvs hedpevkfnw yvdgvevhna ktkpreeqyn
 301 styrvvsvlt vlhqdwlngk eykckvsnka lpapiektis kakgqprepq vytlppsree
 361 mtknqvsltc lvkgfypsdi avewesngqp ennykttppv ldsdgsffly skltvdksrw
 421 qqgnvfscsv mhealhnhyt qkslslspgk
```

Nucleic Acid Sequence Encoding the Full Length Hu01G06 IGHV1-18 Heavy Chain (Humanized Heavy Chain Variable Region and Human IgG1 Constant Region) (SEQ ID NO:177)

```
   1 caagtgcaac ttgtgcagtc gggtgcggaa gtcaaaaagc cgggagcgtc ggtgaaagta
  61 tcgtgtaaag cgtcgggata tacgtttacg gactataaca tggactgggt acgacaggca
 121 ccggggaaat cgttggaatg gatcggacag attaatccga acaatggggg aattttcttt
 181 aatcagaaat tcaaaggacg ggcgacgttg acggtcgata catcgacgaa tacggcgtat
 241 atggaattga ggtcgcttcg ctcggacgat acggcggtct attactgcgc cagggaggcg
 301 atcacgacgg taggggcgat ggattattgg ggacagggga cgcttgtgac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-18 Heavy Chain (Humanized Heavy Chain Variable Region and Human IgG1 Constant Region) (SEQ ID NO:178)

```
  1 qvqlvqsgae vkkpgasvkv sckasgytft dynmdwvrqa pgkslewigq inpnnggiff
 61 nqkfkgratl tvdtstntay melrslrsdd tavyycarea ittvgamdyw gqgtlvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-69 Heavy Chain (Humanized Heavy Chain Variable Region and Human IgG1 Constant Region) (SEQ ID NO:179)

```
   1 caagtccagc ttgtccagtc gggagcggaa gtgaagaaac cggggtcgtc ggtcaaagta
  61 tcgtgtaaag cgtcgggata tacgtttacg gactataaca tggattgggt acgacaggct
 121 ccgggaaaat cattggaatg gattggacag attaatccga ataatggggg tatcttcttt
 181 aatcaaaagt ttaaagggag gcgacgttg acggtggaca atcgacaaa tacggcgtat
 241 atggaattgt cgtcgcttcg gtcggaggac acggcggtgt attactgcgc gagggaggcg
 301 atcacgacgg tcggggcgat ggattattgg gacagggaa cgcttgtgac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt cttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-69 Heavy Chain (Humanized Heavy Chain Variable Region and Human IgG1 Constant Region) (SEQ ID NO:180)

```
  1 qvqlvqsgae vkkpgssvkv sckasgytft dynmdwvrqa pgkslewigq inpnnggiff
 61 nqkfkgratl tvdkstntay melsslrsed tavyycarea ittvgamdyw gqgtlvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh01G06 IGHV1-18 M69L Heavy Chain (Humanized Heavy Chain Variable Region and Human IgG1 Constant Region) (SEQ ID NO:181)

```
   1 caggtccagc ttgtgcaatc gggagcggaa gtgaagaaac cgggagcgtc ggtaaaagtc
  61 tcgtgcaaag cgtcggggta tacgtttacg gactataaca tggactgggt gcgccaagcg
 121 cctggacagg gtcttgaatg gatggggcag attaatccga ataatggagg gatcttcttt
 181 aatcagaaat tcaaaggaag ggtaacgctg acgacagaca cgtcaacatc gacggcctat
 241 atggaattgc ggtcgttgcg atcagatgat acggcggtct actattgtgc gagggaggcg
 301 attacgacgg tgggagcgat ggattattgg ggacagggga cgttggtaac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt cttcctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh01G06 IGHV1-18 M69L Heavy Chain (Humanized Heavy Chain Variable Region and Human IgG1 Constant Region) (SEQ ID NO:182)

```
   1 qvqlvqsgae vkkpgasvkv sckasgytft dynmdwvrqa pgqglewmgq inpnnggiff
  61 nqkfkgrvtl ttdtststay melrslrsdd tavyycarea ittvgamdyw gqgtlvtvss
 121 astkgpsvfp lapsskstsg gtaalgclvk dyfpepvtvs wnsgaltsgv htfpavlqss
 181 glyslssvvt vpssslgtqt yicnvnhkps ntkvdkrvep kscdkthtcp pcpapellgg
 241 psvflfppkp kdtlmisrtp evtcvvvdvs hedpevkfnw yvdgvevhna ktkpreeqyn
 301 styrvvsvlt vlhqdwlngk eykckvsnka lpapiektis kakgqprepq vytlppsree
 361 mtknqvsltc lvkgfypsdi avewesngqp ennykttppv ldsdgsffly skltvdksrw
 421 qqgnvfscsv mhealhnhyt qkslslspgk
```

Nucleic Acid Sequence Encoding the Full Length Sh01G06 IGHV1-18 M69L K64Q G44S Heavy Chain (Humanized Heavy Chain Variable Region and Human IgG1 Constant Region) (SEQ ID NO:183)

```
   1 caggtccagc ttgtgcaatc gggagcggaa gtgaagaaac cgggagcgtc ggtaaaagtc
  61 tcgtgcaaag cgtcggggta tacgtttacg gactataaca tggactgggt gcgccaagcg
 121 cctggacaga gccttgaatg gatggggcag attaatccga ataatggagg gatcttcttt
 181 aatcagaaat tccagggaag ggtaacgctg acgacagaca cgtcaacatc gacggcctat
 241 atggaattgc ggtcgttgcg atcagatgat acggcggtct actattgtgc gagggaggcg
 301 attacgacgg tgggagcgat ggattattgg ggacagggga cgttggtaac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh01G06 IGHV1-18 M69L K64Q G44S Heavy Chain (Humanized Heavy Chain Variable Region and Human IgG1 Constant Region) (SEQ ID NO:184)

```
   1 qvqlvqsgae vkkpgasvkv sckasgytft dynmdwvrqa pgqslewmgq inpnnggiff
  61 nqkfqgrvtl ttdtststay melrslrsdd tavyycarea ittvgamdyw gqgtlvtvss
 121 astkgpsvfp lapsskstsg gtaalgclvk dyfpepvtvs wnsgaltsgv htfpavlqss
 181 glyslssvvt vpssslgtqt yicnvnhkps ntkvdkrvep kscdkthtcp pcpapellgg
 241 psvflfppkp kdtlmisrtp evtcvvvdvs hedpevkfnw yvdgvevhna ktkpreeqyn
 301 styrvvsvlt vlhqdwlngk eykckvsnka lpapiektis kakgqprepq vytlppsree
 361 mtknqvsltc lvkgfypsdi avewesngqp ennykttppv ldsdgsffly skltvdksrw
 421 qqgnvfscsv mhealhnhyt qkslslspgk
```

Nucleic Acid Sequence Encoding the Full Length Sh01G06 IGHV1-18 M69L K64Q Heavy Chain (Humanized Heavy Chain Variable Region and Human IgG1 Constant Region) (SEQ ID NO: 185)

```
   1 caggtccagc ttgtgcaatc gggagcggaa gtgaagaaac cgggagcgtc ggtaaaagtc
  61 tcgtgcaaag cgtcggggta tacgtttacg gactataaca tggactgggt gcgccaagcg
 121 cctggacagg gtcttgaatg gatggggcag attaatccga ataatggagg gatcttcttt
 181 aatcagaaat tccagggaag ggtaacgctg acgacagaca cgtcaacatc gacggcctat
 241 atggaattgc ggtcgttgcg atcagatgat acggcggtct actattgtgc gagggaggcg
 301 attacgacgg tgggagcgat ggattattgg ggacagggga cgttggtaac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh01G06 IGHV1-18 M69L K64Q Heavy Chain (Humanized Heavy Chain Variable Region and Human IgG1 Constant Region) (SEQ ID NO:186)

```
  1 qvqlvqsgae vkkpgasvkv sckasgytft dynmdwvrqa pgqglewmgq inpnnggiff
 61 nqkfqgrvtl ttdtststay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh01G06 IGHV1-69 T30S I69L Heavy Chain (Humanized Heavy Chain Variable Region and Human IgG1 Constant Region) (SEQ ID NO:187)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccga ataatggggg aatcttttc
 181 aatcagaagt ttaaagggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg gggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh01G06 IGHV1-69 T30S I69L Heavy Chain (Humanized Heavy Chain Variable Region and Human IgG1 Constant Region) (SEQ ID NO:188)

```
   1 qvqlvqsgae vkkpgssvkv sckasgytfs dynmdwvrqa pgqglewmgq inpnnggiff
  61 nqkfkgrvtl tadkststay melsslrsed tavyycarea ittvgamdyw gqgtivtvss
 121 astkgpsvfp lapsskstsg gtaalgclvk dyfpepvtvs wnsgaltsgv htfpavlqss
 181 glyslssvvt vpssslgtqt yicnvnhkps ntkvdkrvep kscdkthtcp pcpapellgg
 241 psvflfppkp kdtlmisrtp evtcvvvdvs hedpevkfnw yvdgvevhna ktkpreeqyn
 301 styrvvsvlt vlhqdwlngk eykckvsnka lpapiektis kakgqprepq vytlppsree
 361 mtknqvsltc lvkgfypsdi avewesngqp ennykttppv ldsdgsffly skltvdksrw
 421 qqgnvfscsv mhealhnhyt qkslslspgk
```

Nucleic Acid Sequence Encoding the Full Length Sh01G06 IGHV1-69 T30S K64Q I69L Heavy Chain (Humanized Heavy Chain Variable Region and Human IgG1 Constant Region) (SEQ ID NO: 189)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccga ataatggggg aatcttttc
 181 aatcagaagt ttcaggggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg ggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh01G06 IGHV1-69 T30S K64Q I69L Heavy Chain (Humanized Heavy Chain Variable Region and Human IgG1 Constant Region) (SEQ ID NO:190)

```
   1 qvqlvqsgae vkkpgssvkv sckasgytfs dynmdwvrqa pgqglewmgq inpnnggiff
  61 nqkfqgrvtl tadkststay melsslrsed tavyycarea ittvgamdyw gqgtivtvss
 121 astkgpsvfp lapsskstsg gtaalgclvk dyfpepvtvs wnsgaltsgv htfpavlqss
 181 glyslssvvt vpssslgtqt yicnvnhkps ntkvdkrvep kscdkthtcp pcpapellgg
 241 psvflfppkp kdtlmisrtp evtcvvvdvs hedpevkfnw yvdgvevhna ktkpreeqyn
 301 styrvvsvlt vlhqdwlngk eykckvsnka lpapiektis kakgqprepq vytlppsree
 361 mtknqvsltc lvkgfypsdi avewesngqp ennykttppv ldsdgsffly skltvdksrw
 421 qqgnvfscsv mhealhnhyt qkslslspgk
```

Nucleic Acid Sequence Encoding the Full Length Hu01G06 IGHV1-18 F1 Heavy Chain (Humanized Heavy Chain Variable Region and Human IgG1 Constant Region) (SEQ ID NO:255)

```
   1 caggtccagc ttgtgcaatc gggagcggaa gtgaagaaac cgggagcgtc ggtaaaagtc
  61 tcgtgcaaag cgtcggggta tacgtttacg gactataaca tggactgggt gcgccaagcg
 121 cctggacaga gccttgaatg gatggggcag attaatccgt acaatcacct gatcttcttt
 181 aatcagaaat tccagggaag ggtaacgctg acgacagaca cgtcaacatc gacggcctat
 241 atggaattgc ggtcgttgcg atcagatgat acggcggtct actattgtgc gagggaggcg
 301 attacgacgg tgggagcgat ggattattgg ggacagggga cgttggtaac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc tgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-18 F1 Heavy Chain (Humanized Heavy Chain Variable Region and Human IgG1 Constant Region) (SEQ ID NO:256)

```
  1 qvqlvqsgae vkkpgasvkv sckasgytft dynmdwvrqa pgqslewmgq inpynhliff
 61 nqkfqgrvtl ttdtststay melrslrsdd tavyycarea ittvgamdyw gqgtivtvss
121 astkgpsvfp lapssкstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-18 F2 Heavy Chain (Humanized Heavy Chain Variable Region and Human IgG1 Constant Region) (SEQ ID NO:257)

```
   1 caggtccagc ttgtgcaatc gggagcggaa gtgaagaaac cgggagcgtc ggtaaaagtc
  61 tcgtgcaaag cgtcggggta tacgtttacg gactataaca tggactgggt gcgccaagcg
 121 cctggacaga gccttgaatg gatggggcag attaatccga ataatggact gatcttcttt
 181 aatcagaaat tccagggaag ggtaacgctg acgacagaca cgtcaacatc gacggcctat
 241 atggaattgc ggtcgttgcg atcagatgat acggcggtct actattgtgc gagggaggcg
 301 attacgacgg tgggagcgat ggattattgg ggacagggga cgttggtaac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-18 F2 Heavy Chain (Humanized Heavy Chain Variable Region and Human IgG1 Constant Region) (SEQ ID NO:258)

```
  1 qvqlvqsgae vkkpgasvkv sckasgytft dynmdwvrqa pgqslewmgq inpnngliff
 61 nqkfqgrvtl ttdtststay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-69 F1 Heavy Chain (Humanized Heavy Chain Variable Region and Human IgG1 Constant Region) (SEQ ID NO:259)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccga ataatgggct gatcttttc
 181 aatcagaagt ttaaagggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg gggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-69 F1 Heavy Chain (Humanized Heavy Chain Variable Region and Human IgG1 Constant Region) (SEQ ID NO:260)

```
  1 qvqlvqsgae vkkpgssvkv sckasgytfs dynmdwvrqa pgqglewmgq inpnngliff
 61 nqkfkgrvtl tadkststay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-69 F2 Heavy Chain (Humanized Heavy Chain Variable Region and Human IgG1 Constant Region) (SEQ ID NO:261)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccgt acaatcacct gatcttttc
 181 aatcagaagt ttaaagggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg gggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-69 F2 Heavy Chain (Humanized Heavy Chain Variable Region and Human IgG1 Constant Region) (SEQ ID NO:262)

```
   1 qvqlvqsgae vkkpgssvkv sckasgytfs dynmdwvrqa pgqglewmgq inpynhliff
  61 nqkfkgrvtl tadkststay melsslrsed tavyycarea ittvgamdyw gqgtivtvss
 121 astkgpsvfp lapsskstsg gtaalgclvk dyfpepvtvs wnsgaltsgv htfpavlqss
 181 glyslssvvt vpssslgtqt yicnvnhkps ntkvdkrvep kscdkthtcp pcpapellgg
 241 psvflfppkp kdtlmisrtp evtcvvvdvs hedpevkfnw yvdgvevhna ktkpreeqyn
 301 styrvvsvlt vlhqdwlngk eykckvsnka lpapiektis kakgqprepq vytlppsree
 361 mtknqvsltc lvkgfypsdi avewesngqp ennykttppv ldsdgsffly skltvdksrw
 421 qqgnvfscsv mhealhnhyt qkslslspgk
```

Nucleic Acid Sequence Encoding the Full Length Ch06C11 Chimeric Heavy Chain (Mouse Heavy Chain Variable Region and Human IgG1 Constant Region) (SEQ ID NO:191)

```
   1 caggtgacac tcaaagaatc aggacccgga atccttcagc ccagccagac cttgtcgctg
  61 acttgttcgt tctccggttt cagcctgaat acttatggga tgggtgtgtc atggatcagg
 121 caaccgtccg ggaaaggatt ggagtggctc gcgcacatct actgggacga tgacaaacgc
 181 tacaatcctt cgctgaagag ccgattgacg atttccaagg atgcctcgaa caaccgggta
 241 tttcttaaga tcacgtcggt cgatacggca gacacggcga cctattactg cgcccaaaga
 301 gggtacgatg actattgggg atattggggc caggggacac tcgtcacaat ttcagctgcc
 361 tcaacaaaag gaccaagtgt gttcccactc gcccctagca gcaagagtac atccgggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttcccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc cagcccccta tcgagaagac tattagtaag
1021 gcaaaggggc agcctcgtga accacaggtg tacactctgc cacccagtag agaggaaatg
1081 acaaagaacc aagtctcatt gacctgcctg gtgaaaggct tctacccag cgacatcgcc
1141 gttgagtggg agagtaacgg tcagcctgag aacaattaca agacaacccc cccagtgctg
1201 gatagtgacg ggtctttctt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

Protein Sequence Defining the Full Length Ch06C11 Chimeric Heavy Chain (Mouse Heavy Chain Variable Region and Human IgG1 Constant Region) (SEQ ID NO:192)

```
   1 qvtlkesgpg ilqpsqtlsl tcsfsgfsln tygmgvswir qpsgkglewl ahiywdddkr
  61 ynpslksrlt iskdasnnry flkitsvdta dtatyycaqr gyddywgywg qgtivtisaa
 121 stkgpsvfpl apsskstsgg taalgclvkd yfpepvtvsw nsgaltsgvh tfpavlqssg
 181 lyslssvvtv pssslgtqty icnvnhkpsn tkvdkrvepk scdkthtcpp cpapellggp
 241 svflfppkpk dtlmisrtpe vtcvvvdvsh edpevkfnwy vdgvevhnak tkpreeqyns
 301 tyrvvsvltv lhqdwlngke ykckvsnkal papiektisk akgqprepqv ytlppsreem
 361 tknqvsltcl vkgfypsdia vewesngqpe nnykttppvl dsdgsfflys kltvdksrwq
 421 qgnvfscsvm healhnhytq kslslspgk
```

Nucleic Acid Sequence Encoding the Full Length HE LM 06C11 IGHV2-70 Heavy Chain (Humanized Heavy Chain Variable Region and Human IgG1 Constant Region) (SEQ ID NO:193)

```
   1 caggtgactt tgaaagaatc cggtcccgca ttggtaaagc caacccagac acttacgctc
  61 acatgtacat tttccggatt cagcttgaac acttacggga tgggagtgtc gtggattcgg
 121 caacctccgg ggaaggctct ggagtggctg gcgcacatct actgggatga tgacaaaagg
 181 tataacccct cacttaaaac gagactgacg atctcgaagg acacaagcaa gaatcaggtc
 241 gtcctcacga ttacgaatgt agacccggtg gatactgccg tctattactg cgcgcaacgc
 301 gggtatgatg actactgggg atattggggt cagggcaccc tcgtgaccat ctcgtcagcc
 361 tcaacaaaag gaccaagtgt gttcccactc gcccctagca gcaagagtac atccgggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc ccagccccta tcgagaagac tattagtaag
1021 gcaaaggggc agcctcgtga accacaggtg tacactctgc cacccagtag agaggaaatg
1081 acaaagaacc aagtctcatt gacctgcctg gtgaaaggct tctaccccag cgacatcgcc
1141 gttgagtggg agagtaacgg tcagcctgag aacaattaca agacaacccc cccagtgctg
1201 gatagtgacg gtctttcttt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

Protein Sequence Defining the Full Length HE LM 06C11 IGHV2-70 Heavy Chain (Humanized Heavy Chain Variable Region and Human IgG1 Constant Region) (SEQ ID NO:194)

```
   1 qvtlkesgpa lvkptqtltl tctfsgfsln tygmgvswir qppgkalewl ahiywdddkr
  61 ynpslktrlt iskdtsknqv vltitnvdpv dtavyycaqr gyddywgywg qgtivtissa
 121 stkgpsvfpl apsskstsgg taalgclvkd yfpepvtvsw nsgaltsgvh tfpavlqssg
 181 lyslssvvtv pssslgtqty icnvnhkpsn tkvdkrvepk scdkthtcpp cpapellggp
 241 svflfppkpk dtlmisrtpe vtcvvvdvsh edpevkfnwy vdgvevhnak tkpreeqyns
 301 tyrvvsvltv lhqdwlngke ykckvsnkal papiektisk akgqprepqv ytlppsreem
 361 tknqvsltcl vkgfypsdia vewesngqpe nnykttppvl dsdgsfflys kltvdksrwq
 421 qgnvfscsvm healhnhytq kslslspgk
```

Nucleic Acid Sequence Encoding the Full Length Hu06C11 IGHV2-5 Heavy Chain (Humanized Heavy Chain Variable Region and Human IgG1 Constant Region) (SEQ ID NO:195)

```
   1 caagtaacgc tcaaggagtc cggacccacc ttggtgaagc cgacgcagac cttgactctt
  61 acgtgcactt tctcggggtt ttcactgaat acgtacggga tgggtgtctc atggatcagg
 121 caacctccgg ggaaaggatt ggaatggctg cgcacatct actgggatga cgataagaga
 181 tataacccaa gcctcaagtc gcggctcacc attacaaaag atacatcgaa aaatcaggtc
 241 gtacttacta tcacgaacat ggaccccgtg dacacagcaa catattactg tgcccagcgc
 301 ggctatgacg attattgggg ttactgggga cagggaacac tggtcacggt gtccagcgcc
 361 tcaacaaaag gaccaagtgt gttcccactc gcccctagca gcaagagtac atccgggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttcccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc ccagccccta tcgagaagac tattagtaag
1021 gcaaaggggc agcctcgtga accacaggtg tacactctgc cacccagtag agaggaaatg
1081 acaaagaacc aagtctcatt gacctgcctg gtgaaaggct ctaccccag cgacatcgcc
1141 gttgagtggg agagtaacgg tcagcctgag aacaattaca agacaaccc cccagtgctg
1201 gatagtgacg gtctttctt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

Protein Sequence Defining the Full Length Hu06C11 IGHV2-5 Heavy Chain (Humanized Heavy Chain Variable Region and Human IgG1 Constant Region) (SEQ ID NO:196)

```
   1 qvtlkesgpt lvkptqtltl tctfsgfsln tygmgvswir qppgkglewl ahiywdddkr
  61 ynpslksrlt itkdtsknqv vltitnmdpv dtatyycaqr gyddywgywg qgtlvtvssa
 121 stkgpsvfpl apssktsgg taalgclvkd yfpepvtvsw nsgaltsgvh tfpavlqssg
 181 lyslssvvtv pssslgtqty icnvnhkpsn tkvdkrvepk scdkthtcpp cpapellggp
 241 svflfppkpk dtlmisrtpe vtcvvvdvsh edpevkfnwy vdgvevhnak tkpreeqyns
 301 tyrvvsvltv lhqdwlngke ykckvsnkal papiektisk akgqprepqv ytlppsreem
 361 tknqvsltcl vkgfypsdia vewesngqpe nnykttppvl dsdgsfflys kltvdksrwq
 421 qgnvfscsvm healhnhytq kslslspgk
```

Nucleic Acid Sequence Encoding the Full Length Ch14F11 Chimeric Heavy Chain (Mouse Heavy Chain Variable Region and Human IgG1 Constant Region) (SEQ ID NO:197)

```
   1 caggtcacgc tgaaagagtc aggtcccgga atccttcaac cttcgcagac attgtcactc
  61 acatgttcct tctccgggtt ctcgctctcg acttatggca tgggtgtagg atggattcgg
 121 cagcccagcg ggaagggct tgagtggttg gcggatatct ggtgggacga cgacaaatac
 181 tacaatccga gcctgaagtc ccgcctcacc atttcgaaag atacgtcatc aaacgaagtc
 241 tttttgaaga tcgccatcgt ggacacggcg gatacagcga cgtattactg cgccagaagg
 301 ggacactaca gcgcaatgga ttattgggga caggggacct cggtgactgt gtcgtccgcc
 361 tcaacaaaag gaccaagtgt gttcccactc gcccctagca gcaagagtac atccgggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttcccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc ccagccccta tcgagaagac tattagtaag
1021 gcaaaggggc agcctcgtga accacaggtg tacactctgc cacccagtag agaggaaatg
1081 acaaagaacc aagtctcatt gacctgcctg gtgaaaggct tctacccag cgacatcgcc
1141 gttgagtggg agagtaacgg tcagcctgag aacaattaca agacaacccc cccagtgctg
1201 gatagtgacg ggtctttctt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

Protein Sequence Defining the Full Length Ch14F11 Chimeric Heavy Chain (Mouse Heavy Chain Variable Region and Human IgG1 Constant Region) (SEQ ID NO:198)

```
   1 qvtlkesgpg ilqpsqtlsl tcsfsgfsls tygmgvgwir qpsgkglewl adiwwdddky
  61 ynpslksrlt iskdtssnev flkiaivdta dtatyycarr ghysamdywg qgtsvtvssa
 121 stkgpsvfpl apsskstsgg taalgclvkd yfpepvtvsw nsgaltsgvh tfpavlqssg
 181 lyslssvvtv pssslgtqty icnvnhkpsn tkvdkrvepk scdkthtcpp cpapellggp
 241 svflfppkpk dtlmisrtpe vtcvvvdvsh edpevkfnwy vdgvevhnak tkpreeqyns
 301 tyrvvsvltv lhqdwlngke ykckvsnkal papiektisk akgqprepqv ytlppsreem
 361 tknqvsltcl vkgfypsdia vewesngqpe nnykttppvl dsdgsfflys kltvdksrwq
 421 qgnvfscsvm healhnhytq kslslspgk
```

Nucleic Acid Sequence Encoding the Full Length Sh14F11 IGHV2-5 Heavy Chain (Humanized Heavy Chain Variable Region and Human IgG1 Constant Region) (SEQ ID NO:199)

```
   1 cagatcactt tgaaagaaag cggaccgacc ttggtcaagc ccacacaaac cctcacgctc
  61 acgtgtacat tttcggggtt ctcgctttca acttacggga tgggagtagg gtggattcgc
 121 cagccgcctg gtaaagcgtt ggagtggctt gcagacatct ggtgggacga cgataagtac
 181 tataatccct cgctcaagtc cagactgacc atcacgaaag atacgagcaa gaaccaggtc
 241 gtgctgacaa tgactaacat ggacccagtg gatacggcta catattactg cgccaggcgg
 301 ggtcactact cagcgatgga ttattgggggc cagggaacac tggtaacggt gtcgtccgcc
 361 tcaacaaaag gaccaagtgt gttcccactc gcccctagca gcaagagtac atccggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttcccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc ccagccccta tcgagaagac tattagtaag
1021 gcaaaggggc agcctcgtga accacaggtg tacactctgc cacccagtag agaggaaatg
1081 acaaagaacc aagtctcatt gacctgcctg gtgaaaggct tctaccccag cgacatcgcc
1141 gttgagtggg agagtaacgg tcagcctgag aacaattaca agacaacccc cccagtgctg
1201 gatagtgacg gtctttctt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

Protein Sequence Defining the Full Length Sh14F11 IGHV2-5 Heavy Chain (Humanized Heavy Chain Variable Region and Human IgG1 Constant Region) (SEQ ID NO:200)

```
   1 qitlkesgpt lvkptqtltl tctfsgfsls tygmgvgwir qppgkalewl adiwwdddky
  61 ynpslksrlt itkdtsknqv vltmtnmdpv dtatyycarr ghysamdywg qgtlvtvssa
 121 stkgpsvfpl apsskstsgg taalgclvkd yfpepvtvsw nsgaltsgvh tfpavlqssg
 181 lyslssvvtv pssslgtqty icnvnhkpsn tkvdkrvepk scdkthtcpp cpapellggp
 241 svflfppkpk dtlmisrtpe vtcvvvdvsh edpevkfnwy vdgvevhnak tkpreeqyns
 301 tyrvvsvltv lhqdwlngke ykckvsnkal papiektisk akgqprepqv ytlppsreem
 361 tknqvsltcl vkgfypsdia vewesngqpe nnykttppvl dsdgsfflys kltvdksrwq
 421 qgnvfscsvm healnhhytq kslslspgk
```

Nucleic Acid Sequence Encoding the Full Length Sh14F11 IGHV2-70 Heavy Chain (Humanized Heavy Chain Variable Region and Human IgG1 Constant Region) (SEQ ID NO:201)

```
   1 caagtgactc tcaaggagtc cggacccgcc ctggtcaaac caacgcagac actgacgctc
  61 acatgcacct tcagcggatt ttcgttgtca acgtacggca tgggtgtggg gtggattcgc
 121 cagcctccgg ggaaagccct tgaatggttg gcggacatct ggtgggatga tgacaagtac
 181 tataatccct cacttaagtc acggttgacg atctcgaaag acaccagcaa gaaccaggta
 241 gtgctgacaa tgactaacat ggacccggtc gatacagcgg tctactattg tgctagaagg
 301 ggacactact ccgcaatgga ttattggggt caggggacgc tcgtaaccgt gtcgtcggcc
 361 tcaacaaaag gaccaagtgt gttcccactc gcccctagca gcaagagtac atccgggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttcccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc ccagccccta tcgagaagac tattagtaag
1021 gcaaaggggc agcctcgtga accacaggtg tacactctgc cacccagtag agaggaaatg
1081 acaaagaacc aagtctcatt gacctgcctg gtgaaaggct tctacccag cgacatcgcc
1141 gttgagtggg agagtaacgg tcagcctgag aacaattaca agacaacccc cccagtgctg
1201 gatagtgacg ggtctttctt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

Protein Sequence Defining the Full Length Sh14F11 IGHV2-70 Heavy Chain (Humanized Heavy Chain Variable Region and Human IgG1 Constant Region) (SEQ ID NO:202)

```
  1 qvtlkesgpa lvkptqtltl tctfsgfsls tygmgvgwir qppgkalewl adiwwdddky
 61 ynpslksrlt iskdtsknqv vltmtnmdpv dtavyycarr ghysamdywg qgtlvtvssa
121 stkgpsvfpl apsskstsgg taalgclvkd yfpepvtvsw nsgaltsgvh tfpavlqssg
181 lyslssvvtv psslgtqty icnvnhkpsn tkvdkrvepk scdkthtcpp cpapellggp
241 svflfppkpk dtlmisrtpe vtcvvvdvsh edpevkfnwy vdgvevhnak tkpreeqyns
301 tyrvvsvltv lhqdwlngke ykckvsnkal papiektisk akgqprepqv ytlppsreem
361 tknqvsltcl vkgfypsdia vewesngqpe nnykttppvl dsdgsfflys kltvdksrwq
421 qgnvfscsvm healhnhytq kslslspgk
```

Nucleic Acid Sequence Encoding the Full Length Ch01G06 Chimeric Light Chain (Mouse Kappa Chain Variable Region and Human Kappa Constant Region) (SEQ ID NO:203)

```
  1   gacatccaaa tgacccagtc acccgcgagc ctttcggcgt cggtcggaga aacggtcacg
 61   atcacgtgcc ggacatcaga gaatctccat aactacctcg cgtggtatca acagaagcag
121   gggaagtcgc cccagttgct tgtatacgat gcgaaaacgt tggcggatgg ggtgccgtcc
181   agattctcgg gatcgggctc ggggacgcag tactcgctca agatcaattc gctgcagccg
241   gaggactttg gtcgtacta ttgtcagcat ttttggtcat caccgtatac atttggaggt
301   ggaacgaaac ttgagattaa gcgcacagtt gctgcccca gcgtgttcat tttcccacct
361   agcgatgagc agctgaaaag cggtactgcc tctgtcgtat gcttgctcaa caacttttac
421   ccacgtgagg ctaaggtgca gtggaaagtg gataatgcac ttcaatctgg aaacagtcaa
481   gagtccgtga cagaacagga cagcaaagac tcaacttatt cactctcttc caccctgact
541   ctgtccaagg cagactatga aaacacaag gtatacgcct gcgaggttac acaccagggt
601   ttgtctagtc ctgtcaccaa gtccttcaat aggggcgaat gt
```

Protein Sequence Defining the Full Length Ch01G06 Chimeric Light Chain (Mouse Kappa Chain Variable Region and Human Kappa Constant Region) (SEQ ID NO:204)

```
  1   diqmtqspas lsasvgetvt itcrtsenlh nylawyqqkq gkspqllvyd aktladgvps
 61   rfsgsgsgtq yslkinslqp edfgsyycqh fwsspytfgg gtkleikrtv aapsvfifpp
121   sdeqlksgta svvcllnnfy preakvqwkv dnalqsgnsq esvteqdskd styslsstlt
181   lskadyekhk vyacevthqg lsspvtksfn rgec
```

Nucleic Acid Sequence Encoding the Full Length Hu01G06 IGKV1-39 Light Chain (Humanized Kappa Chain Variable Region and Human Kappa Constant Region) (SEQ ID NO:205)

```
  1   gacatccaaa tgacccagtc gccgtcgtcg ctttcagcgt cggtagggga tcgggtcaca
 61   attacgtgcc gaacgtcaga gaatttgcat aactacctcg cgtggtatca gcagaagccc
121   gggaagtcac cgaaactcct tgtctacgat gcgaaaacgc tggcggatgg agtgccgtcg
181   agattctcgg gaagcggatc cggtacggac tatacgctta cgatctcatc gctccagccc
241   gaggactttg cgacgtacta ttgtcagcat ttttggtcgt cgccctacac atttgggcag
301   gggaccaagt tggaaatcaa gcgcacagtt gctgcccca gcgtgttcat tttcccacct
361   agcgatgagc agctgaaaag cggtactgcc tctgtcgtat gcttgctcaa caacttttac
421   ccacgtgagg ctaaggtgca gtggaaagtg gataatgcac ttcaatctgg aaacagtcaa
481   gagtccgtga cagaacagga cagcaaagac tcaacttatt cactctcttc caccctgact
541   ctgtccaagg cagactatga aaacacaag gtatacgcct gcgaggttac acaccagggt
601   ttgtctagtc ctgtcaccaa gtccttcaat aggggcgaat gt
```

Protein Sequence Defining the Full Length Hu01G06 IGKV1-39 Light Chain (Humanized Kappa Chain Variable Region and Human Kappa Constant Region) (SEQ ID NO:206)

```
  1  diqmtqspss lsasvgdrvt itcrtsenlh nylawyqqkp gkspkllvyd aktladgvps
 61  rfsgsgsgtd ytltisslqp edfatyycqh fwsspytfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Hu01G06 IGKV1-39 S43A V48I Light Chain (Humanized Kappa Chain Variable Region and Human Kappa Constant Region) (Also Referred to Herein as the Full Length Hu01G06 IGFV1-39 F1 Light Chain; SEQ ID NO:207)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaaggccc cgaaactcct tatctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgt cgccctacac atttgggcag
301  gggaccaagt tggaaatcaa gcgcacagtt gctgccccca gcgtgttcat tttcccacct
361  agcgatgagc agctgaaaag cggtactgcc tctgtcgtat gcttgctcaa caactttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Hu01G06 IGKV1-39 S43A V48I Light Chain (Humanized Kappa Chain Variable Region and Human Kappa Constant Region) (Also Referred to Herein as the Full Length Hu01G06 IGFV1-39 F1 Light Chain; SEQ ID NO:208)

```
  1  diqmtqspss lsasvgdrvt itcrtsenlh nylawyqqkp gkapklliyd aktladgvps
 61  rfsgsgsgtd ytltisslqp edfatyycqh fwsspytfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Hu01G06 IGKV1-39 V48I Light Chain (Humanized Kappa Chain Variable Region and Human Kappa Constant Region) (SEQ ID NO:209)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaagtcac cgaaactcct tatctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgt cgccctacac atttgggcag
301  gggaccaagt tggaaatcaa gcgcacagtt gctgccccca gcgtgttcat tttcccacct
```

```
361  agcgatgagc agctgaaaag cggtactgcc tctgtcgtat gcttgctcaa caactttac 421  ccacgtgagg ctaaggtgca gtggaaagtg gataatgcac ttcaatctgg aaacagtcaa 481  gagtccgtga cagaacagga cagcaaagac tcaacttatt cactctcttc caccctgact 541  ctgtccaagg cagactatga aaaacacaag gtatacgcct gcgaggttac acaccagggt 601  ttgtctagtc ctgtcaccaa gtccttcaat aggggcgaat gt
```

Protein Sequence Defining the Full Length Hu01G06 IGKV1-39 V48I Light Chain (Humanized Kappa Chain Variable Region and Human Kappa Constant Region) (SEQ ID NO:210)

```
  1  diqmtqspss lsasvgdrvt itcrtsenlh nylawyqqkp gkspklliyd aktladgvps 61  rfsgsgsgtd ytltisslqp edfatyycqh fwsspytfgq gtkleikrtv aapsvfifpp 121  sdeqlksgta svvcllnnfy preakvqwkv dnalqsgnsq esvteqdskd styslsstlt 181  lskadyekhk vyacevthqg lsspvtksfn rgec
```

Nucleic Acid Sequence Encoding the Full Length Hu01G06 IGKV1-39 F1 Light Chain (Humanized Kappa Chain Variable Region and Human Kappa Constant Region) (Also Referred to Herein as the Full Length Hu01G06 IGKV1-39 S43A V48I Light Chain; SEQ ID NO:207)

```
  1  gacatccaaa tgacccagtc gccgtcgtcg ctttcagcgt cggtagggga tcgggtcaca 61  attacgtgcc gaacgtcaga gaatttgcat aactacctcg cgtggtatca gcagaagccc 121  gggaaggccc cgaaactcct tatctacgat gcgaaaacgc tggcggatgg agtgccgtcg 181  agattctcgg gaagcggatc cggtacggac tatacgctta cgatctcatc gctccagccc 241  gaggactttg cgacgtacta ttgtcagcat ttttggtcgt cgccctacac atttgggcag 301  gggaccaagt tggaaatcaa agcacagtt gctgccccca gcgtgttcat tttcccacct 361  agcgatgagc agctgaaaag cggtactgcc tctgtcgtat gcttgctcaa caactttac 421  ccacgtgagg ctaaggtgca gtggaaagtg gataatgcac ttcaatctgg aaacagtcaa 481  gagtccgtga cagaacagga cagcaaagac tcaacttatt cactctcttc caccctgact 541  ctgtccaagg cagactatga aaaacacaag gtatacgcct gcgaggttac acaccagggt 601  ttgtctagtc ctgtcaccaa gtccttcaat aggggcgaat gt
```

Protein Sequence Defining the Full Length Hu01G06 IGKV1-39 F1 Light Chain (Humanized Kappa Chain Variable Region and Human Kappa Constant Region) (Also Referred to Herein as the Full Length Hu01G06 IGKV1-39 S43A V48I Light Chain; SEQ ID NO:208)

```
  1    diqmtqspss lsasvgdrvt itcrtsenlh nylawyqqkp gkapklliyd aktladgvps 61    rfsgsgsgtd ytltisslqp edfatyycqh fwsspytfgq gtkleikrtv aapsvfifpp 121    sdeqlksgta svvcllnnfy preakvqwkv dnalqsgnsq esvteqdskd styslsstlt 181    lskadyekhk vyacevthqg lsspvtksfn rgec
```

Nucleic Acid Sequence Encoding the Full Length Hu01G06 IGKV1-39 F2 Light Chain (Humanized Kappa Chain Variable Region and Human Kappa Constant Region) (SEQ ID NO:263)

```
  1  gacatccaaa tgacccagtc gccgtcgtcg ctttcagcgt cggtagggga tcgggtcaca
 61  attacgtgcc gaacgtcaga gaatttgcat aactacctcg cgtggtatca gcagaagccc
121  gggaagtcac cgaaactcct tatctacgat gcgaaaacgc tggcggatgg agtgccgtcg
181  agattctcgg gaagcggatc cggtacggac tatacgctta cgatctcatc gctccagccc
241  gaggactttg cgacgtacta ttgtcagcat ttttggtcgg accccatac atttgggcag
301  gggaccaagt tggaaatcaa cgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Hu01G06 IGKV1-39 F2 Light Chain (Humanized Kappa Chain Variable Region and Human Kappa Constant Region) (SEQ ID NO:264)

```
  1  diqmtqspss lsasvgdrvt itcrtsenlh nylawyqqkp gkspklliyd aktladgvps
 61  rfsgsgsgtd ytltisslqp edfatyycqh fwsdpytfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Ch06C11 Chimeric Light Chain (Mouse Kappa Chain Variable Region and Human Kappa Constant Region) (SEQ ID NO:211)

```
  1  gatatcgtca tgacccagtc ccagaagttc atgtcaactt cagtgggaga cagagtgtcc
 61  gtcacatgta agcctcgca aaatgtggga accaacgtag cgtggttcca gcagaaacct
121  ggccaatcac cgaaggcact gatctactcg gccagctata ggtactcggg agtaccagat
181  cggtttacgg ggtcggggag cgggacggac tttatcctca ctatttccaa tgtccagtcg
241  gaggaccttg cggaatactt ctgccagcag tataacaact atcccctcac gtttggtgct
301  ggtacaaaat tggagttgaa gcgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Ch06C11 Chimeric Light Chain (Mouse Kappa Chain Variable Region and Human Kappa Constant Region) (SEQ ID NO:212)

```
  1  divmtqsqkf mstsvgdrvs vtckasqnvg tnvawfqqkp gqspkaliys asyrysgvpd
 61  rftgsgsgtd filtisnvqs edlaeyfcqq ynnypltfga gtklelkrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Sh06C11 IGKV1-16 Light Chain (Humanized Kappa Chain Variable Region and Human Kappa Constant Region) (SEQ ID NO:213)

```
  1  gacatccaaa tgacccaatc gccctcctcc ctctccgcat cagtagggga ccgcgtcaca
 61  attacttgca aagcgtcgca gaacgtcgga acgaatgtgg cgtggtttca gcagaagccc
121  ggaaaagctc cgaagagctt gatctactcg gcctcatata ggtattcggg tgtgccgagc
181  cggtttagcg gtcggggtc aggtactgat ttcacgctca caatttcatc gttgcagcca
241  gaagatttcg ccacatatta ctgtcagcag tacaacaatt accctctgac gttcggccag
301  ggaaccaaac ttgagatcaa gcgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat agggcgaat gt
```

Protein Sequence Defining the Full Length Sh06C11 IGKV1-16 Light Chain (Humanized Kappa Chain Variable Region and Human Kappa Constant Region) (SEQ ID NO:214)

```
  1  diqmtqspss lsasvgdrvt itckasqnvg tnvawfqqkp gkapksliys asyrysgvps
 61  rfsgsgsgtd ftltisslqp edfatyycqq ynnypltfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Ch14F11 Chimeric Light Chain (Mouse Kappa Chain Variable Region and Human Kappa Constant Region) (SEQ ID NO:215)

```
  1  gacatcgtga tgacacagtc acagaaattc atgtccacat ccgtcggtga tagagtatcc
 61  gtcacgtgta aggcctcgca aaacgtagga actaatgtgg cgtggtatca acagaagcca
121  ggacagtcac ccaaagcact catctacagc ccctcatatc ggtacagcgg ggtgccggac
181  aggttcacgg gatcggggag cgggaccgat tttacactga ccatttcgaa tgtccagtcg
241  gaggaccttg cggaatactt ctgccagcag tataactcgt accctcacac gtttggaggt
301  ggcactaagt tggagatgaa acgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
```

Protein Sequence Defining the Full Length Ch14F11 Chimeric Light Chain (Mouse Kappa Chain Variable Region and Human Kappa Constant Region) (SEQ ID NO:216)

```
  1  divmtqsqkf mstsvgdrvs vtckasqnvg tnvawyqqkp gqspkaliys psyrysgvpd
 61  rftgsgsgtd ftltisnvqs edlaeyfcqq ynsyphtfgg gtklemkrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Hu14F11 IGKV1-16 Light Chain (Humanized Kappa Chain Variable Region and Human Kappa Constant Region) (SEQ ID NO:217)

```
  1  gatatccaga tgacacagtc accctcgtcg ctctcagctt ccgtaggcga cagggtcact
 61  attacgtgta aagcatcaca gaacgtcgga acgaatgtgg cgtggtttca gcagaagccc
121  gggaagagcc ccaaagcgct tatctactcc ccgtcgtatc ggtattccgg tgtgccaagc
181  agattttcgg ggtcaggttc gggaactgac tttacccctga ccatctcgtc cctccaaccg
241  gaagatttcg ccacgtactt ctgccagcag tacaacagct atcctcacac attcggacaa
301  gggacaaagt tggagattaa acgcacagtt gctgccccca gcgtgttcat ttttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Hu14F11 IGKV1-16 Light Chain (Humanized Kappa Chain Variable Region and Human Kappa Constant Region) (SEQ ID NO:218)

```
  1  diqmtqspss lsasvgdrvt itckasqnvg tnvawfqqkp gkspkaliys psyrysgvps
 61  rfsgsgsgtd ftltisslqp edfatyfcqq ynsyphtfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Table 22 is a concordance chart showing the SEQ ID NO. of each sequence discussed in this Example.

TABLE 22

| SEQ ID NO. | Nucleic Acid or Protein |
|---|---|
| 171 | Human IgG1 constant - nucleic acid |
| 172 | Human IgG1 constant - protein |
| 173 | Human Kappa constant - nucleic acid |
| 174 | Human Kappa constant - protein |
| 175 | Humanized Ch01G06 Chimeric Heavy Human Variable + Human IgG1 constant - nucleic acid |
| 176 | Humanized Ch01G06 Chimeric Heavy Human Variable + Human IgG1 constant - protein |
| 177 | Humanized Hu01G06 IGHV1-18 Heavy Human Variable + Human IgG1 constant - nucleic acid |

TABLE 22-continued

| SEQ ID NO. | Nucleic Acid or Protein |
|---|---|
| 178 | Humanized Hu01G06 IGHV1-18 Heavy Human Variable + Human IgG1 constant - protein |
| 179 | Humanized Hu01G06 IGHV1-69 Heavy Human Variable + Human IgG1 constant - nucleic acid |
| 180 | Humanized Hu01G06 IGHV1-69 Heavy Human Variable + Human IgG1 constant - protein |
| 181 | Humanized Sh01G06 IGHV1-18 M69L Heavy Human Variable + Human IgG1 constant - nucleic acid |
| 182 | Humanized Sh01G06 IGHV1-18 M69L Heavy Human Variable + Human IgG1 constant - protein |
| 183 | Humanized Sh01G06 IGHV1-18 M69L K64Q G44S Heavy Human Variable + Human IgG1 constant - nucleic acid |
| 184 | Humanized Sh01G06 IGHV1-18 M69L K64Q G44S Heavy Human Variable + Human IgG1 constant - protein |
| 185 | Humanized Sh01G06 IGHV1-18 M69L K64Q Heavy Human Variable + Human IgG1 constant - nucleic acid |
| 186 | Humanized Sh01G06 IGHV1-18 M69L K64Q Heavy Human Variable + Human IgG1 constant - protein |
| 187 | Humanized Sh01G06 IGHV1-69 T30S I69L Heavy Human Variable + Human IgG1 constant - nucleic acid |
| 188 | Humanized Sh01G06 IGHV1-69 T30S I69L Heavy Human Variable + Human IgG1 constant - protein |
| 189 | Humanized Sh01G06 IGHV1-69 T30S K64Q I69L Heavy Human Variable + Human IgG1 constant - nucleic acid |
| 190 | Humanized Sh01G06 IGHV1-69 T30S K64Q I69L Heavy Human Variable + Human IgG1 constant - protein |
| 255 | Humanized Hu01G06 IGHV1-18 F1 Heavy Human Variable + Human IgG1 constant - nucleic acid |
| 256 | Humanized Hu01G06 IGHV1-18 F1 Heavy Human Variable + Human IgG1 constant - protein |
| 257 | Humanized Hu01G06 IGHV1-18 F2 Heavy Human Variable + Human IgG1 constant - nucleic acid |
| 258 | Humanized Hu01G06 IGHV1-18 F2 Heavy Human Variable + Human IgG1 constant - protein |
| 259 | Humanized Hu01G06 IGHV1-69 F1 Heavy Human Variable + Human IgG1 constant - nucleic acid |
| 260 | Humanized Hu01G06 IGHV1-69 F1 Heavy Human Variable + Human IgG1 constant - protein |
| 261 | Humanized Hu01G06 IGHV1-69 F2 Heavy Human Variable + Human IgG1 constant - nucleic acid |
| 262 | Humanized Hu01G06 IGHV1-69 F2 Heavy Human Variable + Human IgG1 constant - protein |
| 191 | Humanized Ch06C11 Chimeric Heavy Human Variable + Human IgG1 constant - nucleic acid |
| 192 | Humanized Ch06C11 Chimeric Heavy Human Variable + Human IgG1 constant - protein |
| 193 | Humanized HE LM 06C11 IGHV2-70 Heavy Human Variable + Human IgG1 constant - nucleic acid |
| 194 | Humanized HE LM 06C11 IGHV2-70 Heavy Human Variable + Human IgG1 constant - protein |
| 195 | Humanized Hu06C11 IGHV2-5 Heavy Human Variable + Human IgG1 constant - nucleic acid |
| 196 | Humanized Hu06C11 IGHV2-5 Heavy Human Variable + Human IgG1 constant - protein |
| 197 | Humanized Ch14F11 Chimeric Heavy Human Variable + Human IgG1 constant - nucleic acid |
| 198 | Humanized Ch14F11 Chimeric Heavy Human Variable + Human IgG1 constant - protein |
| 199 | Humanized Sh14F11 IGHV2-5 Heavy Human Variable + Human IgG1 constant - nucleic acid |
| 200 | Humanized Sh14F11 IGHV2-5 Heavy Human Variable + Human IgG1 constant - protein |
| 201 | Humanized Sh14F11-IGHV2-70 Heavy Human Variable + Human IgG1 constant - nucleic acid |
| 202 | Humanized Sh14F11-IGHV2-70 Heavy Human Variable + Human IgG1 constant - protein |
| 203 | Humanized Ch01G06 Chimeric Human Variable + Human Kappa constant - nucleic acid |
| 204 | Humanized Ch01G06 Chimeric Human Variable + Human Kappa constant - protein |
| 205 | Humanized Hu01G06 IGKV1-39 Human Variable + Human Kappa constant - nucleic acid |
| 206 | Humanized Hu01G06 IGKV1-39 Human Variable + Human Kappa constant - protein |
| 207 | Humanized Hu01G06 IGKV1-39 S43A V48I Human Variable + Human Kappa constant - nucleic acid |
| 208 | Humanized Hu01G06 IGKV1-39 S43A V48I Human Variable + Human Kappa constant - protein |
| 209 | Humanized Hu01G06 IGKV1-39 V48I Human Variable + Human Kappa constant - nucleic acid |
| 210 | Humanized Hu01G06 IGKV1-39 V48I Human Variable + Human Kappa constant - protein |
| 207 | Humanized Hu01G06 IGKV1-39 F1 Human Variable + Human Kappa constant - nucleic acid |
| 208 | Humanized Hu01G06 IGKV1-39 F1 Human Variable + Human Kappa constant - protein |
| 263 | Humanized Hu01G06 IGKV1-39 F2 Human Variable + Human Kappa constant - nucleic acid |
| 264 | Humanized Hu01G06 IGKV1-39 F2 Human Variable + Human Kappa constant - protein |
| 211 | Humanized Ch06C11 Chimeric Human Variable + Human Kappa constant - nucleic acid |
| 212 | Humanized Ch06C11 Chimeric Human Variable + Human Kappa constant - protein |
| 213 | Humanized Sh06C11 IGKV1-16 Human Variable + Human Kappa constant - nucleic acid |
| 214 | Humanized Sh06C11 IGKV1-16 Human Variable + Human Kappa constant - protein |
| 215 | Humanized Ch14F11 Chimeric Human Variable + Human Kappa constant - nucleic acid |
| 216 | Humanized Ch14F11 Chimeric Human Variable + Human Kappa constant - protein |
| 217 | Humanized Hu14F11 IGKV1-16 Human Variable + Human Kappa constant - nucleic acid |
| 218 | Humanized Hu14F11 IGKV1-16 Human Variable + Human Kappa constant - protein |

Table 23 below shows antibodies containing chimeric immunoglobulin heavy and light chains and exemplary combinations of the full-length chimeric or humanized immunoglobulin heavy and light chains.

TABLE 23

| Antibody Name | Light Chain | Heavy Chain |
|---|---|---|
| Hu01G06-1 | Humanized Ch01G06 Chimeric Human Variable + Human Kappa constant (SEQ ID NO: 204) | Humanized Ch01G06 Chimeric Heavy Human Variable + Human IgG1 constant (SEQ ID NO: 176) |
| Hu01G06-46 | Humanized Hu01G06 IGKV1-39 Human Variable + Human Kappa constant (SEQ ID NO: 206) | Humanized Hu01G06 IGHV1-18 Heavy Human Variable + Human IgG1 constant (SEQ ID NO: 178) |
| Hu01G06-52 | Humanized Hu01G06 IGKV1-39 Human Variable + Human Kappa constant (SEQ ID NO: 206) | Humanized Hu01G06 IGHV1-69 Heavy Human Variable + Human IgG1 constant (SEQ ID NO: 180) |
| Hu01G06-100 | Humanized Hu01G06 IGKV1-39 Human Variable + Human Kappa constant (SEQ ID NO: 206) | Humanized Sh01G06 IGHV1-18 M69L Heavy Human Variable + Human IgG1 constant (SEQ ID NO: 182) |

TABLE 23-continued

| Antibody Name | Light Chain | Heavy Chain |
|---|---|---|
| Hu01G06-101 | Humanized Hu01G06 IGKV1-39 Human Variable + Human Kappa constant (SEQ ID NO: 206) | Humanized Sh01G06 IGHV1-18 M69L K64Q Heavy Human Variable + Human IgG1 constant (SEQ ID NO: 186) |
| Hu01G06-102 | Humanized Hu01G06 IGKV1-39 Human Variable + Human Kappa constant (SEQ ID NO: 206) | Humanized Sh01G06 IGHV1-18 M69L K64Q G44S Heavy Human Variable + Human IgG1 constant (SEQ ID NO: 184) |
| Hu01G06-103 | Humanized Hu01G06 IGKV1-39 Human Variable + Human Kappa constant (SEQ ID NO: 206) | Humanized Sh01G06 IGHV1-69 T30S I69L Heavy Human Variable + Human IgG1 constant (SEQ ID NO: 188) |
| Hu01G06-104 | Humanized Hu01G06 IGKV1-39 Human Variable + Human Kappa constant (SEQ ID NO: 206) | Humanized Sh01G06 IGHV1-69 T30S K64Q I69L Heavy Human Variable + Human IgG1 constant (SEQ ID NO: 190) |
| Hu01G06-105 | Humanized Hu01G06 IGKV1-39 V48I Human Variable + Human Kappa constant (SEQ ID NO: 210) | Humanized Sh01G06 IGHV1-18 M69L Heavy Human Variable + Human IgG1 constant (SEQ ID NO: 182) |
| Hu01G06-106 | Humanized Hu01G06 IGKV1-39 V48I Human Variable + Human Kappa constant (SEQ ID NO: 210) | Humanized Sh01G06 IGHV1-18 M69L K64Q Heavy Human Variable + Human IgG1 constant (SEQ ID NO: 186) |
| Hu01G06-107 | Humanized Hu01G06 IGKV1-39 V48I Human Variable + Human Kappa constant (SEQ ID NO: 210) | Humanized Sh01G06 IGHV1-18 M69L K64Q G44S Heavy Human Variable + Human IgG1 constant (SEQ ID NO: 184) |
| Hu01G06-108 | Humanized Hu01G06 IGKV1-39 V48I Human Variable + Human Kappa constant (SEQ ID NO: 210) | Humanized Sh01G06 IGHV1-69 T30S I69L Heavy Human Variable + Human IgG1 constant (SEQ ID NO: 188) |
| Hu01G06-109 | Humanized Hu01G06 IGKV1-39 V48I Human Variable + Human Kappa constant (SEQ ID NO: 210) | Humanized Sh01G06 IGHV1-69 T30S K64Q I69L Heavy Human Variable + Human IgG1 constant (SEQ ID NO: 190) |
| Hu01G06-110 | Humanized Hu01G06 IGKV1-39 S43A V48I Human Variable + Human Kappa constant (SEQ ID NO: 208) | Humanized Sh01G06 IGHV1-18 M69L Heavy Human Variable + Human IgG1 constant (SEQ ID NO: 182) |
| Hu01G06-111 | Humanized Hu01G06 IGKV1-39 S43A V48I Human Variable + Human Kappa constant (SEQ ID NO: 208) | Humanized Sh01G06 IGHV1-18 M69L K64Q Heavy Human Variable + Human IgG1 constant (SEQ ID NO: 186) |
| Hu01G06-112 | Humanized Hu01G06 IGKV1-39 S43A V48I Human Variable + Human Kappa constant (SEQ ID NO: 208) | Humanized Sh01G06 IGHV1-18 M69L K64Q G44S Heavy Human Variable + Human IgG1 constant (SEQ ID NO: 184) |
| Hu01G06-113 | Humanized Hu01G06 IGKV1-39 S43A V48I Human Variable + Human Kappa constant (SEQ ID NO: 208) | Humanized Sh01G06 IGHV1-69 T30S I69L Heavy Human Variable + Human IgG1 constant (SEQ ID NO: 188) |
| Hu01G06-114 | Humanized Hu01G06 IGKV1-39 S43A V48I Human Variable + Human Kappa constant (SEQ ID NO: 208) | Humanized Sh01G06 IGHV1-69 T30S K64Q I69L Heavy Human Variable + Human IgG1 constant (SEQ ID NO: 190) |
| Hu01G06-122 | Humanized Hu01G06 IGKV1-39 F1 Human Variable + Human Kappa constant (SEQ ID NO: 208) | Humanized Hu01G06 IGHV1-18 F1 Heavy Human Variable + Human IgG1 constant (SEQ ID NO: 256) |
| Hu01G06-127 | Humanized Hu01G06 IGKV1-39 F2 Human Variable + Human Kappa constant (SEQ ID NO: 264) | Humanized Hu01G06 IGHV1-18 F2 Heavy Human Variable + Human IgG1 constant (SEQ ID NO: 258) |
| Hu01G06-135 | Humanized Hu01G06 IGKV1-39 F1 Human Variable + Human Kappa constant (SEQ ID NO: 208) | Humanized Hu01G06 IGHV1-69 F1 Heavy Human Variable + Human IgG1 constant (SEQ ID NO: 260) |
| Hu01G06-138 | Humanized Hu01G06 IGKV1-39 F1 Human Variable + Human Kappa constant (SEQ ID NO: 208) | Humanized Hu01G06 IGHV1-69 F2 Heavy Human Variable + Human IgG1 constant (SEQ ID NO: 262) |
| Hu01G06-146 | Humanized Hu01G06 IGKV1-39 F2 Human Variable + Human Kappa constant (SEQ ID NO: 264) | Humanized Hu01G06 IGHV1-69 F2 Heavy Human Variable + Human IgG1 constant (SEQ ID NO: 262) |
| Hu06C11-1 | Humanized Ch06C11 Chimeric Human Variable + Human Kappa constant (SEQ ID NO: 212) | Humanized Ch06C11 Chimeric Heavy Human Variable + Human IgG1 constant (SEQ ID NO: 176) |
| Hu06C11-27 | Humanized Sh06C11 IGKV1-16 Human Variable + Human Kappa constant (SEQ ID NO: 214) | Humanized HE LM 06C11 IGHV2-70 Heavy Human Variable + Human IgG1 constant (SEQ ID NO: 194) |
| Hu06C11-30 | Humanized Sh06C11 IGKV1-16 Human Variable + Human Kappa constant (SEQ ID NO: 214) | Humanized Hu06C11 IGHV2-5 Heavy Human Variable + Human IgG1 constant (SEQ ID NO: 196) |
| Hu14F11-1 | Humanized Ch14F11 Chimeric Human Variable + Human Kappa constant (SEQ ID NO: 216) | Humanized Ch14F11 Chimeric Heavy Human Variable + Human IgG1 constant (SEQ ID NO: 198) |
| Hu14F11-23 | Humanized Ch14F11 Chimeric Human Variable + Human Kappa constant (SEQ ID NO: 216) | Humanized Ch06C11 Chimeric Heavy Human Variable + Human IgG1 constant (SEQ ID NO: 192) |
| Hu14F11-24 | Humanized Ch06C11 Chimeric Human Variable + Human Kappa constant (SEQ ID NO: 212) | Humanized Ch14F11 Chimeric Heavy Human Variable + Human IgG1 constant (SEQ ID NO: 198) |
| Hu14F11-39 | Humanized Hu14F11 IGKV1-16 Human Variable + Human Kappa constant (SEQ ID NO: 218) | Humanized Sh14F11 IGHV2-5 Heavy Human Variable + Human IgG1 constant (SEQ ID NO: 200) |

TABLE 23-continued

| Antibody Name | Light Chain | Heavy Chain |
| --- | --- | --- |
| Hu14F11-47 | Humanized Hu14F11 IGKV1-16 Human Variable + Human Kappa constant (SEQ ID NO: 218) | Humanized Sh14F11-IGHV2-70 Heavy Human Variable + Human IgG1 constant (SEQ ID NO: 202) |

The antibody constructs containing the full length chimeric heavy and light chains are designated below:

Chimeric 01G06 (Hu01G06-1)=Full Length Ch01G06 Chimeric Heavy Chain (Mouse Heavy Chain Variable Region and Human IgG1 Constant Region) (SEQ ID NO:176) plus Full Length Ch01G06 Chimeric Light Chain (Mouse Kappa Chain Variable Region and Human Kappa Constant Region) (SEQ ID NO:204)

Chimeric 06C11 (Hu06C11-1)=Full Length Ch06C11 Chimeric Heavy Chain (Mouse Heavy Chain Variable Region and Human IgG1 Constant Region) (SEQ ID NO:192) plus Full Length Ch06C11 Chimeric Light Chain (Mouse Kappa Chain Variable Region and Human Kappa Constant Region) (SEQ ID NO:212)

Chimeric 14F11 (Hu14F11-1)=Full Length Ch14F11 Chimeric Heavy Chain (Mouse Heavy Chain Variable Region and Human IgG1 Constant Region) (SEQ ID NO:198) plus Full Length Ch4F11 Chimeric Light Chain (Mouse Kappa Chain Variable Region and Human Kappa Constant Region) (SEQ ID NO:216)

Fifteen of the possible antibody constructs containing the full length immunoglobulin heavy and light chains containing humanized variable regions are designated below:

Hu01G06-46=Full Length Hu01G06 IGHV1-18 Heavy Chain (Humanized Heavy Chain Variable Region and Human IgG1 Constant Region) (SEQ ID NO:178) plus Full Length Hu01G06 IGKV1-39 Light Chain (Humanized Kappa Chain Variable Region and Human Kappa Constant Region) (SEQ ID NO:206)

Hu01G06-52=Full Length Hu01G06 IGHV1-69 Heavy Chain (Humanized Heavy Chain Variable Region and Human IgG1 Constant Region) (SEQ ID NO:180) plus Full Length Hu01G06 IGKV1-39 Light Chain (Humanized Kappa Chain Variable Region and Human Kappa Constant Region) (SEQ ID NO:206)

Hu01G06-107=Full Length Sh01G06 IGHV1-18 M69L K64Q G44S Heavy Chain (Humanized Heavy Chain Variable Region and Human IgG1 Constant Region) (SEQ ID NO:184) plus Full Length Hu01G06 IGKV1-39 V48I Light Chain (Humanized Kappa Chain Variable Region and Human Kappa Constant Region) (SEQ ID NO:210)

Hu01G06-108=Full Length Sh01G06 IGHV1-69 T30S I69L Heavy Chain (Humanized Heavy Chain Variable Region and Human IgG1 Constant Region) (SEQ ID NO:188) plus Full Length Hu01G06 IGKV1-39 V48I Light Chain (Humanized Kappa Chain Variable Region and Human Kappa Constant Region) (SEQ ID NO:210)

Hu01G06-112=Full Length Sh01G06 IGHV1-18 M69L K64Q G44S Heavy Chain (Humanized Heavy Chain Variable Region and Human IgG1 Constant Region) (SEQ ID NO:184) plus Full Length Hu01G06 IGKV1-39 S43A V48I Light Chain (Humanized Kappa Chain Variable Region and Human Kappa Constant Region) (SEQ ID NO:208)

Hu01G06-113=Full Length Sh01G06 IGHV1-69 T30S I69L Heavy Chain (Humanized Heavy Chain Variable Region and Human IgG1 Constant Region) (SEQ ID NO:188) plus Full Length Hu01G06 IGKV1-39 S43A V48I Light Chain (Humanized Kappa Chain Variable Region and Human Kappa Constant Region) (SEQ ID NO:208)

Hu01G06-122=Full Length Hu01G06 IGHV1-18 F1 Heavy Chain (Humanized Heavy Chain Variable Region and Human IgG1 Constant Region) (SEQ ID NO:256) plus Full Length Hu01G06 IGKV1-39 F1 Light Chain (Humanized Kappa Chain Variable Region and Human Kappa Constant Region) (SEQ ID NO:208)

Hu01G06-127=Full Length Hu01G06 IGHV1-18 F2 Heavy Chain (Humanized Heavy Chain Variable Region and Human IgG1 Constant Region) (SEQ ID NO:258) plus Full Length Hu01G06 IGKV1-39 F2 Light Chain (Humanized Kappa Chain Variable Region and Human Kappa Constant Region) (SEQ ID NO:264)

Hu01G06-135=Full Length Hu01G06 IGHV1-69 F1 Heavy Chain (Humanized Heavy Chain Variable Region and Human IgG1 Constant Region) (SEQ ID NO:260) plus Full Length Hu01G06 IGKV1-39 F1 Light Chain (Humanized Kappa Chain Variable Region and Human Kappa Constant Region) (SEQ ID NO:208)

Hu01G06-138=Full Length Hu01G06 IGHV1-69 F2 Heavy Chain (Humanized Heavy Chain Variable Region and Human IgG1 Constant Region) (SEQ ID NO:262) plus Full Length Hu01G06 IGKV1-39 F1 Light Chain (Humanized Kappa Chain Variable Region and Human Kappa Constant Region) (SEQ ID NO:208)

Hu01G06-146=Full Length Hu01G06 IGHV1-69 F2 Heavy Chain (Humanized Heavy Chain Variable Region and Human IgG1 Constant Region) (SEQ ID NO:262) plus Full Length Hu01G06 IGKV1-39 F2 Light Chain (Humanized Kappa Chain Variable Region and Human Kappa Constant Region) (SEQ ID NO:264)

Hu06C11-27=Full Length HE LM 06C11 IGHV2-70 Heavy Chain (Humanized Heavy Chain Variable Region and Human IgG1 Constant Region) (SEQ ID NO:194) plus Full Length Sh06C11 IGKV1-16 Light Chain (Humanized Kappa Chain Variable Region and Human Kappa Constant Region) (SEQ ID NO:214)

Hu06C11-30=Full Length Hu06C11 IGHV2-5 Heavy Chain (Humanized Heavy Chain Variable Region and Human IgG1 Constant Region) (SEQ ID NO:196) plus Full Length Sh06C11 IGKV1-16 Light Chain (Humanized Kappa Chain Variable Region and Human Kappa Constant Region) (SEQ ID NO:214)

Hu14F11-39=Full Length Sh14F11 IGHV2-5 Heavy Chain (Humanized Heavy Chain Variable Region and Human IgG1 Constant Region) (SEQ ID NO:200) plus Full Length Hu14F11 IGKV1-16 Light Chain (Humanized Kappa Chain Variable Region and Human Kappa Constant Region) (SEQ ID NO:218)

Hu14F11-47=Full Length Sh14F11-IGHV2-70 Heavy Chain (Humanized Heavy Chain Variable Region and Human IgG1 Constant Region) (SEQ ID NO:202) plus Full Length Hu14F11 IGKV1-16 Light Chain (Humanized Kappa Chain Variable Region and Human Kappa Constant Region) (SEQ ID NO:218)

Example 15: Binding Affinities of Humanized and Chimeric Anti-GDF15 Monoclonal Antibodies The binding affinities and kinetics of binding of chimeric and humanized antibodies to mFc-rhGDF15 were measured by surface plasmon resonance, using a BIAcore® T100 instrument (GE Healthcare, Piscataway, NJ).

Goat anti-human IgGs (Fc fragment specific, Jackson ImmunoResearch, West Grove, PA) were immobilized on carboxymethylated dextran CM4 sensor chips by amine coupling, according to a standard protocol. Analyses were performed at 37° C. using PBS containing 0.05% surfactant P20 as running buffer. The antibodies were captured in individual flow cells at a flow rate of 10 µL/minute. Injection time was varied for each antibody to yield an Rmax between 30 and 60 RU. Buffer or mFc-rhGDF15 diluted in running buffer was injected sequentially over a reference surface (no antibody captured) and the active surface (antibody to be tested) for 240 seconds at 60 µL/minute. The dissociation phase was monitored for up to 1200 seconds. The surface was then regenerated with two 60-second injections of 10 mM Glycine-HCl, pH 2.25, at a flow rate of 30 µL/minute. The GDF15 concentration range tested was 20 nM to 0.625 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined. Kinetic values of purified monoclonal antibodies on mFc-rhGDF15 are summarized in Table 24.

TABLE 24

| Antibody | $k_a$ (1/Ms) | $k_d$ (1/s) | $K_D$ (M) | n |
|---|---|---|---|---|
| Hu01G06-1 | 4.2E+06 | 6.4E−04 | 1.6E−10 | 8 |
| Hu01G06-46 | 3.6E+06 | 3.8E−04 | 1.1E−10 | 11 |
| Hu01G06-52 | 3.6E+06 | 3.6E−04 | 9.9E−11 | 10 |
| Hu06C11-1 | 5.3E+06 | 8.4E−04 | 1.8E−10 | 2 |
| Hu06C11-27 | 4.7E+06 | 8.2E−04 | 1.8E−10 | 2 |
| Hu06C11-30 | 4.8E+06 | 8.7E−04 | 1.8E−10 | 2 |
| Hu14F11-1 | 3.0E+06 | 4.6E−04 | 1.6E−10 | 2 |
| Hu14F11-39 | 3.0E+06 | 1.9E−04 | 6.6E−11 | 2 |
| Hu14F11-47 | 3.3E+06 | 1.8E−04 | 6.5E−11 | 2 |

The results in Table 24 demonstrate that the chimeric and each of the humanized antibodies, have fast association rates ($k_a$), very slow disassociation rates ($k_d$) and very high affinities ($K_D$). In particular, the antibodies have affinities ranging from about 65 pM to about 200 pM.

Kinetic values of chimeric 01G06 (Hu01G06-1), two initial lead humanized 01G06 monoclonal antibodies (Hu01G06-46 and -52), and sequence optimized humanized 01G06 monoclonal antibody variants Hu01G06-100 through -114 (in supernatant) on mFc-rhGDF15 are summarized in Table 25.

TABLE 25

| Antibody | $k_a$ (1/Ms) | $k_d$ (1/s) | $K_D$ (M) | n |
|---|---|---|---|---|
| Hu01G06-1 | 4.9E+06 | 7.1E−04 | 1.4E−10 | 3 |
| Hu01G06-46 | 4.1E+06 | 4.3E−04 | 1.0E−10 | 3 |
| Hu01G06-52 | 5.0E+06 | 4.4E−04 | 8.9E−11 | 3 |
| Hu01G06-100 | 4.1E+06 | 6.2E−04 | 1.5E−10 | 3 |
| Hu01G06-101 | 4.4E+06 | 6.3E−04 | 1.4E−10 | 3 |
| Hu01G06-102 | 4.4E+06 | 4.6E−04 | 1.1E−10 | 3 |
| Hu01G06-103 | 4.4E+06 | 4.7E−04 | 1.1E−10 | 3 |
| Hu01G06-104 | 4.5E+06 | 5.2E−04 | 1.2E−10 | 3 |
| Hu01G06-105 | 4.3E+06 | 5.6E−04 | 1.3E−10 | 3 |
| Hu01G06-106 | 4.3E+06 | 7.0E−04 | 1.6E−10 | 3 |
| Hu01G06-107 | 4.1E+06 | 4.7E−04 | 1.2E−10 | 3 |
| Hu01G06-108 | 4.2E+06 | 4.6E−04 | 1.2E−10 | 3 |
| Hu01G06-109 | 4.6E+06 | 5.6E−04 | 1.3E−10 | 4 |
| Hu01G06-110 | 4.3E+06 | 5.8E−04 | 1.4E−10 | 4 |
| Hu01G06-111 | 4.3E+06 | 6.6E−04 | 1.6E−10 | 3 |
| Hu01G06-112 | 4.7E+06 | 5.3E−04 | 1.2E−10 | 3 |
| Hu01G06-113 | 4.5E+06 | 4.8E−04 | 1.1E−10 | 3 |
| Hu01G06-114 | 4.5E+06 | 5.4E−04 | 1.3E−10 | 3 |

The results in Table 25 demonstrate that the sequence optimized antibodies, Hu01G06-100 through -114, have binding affinities ranging from about 89 pM to about 160 pM.

Binding affinities and binding kinetics of mFc-rhGDF15 with chimeric 14F11 (Hu14F11-1), chimeric light 14F11 with chimeric heavy 06C11 (Hu14F11-23), and chimeric light 06C11 with chimeric heavy 14F11 (Hu14F11-24) heavy monoclonal antibody variants (in supernatant) were measured using biolayer interferometry (BLI) on an Octet™ QK instrument (ForteBio, Inc., Menlo Park, CA). The Octet analysis was performed at 30° C. using 1× Kinetics Buffer (ForteBio, Inc.) as assay buffer. Anti-human IgG Fc Capture (AHC) biosensors (ForteBio, Inc.) were used to capture human antibodies onto the sensors. Sensors were saturated in assay buffer for at 300 seconds before the assay. Antibodies were loaded onto sensors by dipping the sensors into antibody supernatant solution for 220 seconds, which typically resulted in capture levels of 1.5-2 nm. Baseline was established by dipping the sensors into 1× assay buffer for 200 seconds. Next, association was monitored for 220 seconds in 400 nM mFc-rhGDF15 protein, and dissociation was followed for 600 seconds in buffer alone.

Kinetic parameters for Hu14F11-1, Hu14F11-23, and Hu14F11-24 were determined using the kinetic function of the ForteBio Analysis Software Version 7.0. Kinetic parameters of the antibody, $k_a$, $k_d$, and $K_D$ were determined.

Kinetic values of Hu14F11-1, Hu14F11-23, and Hu14F11-24 heavy monoclonal antibody variants (in supernatant) on mFc-rhGDF15 are summarized in Table 26.

TABLE 26

| Antibody | $k_a$ (1/Ms) | $k_d$ (1/s) | $K_D$ (M) | n |
|---|---|---|---|---|
| Hu14F11-1 | 6.3E+05 | 1.9E−05 | 3.2E−11 | 3 |
| Hu14F11-23 | 3.4E+05 | 6.2E−05 | 1.8E−10 | 1 |
| Hu14F11-24 | 7.1E+05 | 2.2E−04 | 3.1E−10 | 1 |

The results in Table 26 demonstrate that Hu14F11-23 and Hu14F11-24, (i.e., antibodies that consist of one chimeric 06C11 chain (heavy or light) mixed with one chimeric 14F11 chain (heavy or light)), retain binding to GDF15. In particular, these antibodies have high affinities ranging from about 180 pM to about 310 pM.

Example 16: Binding Affinities of Affinity Matured Humanized Anti-GDF15 Monoclonal Antibodies The binding affinities and kinetics of binding of chimeric and humanized antibodies to mFc-rhGDF15, cleaved-rhGDF15, rabbit Fc mature recombinant mouse GDF15 (rFc-rmGDF15), and mouse Fc mature recombinant cynomolgus monkey GDF15 (mFc-rcGDF15) were measured by surface plasmon resonance, using a BIAcore® T100 instrument (GE Healthcare, Piscataway, NJ).

Goat anti-human IgGs (Fc fragment specific, Jackson ImmunoResearch, West Grove, PA) were immobilized on carboxymethylated dextran CM4 sensor chips by amine coupling, according to a standard protocol. Analyses were performed at 37° C. using PBS containing 0.05% surfactant P20 as running buffer. The antibodies were captured in individual flow cells at a flow rate of 10 μL/minute. Injection time was varied for each antibody to yield an Rmax between 30 and 60 RU. Buffer, mFc-rhGDF15, cleaved-rhGDF15, rFc-rmGDF15, or mFc-rcGDF15 diluted in running buffer was injected sequentially over a reference surface (no antibody captured) and the active surface (antibody to be tested) for 240 seconds at 60 μL/minute. The dissociation phase was monitored for up to 1500 seconds. The surface was then regenerated with two 60-second injections of 10 mM Glycine-HCl, pH 2.25, at a flow rate of 30 μL/minute. The GDF15 concentration range tested for each GDF15 protein was 5 nM to 0.3125 nM (two-fold dilutions).

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined. Kinetic values of purified monoclonal antibodies on mFc-rhGDF15, mature human GDF15, rFc-rmGDF15, and mFc-rcGDF15 are summarized in Table 27.

TABLE 27

| Protein | Antibody | $k_a$ (1/Ms) | $k_d$ (1/s) | $K_D$ (M) | n |
|---|---|---|---|---|---|
| mFc-rhGDF15 | Hu01G06-122 | 5.9E+06 | 2.1E−05 | 6.5E−12 | 5 |
| | Hu01G06-127 | 4.6E+06 | 4.2E−05 | 1.8E−11 | 4 |
| | Hu01G06-135 | 5.3E+06 | 4.4E−05 | 1.4E−11 | 5 |
| | Hu01G06-138 | 5.9E+06 | 4.1E−05 | 1.1E−11 | 5 |
| | Hu01G06-146 | 5.3E+06 | 2.6E−05 | 9.3E−12 | 5 |
| Cleaved-rhGDF15 | Hu01G06-122 | 7.9E+06 | 3.4E−05 | 7.9E−12 | 4 |
| | Hu01G06-127 | 6.1E+06 | 3.6E−05 | 1.0E−11 | 4 |
| | Hu01G06-135 | 7.3E+06 | 6.2E−05 | 1.0E−11 | 4 |
| | Hu01G06-138 | 7.9E+06 | 2.5E−05 | 4.5E−12 | 4 |
| | Hu01G06-146 | 6.5E+06 | 5.2E−05 | 1.1E−11 | 4 |
| mFc-rcGDF15 | Hu01G06-122 | 2.3E+06 | 2.4E−05 | 1.0E−11 | 4 |
| | Hu01G06-127 | 1.8E+06 | 1.6E−05 | 9.5E−12 | 4 |
| | Hu01G06-135 | 2.2E+06 | 7.9E−05 | 3.8E−11 | 4 |
| | Hu01G06-138 | 2.3E+06 | 5.3E−05 | 2.5E−11 | 4 |
| | Hu01G06-146 | 2.0E+06 | 1.5E−05 | 8.0E−12 | 4 |
| rFc-rmGDF15 | Hu01G06-122 | 2.2E+07 | 1.4E−03 | 6.3E−11 | 2 |
| | Hu01G06-127 | 3.9E+07 | 2.1E−03 | 5.1E−11 | 2 |
| | Hu01G06-135 | 3.7E+07 | 1.9E−03 | 5.5E−11 | 2 |
| | Hu01G06-138 | 1.9E+07 | 8.0E−04 | 4.4E−11 | 2 |
| | Hu01G06-146 | 1.1E+07 | 7.2E−04 | 6.3E−11 | 2 |

The results in Table 27 demonstrate that the chimeric and each of the humanized antibodies, have fast association rates ($k_a$), very slow disassociation rates ($k_d$) and very high affinities ($K_D$). In particular, the antibodies have affinities ranging from less than 5 pM (e.g., about 4.5 pM) to about 65 pM.

Example 17: Reversal of Cachexia in an HT-1080 Fibrosarcoma Xenograft Model

Figure 23:
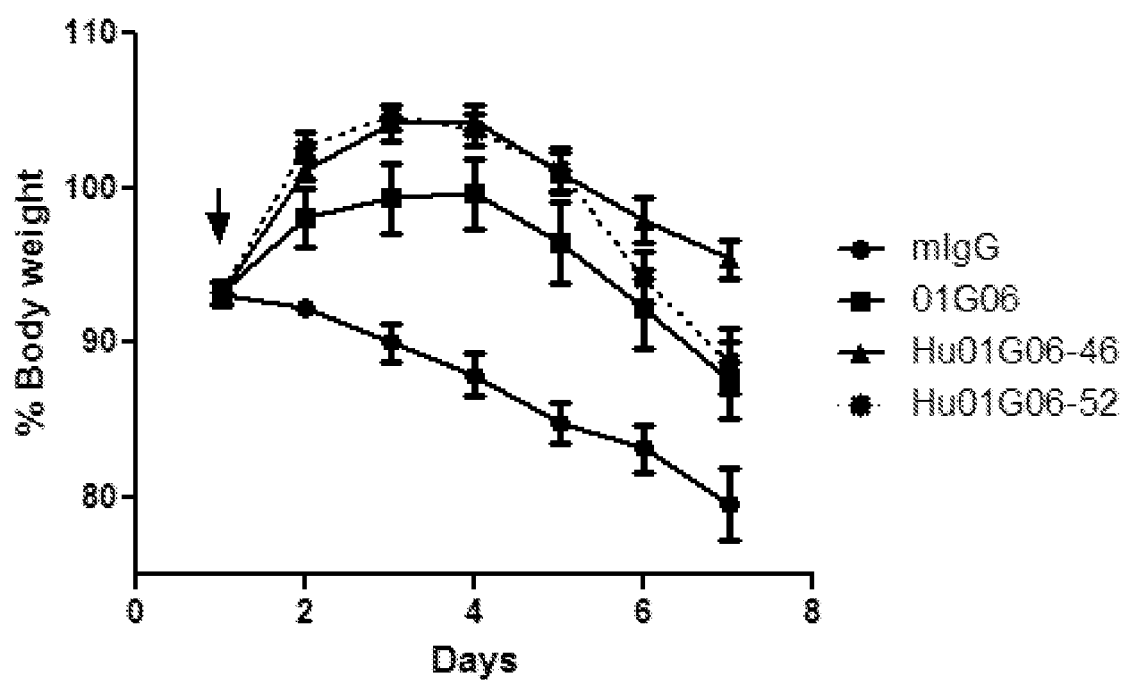
FIG. 23 is a graph summarizing results from an experiment to measure cachectic inhibitory activity of anti-GDF15 antibodies 01G06 (■), Hu01G06-46 (▲), and Hu01G06-52 (*), and a murine IgG control (●) dosed at 2 mg/kg in an HT-1080 fibrosarcoma tumor xenograft model in ICR-SCID mice. The arrow indicates intra-peritoneal injection of antibody.

This Example demonstrates the reversal of cachexia (as indicated by body weight loss) by humanized 01G06, 06C11, 14F11 antibodies in an HT-1080 fibrosarcoma xenograft model. HT-1080 cells were grown in culture at 37° C. and inoculated subcutaneously into the flank of 8-week old female ICR-SCID mice as described above in Example 10. Body weight was measured daily. When body weight reached 93%, the mice were randomly divided into groups of ten mice each. Each group received one of the following treatments: murine IgG control, 01G06, 06C11, 14F11, and their respective humanized versions at 2 mg/kg. Treatment was administered once a day by intra-peritoneal injection. Antibody treatment with 01G06, Hu01G06-46 and Hu01G06-52 resulted in body weight increase to initial weight or 100% (p<0.001) (FIG. 23). Statistical analysis was performed using ANOVA. Results for reversal of body weight on day in the HT-1080 model are shown in FIG. 23 and Table 28, respectively.

TABLE 28

| | Treatment | | % Body | ANOVA Analysis |
|---|---|---|---|---|
| Gr. | Agent | mg/kg | weight | (compared to mIgG) |
| 1 | mIgG | 2 | 79.5 | NA |
| 2 | 01G06 | 2 | 87.6 | p < 0.001 |
| 3 | Hu01G06-46 | 2 | 95.4 | p < 0.001 |
| 4 | Hu01G06-52 | 2 | 87.8 | p < 0.001 |

The data in FIG. 23 and Table 28 indicated that antibodies 01G06, Hu01G06-46 and Hu01G06-52 can reverse cachexia in an HT-1080 fibrosarcoma xenograft model.

Figure 24:
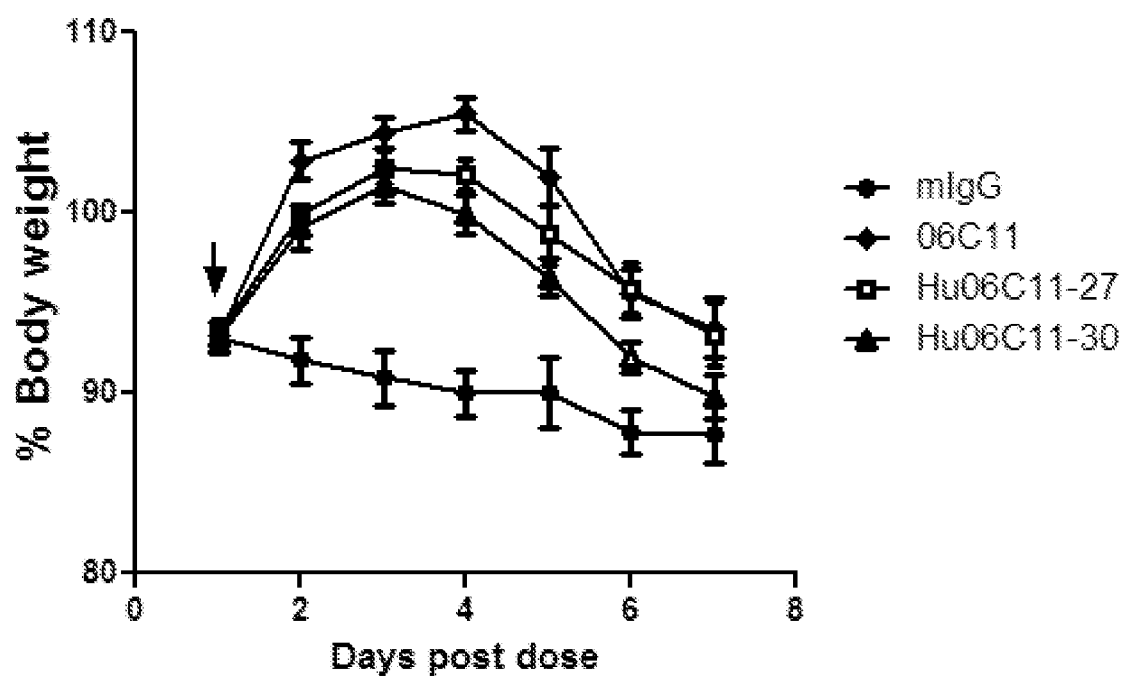
FIG. 24 is a graph summarizing results from an experiment to measure cachectic inhibitory activity of anti-GDF15 antibodies 06C11 (♦), Hu06C11-27 (□), and Hu06C11-30 (▲), and a murine IgG control (●) dosed at 2 mg/kg in an HT-1080 fibrosarcoma tumor xenograft model in ICR-SCID mice. The arrow indicates intra-peritoneal injection of antibody.

Antibody treatment with 06C11, Hu06C11-27, and Hu06C11-30 resulted in body weight increase relative to initial weight or about 100% (p<0.001) (FIG. 24). Statistical analysis was performed using ANOVA. Results for reversal of body weight in the HT-1080 model are shown in FIG. 24 and Table 29.

TABLE 29

| | Treatment | | % Body | ANOVA Analysis |
|---|---|---|---|---|
| Gr. | Agent | mg/kg | weight | (compared to mIgG) |
| 1 | mIgG | 2 | 87.7 | NA |
| 2 | 01G06 | 2 | 93.6 | p < 0.001 |
| 3 | Hu06C11-27 | 2 | 93.2 | p < 0.001 |
| 4 | Hu06C11-30 | 2 | 89.8 | p < 0.001 |

The data in FIG. 24 and Table 29 indicate that antibodies 06C11, Hu06C11-27, and Hu06C11-30 can reverse cachexia in an HT-1080 fibrosarcoma xenograft model.

Figure 25:
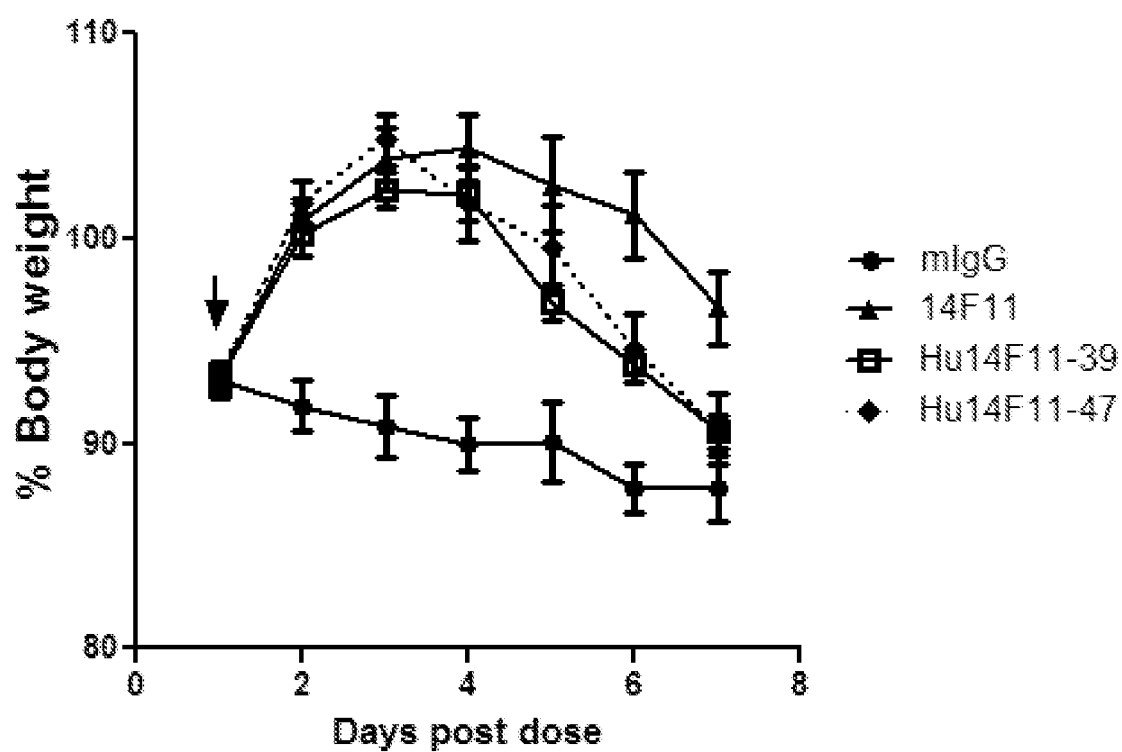
FIG. 25 is a graph summarizing results from an experiment to measure cachectic inhibitory activity of anti-GDF15 antibodies 14F11 (▲), Hu14F11-39 (□), and Hu14F11-47 (♦), and a murine IgG control (●) dosed at 2 mg/kg in an HT-1080 fibrosarcoma tumor xenograft model in ICR-SCID mice. The arrow indicates intra-peritoneal injection of antibody.

Antibody treatment with 14F11, Hu14F11-39, and Hu14F11-47 resulted in body weight increase relative to initial weight or about 100% (p<0.001) (FIG. 25). Statistical analysis was performed using ANOVA. Results for reversal of body weight in the HT-1080 model are shown in FIG. 25 and Table 30.

TABLE 30

| | Treatment | | % Body | ANOVA Analysis |
|---|---|---|---|---|
| Gr. | Agent | mg/kg | weight | (compared to mIgG) |
| 1 | mIgG | 2 | 87.7 | NA |
| 2 | 14F11 | 2 | 96.6 | p < 0.001 |
| 3 | Hu14F11-39 | 2 | 90.5 | p < 0.001 |
| 4 | Hu14F11-47 | 2 | 90.7 | p < 0.001 |

The data in FIG. 25 and Table 30 indicated that antibodies 14F11, Hu14F11-39, and Hu14F11-47 can reverse cachexia in an HT-1080 fibrosarcoma xenograft model.

Figure 26:
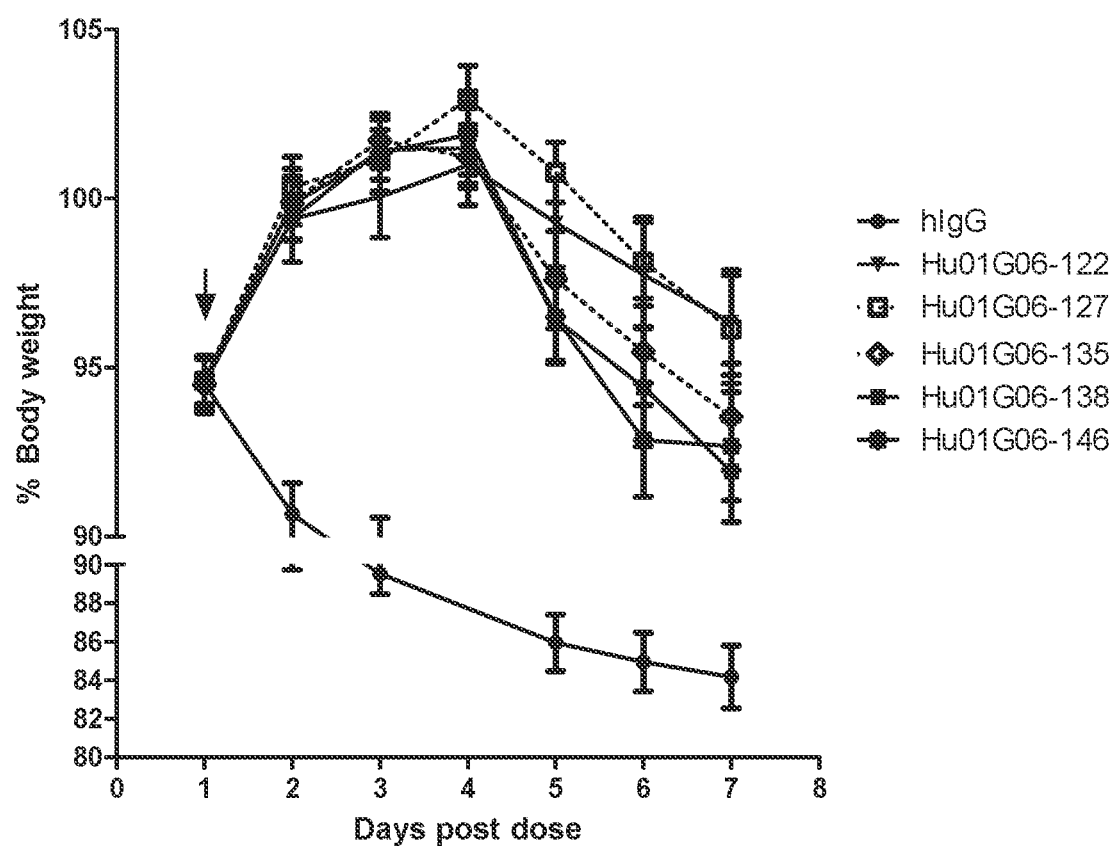
FIG. 26 is a graph summarizing results from an experiment to measure cachectic inhibitory activity of anti-GDF15 antibodies Hu01G06-122 (▼), Hu01G06-127 (□), Hu01G06-135 (◇), Hu01G06-138 (■), and Hu01G06-146 (*), and a human IgG control (●) dosed at 2 mg/kg in an HT-1080 fibrosarcoma tumor xenograft model in ICR-SCID mice. The arrow indicates intra-peritoneal injection of antibody.

Antibody treatment with humanized 01G06 antibodies (i.e., antibodies Hu01G06-122, Hu01G06-127, Hu01G06-135, Hu01G06-138 and Hu01G06-146) resulted in body weight increase relative to initial weight or about 1009. (p<7.0) (FIG. 26). Statistical analysis was performed using ANOVA. Treatment with human IgG (hIgG) was used as a control. Results for reversal of body weights in the HT-1080 model are shown in FIG. 26 and Table 31.

TABLE 31

| Gr. | Treatment Agent | mg/kg | % Body weight | ANOVA Analysis (compared to mIgG) |
|---|---|---|---|---|
| 1 | mIgG | 2 | 84.2 | NA |
| 2 | Hu01G06-122 | 2 | 96.3 | p < 0.001 |
| 3 | Hu01G06-127 | 2 | 96.1 | p < 0.001 |
| 4 | Hu01G06-135 | 2 | 93.5 | p < 0.001 |
| 5 | Hu01G06-138 | 2 | 91.9 | p < 0.001 |
| 6 | Hu01G06-146 | 2 | 92.7 | p < 0.001 |

The data in FIG. 26 and Table 31 indicated that humanized anti-GDF15 antibodies Hu01G06-122, Hu01G06-127, Hu01G06-135, Hu01G06-138 and Hu01G06-146 can reverse cachexia in an HT-1080 fibrosarcoma xenograft model.

Example 18: Reversal of Cachexia in an mFc-rhGDF15-Induced Model

This Example demonstrates the reversal of cachexia (as indicated by body weight loss) by humanized 01G06 antibodies (i.e., antibody Hu01G06-122, Hu01G06-127, Hu01G06-135, Hu01G06-138, or Hu01G06-146) in an mFc-rhGDF15-induced cachexia model. mFc-rhGDF15 (1 μg/g) was administered subcutaneously into the flank of 8-week old female ICR-SCID mice. Body weight was measured daily. When body weight reached 93%, the mice were randomly divided into six groups of ten mice each. Each group received one of the following treatments: human IgG control (hIgG), Hu01G06-122, Hu01G06-127, Hu01G06-135, Hu01G06-138 or Hu01G06-146 at 2 mg/kg. Treatment was administered once by intra-peritoneal injection. Treatment with antibody Hu01G06-122, Hu01G06-127, Hu01G06-135, Hu01G06-138 or Hu01G06-146 resulted in body weight increase relative to initial weight or about 100% (p<0.001) (FIG. 27 and Table 32).

TABLE 32

| Gr. | Treatment Agent | mg/kg | % Body weight | ANOVA Analysis (compared to mIgG) |
|---|---|---|---|---|
| 1 | mIgG | 2 | 70.6 | NA |
| 2 | Hu01G06-122 | 2 | 101.7 | p < 0.001 |
| 3 | Hu01G06-127 | 2 | 103.2 | p < 0.001 |
| 4 | Hu01G06-135 | 2 | 102.5 | p < 0.001 |
| 5 | Hu01G06-138 | 2 | 101.8 | p < 0.001 |
| 6 | Hu01G06-146 | 2 | 102.5 | p < 0.001 |

Figure 27:
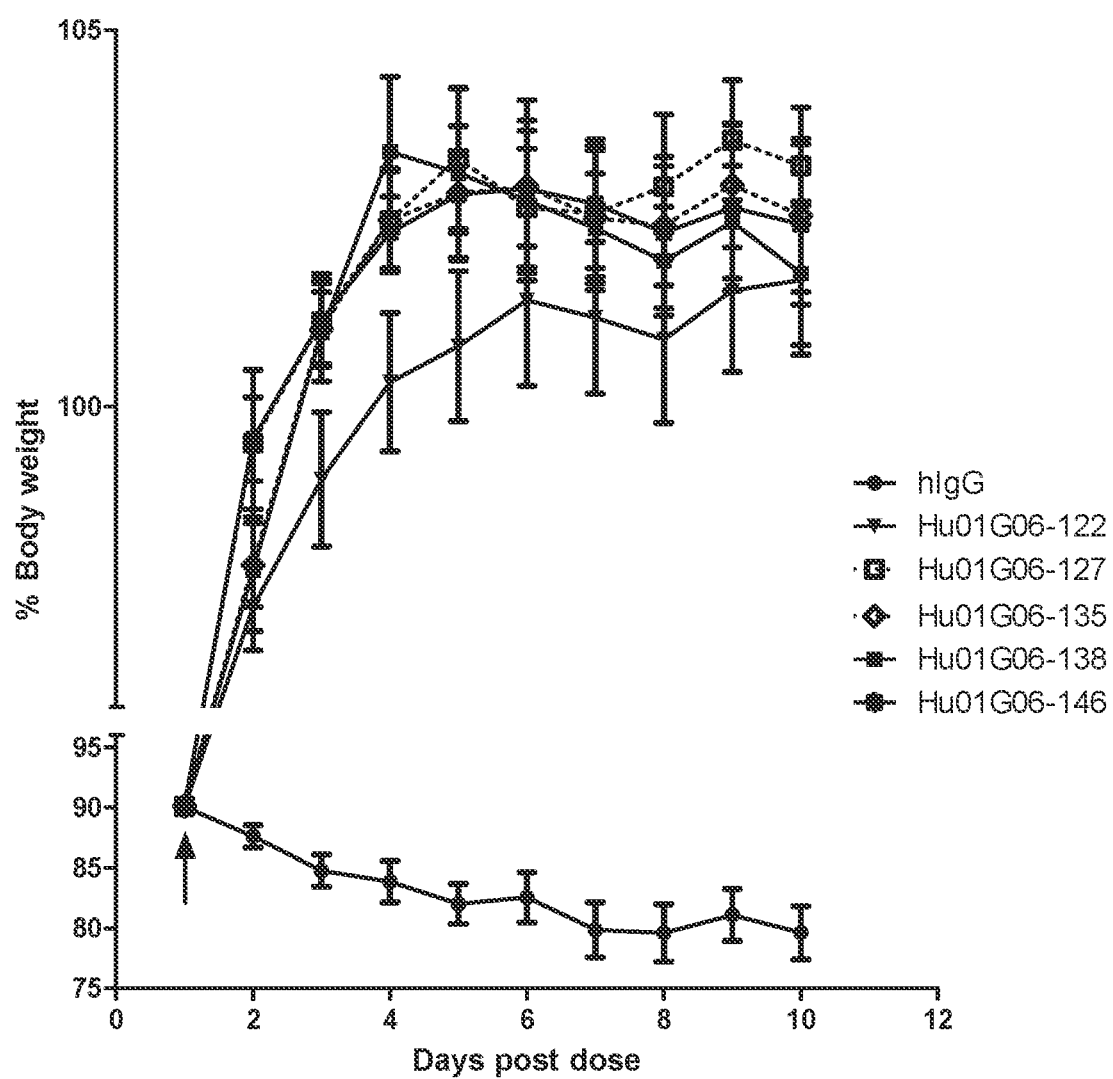
FIG. 27 is a graph summarizing results from an experiment to measure cachectic inhibitory activity of anti-GDF15 antibodies Hu01G06-122 (▼), Hu01G06-127 (□), Hu01G06-135 (◇), Hu01G06-138 (■), and Hu01G06-146 (*), and a human IgG control (●) dosed at 2 mg/kg in an mFc-rhGDF15 cachectic model in ICR-SCID mice. The arrow indicates intra-peritoneal injection of antibody.

The data in FIG. 27 and Table 32 indicate that the disclosed anti-GDF15 antibodies can reverse cachexia in an mFc-rhGDF15-induced mouse model (i.e., a non-tumor bearing mouse model).

These results indicate that humanized anti-GDF15 antibodies can reverse cachexia in an mFc-rhGDF15-induced cachexia model.

Figure 28:
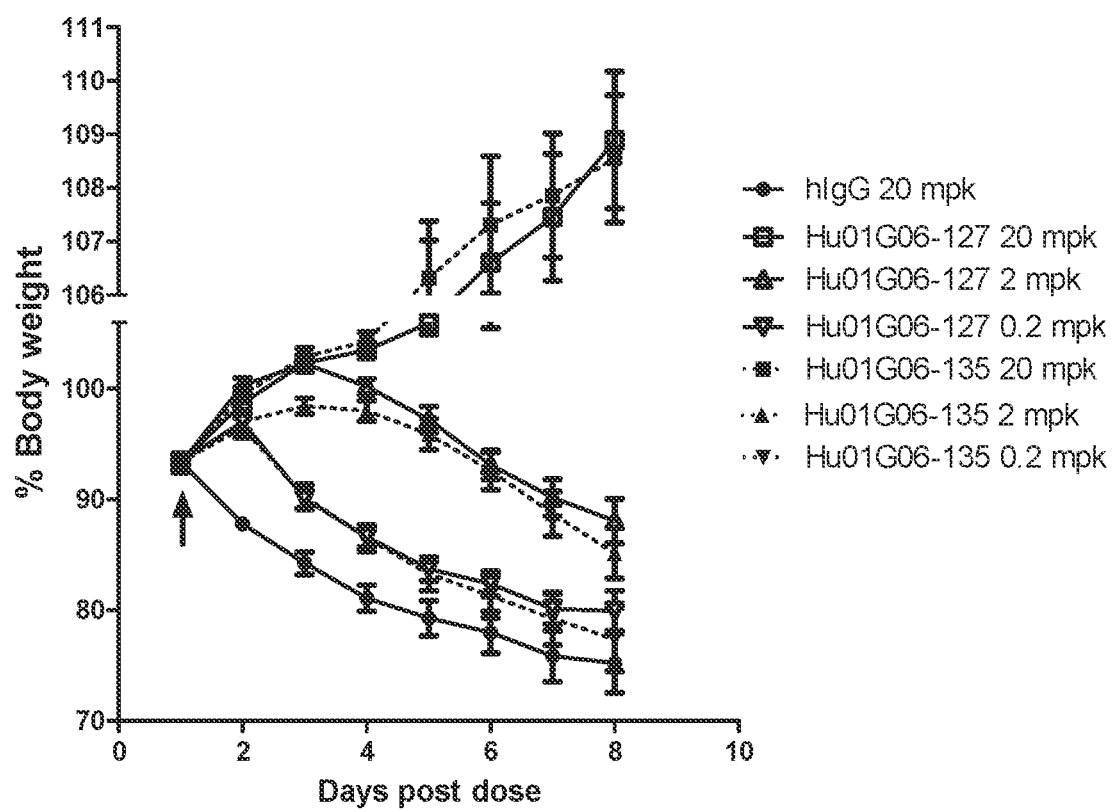
FIG. 28 is a graph summarizing results from an experiment to measure cachectic dose response inhibitory activity of anti-GDF15 antibodies Hu01G06-127 dosed at 20 mg/kg (□), 2 mg/kg (Δ), and 0.2 mg/kg (∇); Hu01G06-135 at 20 mg/kg (■), 2 mg/kg (▲), and 0.2 mg/kg (▼), and a human IgG control at 20 mg/kg (●) in an HT-1080 fibrosarcoma tumor xenograft model in ICR-SCID mice. The arrow indicates intravenous injection of antibody.

Example 19: Dose Response Reversal of Cachexia in an HT-1080 Fibrosarcoma Xenograft Model This Example demonstrates the dose response reversal of cachexia (as indicated by body weight loss) by humanized Hu01G06-127 and Hu01G06-135 antibodies in an HT-1080 fibrosarcoma xenograft model. HT-1080 cells were grown in culture at 37° C. and inoculated subcutaneously into the flank of 8-week old female ICR-SCID mice as described above in Example 10. Body weight was measured daily. When body weight reached 93%, the mice were randomly divided into groups of ten mice each. Each group received one of the following treatments: human IgG control (hIgG; 20 mg/kg), Hu01G06-127 (20 mg/kg, 2 mg/kg, or 0.2 mg/kg) and Hu01G06-135 (20 mg/kg, 2 mg/kg, or 0.2 mg/kg). Treatment was administered once a day by intravenous injection. Antibody treatment with Hu01G06-127 and Hu01G06-135 at 20 mg/kg resulted in body weight increase above the initial weight or 108% (p<0.001) (FIG. 28). Antibody treatment with Hu01G06-127 and Hu01G06-135 at 2 mg/kg resulted in limited body weight decrease compare to control (hIgG) from the initial weight or 88-85% (p<0.001) (FIG. 28). Statistical analysis was performed using ANOVA. Results for changes of body weight at the end of the study in the HT-1080 model are shown in FIG. 28 and Table 33.

TABLE 33

| Gr. | Treatment Agent | mg/kg | % Body weight | ANOVA Analysis (compared to mIgG) |
|---|---|---|---|---|
| 1 | mIgG | 20 | 75.2 | NA |
| 2 | Hu01G06-127 | 20 | 108.9 | p < 0.001 |
| 3 | Hu01G06-127 | 2.0 | 88.1 | p < 0.001 |
| 4 | Hu01G06-127 | 0.2 | 80.0 | NS |
| 5 | Hu01G06-135 | 20 | 108.6 | p < 0.001 |
| 6 | Hu01G06-135 | 2.0 | 85.2 | p < 0.001 |
| 7 | Hu01G06-135 | 0.2 | 77.3 | NS |

The data in FIG. 28 and Table 33 indicated that antibodies Hu01G06-127 and Hu01G06-135 can reverse cachexia in an HT-1080 fibrosarcoma xenograft model in a dose-dependent manner.

Example 20: Reversal of Muscle and Fat Loss in an HT-1080 Xenograft Tumor Model

This Example demonstrates the reversal of cachexia (as indicated by body weight loss, muscle mass loss and fat mass loss) by antibody 01G06 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5 \times 10^6$ cells per mouse in 50% matrigel. A cohort of ten 8-week old female ICR SCID mice with the same body weight was selected for subcutaneous inoculation into the flank with matrigel, as a non tumor (SHAM) control arm. Body weight was measured daily. When body weight reached 91% in the tumor bearing mice, the mice were randomly divided into two groups of ten mice each. Each group received one of the following treatments: human IgG control (hIgG) or Hu01G06-127 10 mg/kg on day 1, day 3 and day 6. Treatment was administered by intra-peritoneal injection. Treatment with antibody Hu01G06-127 resulted in body weight increase to 105% of initial weight compared to non-tumor bearing control mice (SHAM; p<0.001) (FIG. 29A and Table 34).

TABLE 34

| Gr. | Agent | mg/kg | % Body weight | ANOVA Analysis (compared to hIgG) |
|---|---|---|---|---|
| 1 | hIgG | 10 | 84.3 | NA |
| 2 | Hu01G06-127 | 10 | 105.4 | p < 0.001 |
| 2 | SHAM no tumor control | none | 101.9 | p < 0.001 |

Figure 29A:
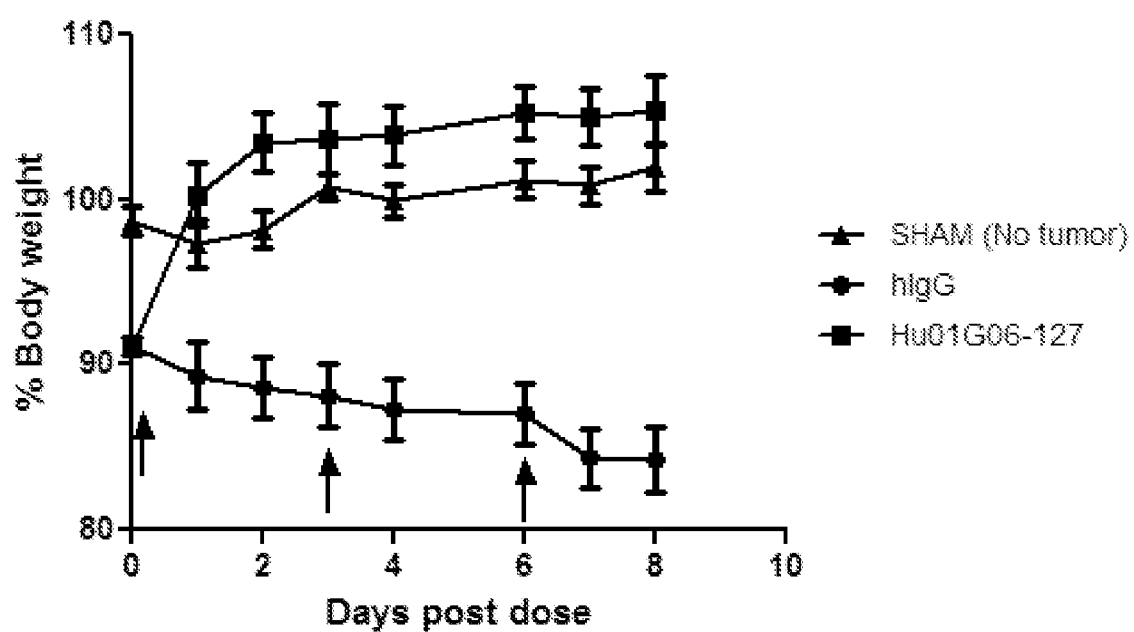
FIGS. 29A-29C are graphs summarizing results from an experiment to demonstrate anti-cachectic activity of anti-GDF15 antibodies Hu01G06-127 (■), dosed at 10 mg/kg, in immune-incompetent mice (ICR-SCID) bearing an HT-1080 fibrosarcoma tumor xenograft model. Treatment with antibody Hu01G06-127 reversed body weight loss (FIG. 29A); induced a gain of gonadal fat mass (FIG. 29B); and induced a gain of muscle mass of gastrocnemius muscle (FIG. 29 C) compared to negative control (hIgG (●)

The data in FIG. 29A and Table 34 indicate that the disclosed anti-GDF15 antibody can completely reverse cachexia in an HT-1080 fibrosarcoma xenograft model.

Figure 29B:
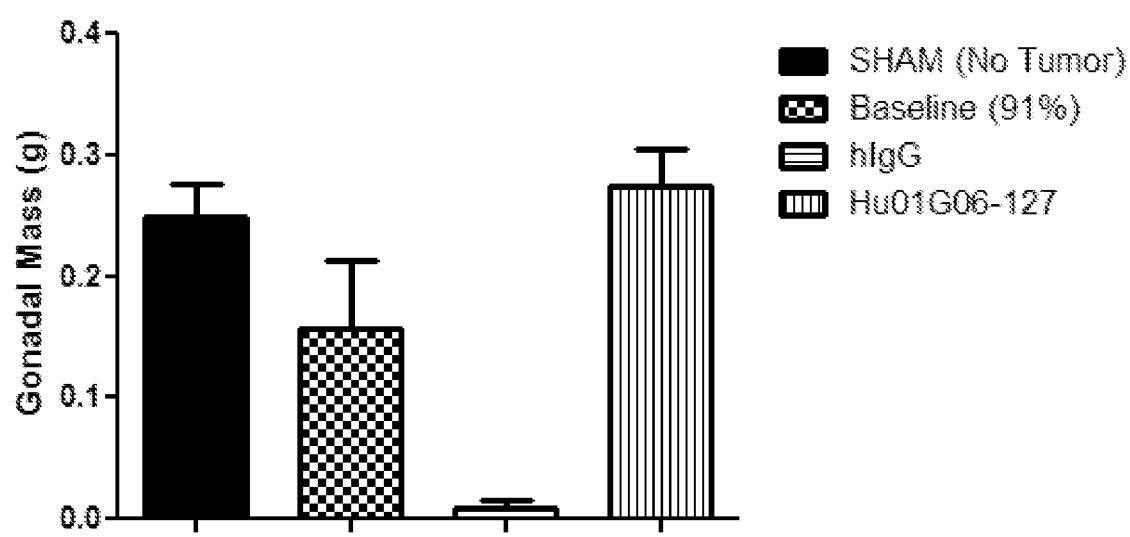
Figure 29C:
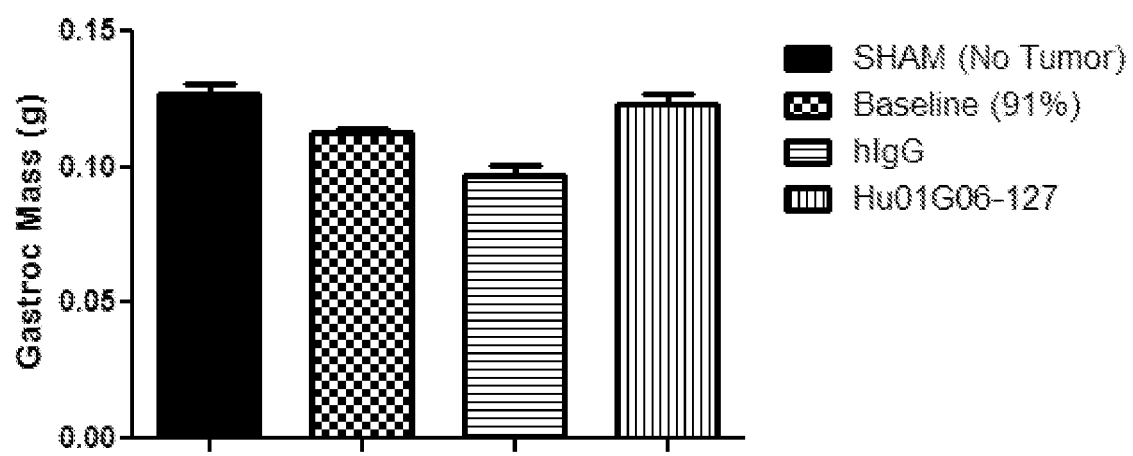

In this experiment, a group of ten mice were sacrificed at the time of dosing (baseline or 91% body weight loss, without treatment) and at the end of the study (eight days post dose, either hIgG or Hu01G06-127 as well SHAM non tumor control mice). Gonadal fat and the gastrocnemius muscles were removed surgically and weighed. As shown in FIG. 29B, significant gonadal fat mass loss was observed seven days post dose with hIgG, but not in the group treated with antibody Hu01G06-127 compared to baseline control (91% body weight loss). Moreover, treatment with Hu01G06-127 not only prevented further fat loss (compared to baseline group), but also, was able to restore the normal levels of gonadal fat (compared to SHAM non-tumor control) (FIG. 29B). In addition, significant gastrocnemius muscle mass loss was observed seven days post dose with hIgG, but not in the group treated with antibody Hu01G06-127 compared to baseline control (91% body weight loss) (FIG. 29C). Treatment with Hu01G06-127 not only prevented further muscle loss (compare to baseline group), but also was able to restore the normal levels of gastrocnemius muscle (compared to SHAM non tumor control) (FIG. 29C).

These results indicate that the disclosed anti-GDF15 antibodies can completely reverse cachexia measured by the loss of muscle mass, loss of fat and involuntary weight loss in an HT-1080 xenograft tumor model.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

SEQUENCE LISTING

```
Sequence total quantity: 266
SEQ ID NO: 1              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 1
DYNMD                                                                     5

SEQ ID NO: 2              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 2
SYWIH                                                                     5

SEQ ID NO: 3              moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 3
TYGMGVT                                                                   7

SEQ ID NO: 4              moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 4
TYGMGVS                                                                   7

SEQ ID NO: 5              moltype = AA  length = 7
FEATURE                   Location/Qualifiers
```

```
REGION                    1..7
                          note = Description of Artificial Sequence: Synthetic peptide
source                    1..7
                          mol_type = protein
                          organism = synthetic construct
SEQUENCE: 5
TYGMGVG                                                                              7

SEQ ID NO: 6              moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 6
TSGMGVS                                                                              7

SEQ ID NO: 7              moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 7
QINPNNGGIF FNQKFKG                                                                  17

SEQ ID NO: 8              moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 8
DINPSNGRSK YNEKFKN                                                                  17

SEQ ID NO: 9              moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 9
HIYWDDDKRY NPSLKS                                                                   16

SEQ ID NO: 10             moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 10
EINPNNGGTF YNQKFKG                                                                  17

SEQ ID NO: 11             moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 11
DIWWDDDKYY NPSLKS                                                                   16

SEQ ID NO: 12             moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 12
HNDWDDDKRY KSSLKS                                                                   16

SEQ ID NO: 13             moltype = AA  length = 17
```

```
                        -continued

FEATURE                 Location/Qualifiers
REGION                  1..17
                        note = Description of Artificial Sequence: Synthetic peptide
source                  1..17
                        mol_type = protein
                        organism = synthetic construct
SEQUENCE: 13
QINPNNGGIF FNQKFQG                                                           17

SEQ ID NO: 14           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 14
HIYWDDDKRY NPSLKT                                                            16

SEQ ID NO: 15           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 15
EAITTVGAMD Y                                                                 11

SEQ ID NO: 16           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 16
EVLDGAMDY                                                                    9

SEQ ID NO: 17           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 17
TGYSNLFAY                                                                    9

SEQ ID NO: 18           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 18
RGYDDYWGY                                                                    9

SEQ ID NO: 19           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 19
RGHYSAMDY                                                                    9

SEQ ID NO: 20           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 20
RVGGLEGYFD Y                                                                 11
```

| | | |
|---|---|---|
| SEQ ID NO: 21 | moltype = AA length = 11 | |
| FEATURE | Location/Qualifiers | |
| REGION | 1..11 | |
| | note = Description of Artificial Sequence: Synthetic peptide | |
| source | 1..11 | |
| | mol_type = protein | |
| | organism = synthetic construct | |
| SEQUENCE: 21 | | |
| RTSENLHNYL A | | 11 |
| SEQ ID NO: 22 | moltype = AA length = 15 | |
| FEATURE | Location/Qualifiers | |
| REGION | 1..15 | |
| | note = Description of Artificial Sequence: Synthetic peptide | |
| source | 1..15 | |
| | mol_type = protein | |
| | organism = synthetic construct | |
| SEQUENCE: 22 | | |
| RASESVDNYG ISFMN | | 15 |
| SEQ ID NO: 23 | moltype = AA length = 11 | |
| FEATURE | Location/Qualifiers | |
| REGION | 1..11 | |
| | note = Description of Artificial Sequence: Synthetic peptide | |
| source | 1..11 | |
| | mol_type = protein | |
| | organism = synthetic construct | |
| SEQUENCE: 23 | | |
| KASQNVGTNV A | | 11 |
| SEQ ID NO: 24 | moltype = AA length = 11 | |
| FEATURE | Location/Qualifiers | |
| REGION | 1..11 | |
| | note = Description of Artificial Sequence: Synthetic peptide | |
| source | 1..11 | |
| | mol_type = protein | |
| | organism = synthetic construct | |
| SEQUENCE: 24 | | |
| RASGNIHNYL A | | 11 |
| SEQ ID NO: 25 | moltype = AA length = 15 | |
| FEATURE | Location/Qualifiers | |
| REGION | 1..15 | |
| | note = Description of Artificial Sequence: Synthetic peptide | |
| source | 1..15 | |
| | mol_type = protein | |
| | organism = synthetic construct | |
| SEQUENCE: 25 | | |
| RASQSVSTSR FSYMH | | 15 |
| SEQ ID NO: 26 | moltype = AA length = 7 | |
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 26 | | |
| DAKTLAD | | 7 |
| SEQ ID NO: 27 | moltype = AA length = 7 | |
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 27 | | |
| AASNQGS | | 7 |
| SEQ ID NO: 28 | moltype = AA length = 7 | |
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 28 | | |
| SASYRYS | | 7 |

-continued

```
SEQ ID NO: 29          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 29
NAKTLAD                                                                         7

SEQ ID NO: 30          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 30
SPSYRYS                                                                         7

SEQ ID NO: 31          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 31
YASNLES                                                                         7

SEQ ID NO: 32          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 32
QHFWSSPYT                                                                       9

SEQ ID NO: 33          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 33
QQSKEVPWT                                                                       9

SEQ ID NO: 34          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 34
QQYNSYPYT                                                                       9

SEQ ID NO: 35          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 35
QQYNNYPLT                                                                       9

SEQ ID NO: 36          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 36
```

```
QQYNSYPHT                                                             9

SEQ ID NO: 37           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 37
QHSWEIPYT                                                             9

SEQ ID NO: 38           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 38
GYTFTDY                                                               7

SEQ ID NO: 39           moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 39
gaggtcctgc tgcaacagtc tggacctgag ctggtgaagc ctggggcttc agtgaagata      60
ccctgcaagg cttctggata cacattcact gactacaaca tggactgggt gaagcagagc    120
catggaaaga gccttgagtg gattggacaa attaatccta caaatggtgg tatttttcttc   180
aaccagaagt tcaagggcaa ggccacattg actgtagaca gtgcctccaa tacagccttc    240
atggaggtcc gcagcctgac atctgaggac actgcagtct attactgtgc aagagaggca    300
attactacgg taggcgctat ggactactgg ggtcaaggaa cctcagtcac cgtctcctca    360

SEQ ID NO: 40           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 40
EVLLQQSGPE LVKPGASVKI PCKASGYTFT DYNMDWVKQS HGKSLEWIGQ INPNNGGIFF      60
NQKFKGKATL TVDKSSNTAF MEVRSLTSED TAVYYCAREA ITTVGAMDYW GQGTSVTVSS    120

SEQ ID NO: 41           moltype = DNA  length = 354
FEATURE                 Location/Qualifiers
misc_feature            1..354
                        note = Description of Artificial Sequence: Synthetic
                         polynucleotide
source                  1..354
                        mol_type = other DNA
                        organism = synthetic construct
SEQUENCE: 41
caggtccaac tgcagcagcc tggggctgaa ctggtgaagc ctggggcttc agtgaagctg      60
tcctgcaagg cttctggcta caccttcacc agctactgga ttcactgggt gaaccagagg    120
cctggacaag gccttgagtg gattggagac attaatccta gcaacggccg tagtaagtat    180
aatgagaagt tcaagaacaa ggccacaatg actgcagaca atcctccaa cacagcctac     240
atgcaactca gcagcctgac atctgaggac tctgcggtct attactgtgc aagagaggtt    300
ctggatggtg ctatggacta ctggggtcaa ggaacctcag tcaccgtctc ctca          354

SEQ ID NO: 42           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 42
QVQLQQPGAE LVKPGASVKL SCKASGYTFT SYWIHWVNQR PGQGLEWIGD INPSNGRSKY      60
NEKFKNKATM TADKSSNTAY MQLSSLTSED SAVYYCAREV LDGAMDYWGQ GTSVTVSS      118

SEQ ID NO: 43           moltype = DNA  length = 357
```

| FEATURE | Location/Qualifiers |
|---|---|
| misc_feature | 1..357 |
| | note = Description of Artificial Sequence: Synthetic polynucleotide |
| source | 1..357 |
| | mol_type = other DNA |
| | organism = synthetic construct |

SEQUENCE: 43
```
caggttactc tgaaagagtc tggccctggg atattgcagc cctcccagac cctcagtctg   60
acttgttctt tctctgggtt ttcactgagc acttatggta tgggtgtgac ctggattcgt  120
cagccttcag gaaagggtct ggagtggctg gcacacattt actgggatga tgacaagcgc  180
tataaccat  ccctgaagag ccggctcaca atctccaagg atacctccaa caaccaggta  240
ttcctcaaga tcaccagtgt ggacactgca gatactgcca catactactg tgctcaaacg  300
gggtatagta acttgtttgc ttactggggc caagggactc tggtcactgt ctctgca     357
```

| SEQ ID NO: 44 | moltype = AA length = 119 |
|---|---|
| FEATURE | Location/Qualifiers |
| REGION | 1..119 |
| | note = Description of Artificial Sequence: Synthetic polypeptide |
| source | 1..119 |
| | mol_type = protein |
| | organism = synthetic construct |

SEQUENCE: 44
```
QVTLKESGPG ILQPSQTLSL TCSFSGFSLS TYGMGVTWIR QPSGKGLEWL AHIYWDDDKR   60
YNPSLKSRLT ISKDTSNNQV FLKITSVDTA DTATYYCAQT GYSNLFAYWG QGTLVTVSA   119
```

| SEQ ID NO: 45 | moltype = DNA length = 357 |
|---|---|
| FEATURE | Location/Qualifiers |
| misc_feature | 1..357 |
| | note = Description of Artificial Sequence: Synthetic polynucleotide |
| source | 1..357 |
| | mol_type = other DNA |
| | organism = synthetic construct |

SEQUENCE: 45
```
caggttactc tgaaagagtc tggccctggg atattgcagc cctcccagac cctcagtctg   60
acttgttctt tctctgggtt ttcactgaac acttatggta tgggtgtgag ctggattcgt  120
cagccttcag gaaagggtct ggagtggctg gcacacattt actgggatga tgacaagcgc  180
tataaccat  ccctgaagag ccggctcaca atctccaagg atgcctccaa caaccgggtc  240
ttcctcaaga tcaccagtgt ggacactgca gatactgcca catactactg tgctcaaaga  300
ggttatgatg attactgggg ttactggggc caagggactc tggtcactat ctctgca     357
```

| SEQ ID NO: 46 | moltype = AA length = 119 |
|---|---|
| FEATURE | Location/Qualifiers |
| REGION | 1..119 |
| | note = Description of Artificial Sequence: Synthetic polypeptide |
| source | 1..119 |
| | mol_type = protein |
| | organism = synthetic construct |

SEQUENCE: 46
```
QVTLKESGPG ILQPSQTLSL TCSFSGFSLN TYGMGVSWIR QPSGKGLEWL AHIYWDDDKR   60
YNPSLKSRLT ISKDASNNRV FLKITSVDTA DTATYYCAQR GYDDYWGYWG QGTLVTISA   119
```

| SEQ ID NO: 47 | moltype = DNA length = 360 |
|---|---|
| FEATURE | Location/Qualifiers |
| misc_feature | 1..360 |
| | note = Description of Artificial Sequence: Synthetic polynucleotide |
| source | 1..360 |
| | mol_type = other DNA |
| | organism = synthetic construct |

SEQUENCE: 47
```
gaggtcctgc tgcaacagtc tggacctgag gtggtgaagc ctggggcttc agtgaagata   60
ccctgcaagg cttctggata cacattcact gactacaaca tggactgggt gaagcagagc  120
catggaaaga gccttgagtg gattggagag attaatccta caatggtgg  tacttctac   180
aaccagaagt tcaagggcaa ggccacattg actgtagaca gtcctccag  cacagcctac  240
atggagctcc gcagcctgac atctgaggac actgcagtct attactgtgc aagagaggca  300
attactacgg taggcgctat ggactactgg ggtcaaggaa cctcagtcac cgtctcctca  360
```

| SEQ ID NO: 48 | moltype = AA length = 120 |
|---|---|
| FEATURE | Location/Qualifiers |
| REGION | 1..120 |
| | note = Description of Artificial Sequence: Synthetic polypeptide |
| source | 1..120 |
| | mol_type = protein |
| | organism = synthetic construct |

```
SEQUENCE: 48
EVLLQQSGPE VVKPGASVKI PCKASGYTFT DYNMDWVKQS HGKSLEWIGE INPNNGGTFY    60
NQKFKGKATL TVDKSSSTAY MELRSLTSED TAVYYCAREA ITTVGAMDYW GQGTSVTVSS   120

SEQ ID NO: 49           moltype = DNA   length = 357
FEATURE                 Location/Qualifiers
misc_feature            1..357
                        note = Description of Artificial Sequence: Synthetic
                        polynucleotide
source                  1..357
                        mol_type = other DNA
                        organism = synthetic construct
SEQUENCE: 49
caggttactc tgaaagagtc tggccctgga atattgcagc cctcccagac cctcagtctg    60
acttgttctt tctctgggtt ttcactgagc acttatggta tgggtgtagg ctggattcgt   120
cagccttcag gaaagggtct agagtggctg gcagacattt ggtgggatga cgataagtac   180
tataacccat ccctgaagag ccggctcaca atctccaagg atacctccag caatgaggta   240
ttcctcaaga tcgccattgt ggacactgca gatactgcca cttactactg tgctcgaaga   300
ggtcactact ctgctatgga ctactgggt caaggaacct cagtcaccgt ctcctca      357

SEQ ID NO: 50           moltype = AA   length = 119
FEATURE                 Location/Qualifiers
REGION                  1..119
                        note = Description of Artificial Sequence: Synthetic
                        polypeptide
source                  1..119
                        mol_type = protein
                        organism = synthetic construct
SEQUENCE: 50
QVTLKESGPG ILQPSQTLSL TCSFSGFSLS TYGMGVGWIR QPSGKGLEWL ADIWWDDDKY    60
YNPSLKSRLT ISKDTSSNEV FLKIAIVDTA DTATYYCARR GHYSAMDYWG QGTSVTVSS    119

SEQ ID NO: 51           moltype = DNA   length = 363
FEATURE                 Location/Qualifiers
misc_feature            1..363
                        note = Description of Artificial Sequence: Synthetic
                        polynucleotide
source                  1..363
                        mol_type = other DNA
                        organism = synthetic construct
SEQUENCE: 51
caggttactc tgaaagagtc tggccctggg atattgcagc cctcccagac cctcagtctg    60
acttgttctt tctctgggtt ttcactgagc acttctggta tgggtgtgag ttggattcgt   120
cagccttcag gaaagggtct ggagtggctg gcacacaatg actgggatga tgacaagcgc   180
tataagtcat ccctgaagag ccggctcaca atatccaagg atacctccag aaaccaggta   240
ttcctcaaga tcaccagtgt ggacactgca gatactgcca catactactg tgctcgaaga   300
gttggggat tagagggcta ttttgattac tggggccaag caccactct cacagtctcc    360
tca                                                                363

SEQ ID NO: 52           moltype = AA   length = 121
FEATURE                 Location/Qualifiers
REGION                  1..121
                        note = Description of Artificial Sequence: Synthetic
                        polypeptide
source                  1..121
                        mol_type = protein
                        organism = synthetic construct
SEQUENCE: 52
QVTLKESGPG ILQPSQTLSL TCSFSGFSLS TSGMGVSWIR QPSGKGLEWL AHNDWDDDKR    60
YKSSLKSRLT ISKDTSRNQV FLKITSVDTA DTATYYCARR VGGLEGYFDY WGQGTTLTVS   120
S                                                                  121

SEQ ID NO: 53           moltype = DNA   length = 360
FEATURE                 Location/Qualifiers
misc_feature            1..360
                        note = Description of Artificial Sequence: Synthetic
                        polynucleotide
source                  1..360
                        mol_type = other DNA
                        organism = synthetic construct
SEQUENCE: 53
caagtgcaac ttgtgcagtc gggtgcggaa gtcaaaaagc cggagcgtc ggtgaaagta     60
tcgtgtaaag cgtcgggata tacgtttacg gactataaca tggactgggt acgacaggca   120
ccggggaaat cgttggaatg gatcggacag attaatccga acaatggggg aatttttcttt   180
aatcagaaat tcaaaggacg ggcgacgttg acggtcgata catcgacgaa tacggctat   240
atggaattga ggtcgcttcg ctcggacgat acggcggtct attactcgc cagggaggcg   300
atcacgacg taggggcgat ggattattgg ggacagggga cgcttgtgac ggtatcgtcg   360

SEQ ID NO: 54           moltype = AA   length = 120
```

```
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 54
QVQLVQSGAE VKKPGASVKV SCKASGYTFT DYNMDWVRQA PGKSLEWIGQ INPNNGGIFF    60
NQKFKGRATL TVDTSTNTAY MELRSLRSDD TAVYYCAREA ITTVGAMDYW GQGTLVTVSS   120

SEQ ID NO: 55           moltype = DNA   length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 55
caagtccagc ttgtccagtc gggagcggaa gtgaagaaac cggggtcgtc ggtcaaagta    60
tcgtgtaaag cgtcgggata tacgtttacg gactataatg tggattgggt acgacaggct   120
ccggaaaaat cattggaatg gattggacag attaatccga ataatggggg tatcttcttt   180
aatcaaaagt ttaaagggag ggcgacgttg acggtggaca aatcgacaaa tacggcgtat   240
atggaattgt cgtcgcttcg gtcggaggac acggcggtgt attactgcgc gagggaggcg   300
atcacgacgg tcggggcgat ggattattgg ggacagggaa cgcttgtgac ggtatcgtcg   360

SEQ ID NO: 56           moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 56
QVQLVQSGAE VKKPGSSVKV SCKASGYTFT DYNMDWVRQA PGKSLEWIGQ INPNNGGIFF    60
NQKFKGRATL TVDKSTNTAY MELSSLRSED TAVYYCAREA ITTVGAMDYW GQGTLVTVSS   120

SEQ ID NO: 57           moltype = DNA   length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 57
caggtccagc ttgtgcaatc gggagcggaa gtgaagaaac cgggagcgtc ggtaaaagtc    60
tcgtgcaaag cgtcggggta tacgtttacg gactataaca tggactgggt cgccaagcg   120
cctggacagg tcttgaatg gatgggggcag attaatccga ataatggagg gatcttcttt   180
aatcagaaat tcaaaggaag ggtaacgctg acgacagaca cgtcaacatc gacggcgtat   240
atggaattgc ggtcgttgcg atcagatgat acggcggtct actattgtgc gagggaggcg   300
attacgacgg tgggagcgat ggattattgg ggacaggggg acgttggtaac ggtatcgtcg   360

SEQ ID NO: 58           moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 58
QVQLVQSGAE VKKPGASVKV SCKASGYTFT DYNMDWVRQA PGQGLEWMGQ INPNNGGIFF    60
NQKFKGRVTL TTDTSTSTAY MELRSLRSDD TAVYYCAREA ITTVGAMDYW GQGTLVTVSS   120

SEQ ID NO: 59           moltype = DNA   length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 59
caggtccagc ttgtgcaatc gggagcggaa gtgaagaaac cgggagcgtc ggtaaaagtc    60
tcgtgcaaag cgtcggggta tacgtttacg gactataaca tggactgggt cgccaagcg   120
cctggacaga gccttgaatg gatgggggcag attaatccga ataatggagg gatcttcttt   180
```

```
aatcagaaat tccagggaag gtaacgctg acgacagaca cgtcaacatc gacggcctat   240
atggaattgc ggtcgttgcg atcagatgat acggcggtct actattgtgc gagggaggcg   300
attacgacgg tgggagcgat ggattattgg ggacagggga cgttggtaac ggtatcgtcg   360

SEQ ID NO: 60            moltype = AA   length = 120
FEATURE                  Location/Qualifiers
REGION                   1..120
                         note = Description of Artificial Sequence: Synthetic
                         polypeptide
source                   1..120
                         mol_type = protein
                         organism = synthetic construct
SEQUENCE: 60
QVQLVQSGAE VKKPGASVKV SCKASGYTFT DYNMDWVRQA PGQSLEWMGQ INPNNGGIFF    60
NQKFQGRVTL TTDTSTSTAY MELRSLRSDD TAVYYCAREA ITTVGAMDYW GQGTLVTVSS   120

SEQ ID NO: 61            moltype = DNA   length = 360
FEATURE                  Location/Qualifiers
misc_feature             1..360
                         note = Description of Artificial Sequence: Synthetic
                         polynucleotide
source                   1..360
                         mol_type = other DNA
                         organism = synthetic construct
SEQUENCE: 61
caggtccagc ttgtgcaatc gggagcggaa gtgaagaaac cgggagcgtc ggtaaaagtc    60
tcgtgcaaag cgtcggggta tacgtttacg gactataaca tggactgggt gcgccaagcg   120
cctggacagg tcttgaatg gatggggcag attaatccga ataatggagg gatcttcttt   180
aatcagaaat tccagggaag ggtaacgctg acgacagaca cgtcaacatc gacggcctat   240
atggaattgc ggtcgttgcg atcagatgat acggcggtct actattgtgc gagggaggcg   300
attacgacgg tgggagcgat ggattattgg ggacagggga cgttggtaac ggtatcgtcg   360

SEQ ID NO: 62            moltype = AA   length = 120
FEATURE                  Location/Qualifiers
REGION                   1..120
                         note = Description of Artificial Sequence: Synthetic
                         polypeptide
source                   1..120
                         mol_type = protein
                         organism = synthetic construct
SEQUENCE: 62
QVQLVQSGAE VKKPGASVKV SCKASGYTFT DYNMDWVRQA PGQGLEWMGQ INPNNGGIFF    60
NQKFQGRVTL TTDTSTSTAY MELRSLRSDD TAVYYCAREA ITTVGAMDYW GQGTLVTVSS   120

SEQ ID NO: 63            moltype = DNA   length = 360
FEATURE                  Location/Qualifiers
misc_feature             1..360
                         note = Description of Artificial Sequence: Synthetic
                         polynucleotide
source                   1..360
                         mol_type = other DNA
                         organism = synthetic construct
SEQUENCE: 63
caagtacagc ttgtacagtc gggagcggaa gtcaagaaac cgggatcgtc ggtcaaagtg    60
tcgtgtaaag cgtcggggata tacgtttagc gactataaca tggattgggt gcgacaagcg   120
cctgggcagg gacttgaatg gatgggtcag atcaatccga ataatggggg aatcttttc   180
aatcagaagt ttaaagggag ggtaacgctg acgcggata aaagcacgtc aacggcgtat   240
atggagttgt cgtcgttgcg gtcggaggac acggcggtct attactgcgc gagggaagcg   300
attacgacgg tgggagcgat ggattattgg ggcagggaa cgcttgtaac ggtgtcatcg   360

SEQ ID NO: 64            moltype = AA   length = 120
FEATURE                  Location/Qualifiers
REGION                   1..120
                         note = Description of Artificial Sequence: Synthetic
                         polypeptide
source                   1..120
                         mol_type = protein
                         organism = synthetic construct
SEQUENCE: 64
QVQLVQSGAE VKKPGSSVKV SCKASGYTFS DYNMDWVRQA PGQGLEWMGQ INPNNGGIFF    60
NQKFKGRVTL TADKSTSTAY MELSSLRSED TAVYYCAREA ITTVGAMDYW GQGTLVTVSS   120

SEQ ID NO: 65            moltype = DNA   length = 360
FEATURE                  Location/Qualifiers
misc_feature             1..360
                         note = Description of Artificial Sequence: Synthetic
                         polynucleotide
source                   1..360
                         mol_type = other DNA
```

```
                        organism = synthetic construct
SEQUENCE: 65
caagtacagc ttgtacagtc gggagcggaa gtcaagaaac cgggatcgtc ggtcaaagtg    60
tcgtgtaaag cgtcgggata tacgtttagc gactataaca tggattgggt gcgacaagcg   120
cctgggcagg gacttgaatg gatgggtcag atcaatcaga ataatggggg aatcttttc    180
aatcagaagt tcaggggag ggtaacgctg acggcggata aaagcacgtc aacggcgtat    240
atggagttgt cgtcgttgcg gtcggaggac acggcggtct attactcgcg gagggaagcg   300
attacgacgg tggagcgat ggattattgg gggcaggaaa cgcttgtaac ggtgtcatcg    360

SEQ ID NO: 66          moltype = AA   length = 120
FEATURE                Location/Qualifiers
REGION                 1..120
                        note = Description of Artificial Sequence: Synthetic
                         polypeptide
source                 1..120
                        mol_type = protein
                        organism = synthetic construct
SEQUENCE: 66
QVQLVQSGAE VKKPGSSVKV SCKASGYTFS DYNMDWVRQA PGQGLEWMGQ INPNNGGIFF     60
NQKFQGRVTL TADKSTSTAY MELSSLRSED TAVYYCAREA ITTVGAMDYW GQGTLVTVSS    120

SEQ ID NO: 67          moltype = DNA   length = 357
FEATURE                Location/Qualifiers
misc_feature           1..357
                        note = Description of Artificial Sequence: Synthetic
                         polynucleotide
source                 1..357
                        mol_type = other DNA
                        organism = synthetic construct
SEQUENCE: 67
caggtgactt tgaaagaatc cggtcccgca ttggtaaagc caacccagac acttacgctc     60
acatgtacat tttccggatt cagcttgaac acttacggga tgggagtgtc gtggattcgg   120
caacctccgg ggaaggctct ggagtggctg gcgcacatct actgggatga tgacaaaagg   180
tataacccct cacttaaaac gagactgacg atctcgaagg acacaagcaa gaatcaggtc   240
gtcctcacga ttacgaatgt agacccggtg gatactgcct ctattactg cgcgcaacgc   300
gggtatgatg actactgggg atattggggt cagggcaccc tcgtgaccat ctcgtca     357

SEQ ID NO: 68          moltype = AA   length = 119
FEATURE                Location/Qualifiers
REGION                 1..119
                        note = Description of Artificial Sequence: Synthetic
                         polypeptide
source                 1..119
                        mol_type = protein
                        organism = synthetic construct
SEQUENCE: 68
QVTLKESGPA LVKPTQTLTL TCTFSGFSLN TYGMGVSWIR QPPGKALEWL AHIYWDDDKR     60
YNPSLKTRLT ISKDTSKNQV VLTITNVDPV DTAVYYCAQR GYDDYWGYWG QGTLVTISS    119

SEQ ID NO: 69          moltype = DNA   length = 357
FEATURE                Location/Qualifiers
misc_feature           1..357
                        note = Description of Artificial Sequence: Synthetic
                         polynucleotide
source                 1..357
                        mol_type = other DNA
                        organism = synthetic construct
SEQUENCE: 69
caagtaacgc tcaaggagtc cggacccacc ttggtgaagc cgacgcagac cttgactctt     60
acgtgcactt tctcgggtt ttcactgaat acgtacggga tgggtgtctc atggatcagg   120
caacctccgg ggaaaggatt ggaatggctg gcgcacatct actgggatga cgataagaga   180
tataacccaa gcctcaagtc gcggctcacc attacaaaag atacatcgaa aaatcaggtc   240
gtacttacta tcacgaacat ggaccccgtg gacacagcaa catattactg tgcccagcgc   300
ggctatgacg attattgggg ttactgggga cagggaacac tggtcacggt gtccagc      357

SEQ ID NO: 70          moltype = AA   length = 119
FEATURE                Location/Qualifiers
REGION                 1..119
                        note = Description of Artificial Sequence: Synthetic
                         polypeptide
source                 1..119
                        mol_type = protein
                        organism = synthetic construct
SEQUENCE: 70
QVTLKESGPT LVKPTQTLTL TCTFSGFSLN TYGMGVSWIR QPPGKGLEWL AHIYWDDDKR     60
YNPSLKSRLT ITKDTSKNQV VLTITNMDPV DTATYYCAQR GYDDYWGYWG QGTLVTVSS    119

SEQ ID NO: 71          moltype = DNA   length = 357
FEATURE                Location/Qualifiers
```

```
misc_feature           1..357
                       note = Description of Artificial Sequence: Synthetic
                         polynucleotide
source                 1..357
                       mol_type = other DNA
                       organism = synthetic construct
SEQUENCE: 71
cagatcactt tgaaagaaag cggaccgacc ttggtcaagc ccacacaaac cctcacgctc   60
acgtgtacat tttcgggggtt ctcgctttca acttacggga tgggagtagg gtggattcgc  120
cagccgcctg gtaaagcgtt ggagtggctt gcagacatct ggtgggacga cgataagtac  180
tataatccct cgctcaagtc cagactgacc atcacgaaag atacgagcaa gaaccaggtc  240
gtgctgacaa tgactaacat ggacccagtg gatacggcta catattactg cgccaggcgg  300
ggtcactact cagcgatgga ttattgggggc cagggaacac tggtaacggt gtcgtcc    357

SEQ ID NO: 72          moltype = AA  length = 119
FEATURE                Location/Qualifiers
REGION                 1..119
                       note = Description of Artificial Sequence: Synthetic
                         polypeptide
source                 1..119
                       mol_type = protein
                       organism = synthetic construct
SEQUENCE: 72
QITLKESGPT LVKPTQTLTL TCTFSGFSLS TYGMGVGWIR QPPGKALEWL ADIWWDDDKY   60
YNPSLKSRLT ITKDTSKNQV VLTMTNMDPV DTATYYCARR GHYSAMDYWG QGTLVTVSS   119

SEQ ID NO: 73          moltype = DNA  length = 357
FEATURE                Location/Qualifiers
misc_feature           1..357
                       note = Description of Artificial Sequence: Synthetic
                         polynucleotide
source                 1..357
                       mol_type = other DNA
                       organism = synthetic construct
SEQUENCE: 73
caagtgactc tcaaggagtc cggaccgcc ctggtcaaac caacgcagac actgacgctc    60
acatgcacct tcagcggatt ttcgttgtca acgtacggca tgggtgtggg gtggattcgc  120
cagcctccgg ggaaagccct tgaatggttg gcggacatct ggtgggatga tgacaagtac  180
tataatccct cacttaagtc acggttgacg atctcgaaag acaccagcaa gaaccaggta  240
gtgctgacaa tgactaacat ggacccggtc gatacagcgg tctactattg tgctagaagg  300
ggacactact ccgcaatgga ttattgggggt caggggacgc tcgtaaccgt gtcgtcg    357

SEQ ID NO: 74          moltype = AA  length = 119
FEATURE                Location/Qualifiers
REGION                 1..119
                       note = Description of Artificial Sequence: Synthetic
                         polypeptide
source                 1..119
                       mol_type = protein
                       organism = synthetic construct
SEQUENCE: 74
QVTLKESGPA LVKPTQTLTL TCTFSGFSLS TYGMGVGWIR QPPGKALEWL ADIWWDDDKY   60
YNPSLKSRLT ISKDTSKNQV VLTMTNMDPV DTAVYYCARR GHYSAMDYWG QGTLVTVSS   119

SEQ ID NO: 75          moltype = DNA  length = 321
FEATURE                Location/Qualifiers
misc_feature           1..321
                       note = Description of Artificial Sequence: Synthetic
                         polynucleotide
source                 1..321
                       mol_type = other DNA
                       organism = synthetic construct
SEQUENCE: 75
gacatccaga tgactcagtc tccagcctcc ctatctgcat ctgtgggaga aactgtcacc   60
atcacatgtc gaacaagtga gaatcttcac aattatttag catggtatca gcagaaacag  120
ggaaaatctc ctcagctcct ggtctatgat gcaaaaacct tagcagatgg tgtgccatca  180
aggttcagtg gcagtggatc aggaacacaa tattctctca agatcaacag cctgcagcct  240
gaagattttg ggagttatta ctgtcaacat ttttggagta gtccttacac gttcggaggg  300
gggaccaagc tggaaataaa a                                            321

SEQ ID NO: 76          moltype = AA  length = 107
FEATURE                Location/Qualifiers
REGION                 1..107
                       note = Description of Artificial Sequence: Synthetic
                         polypeptide
source                 1..107
                       mol_type = protein
                       organism = synthetic construct
SEQUENCE: 76
```

```
DIQMTQSPAS LSASVGETVT ITCRTSENLH NYLAWYQQKQ GKSPQLLVYD AKTLADGVPS    60
RFSGSGSGTQ YSLKINSLQP EDFGSYYCQH FWSSPYTFGG GTKLEIK                 107

SEQ ID NO: 77           moltype = DNA   length = 333
FEATURE                 Location/Qualifiers
misc_feature            1..333
                        note = Description of Artificial Sequence: Synthetic
                        polynucleotide
source                  1..333
                        mol_type = other DNA
                        organism = synthetic construct
SEQUENCE: 77
gacattgtgt tgacccaatc tccagcttct ttggctgtgt ctctagggca gagggccacc    60
atctcctgca gagccagcga aagtgttgat aattatggca ttagttttat gaactggttc   120
caacagaaac caggacagcc acccaaactc ctcatctatg ctgcatccaa ccaaggctcc   180
ggggtccctg ccaggtttag tggcagtggg tctgggacag acttcagcct caacatccat   240
cctatggagg aggatgatac tgcaatgtat ttctgtcagc aaagtaagga ggttccgtgg   300
acgttcggtg gaggctccaa gctggaaatc aaa                                333

SEQ ID NO: 78           moltype = AA    length = 111
FEATURE                 Location/Qualifiers
REGION                  1..111
                        note = Description of Artificial Sequence: Synthetic
                        polypeptide
source                  1..111
                        mol_type = protein
                        organism = synthetic construct
SEQUENCE: 78
DIVLTQSPAS LAVSLGQRAT ISCRASESVD NYGISFMNWF QQKPGQPPKL LIYAASNQGS    60
GVPARFSGSG SGTDFSLNIH PMEEDDTAMY FCQQSKEVPW TFGGGSKLEI K            111

SEQ ID NO: 79           moltype = DNA   length = 321
FEATURE                 Location/Qualifiers
misc_feature            1..321
                        note = Description of Artificial Sequence: Synthetic
                        polynucleotide
source                  1..321
                        mol_type = other DNA
                        organism = synthetic construct
SEQUENCE: 79
gacattgtga tgacccagtc tcaaaaattc atgtccacat cagtaggaga cagggtcagc    60
gtcacctgca aggccagtca gaatgtgggt actaatgtag cctggtatca acagaaatta   120
ggacaatctc ctaaaacact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atccgtacac gttcggaggg   300
gggaccaagc tggaaataaa a                                             321

SEQ ID NO: 80           moltype = AA    length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 80
DIVMTQSQKF MSTSVGDRVS VTCKASQNVG TNVAWYQQKL GQSPKTLIYS ASYRYSGVPD    60
RFTGSGSGTD FTLTISNVQS EDLAEYFCQQ YNSYPYTFGG GTKLEIK                 107

SEQ ID NO: 81           moltype = DNA   length = 321
FEATURE                 Location/Qualifiers
misc_feature            1..321
                        note = Description of Artificial Sequence: Synthetic
                        polynucleotide
source                  1..321
                        mol_type = other DNA
                        organism = synthetic construct
SEQUENCE: 81
gacattgtga tgacccagtc tcaaaaattc atgtccacat cagtaggaga cagggtcagc    60
gtcacctgca aggccagtca gaatgtgggt actaatgtag cctggtttca acagaaacca   120
ggtcaatctc ctaaagcact gatttactcg gcatcttacc ggtacagtgg agtccctgat   180
cgcttcacag gcagtggatc tgggacagat ttcattctca ccatcagcaa tgtgcagtct   240
gaagacttgg cagagtattt ctgtcagcaa tataacaact atcctctcac gttcggtgct   300
gggaccaagc tggagctgaa a                                             321

SEQ ID NO: 82           moltype = AA    length = 107
FEATURE                 Location/Qualifiers
REGION                  1..107
                        note = Description of Artificial Sequence: Synthetic
```

```
                        polypeptide
source                  1..107
                        mol_type = protein
                        organism = synthetic construct
SEQUENCE: 82
DIVMTQSQKF MSTSVGDRVS VTCKASQNVG TNVAWFQQKP GQSPKALIYS ASYRYSGVPD    60
RFTGSGSGTD FILTISNVQS EDLAEYFCQQ YNNYPLTFGA GTKLELK                 107

SEQ ID NO: 83           moltype = DNA  length = 321
FEATURE                 Location/Qualifiers
misc_feature            1..321
                        note = Description of Artificial Sequence: Synthetic
                        polynucleotide
source                  1..321
                        mol_type = other DNA
                        organism = synthetic construct
SEQUENCE: 83
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcagctcct ggtctataat gcaaaaacct tagcagatgg tgtgccatca   180
aggttcagtg gcagtggatc aggaacacaa tattctctca agatcaacag cctgcagcct   240
gaagattttg ggagttatta ctgtcaacat ttttggagtt ctccttacac gttcggaggg   300
gggaccaagc tggaaataaa a                                             321

SEQ ID NO: 84           moltype = AA  length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 84
DIQMTQSPAS LSASVGETVT ITCRASGNIH NYLAWYQQKQ GKSPQLLVYN AKTLADGVPS    60
RFSGSGSGTQ YSLKINSLQP EDFGSYYCQH FWSSPYTFGG GTKLEIK                 107

SEQ ID NO: 85           moltype = DNA  length = 321
FEATURE                 Location/Qualifiers
misc_feature            1..321
                        note = Description of Artificial Sequence: Synthetic
                        polynucleotide
source                  1..321
                        mol_type = other DNA
                        organism = synthetic construct
SEQUENCE: 85
gacattgtaa tgacccagtc tcaaaaattc atgtccacat cagtaggaga cagggtcagc    60
gtcacctgca aggccagtca gaatgtgggt actaatgtag cctggtatca acagaaacca   120
gggcaatctc ctaaagcact gatttactcg ccatcctacc ggtacagtgg agtccctgat   180
cgcttcacag gcagtggatc tgggacagat ttcactctca ccatcagcaa tgtgcagtct   240
gaagacttgg cagaatattt ctgtcagcaa tataacagct atcctcacac gttcggaggg   300
gggaccaagc tggaaatgaa a                                             321

SEQ ID NO: 86           moltype = AA  length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 86
DIVMTQSQKF MSTSVGDRVS VTCKASQNVG TNVAWYQQKP GQSPKALIYS PSYRYSGVPD    60
RFTGSGSGTD FTLTISNVQS EDLAEYFCQQ YNSYPHTFGG GTKLEMK                 107

SEQ ID NO: 87           moltype = DNA  length = 333
FEATURE                 Location/Qualifiers
misc_feature            1..333
                        note = Description of Artificial Sequence: Synthetic
                        polynucleotide
source                  1..333
                        mol_type = other DNA
                        organism = synthetic construct
SEQUENCE: 87
gacattgtgc tgacacagtc tcctgcttcc ttagctgtat ctctggggca gagggccacc    60
atctcatgca gggccagcca aagtgtcagt acatctaggt ttagttatat gcactggttc   120
caacagaaac caggacaggc acccaaactc ctcatcaagt atgcatccaa cctagaatct   180
ggggtccctg ccaggttcag tggcagtggg tctgggacag acttcaccct caacatccat   240
cctgtggagg gggaggatac tgcaacatat tactgtcagc acagtgggga gattcgtac   300
acgttcggag gggggaccaa gctggaaata aaa                                333
```

```
SEQ ID NO: 88            moltype = AA   length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 88
DIVLTQSPAS LAVSLGQRAT ISCRASQSVS TSRFSYMHWF QQKPGQAPKL LIKYASNLES   60
GVPARFSGSG SGTDFTLNIH PVEGEDTATY YCQHSWEIPY TFGGGTKLEI K           111

SEQ ID NO: 89            moltype = DNA   length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 89
gacatccaaa tgacccagtc gccgtcgtcg ctttcagcgt cggtagggga tcgggtcaca    60
attacgtgcc gaacgtcaga gaatttgcat aactacctcg cgtggtatca gcagaagccc   120
gggaagtcac cgaaactcct tgtctacgat gcgaaaacgc tggcggatgg agtgccgtcg   180
agattctcgg gaagcggatc cggtacggac tatacgctta cgatctcatc gctccagccc   240
gaggactttg cgacgtacta ttgtcagcat ttttggtcgt cgccctacac atttgggcag   300
gggaccaagt tggaaatcaa g                                             321

SEQ ID NO: 90            moltype = AA   length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 90
DIQMTQSPSS LSASVGDRVT ITCRTSENLH NYLAWYQQKP GKSPKLLVYD AKTLADGVPS    60
RFSGSGSGTD YTLTISSLQP EDFATYYCQH FWSSPYTFGQ GTKLEIK                 107

SEQ ID NO: 91            moltype = DNA   length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 91
gacatccaaa tgacccagtc gccgtcgtcg ctttcagcgt cggtagggga tcgggtcaca    60
attacgtgcc gaacgtcaga gaatttgcat aactacctcg cgtggtatca gcagaagccc   120
gggaaggccc cgaaactcct tatctacgat gcgaaaacgc tggcggatgg agtgccgtcg   180
agattctcgg gaagcggatc cggtacggac tatacgctta cgatctcatc gctccagccc   240
gaggactttg cgacgtacta ttgtcagcat ttttggtcgt cgccctacac atttgggcag   300
gggaccaagt tggaaatcaa g                                             321

SEQ ID NO: 92            moltype = AA   length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 92
DIQMTQSPSS LSASVGDRVT ITCRTSENLH NYLAWYQQKP GKAPKLLIYD AKTLADGVPS    60
RFSGSGSGTD YTLTISSLQP EDFATYYCQH FWSSPYTFGQ GTKLEIK                 107

SEQ ID NO: 93            moltype = DNA   length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 93
gacatccaaa tgacccagtc gccgtcgtcg ctttcagcgt cggtagggga tcgggtcaca    60
```

```
attacgtgcc gaacgtcaga gaatttgcat aactacctcg cgtggtatca gcagaagccc    120
gggaagtcac cgaaactcct tatctacgat gcgaaaacgc tggcggatgg agtgccgtcg    180
agattctcgg gaagcggatc cggtacggac tatacgctta cgatctcatc gctccagccc    240
gaggactttg cgacgtacta ttgtcagcat ttttggtcgt cgccctacac atttgggcag    300
gggaccaagt tggaaatcaa g                                              321

SEQ ID NO: 94           moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 94
DIQMTQSPSS LSASVGDRVT ITCRTSENLH NYLAWYQQKP GKSPKLLIYD AKTLADGVPS    60
RFSGSGSGTD YTLTISSLQP EDFATYYCQH FWSSPYTFGQ GTKLEIK                  107

SEQ ID NO: 95           moltype = DNA   length = 321
FEATURE                 Location/Qualifiers
misc_feature            1..321
                        note = Description of Artificial Sequence: Synthetic
                        polynucleotide
source                  1..321
                        mol_type = other DNA
                        organism = synthetic construct
SEQUENCE: 95
gacatccaaa tgacccaatc gccctcctcc ctctccgcat cagtagggga ccgcgtcaca    60
attacttgca aagcgtcgca gaacgtcgga acgaatgtgg cgtggtttca gcagaagccc    120
ggaaaagctc cgaagagctt gatctactcg gcctcatata ggtattcggg tgtgccgagc    180
cggtttagcg ggtcggggtc aggtactgat ttcacgctca caatttcatc gttccagcca    240
gaagatttcg ccacatatta ctgtcagcag tacaacaatt accctctgac gttcggccag    300
ggaaccaaac ttgagatcaa g                                              321

SEQ ID NO: 96           moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 96
DIQMTQSPSS LSASVGDRVT ITCKASQNVG TNVAWFQQKP GKAPKSLIYS ASYRYSGVPS    60
RFSGSGSGTD FTLTISSLQP EDFATYYCQQ YNNYPLTFGQ GTKLEIK                  107

SEQ ID NO: 97           moltype = DNA   length = 321
FEATURE                 Location/Qualifiers
misc_feature            1..321
                        note = Description of Artificial Sequence: Synthetic
                        polynucleotide
source                  1..321
                        mol_type = other DNA
                        organism = synthetic construct
SEQUENCE: 97
gatatccaga tgacacagtc accctcgtcg ctctcagctt ccgtaggcga cagggtcact    60
attacgtgta aagcatcaca gaacgtcgga acgaatgtgg cgtggtttca gcagaagccc    120
gggaagagcc ccaaagcgct tatctactcc cgtcgtatc ggtattccgg tgtgccaagc    180
agattttcgg ggtcaggttc gggaactgac tttaccctga ccatctcgtc cctccaaccg    240
gaagatttcg ccacgtactt ctgccagcag tacaacagct atcctcacac attcggacaa    300
gggacaaagt tggagattaa a                                              321

SEQ ID NO: 98           moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 98
DIQMTQSPSS LSASVGDRVT ITCKASQNVG TNVAWFQQKP GKSPKALIYS PSYRYSGVPS    60
RFSGSGSGTD FTLTISSLQP EDFATYFCQQ YNSYPHTFGQ GTKLEIK                  107

SEQ ID NO: 99           moltype = DNA   length = 1332
FEATURE                 Location/Qualifiers
misc_feature            1..1332
                        note = Description of Artificial Sequence: Synthetic
                        polynucleotide
```

| | | |
|---|---|---|
| source | 1..1332<br>mol_type = other DNA<br>organism = synthetic construct | |
| SEQUENCE: 99 | | |
| gaggtcctgc tgcaacagtc tggacctgag ctggtgaagc ctggggcttc agtgaagata | | 60 |
| ccctgcaagg cttctggata cacattcact gactacaaca tggactgggt gaagcagagc | | 120 |
| catggaaaga gccttgagtg gattggacaa attaatccta caatggtgg tatttcttc | | 180 |
| aaccagaagt tcaagggcaa ggccacattg actgtagaca gtcctccaa tacagccttc | | 240 |
| atggaggtcc gcagcctgac atctgaggac actgcagtct attactgtgc aagagaggca | | 300 |
| attactacgg taggcgctat ggactactgg ggtcaaggaa cctcagtcac cgtctcctca | | 360 |
| gccaaaacga caccccatc tgtctatcca ctggcccctg gatctgctgc ccaaactaac | | 420 |
| tccatggtga ccctgggatg cctggtcaag ggctatttcc ctgagccagt gacagtgacc | | 480 |
| tggaactctg gatccctgtc cagcggtgtg cacaccttcc cagctgtcct gcagtctgac | | 540 |
| ctctacactc tgagcagctc agtgactgtc ccctccagca cctggcccag cgagaccgtc | | 600 |
| acctgcaacg ttgcccaccc ggccagcagc accaaggtgg acaagaaaat tgtgcccagg | | 660 |
| gattgtggtt gtaagccttg catatgtaca gtcccagaag tatcatctgt cttcatcttc | | 720 |
| cccccaaagc caaggatgt gctcaccatt actctgactc ctaaggtcac gtgtgttgtg | | 780 |
| gtagacatca gcaaggatga tcccgaggtc cagttcagtt ggtttgtaga tgatgtggag | | 840 |
| gtgcacacag ctcagacgca accccgggag gagcagttca acagcacttt ccgctcagtc | | 900 |
| agtgaacttc ccatcatgca ccaggactgg ctcaatggca aggagttcaa atgcagggtc | | 960 |
| aacagtgcag ctttccctgc ccccatcgag aaaaccatct ccaaaaccaa aggcagaccg | | 1020 |
| aaggctccac aggtgtacac cattccacct cccaaggagc agatggcaa ggataaagtc | | 1080 |
| agtctgacct gcatgataac agacttcttc cctgaagaca ttactgtgga gtggcagtgg | | 1140 |
| aatgggcagc cagcggagaa ctacaagaac actcagccca tcatgacac agatggctct | | 1200 |
| tacttcgtct acagcaagct caatgtgcag aagagcaact gggaggcagg aaatactttc | | 1260 |
| acctgctctg tgttacatga gggcctgcac aaccaccata tgagaagag cctctcccac | | 1320 |
| tctccctggta aa | | 1332 |
| SEQ ID NO: 100 | moltype = AA length = 444 | |
| FEATURE | Location/Qualifiers | |
| REGION | 1..444<br>note = Description of Artificial Sequence: Synthetic<br>polypeptide | |
| source | 1..444<br>mol_type = protein<br>organism = synthetic construct | |
| SEQUENCE: 100 | | |
| EVLLQQSGPE LVKPGASVKI PCKASGYTFT DYNMDWVKQS HGKSLEWIGQ INPNNGGIFF | | 60 |
| NQKFKGKATL TVDKSSNTAF MEVRSLTSED TAVYYCAREA ITTVGAMDYW GQGTSVTVSS | | 120 |
| AKTTPPSVYP LAPGSAAQTN SMVTLGCLVK GYFPEPVTVT WNSGSLSSGV HTFPAVLQSD | | 180 |
| LYTLSSSVTV PSSTWPSETV TCNVAHPASS TKVDKKIVPR DCGCKPCICT VPEVSSVFIF | | 240 |
| PPKPKDVLTI TLTPKVTCVV VDISKDDPEV QFSWFVDDVE VHTAQTQPRE EQFNSTFRSV | | 300 |
| SELPIMHQDW LNGKEFKCRV NSAAFPAPIE KTISKTKGRP KAPQVYTIPP PKEQMAKDKV | | 360 |
| SLTCMITDFF PEDITVEWQW NGQPAENYKN TQPIMDTDGS YFVYSKLNVQ KSNWEAGNTF | | 420 |
| TCSVLHEGLH NHHTEKSLSH SPGK | | 444 |
| SEQ ID NO: 101 | moltype = DNA length = 642 | |
| FEATURE | Location/Qualifiers | |
| misc_feature | 1..642<br>note = Description of Artificial Sequence: Synthetic<br>polynucleotide | |
| source | 1..642<br>mol_type = other DNA<br>organism = synthetic construct | |
| SEQUENCE: 101 | | |
| gacatccaga tgactcagtc tccagcctcc ctatctgcat ctgtgggaga aactgtcacc | | 60 |
| atcacatgtc gaacaagtga gaatcttcac aattatttag catggtatca gcagaaacag | | 120 |
| ggaaaatctc ctcagctcct ggtctatgat gcaaaaacct agcagatgg tgtgccatca | | 180 |
| aggttcagtg gcagtggatc aggaacacaa tattctctca agatcaacag cctgcagcct | | 240 |
| gaagattttg ggagttatta ctgtcaacat ttttggagta gtccttacac gttcggaggg | | 300 |
| gggaccaagc tggaaataaa acgggctgat gctgcaccaa ctgtatccat cttcccacca | | 360 |
| tccagtgagc agttaacatc tggaggtgcc tcagtcgtgt gcttcttgaa caacttctac | | 420 |
| cccaaagaca tcaatgtcaa gtggaagatt gatggcagtg aacgacaaaa tggcgtcctg | | 480 |
| aacagttgga ctgatcagga cagcaaagac agcacctaca gcatgagcag cacccteacg | | 540 |
| ttgaccaagg acgagtatga acgacataac agctatacct gtgaggccac tcacaagaca | | 600 |
| tcaacttcac ccattgtcaa gagcttcaac aggaatgagt gt | | 642 |
| SEQ ID NO: 102 | moltype = AA length = 214 | |
| FEATURE | Location/Qualifiers | |
| REGION | 1..214<br>note = Description of Artificial Sequence: Synthetic<br>polypeptide | |
| source | 1..214<br>mol_type = protein<br>organism = synthetic construct | |
| SEQUENCE: 102 | | |
| DIQMTQSPAS LSASVGETVT ITCRTSENLH NYLAWYQQKQ GKSPQLLVYD AKTLADGVPS | | 60 |
| RFSGSGSGTQ YSLKINSLQP EDFGSYYCQH FWSSPYTFGG GTKLEIKRAD AAPTVSIFPP | | 120 |
| SSEQLTSGGA SVVCFLNNFY PKDINVKWKI DGSERQNGVL NSWTDQDSKD STYSMSSTLT | | 180 |

LTKDEYERHN SYTCEATHKT STSPIVKSFN RNEC                                          214

```
SEQ ID NO: 103            moltype = DNA   length = 1326
FEATURE                   Location/Qualifiers
misc_feature              1..1326
                          note = Description of Artificial Sequence: Synthetic
                            polynucleotide
source                    1..1326
                          mol_type = other DNA
                          organism = synthetic construct
SEQUENCE: 103
caggtccaac tgcagcagcc tggggctgaa ctggtgaagc tgggggcttc agtgaagctg    60
tcctgcaagg cttctggcta caccttcacc agctactgga ttcactgggt gaaccagagg   120
cctggacaag gccttgagtg gattggagac attaatccta gcaacggccg tagtaagtat   180
aatgagaagt tcaagaacaa ggccacaatg actgcagaca aatcctccaa cacagcctac   240
atgcaactca gcagcctgac atctgaggac tctgcggtct attactgtgc aagagaggtt   300
ctggatggtt ctatggacta ctggggtcaa ggaacctcag tcaccgtctc ctcagccaaa   360
acgacaccca catctgtcta tccactggcc cctggatctg ctgcccaaac taactccatg   420
gtgaccctgg gatgcctggt caagggctat ttccctgagc cagtgacagt gacctggaac   480
tctggatccc tgtccagcgg tgtgcacacc ttcccagctg tcctgcagtc tgacctctac   540
actctgagca gctcagtgac tgtcccctcc agcacctggc ccagcgagac cgtcacctgc   600
aacgttgccc acccggccag cagcaccaag gtggacaaga aaattgtgcc cagggattgt   660
ggttgtaagc cttgcatatg tacagtccca gaagtatcat ctgtcttcat cttcccccca   720
aagcccaagg atgtgctcac cattactctg actcctaagg tcacgtgtgt tgtggtagac   780
atcagcaagg atgatcccga ggtccagttc agctggtttg tagatgatgt ggaggtgcac   840
acagctcaga cgcaacccag ggaggagcag ttcaacagca cttttcgctc agtcagtgaa   900
cttcccatca tgcaccagga ctggctcaat ggcaaggagt tcaaatgcag ggtcaacagt   960
gcagctttcc ctgcccccat cgagaaaacc atctccaaaa ccaaggcagc cgaaggct    1020
ccacaggtgt acaccattcc acctcccaag gagcagatgg ccaaggataa agtcagtctg  1080
acctgcatga taacagactt cttccctgaa gacattactg tggagtggca gtggaatggg  1140
cagccagcgg agaactacaa gaacactcag cccatcatgg acacagatgg ctcttacttc  1200
gtctacagca agctcaatgt gcagaagagc aactgggagg caggaaatac tttcacctgc  1260
tctgtgttac atgagggcct gcacaaccac catactgaga gagcctctc ccactctcct   1320
ggtaaa                                                             1326

SEQ ID NO: 104            moltype = AA   length = 442
FEATURE                   Location/Qualifiers
REGION                    1..442
                          note = Description of Artificial Sequence: Synthetic
                            polypeptide
source                    1..442
                          mol_type = protein
                          organism = synthetic construct
SEQUENCE: 104
QVQLQQPGAE LVKPGASVKL SCKASGYTFT SYWIHWVNQR PGQGLEWIGD INPSNGRSKY    60
NEKFKNKATM TADKSSNTAY MQLSSLTSED SAVYYCAREV LDGAMDYWGQ GTSVTVSSAK   120
TTPPSVYPLA PGSAAQTNSM VTLGCLVKGY FPEPVTVTWN SGSLSSGVHT FPAVLQSDLY   180
TLSSSVTVPS STWPSETVTC NVAHPASSTK VDKKIVPRDC GCKPCICTVP EVSSVFIFPP   240
KPKDVLTITL TPKVTCVVVD ISKDDPEVQF SWFVDDVEVH TAQTQPREEQ FNSTFRSVSE   300
LPIMHQDWLN GKEFKCRVNS AAFPAPIEKT ISKTKGRPKA PQVYTIPPPK EQMAKDKVSL   360
TCMITDFFPE DITVEWQWNG QPAENYKNTQ PIMDTDGSYF VYSKLNVQKS NWEAGNTFTC   420
SVLHEGLHNH HTEKSLSHSP GK                                           442

SEQ ID NO: 105            moltype = DNA   length = 654
FEATURE                   Location/Qualifiers
misc_feature              1..654
                          note = Description of Artificial Sequence: Synthetic
                            polynucleotide
source                    1..654
                          mol_type = other DNA
                          organism = synthetic construct
SEQUENCE: 105
gacattgtgt tgacccaatc tccagcttct ttggctgtgt ctctagggca gagggccacc    60
atctcctgca gagccagcga aagtgttgat aattatgca ttagtttat gaactggttc    120
caacagaaac caggacagcc acccaaactc ctcatctatg ctgcatccaa ccaaggctcc   180
ggggtccctg ccaggtttag tggcagtggg tctgggacag acttcagcct caacatccat   240
cctatggagg aggatgatac tgcaatgtat ttctgtcagc aaagtaagga ggttccgtgg   300
acgttcggtg gaggctccaa gctggaaatc aaacgggctg atgctgcacc aactgtatcc   360
atcttcccac catccagtga gcagttaaca tctggaggtg cctcagtcgt gtgcttcttg   420
aacaacttct accccaaaga catcaatgtc aagtggaaga ttgatggcag tgaacgacaa   480
aatggcgtcc tgaacagttg gactgatcag gacagcaaag acagcaccta cagcatgagc   540
agcaccctca cgttgaccaa ggacgagtat gaacgacata acagctatac ctgtgaggcc   600
actcacaaga catcaacttc acccattgtc aagagcttca caggaatga gtgt          654

SEQ ID NO: 106            moltype = AA   length = 218
FEATURE                   Location/Qualifiers
REGION                    1..218
                          note = Description of Artificial Sequence: Synthetic
                            polypeptide
```

```
source                      1..218
                            mol_type = protein
                            organism = synthetic construct
SEQUENCE: 106
DIVLTQSPAS LAVSLGQRAT ISCRASESVD NYGISFMNWF QQKPGQPPKL LIYAASNQGS      60
GVPARFSGSG SGTDFSLNIH PMEEDDTAMY FCQQSKEVPW TFGGGSKLEI KRADAAPTVS     120
IFPPSSEQLT SGGASVVCFL NNFYPKDINV KWKIDGSERQ NGVLNSWTDQ DSKDSTYSMS     180
STLTLTKDEY ERHNSYTCEA THKTSTSPIV KSFNRNEC                             218

SEQ ID NO: 107              moltype = DNA  length = 1329
FEATURE                     Location/Qualifiers
misc_feature                1..1329
                            note = Description of Artificial Sequence: Synthetic
                            polynucleotide
source                      1..1329
                            mol_type = other DNA
                            organism = synthetic construct
SEQUENCE: 107
caggttactc tgaaagagtc tggccctggg atattgcagc cctcccagac cctcagtctg       60
acttgttctt tctctgggtt ttcactgagc acttatggta tgggtgtgac ctggattcgt      120
cagccttcag gaaagggtct ggagtggctg gcacacattt actgggatga tgacaagcgc      180
tataacccat ccctgaagag ccggctcaca atctccagtg ataccccaa caaccaggta       240
ttcctcaaga tcaccagtgt ggacactgca gatactgcca catactactg tgctcaaacg      300
gggtatagta acttgtttgc ttactggggc caagggactc tggtcactgt ctctgcagcc      360
aaaacgacac ccccatctgt ctatccactg gcccctggat ctgctgccca aactaactcc      420
atggtgaccc tgggatgcct ggtcaagggc tatttccctg agccagtgac agtgacctgg      480
aactctggat ccctgtccag cggtgtgcac accttcccag ctgtcctgca gtctgacctc      540
tacactctga gcagctcagt gactgtcccc tccagcacct ggcccagcga gaccgtcacc      600
tgcaacgttg cccacccggc cagcagcacc aaggtggaca gaaaattgt gcccagggat       660
tgtggttgta agccttgcat atgtacagtc cagaagtat catctgtctt catcttcccc       720
ccaaagccca aggatgtgct caccattact ctgactccta aggtcacgtg tgttgtggta      780
gacatcagca aggatgatcc cgaggtccag ttcagctggt ttgtagatga tgtggaggtg      840
cacacagctc agacgcaacc ccgggaggag cagttcaaca gcactttccg ctcagtcagt      900
gaacttccca tcatgcacca ggactggctc aatggcaagg agttcaagtg cagggtcaac      960
agtgcagctt tccctgcccc catccgagaa accatctcca aaaccaaagg cagaccgaag     1020
gctccacagg tgtacaccat tccacctccc aaggagcaga tggccaagga taaagtcagt     1080
ctgacctgca tgataacaga cttcttccct gaagacattc tgtggagtg gcagtggaat     1140
gggcagccag cggagaacta caagaacact cagcccatca tggacacaga tggctcttac     1200
ttcgtctaca gcaagctcaa tgtgcagaag agcaactggg aggcaggaaa tactttcacc     1260
tgctctgtgt tacatgaggg cctgcacaac caccatactg agaagagcct ctcccactct     1320
cctggtaaa                                                            1329

SEQ ID NO: 108              moltype = AA  length = 443
FEATURE                     Location/Qualifiers
REGION                      1..443
                            note = Description of Artificial Sequence: Synthetic
                            polypeptide
source                      1..443
                            mol_type = protein
                            organism = synthetic construct
SEQUENCE: 108
QVTLKESGPG ILQPSQTLSL TCSFSGFSLS TYGMGVTWIR QPSGKGLEWL AHIYWDDDKR      60
YNPSLKSRLT ISKDTSNNQV FLKITSVDTA DTATYYCQT GYSNLFAYWG QGTLVTVSAA     120
KTTPPSVYPL APGSAAQTNS MVTLGCLVKG YFPEPVTVTW NSGSLSSGVH TFPAVLQSDL     180
YTLSSSVTVP SSTWPSETVT CNVAHPASST KVDKKIVPRD CGCKPCICTV PEVSSVFIFP     240
PKPKDVLTIT LTPKVTCVVV DISKDDPEVQ FSWFVDDVEV HTAQTQPREE QFNSTFRSVS     300
ELPIMHQDWL NGKEFKCRVN SAAFPAPIEK TISKTKGRPK APQVYTIPPP KEQMAKDKVS     360
LTCMITDFFP EDITVEWQWN GQPAENYKNT QPIMDTDGSY FVYSKLNVQK SNWEAGNTFT     420
CSVLHEGLHN HHTEKSLSHS PGK                                             443

SEQ ID NO: 109              moltype = DNA  length = 642
FEATURE                     Location/Qualifiers
misc_feature                1..642
                            note = Description of Artificial Sequence: Synthetic
                            polynucleotide
source                      1..642
                            mol_type = other DNA
                            organism = synthetic construct
SEQUENCE: 109
gacattgtga tgacccagtc tcaaaaattc atgtccacat cagtaggaga cagggtcagc       60
gtcacctgca aggccagtca gaatgtgggt actaatgtag cctggtatca acagaaatta      120
ggacaatctc ctaaaacact gatttactcg gcatcctacc ggtacagtgg agtccctgat      180
cgcttcacag gcagtggatc tgggacagat ttcactctca ccatcagcaa tgtgcagtct      240
gaagacttgg cagagtattt ctgtcagcaa tataacagct atccgtacac gttcggaggg      300
gggaccaagc tggaaataaa acgggctgat gctgcaccaa ctgtatccat cttcccacca      360
tccagtgagc agttaacatc tggaggtgcc tcagtcgtgt gcttcttgaa caacttctac      420
cccaaagaca tcaatgtcaa gtggaagatt gatggcagtg aacgacaaaa tggcgtcctg      480
aacagttgga ctgatcagga cagcaaagac agcacctaca gcatgagcag caccctcacg      540
ttgaccaagg acgagtatga acgacataac agctatacct gtgaggccac tcacaagaca      600
```

```
tcaacttcac ccattgtcaa gagcttcaac aggaatgagt gt                642
```

SEQ ID NO: 110          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 110
```
DIVMTQSQKF MSTSVGDRVS VTCKASQNVG TNVAWYQQKL GQSPKTLIYS ASYRYSGVPD   60
RFTGSGSGTD FTLTISNVQS EDLAEYFCQQ YNSYPYTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214
```

SEQ ID NO: 111          moltype = DNA   length = 1329
FEATURE                 Location/Qualifiers
misc_feature            1..1329
                        note = Description of Artificial Sequence: Synthetic
                         polynucleotide
source                  1..1329
                        mol_type = other DNA
                        organism = synthetic construct
SEQUENCE: 111
```
caggttactc tgaaagagtc tggccctggg atattgcagc cctcccagac cctcagtctg   60
acttgttctt tctctgggtt ttcactgaac acttatggta tgggtgtgag ctggattcgt  120
cagccttcag gaaagggtct ggagtggctg gcacacattt actgggatga tgacaagcgc  180
tataacccat ccctgaagag ccggctcaca atctccaagg atgcctccaa caccgggtc   240
ttcctcaaga tcaccagtgt ggacactgca gatactgcca catactactg tgctcaaaga  300
ggttatgatg attactgggg ttactgggc caagggactc tggtcactat ctctgcagcc   360
aaaacgacac cccatctgt ctatccactg gcccctggat ctgctgccca aactaactcc   420
atggtgaccc tgggatgcct ggtcaagggc tatttccctg agccagtgac agtgacctgg   480
aactctggat ccctgtccag cggtgtgcac accttccag ctgtcctgca gtctgacctc   540
tacactctga gcagtcagt gactgtcccc tccagcacct gggcccagca gaccgtcacc   600
tgcaacgttg cccaccccgc cagcagcacc aaggtggaca gaaaattgt gcccagggat   660
tgtggttgta agccttgcat atgtacagtc ccagaagtat catctgtctt catcttcccc   720
ccaaagccca aggatgtgct caccattact ctgactccta aggtcacgtg tgttgtggta   780
gacatcagca aggatgatcc cgaggtccag ttcagctggt ttgtagatga tgtggaggtg   840
cacacagctc agacgcaacc ccgggaggag cagttcaaca gcactttccg ctcagtcagt   900
gaacttccca tcatgcacca ggactggctc aatggcaagg agttcaaatg cagggtcaac   960
agtgcagctt ccctgccccc catcgagaaa accatctcca aaaccaaagg cagaccgaag  1020
gctccacagg tgtacaccat tccacctccc aaggagcaga tggccaaaga taaagtcagt  1080
ctgacctgca tgataacaga cttcttccct gaagacatta ctgtggagtg cagtggaat  1140
gggcagccag cggagaacta caagaacact cagcccatca tggacacaga tggctcttac  1200
ttcgtctaca gcaagctcaa tgtgcagaag agcaactggg aggcaggaaa tacttttacc  1260
tgctctctgt tacatgaggg cctgcacaac caccatactg agaagagcct ctcccactct  1320
cctggtaaa                                                         1329
```

SEQ ID NO: 112          moltype = AA   length = 443
FEATURE                 Location/Qualifiers
REGION                  1..443
                        note = Description of Artificial Sequence: Synthetic
                         polypeptide
source                  1..443
                        mol_type = protein
                        organism = synthetic construct
SEQUENCE: 112
```
QVTLKESGPG ILQPSQTLSL TCSFSGFSLN TYGMGVSWIR QPSGKGLEWL AHIYWDDDKR   60
YNPSLKSRLT ISKDASNNRV FLKITSVDTA DTATYYCAQR GYDDYWGYWG QGTLVTISAA  120
KTTPPSVYPL APGSAAQTNS MVTLGCLVKG YFPEPVTVTW NSGSLSSGVH TFPAVLQSDL  180
YTLSSSVTVP SSTWPSETVT CNVAHPASST KVDKKIVPRD CGCKPCICTV PEVSSVFIFP  240
PKPKDVLTIT LTPKVTCVVV DISKDDPEVQ FSWFVDDVEV HTAQTQPREE QFNSTFRSVS  300
ELPIMHQDWL NGKEFKCRVN SAAFPAPIEK TISKTKGRPK APQVYTIPPP KEQMAKDKVS  360
LTCMITDFFP EDITVEWQWN GQPAENYKNT QPIMDTDGSY FVYSKLNVQK SNWEAGNTFT  420
CSVLHEGLHN HHTEKSLSHS PGK                                          443
```

SEQ ID NO: 113          moltype = DNA   length = 642
FEATURE                 Location/Qualifiers
misc_feature            1..642
                        note = Description of Artificial Sequence: Synthetic
                         polynucleotide
source                  1..642
                        mol_type = other DNA
                        organism = synthetic construct
SEQUENCE: 113
```
gacattgtga tgacccagtc tcaaaaattc atgtccacat cagtaggaga cagggtcagc   60
gtcacctgca aggccagtca gaatgtgggt actaatgtag cctggtttca acagaaacca  120
ggtcaatctc ctaaagcact gatttactcg gcatcttacc ggtacagtgg agtccctgat  180
```

```
cgcttcacag gcagtggatc tgggacagat tcattctca ccatcagcaa tgtgcagtct    240
gaagacctgg cagagtattt ctgtcagcaa tataacaact atcctctcac gttcggtgct    300
gggaccaagc tggagctgaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642

SEQ ID NO: 114          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 114
DIVMTQSQKF MSTSVGDRVS VTCKASQNVG TNVAWFQQKP GQSPKALIYS ASYRYSGVPD     60
RFTGSGSGTD FILTISNVQS EDLAEYFCQQ YNNYPLTFGA GTKLELKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 115          moltype = DNA   length = 1368
FEATURE                 Location/Qualifiers
misc_feature            1..1368
                        note = Description of Artificial Sequence: Synthetic
                         polynucleotide
source                  1..1368
                        mol_type = other DNA
                        organism = synthetic construct
SEQUENCE: 115
gaggtcctgc tgcaacagtc tggacctgag gtggtgaagc ctggggcttc agtgaagata     60
ccctgcaagg cttctggata cacattcact gactacaaca tggactgggt gaagcagagc    120
catggaaaga gccttgagtg gattggagag attaatccta acaatggtgg tactttctac    180
aaccagaagt tcaagggcaa ggccacattg actgtagaca gtcctccag cacagcctac    240
atggagctcc gcagcctgac atctgaggac actgcagtct attactgtgc aagagaggca    300
attactacgg taggcgctat ggactactgg ggtcaaggaa cctcagtcac cgtctcctca    360
gccaaaacaa caccccatc agtctatcca ctggcccctg ggtgtggaga tacaactggt    420
tcctccgtga ctctgggatg cctggtcaag ggctacttcc ctgagtcagt gactgtgact    480
tggaactctg gatccctgtc cagcagtgtg cacaccttcc cagctctcct gcagtctgga    540
ctctacacta tgagcagctc agtgactgtc cctccagca cctggccaag tcagaccgtc    600
acctgcagcg ttgctcaccc agccagcagc accacgtggg acaaaaaact tgagcccagc    660
gggcccattt caacaatcaa cccctgtcct ccatgcaagg agtgtcacaa atgcccagct    720
cctaacctcg agggtggacc atccgtcttc atcttccctc caaatatcaa ggatgtactc    780
atgatctccc tgacacccaa ggtcacgtgt gtggtggtgg atgtgagcga ggatgaccca    840
gacgtccaga tcagctggtt tgtgaacaac gtggaagtac acacagctca gacacaaacc    900
catagagagg attacaacag tactatccgg gtggtcagca ccctccccat ccagcaccag    960
gactggatga gtggcaagga gttcaaatgc aaggtcaaca acaaagacct cccatcaccc   1020
atcgagagaa ccatctcaaa aattaaaggg ctagtcagag ctccacaagt atacatcttg   1080
ccgccaccag cagagcagtt gtccaggaaa gatgtcagtc tcacttgcct ggtcgtgggc   1140
ttcaaccctg gagacatcag tgtggagtgg accagcaatg ggcatacaga ggagaactac   1200
aaggacaccg caccagtcct agactctgac ggttcttact tcatatatag caagctcaat   1260
atgaaaacaa gcaagtggga aaaaacagat tccttctcat gcaacgtgag acacgagggt   1320
ctgaaaaatt actacctgaa gaagaccatc tcccggtctc cgggtaaa                1368

SEQ ID NO: 116          moltype = AA   length = 456
FEATURE                 Location/Qualifiers
REGION                  1..456
                        note = Description of Artificial Sequence: Synthetic
                         polypeptide
source                  1..456
                        mol_type = protein
                        organism = synthetic construct
SEQUENCE: 116
EVLLQQSGPE VVKPGASVKI PCKASGYTFT DYNMDWVKQS HGKSLEWIGE INPNNGGTFY     60
NQKFKGKATL TVDKSSSTAY MELRSLTSED TAVYYCAREA ITTVGAMDYW GQGTSVTVSS    120
AKTTPPSVYP LAPGCGDTTG SSVTLGCLVK GYFPESVTVT WNSGSLSSSV HTFPALLQSG    180
LYTMSSSVTV PSSTWPSQTV TCSVAHPASS TTVDKKLEPS GPISTINPCP PCKECHKCPA    240
PNLEGGPSVF IFPPNIKDVL MISLTPKVTC VVVDVSEDDP DVQISWFVNN VEVHTAQTQT    300
HREDYNSTIR VVSTLPIQHQ DWMSGKEFKC KVNNKDLPSP IERTISKIKG LVRAPQVYIL    360
PPPAEQLSRK DVSLTCLVVG FNPGDISVEW TSNGHTEENY KDTAPVLDSD GSYFIYSKLN    420
MKTSKWEKTD SFSCNVRHEG LKNYYLKKTI SRSPGK                              456

SEQ ID NO: 117          moltype = DNA   length = 642
FEATURE                 Location/Qualifiers
misc_feature            1..642
                        note = Description of Artificial Sequence: Synthetic
                         polynucleotide
```

```
source                     1..642
                           mol_type = other DNA
                           organism = synthetic construct
SEQUENCE: 117
gacatccaga tgactcagtc tccagcctcc ctatctgcat ctgtgggaga aactgtcacc   60
atcacatgtc gagcaagtgg gaatattcac aattatttag catggtatca gcagaaacag  120
ggaaaatctc ctcagctcct ggtctataat gcaaaaacct tagcagatgg tgtgccatca  180
aggttcagtg gcagtggatc aggaacacaa tattctctca agatcaacag cctgcagcct  240
gaagattttg ggagttatta ctgtcaacat ttttggagtt ctccttacac gttcggaggg  300
gggaccaagc tggaaataaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag cacactcacg  540
ttgaccaagg acgagtatga acgacataac agctatacct gtgaggccac tcacaagaca  600
tcaacttcac ccattgtcaa gagcttcaac aggaatgagt gt                     642

SEQ ID NO: 118              moltype = AA  length = 214
FEATURE                     Location/Qualifiers
REGION                      1..214
                            note = Description of Artificial Sequence: Synthetic
                            polypeptide
source                      1..214
                            mol_type = protein
                            organism = synthetic construct
SEQUENCE: 118
DIQMTQSPAS LSASVGETVT ITCRASGNIH NYLAWYQQKQ GKSPQLLVYN AKTLADGVPS   60
RFSGSGSGTQ YSLKINSLQP EDFGSYYCQH FWSSPYTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 119              moltype = DNA  length = 1329
FEATURE                     Location/Qualifiers
misc_feature                1..1329
                            note = Description of Artificial Sequence: Synthetic
                            polynucleotide
source                      1..1329
                            mol_type = other DNA
                            organism = synthetic construct
SEQUENCE: 119
caggttactc tgaaagagtc tggccctgga atattgcagc cctcccagac cctcagtctg   60
acttgttctt tctctgggtt ttcactgagc acttatggta tgggtgtagg ctggattcgt  120
cagccttcag gaaagggtct agagtggctg gcagacattt ggtgggatga cgataagtac  180
tataacccat ccctgaagag ccggctcaca atctccaagg atacctccag caatgaggta  240
ttcctcaaga tcgccattgt ggacactgca gatactgcca cttactactg tgctcgaaga  300
ggtcactact ctgctatgga ctactggggt caaggaacct cagtcaccgt ctcctcagcc  360
aaaacgacac ccccatctgt ctatccactg gcccctggat ctgctgccca aactaactcc  420
atggtgaccc tgggatgcct ggtcaagggc tatttccctg agccagtgac ggtgacctgg  480
aactctggat ccctgtccag cggtgtgcac accttcccag ctgtcctgca gtctgacctc  540
tacactctga gcagctcagt gactgtcccc tccagcacct ggcccagcga gaccgtcacc  600
tgcaacgttg cccacccggc cagcagcacc aaggtggaca gaaaaattgt gcccagggat  660
tgtggttgta agccttgcat atgtacagtc cagaagtat catctgtctt catcttcccc  720
ccaaagccca aggatgtgct caccattact ctgactccta aggtcacgtg tgttgtggta  780
gacatcagca aggatgatcc cgaggtccag ttcagctggt ttgtagatga tgtggaggtg  840
cacacagctc agacgcaacc ccgggaggag cagttcaaca gcactttccg ctcagtcagt  900
gaacttccca tcatgcacca ggactggctc aatggcaagg agttcaaatg cagggtcaac  960
agtgcagctt ccctgccccc catcgagaaa accatctcca aaaccaaagg cagaccgaag 1020
gctccacagg tgtacaccat tccacctccc aaggagcaga tggccaagga taaagtcagt 1080
ctgacctgca tgataacaga cttcttccct gaagacatta ctgtggagtg gcagtggaat 1140
gggcagccag cggagaacta caagaacact cagcccatca tggacacaga tggctcttac 1200
ttcgtctaca gcaagctcaa tgtgcagaag agcaactggg aggcaggaaa tacttttacc 1260
tgctctgtgt tacatgaggg cctgcacaac caccatactg agaagagcct ctcccactct 1320
cctggtaaa                                                         1329

SEQ ID NO: 120              moltype = AA  length = 443
FEATURE                     Location/Qualifiers
REGION                      1..443
                            note = Description of Artificial Sequence: Synthetic
                            polypeptide
source                      1..443
                            mol_type = protein
                            organism = synthetic construct
SEQUENCE: 120
QVTLKESGPG ILQPSQTLSL TCSFSGFSLS TYGMGVGWIR QPSGKGLEWL ADIWWDDDKY   60
YNPSLKSRLT ISKDTSSNEV FLKIAIVDTA DTATYYCARR GHYSAMDYWG QGTSVTVSSA  120
KTTPPSVYPL APGSAAQTNS MVTLGCLVKG YFPEPVTVTW NSGSLSSGVH TFPAVLQSDL  180
YTLSSSVTVP SSTWPSETVT CNVAHPASST KVDKKIVPRD CGCKPCICTV PEVSSVFIFP  240
PKPKDVLTIT LTPKVTCVVV DISKDDPEVQ FSWFVDDVEV HTAQTQPREE QFNSTFRSVS  300
ELPIMHQDWL NGKEFKCRVN SAAFPAPIEK TISKTKGRPK APQVYTIPPP KEQMAKDKVS  360
LTCMITDFFP EDITVEWQWN GQPAENYKNT QPIMDTDGSY FVYSKLNVQK SNWEAGNTFT  420
```

```
CSVLHEGLHN HHTEKSLSHS PGK                                              443

SEQ ID NO: 121           moltype = DNA  length = 642
FEATURE                  Location/Qualifiers
misc_feature             1..642
                         note = Description of Artificial Sequence: Synthetic
                         polynucleotide
source                   1..642
                         mol_type = other DNA
                         organism = synthetic construct
SEQUENCE: 121
gacattgtaa tgacccagtc tcaaaaattc atgtccacat cagtaggaga cagggtcagc   60
gtcacctgca aggccagtca gaatgtgggt actaatgtag cctggtatca acagaaacca  120
gggcaatctc ctaaagcact gatttactcg ccatcctacc gatacagtgg agtccctgat  180
cgcttcacag gcagtggatc tgggacagat ttcactctca ccatcagcaa tgtgcagtct  240
gaagacttgg cagaatattt ctgtcagcaa tataacagct atcctcacac gttcggaggg  300
gggaccaagc tggaaatgaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag cacccctacg  540
ttgaccaagg acgagtatga acgacataac agctatacct gtgaggccac tcacaagaca  600
tcaacttcac ccattgtcaa gagcttcaac aggaatgagt gt                     642

SEQ ID NO: 122           moltype = AA  length = 214
FEATURE                  Location/Qualifiers
REGION                   1..214
                         note = Description of Artificial Sequence: Synthetic
                         polypeptide
source                   1..214
                         mol_type = protein
                         organism = synthetic construct
SEQUENCE: 122
DIVMTQSQKF MSTSVGDRVS VTCKASQNVG TNVAWYQQKP GQSPKALIYS PSYRYSGVPD   60
RFTGSGSGTD FTLTISNVQS EDLAEYFCQQ YNSYPHTFGG GTKLEMKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 123           moltype = DNA  length = 1335
FEATURE                  Location/Qualifiers
misc_feature             1..1335
                         note = Description of Artificial Sequence: Synthetic
                         polynucleotide
source                   1..1335
                         mol_type = other DNA
                         organism = synthetic construct
SEQUENCE: 123
caggttactc tgaaagagtc tggccctggg atattgcagc cctcccagac cctcagtctg   60
acttgttctt tctctgggtt ttcactgagc acttctggta tgggtgtgag ttggattcgt  120
cagccttcag gaaagggtct ggagtggctg gcacacaatg actgggatga tgacaagcgc  180
tataagtcat ccctgaagag ccggctcaca atatccaagg atacctccag aaaccaggta  240
ttcctcaaga tcaccagtgt ggacactgca gatactgcca catactactg tgctcgaaga  300
gttggggggat tagagggcta ttttgattac tggggccaag gcaccactct cacagtctcc  360
tcagccaaaa cgacaccccc atctgtctat ccactggccc ctggatctgc tgcccaaact  420
aactccatgt gaccctgggg atgcctggtc aagggctatt ccctgagcc agtgacagtg  480
acctggaact ctgatcccct gtccagcggt gtgcacacct tcccagctgt cctgcagtct  540
gacctctaca ctctgagcag ctcagtgact gtcccctcca gcacctgcc cagcagacc  600
gtcacctgca acgttgccca ccggccagc agcaccaagg tggacaagaa atttgtgccc  660
agggattgtg gttgtaagcc ttgcatatgt acagtcccag aagtatcatc tgtcttcatc  720
ttcccccaa agcccaagga tgtgctcacc attactctga ctcctaaggt cacgtgtgtt  780
gtggtagaca tcagcaagga tgatcccgag gtccagttca gctggtttgt agatgatgtg  840
gaggtgcaca cagctcagac gcaacccgg gaggagcagt tcaacagcac tttccgctca  900
gtcagtgaac ttcccatcat gcaccaggac tggctcaatg gcaaggagtt caaatgcagg  960
gtcaacagtg cagcttttcc tgcccccatc gagaaaacca tctccaaaac caaaggcaga 1020
ccgaaggctc cacaggtgta caccattcca cctcccaagg agcagatggc caaggataaa 1080
gtcagtctga cctgcatgat aacagacttc ttccctgaag acattactgt ggagtggcag 1140
tggaatgggc agccagcgga gaactacaag aacactcagc ccatcatgga cacagatggc 1200
tcttacttcg tctacagcaa gctcaatgtg cagaagagca ctgggaggc aggaaatact 1260
ttcacctgct ctgtgttaca tgagggcctg cacaaccacc atactgagaa gagcctctcc 1320
cactctcctg gtaaa                                                  1335

SEQ ID NO: 124           moltype = AA  length = 445
FEATURE                  Location/Qualifiers
REGION                   1..445
                         note = Description of Artificial Sequence: Synthetic
                         polypeptide
source                   1..445
                         mol_type = protein
                         organism = synthetic construct
SEQUENCE: 124
```

```
QVTLKESGPG ILQPSQTLSL TCSFSGFSLS TSGMGVSWIR QPSGKGLEWL AHNDWDDDKR    60
YKSSLKSRLT ISKDTSRNQV FLKITSVDTA DTATYYCARR VGGLEGYFDY WGQGTTLTVS   120
SAKTTPPSVY PLAPGSAAQT NSMVTLGCLV KGYFPEPVTV TWNSGSLSSG VHTFPAVLQS   180
DLYTLSSSVT VPSSTWPSET VTCNVAHPAS STKVDKKIVP RDCGCKPCIC TVPEVSSVFI   240
FPPKPKDVLT ITLTPKVTCV VVDISKDDPE VQFSWFVDDV EVHTAQTQPR EEQFNSTFRS   300
VSELPIMHQD WLNGKEFKCR VNSAAFPAPI EKTISKTKGR PKAPQVYTIP PPKEQMAKDK   360
VSLTCMITDF FPEDITVEWQ WNGQPAENYK NTQPIMDTDG SYFVYSKLNV QKSNWEAGNT   420
FTCSVLHEGL HNHHTEKSLS HSPGK                                        445

SEQ ID NO: 125          moltype = DNA  length = 654
FEATURE                 Location/Qualifiers
misc_feature            1..654
                        note = Description of Artificial Sequence: Synthetic
                         polynucleotide
source                  1..654
                        mol_type = other DNA
                        organism = synthetic construct
SEQUENCE: 125
gacattgtgc tgacacagtc tcctgcttcc ttagctgtat ctctggggca gagggccacc    60
atctcatgca gggccagcca aagtgtcagt acatctaggt ttagttatat gcactggttc   120
caacagaaac caggacaggc acccaaactc ctcatcaagt atgcatccaa cctagaatct   180
ggggtccctg ccaggttcag tggcagtggg tctgggacag acttcaccct caacatccat   240
cctgtggagg gggaggatac tgcaacatat tactgtcagc acagttggga gattccgtac   300
acgttcggag ggggaccaa gctggaaata aaacgggctg atgctgcacc aactgtatcc    360
atcttcccac catccagtga gcagttaaca tctgaggtg cctcagtcgt gtgcttcttg   420
aacaacttct accccaaaga catcaatgtc aagtggaaga ttgatggcag tgaacgacaa   480
aatggcgtcc tgaacagttg gactgatcag gacagcaaag acagcaccta cagcatgagc   540
agcaccctca cgttgaccaa ggacgagtat gaacgacata acagctatac ctgtgaggcc   600
actcacaaga catcaacttc acccattgtc aagagcttca caggaatga gtgt           654

SEQ ID NO: 126          moltype = AA  length = 218
FEATURE                 Location/Qualifiers
REGION                  1..218
                        note = Description of Artificial Sequence: Synthetic
                         polypeptide
source                  1..218
                        mol_type = protein
                        organism = synthetic construct
SEQUENCE: 126
DIVLTQSPAS LAVSLGQRAT ISCRASQSVS TSRFSYMHWF QQKPGQAPKL LIKYASNLES    60
GVPARFSGSG SGTDFTLNIH PVEGEDTATY YCQHSWEIPY TFGGGTKLEI KRADAAPTVS   120
IFPPSSEQLT SGGASVVCFL NNFYPKDINV KWKIDGSERQ NGVLNSWTDQ DSKDSTYSMS   180
STLTLTKDEY ERHNSYTCEA THKTSTSPIV KSFNREC                             218

SEQ ID NO: 127          moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 127
gaagtgttgt tgcagcagtc agggccggag ttggtaaaac cgggagcgtc ggtgaaaatc    60
ccgtgcaaag cgtcggggta tacgtttacg gactataaca tggattgggt gaaacagtcg   120
catgggaaat cgcttgaatg gattggtcag atcaatccga ataatggagg aatcttcttt   180
aatcagaagt ttaaaggaaa agcgacgctt acagtcgata gtcgtcgaa cacggcgttc   240
atggaagtac ggtcgcttac gtcggaagat acggcggtct attactgtgc gagggaggcg   300
attacgacgg tgggagcgat ggactattgg ggacaaggga cgtcggtcac ggtatcgtcg   360

SEQ ID NO: 128          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 128
GYTFTSY                                                                7

SEQ ID NO: 129          moltype = DNA  length = 357
FEATURE                 Location/Qualifiers
misc_feature            1..357
                        note = Description of Artificial Sequence: Synthetic
                         polynucleotide
source                  1..357
                        mol_type = other DNA
                        organism = synthetic construct
SEQUENCE: 129
```

```
caggtgacac tcaaagaatc aggacccgga atccttcagc ccagccagac cttgtcgctg    60
acttgttcgt tctccggttt cagcctgaat acttatggga tgggtgtgtc atggatcagg   120
caaccgtccg ggaaaggatt ggagtggctc gcgcacatct actgggacga tgacaaacgc   180
tacaatcctt cgctgaagag ccgattgacg atttccaagg atgcctcgaa caaccgggta   240
tttcttaaga tcacgtcggt cgatacggca gacacggcga cctattactg cgcccaaaga   300
gggtacgatg actattgggg atattgggc aggggacac tcgtcacaat ttcagct       357
```

SEQ ID NO: 130  moltype = AA length = 9
FEATURE     Location/Qualifiers
REGION      1..9
         note = Description of Artificial Sequence: Synthetic peptide
source      1..9
         mol_type = protein
         organism = synthetic construct
SEQUENCE: 130
GFSLSTYGM                                   9

SEQ ID NO: 131  moltype = DNA length = 357
FEATURE     Location/Qualifiers
misc_feature   1..357
         note = Description of Artificial Sequence: Synthetic
         polynucleotide
source      1..357
         mol_type = other DNA
         organism = synthetic construct
SEQUENCE: 131

```
caggtcacgc tgaaagagtc aggtcccgga atccttcaac cttgcagac attgtcactc     60
acatgttcct tctccgggtt ctcgctctcg acttatggca tgggtgtagg atggattcgg   120
cagcccagcg ggaaggggct tgagtggttg gcggatatct ggtgggacga cgacaaatac   180
tacaatccga gcctgaagtc ccgcctcacc atttgcaaag atacgtcatc aaacgaagtc   240
tttttgaaga tcgccatcgt ggacacggcg gatacagcga cgtattactg cgccagaagg   300
ggacactaca gcgcaatgga ttattgggga caggggacct cggtgactgt gtcgtcc     357
```

SEQ ID NO: 132  moltype = AA length = 9
FEATURE     Location/Qualifiers
REGION      1..9
         note = Description of Artificial Sequence: Synthetic peptide
source      1..9
         mol_type = protein
         organism = synthetic construct
SEQUENCE: 132
GFSLNTYGM                                   9

SEQ ID NO: 133  moltype = DNA length = 321
FEATURE     Location/Qualifiers
misc_feature   1..321
         note = Description of Artificial Sequence: Synthetic
         polynucleotide
source      1..321
         mol_type = other DNA
         organism = synthetic construct
SEQUENCE: 133

```
gacatccaaa tgacccagtc acccgcgagc ctttcggcgt cggtcggaga acggtcacg     60
atcacgtgcc ggacatcaga gaatctccat aactacctcg cgtggtatca acagaagcag   120
gggaagtcgc cccagttgct tgtatacgat gcgaaaacgt tgccggatgg ggtgccgtcc   180
agattctcgg gatcgggctc ggggacgcag tactcgctca agatcaattc gctgcagcg   240
gaggactttg ggtcgtacta ttgtcagcat ttttggtcat caccgtatac atttggaggt   300
ggaacgaaac ttgagattaa g                                            321
```

SEQ ID NO: 134  moltype = AA length = 9
FEATURE     Location/Qualifiers
REGION      1..9
         note = Description of Artificial Sequence: Synthetic peptide
source      1..9
         mol_type = protein
         organism = synthetic construct
SEQUENCE: 134
GFSLSTSGM                                  9

SEQ ID NO: 135  moltype = DNA length = 321
FEATURE     Location/Qualifiers
misc_feature   1..321
         note = Description of Artificial Sequence: Synthetic
         polynucleotide
source      1..321
         mol_type = other DNA
         organism = synthetic construct
SEQUENCE: 135
```
gatatcgtca tgacccagtc ccagaagttc atgtcaactt cagtgggaga cagagtgtcc    60
```

```
gtcacatgta aagcctcgca aaatgtggga accaacgtag cgtggttcca gcagaaacct   120
ggccaatcac cgaaggcact gatctactcg gccagctata ggtactcggg agtaccagat   180
cggtttacgg ggtcggggag cgggacggac tttatcctca ctatttccaa tgtccagtcg   240
gaggaccttg cggaatactt ctgccagcag tataacaact atccoctcac gtttggtgct   300
ggtacaaaat tggagttgaa g                                             321
```

```
SEQ ID NO: 136          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 136
GYTFTDYN                                                            8

SEQ ID NO: 137          moltype = DNA  length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 137
gacatcgtga tgacacagtc acagaaattc atgtccacat ccgtcggtga tagagtatcc   60
gtcacgtgta aggcctcgca aaacgtagga actaatgtgg cgtggtatca acagaagcca   120
ggacagtcac ccaaagcact catctacagc ccctcatatc ggtacagcgg ggtgccggac   180
aggttcacgg gatcggggag cgggaccgat tttacactga ccatttcgaa tgtccagtcg   240
gaggaccttg cggaatactt ctgccagcag tataactcgt accctcacac gtttggaggt   300
ggcactaagt tggagatgaa a                                             321

SEQ ID NO: 138          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 138
GYTFTSYW                                                            8

SEQ ID NO: 139          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 139
GGGGS                                                               5

SEQ ID NO: 140          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 140
GFSLSTYGMG                                                          10

SEQ ID NO: 141          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 141
GFSLNTYGMG                                                          10

SEQ ID NO: 142          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
```

```
SEQUENCE: 142
GFSLSTSGMG                                                              10

SEQ ID NO: 143        moltype = AA  length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 143
NPNNGG                                                                  6

SEQ ID NO: 144        moltype = AA  length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 144
NPSNGR                                                                  6

SEQ ID NO: 145        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 145
YWDDD                                                                   5

SEQ ID NO: 146        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 146
WWDDD                                                                   5

SEQ ID NO: 147        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 147
DWDDD                                                                   5

SEQ ID NO: 148        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 148
INPNNGGI                                                                8

SEQ ID NO: 149        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 149
INPSNGRS                                                                8

SEQ ID NO: 150        moltype = AA  length = 7
FEATURE               Location/Qualifiers
REGION                1..7
                      note = Description of Artificial Sequence: Synthetic peptide
source                1..7
                      mol_type = protein
```

```
                        organism = synthetic construct
SEQUENCE: 150
IYWDDDK                                                                      7

SEQ ID NO: 151          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 151
INPNNGGT                                                                     8

SEQ ID NO: 152          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 152
IWWDDDK                                                                      7

SEQ ID NO: 153          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 153
NDWDDDK                                                                      7

SEQ ID NO: 154          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 154
AREAITTVGA MDY                                                              13

SEQ ID NO: 155          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 155
AREVLDGAMD Y                                                                11

SEQ ID NO: 156          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 156
AQTGYSNLFA Y                                                                11

SEQ ID NO: 157          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 157
AQRGYDDYWG Y                                                                11

SEQ ID NO: 158          moltype = AA  length = 11
FEATURE                 Location/Qualifiers
REGION                  1..11
                        note = Description of Artificial Sequence: Synthetic peptide
source                  1..11
```

```
                         mol_type = protein
                         organism = synthetic construct
SEQUENCE: 158
ARRGHYSAMD Y                                                              11

SEQ ID NO: 159           moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 159
ARRVGGLEGY FDY                                                            13

SEQ ID NO: 160           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 160
ENLHNY                                                                     6

SEQ ID NO: 161           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 161
ESVDNYGISF                                                                10

SEQ ID NO: 162           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 162
QNVGTN                                                                     6

SEQ ID NO: 163           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 163
GNIHNY                                                                     6

SEQ ID NO: 164           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 164
QSVSTSRFSY                                                                10

SEQ ID NO: 165           moltype = DNA   length = 972
FEATURE                  Location/Qualifiers
source                   1..972
                         mol_type = genomic DNA
                         organism = Mus sp.
SEQUENCE: 165
gccaaaacga caccccatc tgtctatcca ctggccctg atctgctgc ccaaactaac            60
tccatggtga ccctgggatg cctggtcaag ggctatttcc ctgagccagt gacagtgacc        120
tggaactctg gatccctgtc cagcggtgtg cacaccttcc cagctgtcct gcagtctgac        180
ctctacactc tgagcagctc agtgactgtc ccctccagca cctggcccag cgagaccgtc        240
acctgcaacg ttgcccaccc ggccagcagc accaaggtgg acaagaaaat tgtgcccagg        300
gattgtggtt gtaagccttg catatgtaca gtcccagaag tatcatctgt cttcatcttc        360
cccccaaage ccaaggatgt gctcaccatt actctgactc ctaaggtcac gtgtgttgtg        420
gtagacatca gcaaggatga tcccgaggtc cagttcagct ggtttgtaga tgatgtggag        480
```

```
gtgcacacag ctcagacgca accccgggag gagcagttca acagcacttt ccgctcagtc   540
agtgaacttc ccatcatgca ccaggactgg ctcaatggca aggagttcaa atgcagggtc   600
aacagtgcag cttttccctgc ccccatcgag aaaaccatct ccaaaaccaa aggcagaccg   660
aaggctccac aggtgtacac cattccacct cccaaggagc agatggccaa ggataaagtc   720
agtctgacct gcatgataac agacttcttc cctgaagaca ttactgtgga gtggcagtgg   780
aatgggcagc cagcggagaa ctacaagaac actcagccca tcatggacac agatggctct   840
tacttcgtct acagcaagct caatgtgcag aagagcaact gggaggcagg aaatactttc   900
acctgctctg tgttacatga gggcctgcac aaccaccata ctgagaagag cctctcccac   960
tctcctggta aa                                                       972

SEQ ID NO: 166           moltype = AA  length = 324
FEATURE                  Location/Qualifiers
source                   1..324
                         mol_type = protein
                         organism = Mus sp.
SEQUENCE: 166
AKTTPPSVYP LAPGSAAQTN SMVTLGCLVK GYFPEPVTVT WNSGSLSSGV HTFPAVLQSD    60
LYTLSSSVTV PSSTWPSETV TCNVAHPASS TKVDKKIVPR DCGCKPCICT VPEVSSVFIF   120
PPKPKDVLTI TLTPKVTCVV VDISKDDPEV QFSWFVDDVE VHTAQTQPRE EQFNSTFRSV   180
SELPIMHQDW LNGKEFKCRV NSAAFPAPIE KTISKTKGRP KAPQVYTIPP PKEQMAKDKV   240
SLTCMITDFF PEDITVEWQW NGQPAENYKN TQPIMDTDGS YFVYSKLNVQ KSNWEAGNTF   300
TCSVLHEGLH NHHTEKSLSH SPGK                                         324

SEQ ID NO: 167           moltype = DNA  length = 1008
FEATURE                  Location/Qualifiers
source                   1..1008
                         mol_type = genomic DNA
                         organism = Mus sp.
SEQUENCE: 167
gccaaaacaa caccccccatc agtctatcca ctggcccctg ggtgtggaga tacaactggt    60
tcctccgtga ctctgggatg cctggtcaag ggctacttcc ctgagtcagt gactgtgact   120
tggaactctg gatccctgtc cagcagtgtg cacaccttcc cagctctcct gcagtctgga   180
ctctacacta tgagcagctc agtgactgtc ccctccagca cctggccaag tcagaccgtc   240
acctgcagcg ttgctcaccc agccagcagc accacggtgg acaaaaaact tgagcccagc   300
gggcccattt caacaatcaa cccctgtcct ccatgcacaa agtgtcacaa atgcccagct   360
cctaacctcg agggtggacc atccgtcttc atcttccctc caaatatcaa ggatgtactc   420
atgatctccc tgacacccaa ggtcacgtgt gtggtggtgg atgtgagcga ggatgaccca   480
gacgtccaga tcagctggtt tgtgaacaac gtggaagtac acacagctca gacacaaacc   540
catagagagg attacaacag tactatccgg gtggtcagca ccctccccat ccagcaccag   600
gactggatga gtggcaagga gttcaaatgc aaggtcaaca caaagacctc ccatcaccc    660
atcgagagaa ccatctcaaa aattaaaggg ctagtcagag ctccacaagt atacatcttg   720
ccgccaccag cagagcagtt gtccaggaaa gatgtcagtc tcacttgcct ggtcgtgggc   780
ttcaaccctg gagacatcag tgtggagtgg accagcaatg ggcatacaga ggagaactac   840
aaggacaccg caccagtcct agactctgac ggttcttact tcatatatag caagctcaat   900
atgaaaacaa gcaagtggga gaaaacagat tccttctcat gcaacgtgag acacgagggt   960
ctgaaaaatt actacctgaa gaagaccatc tcccggtctc cgggtaaa              1008

SEQ ID NO: 168           moltype = AA  length = 336
FEATURE                  Location/Qualifiers
source                   1..336
                         mol_type = protein
                         organism = Mus sp.
SEQUENCE: 168
AKTTPPSVYP LAPGCGDTTG SSVTLGCLVK GYFPESVTVT WNSGSLSSSV HTFPALLQSG    60
LYTMSSSVTV PSSTWPSQTV TCSVAHPASS TTVDKKLEPS GPISTINPCP PCKECHKCPA   120
PNLEGGPSVF IFPPNIKDVL MISLTPKVTC VVVDVSEDDP DVQISWFVNN VEVHTAQTQT   180
HREDYNSTIR VVSTLPIQHQ DWMSGKEFKC KVNNKDLPSP IERTISKIKG LVRAPQVYIL   240
PPPAEQLSRK DVSLTCLVVG FNPGDISVEW TSNGHTEENY KDTAPVLDSD GSYFIYSKLN   300
MKTSKWEKTD SFSCNVRHEG LKNYYLKKTI SRSPGK                            336

SEQ ID NO: 169           moltype = DNA  length = 321
FEATURE                  Location/Qualifiers
source                   1..321
                         mol_type = genomic DNA
                         organism = Mus sp.
SEQUENCE: 169
cgggctgatg ctgcaccaac tgtatccatc ttcccaccat ccagtgagca gttaacatct    60
ggaggtgcct cagtcgtgtg cttcttgaac aacttctacc ccaaagacat caatgtcaag   120
tggaagattg atggcagtga acgacaaaat ggcgtcctga acagttggac tgatcaggac   180
agcaaagaca gcacctacag catgagcagc accctcacgt tgaccaagga cgagtatgaa   240
cgacataaca gctataccctg tgaggccact cacaagacat caacttcacc cattgtcaag   300
agcttcaaca ggaatgagtg t                                             321

SEQ ID NO: 170           moltype = AA  length = 107
FEATURE                  Location/Qualifiers
source                   1..107
                         mol_type = protein
                         organism = Mus sp.
SEQUENCE: 170
```

```
RADAAPTVSI FPPSSEQLTS GGASVVCFLN NFYPKDINVK WKIDGSERQN GVLNSWTDQD    60
SKDSTYSMSS TLTLTKDEYE RHNSYTCEAT HKTSTSPIVK SFNRNEC                107

SEQ ID NO: 171            moltype = DNA  length = 990
FEATURE                   Location/Qualifiers
source                    1..990
                          mol_type = genomic DNA
                          organism = Homo sapiens
SEQUENCE: 171
gcctcaacaa aaggaccaag tgtgttccca ctcgcccta gcagcaagag tacatccggg     60
ggcactgcag cactcggctg cctcgtcaag gattattttc cagagccagt aaccgtgagc   120
tggaacagtg gagcactcac ttctggtgtc catactttc ctgctgtcct gcaaagctct    180
ggcctgtact cactcagctc cgtcgtgacc gtgccatctt catctctggg cactcagacc   240
tacatctgta atgtaaacca caagcctagc aatactaagg tcgataagcg ggtggaaccc   300
aagagctgcg acaagactca cacttgtccc ccatgccctg ccctgaact tctgggcggt    360
cccagcgtct ttttgttccc accaaagcct aaagatactc tgatgataag tagaacaccc   420
gaggtgacat gtgttgttgt agacgtttcc cacgaggacc cagaggttaa gttcaactgg   480
tacgttgatg gagtcgaagt acataatgct aagaccaagc ctagagagga gcagtataat   540
agtacatacc gtgtagtcag tgttctcaca gtgctgcacc aagactggct caacggcaaa   600
gaatacaaat gcaaagtgtc caacaaagca ctcccagccc ctatcgagaa gactattagt   660
aaggcaaagg ggcagcctcg tgaaccacag tgtacactc tgccacccag tagagaggaa    720
atgacaaaga accaagtctc attgacctgc ctggtgaaga gcttctaccc cagcgacatc   780
gccgttgagt gggagagtaa cggtcagcct gagaacaatt acaagacaac ccccccagtg   840
ctggatagtg acgggtcttt ctttctgtac agtaagctga ctgtggacaa gtcccgctgg   900
cagcagggta acgtcttcag ctgttccgtg atgcacgagg cattgcacaa ccactacacc   960
cagaagtcac tgagcctgag cccagggaag                                    990

SEQ ID NO: 172            moltype = AA  length = 330
FEATURE                   Location/Qualifiers
source                    1..330
                          mol_type = protein
                          organism = Homo sapiens
SEQUENCE: 172
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 173            moltype = DNA  length = 321
FEATURE                   Location/Qualifiers
source                    1..321
                          mol_type = genomic DNA
                          organism = Homo sapiens
SEQUENCE: 173
cgcacagttg ctgccccag cgtgttcatt ttcccaccta gcgatgagca gctgaaaagc     60
ggtactgcct ctgtcgtatg cttgctcaac aacttttacc cacgtgaggc taaggtgcag   120
tggaaagtgg ataatgcact tcaatctgga aacagtcaag agtccgtgac agaacaggac   180
agcaaagact caacttattc actctcttcc accctgactc tgtccaaggc agactatgaa   240
aaaacacaag tatacgcctg cgaggttaca caccagggt tgtctagtcc tgtcaccaag   300
tccttcaata ggggcgaatg t                                              321

SEQ ID NO: 174            moltype = AA  length = 107
FEATURE                   Location/Qualifiers
source                    1..107
                          mol_type = protein
                          organism = Homo sapiens
SEQUENCE: 174
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 175            moltype = DNA  length = 1350
FEATURE                   Location/Qualifiers
misc_feature              1..1350
                          note = Description of Artificial Sequence: Synthetic
                          polynucleotide
source                    1..1350
                          mol_type = other DNA
                          organism = synthetic construct
SEQUENCE: 175
gaagtgttgt tgcagcagtc agggccggag ttggtaaaac cggagcgtc ggtgaaaatc     60
ccgtgcaaag cgtcggggta tacgtttacg gactataaca tggattgggt gaaacagtcg   120
catgggaaat cgcttgaatg gattggtcag atcaatccga ataatggagg aatcttcttt   180
aatcagaagt ttaaaggaaa agcgacgctt acagtcgata gtcgtcgaa cacggcgttc   240
atggaagtac ggtcgcttac gtcggaagat acggcggtct attactgtgc gagggaggcg   300
attacgacgg tgggagcgat ggactattgg ggacaaggga cgtcggtcac ggtatcgtcg   360
gcctcaacaa aaggaccaag tgtgttccca ctcgcccta gcagcaagag tacatccggg   420
ggcactgcag cactcggctg cctcgtcaag gattattttc cagagccagt aaccgtgagc   480
```

-continued

```
tggaacagtg gagcactcac ttctggtgtc catactttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct ttttgttccc accaaagcct aaagatactc tgatgataag tagaacaccc    780
gaggtgacat gtgttgttgt agacgttccc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagcca ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

| | | |
|---|---|---|
| SEQ ID NO: 176 | moltype = AA length = 450 | |
| FEATURE | Location/Qualifiers | |
| REGION | 1..450 | |
| | note = Description of Artificial Sequence: Synthetic polypeptide | |
| source | 1..450 | |
| | mol_type = protein | |
| | organism = synthetic construct | |

SEQUENCE: 176
```
EVLLQQSGPE LVKPGASVKI PCKASGYTFT DYNMDWVKQS HGKSLEWIGQ INPNNGGIFF     60
NQKFKGKATL TVDKSSNTAF MEVRSLTSED TAVYYCAREA ITTVGAMDYW GQGTSVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKRVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450
```

| | | |
|---|---|---|
| SEQ ID NO: 177 | moltype = DNA length = 1350 | |
| FEATURE | Location/Qualifiers | |
| misc_feature | 1..1350 | |
| | note = Description of Artificial Sequence: Synthetic polynucleotide | |
| source | 1..1350 | |
| | mol_type = other DNA | |
| | organism = synthetic construct | |

SEQUENCE: 177
```
caagtgcaac ttgtgcagtc gggtgcggaa gtcaaaaagc cgggagcgtc ggtgaaagta     60
tcgtgtaaag cgtcgggata tacgtttacg gactataaca tggactgggt acgacaggca    120
ccggggaaat cgttggaatg gatcggacag attaatccga acaatggggg aattttcttt    180
aatcagaaat tcaaaggacg ggcgacgttg acggtcgata catcgacaaa tacggcgtat    240
atggaattga gtcgcttcg ctcggacgat acgcggtct attactgcgc cagggaggcg    300
atcacgacgg taggggcgat ggattattgg ggacagggga cgcttgtgac ggtatcgtcg    360
gcctcaacaa aggaccaag tgtgttccca ctcgccccta gcagcaagag tacatccggg    420
ggcactgcag cactcggctg cctcgtcaag gattattttc cagagccagt aaccgtgtcg    480
tggaacagtg gagcactcac ttctggtgtc catactttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct ttttgttccc accaaagcct aaagatactc tgatgataag tagaacaccc    780
gaggtgacat gtgttgttgt agacgttccc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

| | | |
|---|---|---|
| SEQ ID NO: 178 | moltype = AA length = 450 | |
| FEATURE | Location/Qualifiers | |
| REGION | 1..450 | |
| | note = Description of Artificial Sequence: Synthetic polypeptide | |
| source | 1..450 | |
| | mol_type = protein | |
| | organism = synthetic construct | |

SEQUENCE: 178
```
QVQLVQSGAE VKKPGASVKV SCKASGYTFT DYNMDWVRQA PGKSLEWIGQ INPNNGGIFF     60
NQKFKGRATL TVDTSTNTAY MELRSLRSDD TAVYYCAREA ITTVGAMDYW GQGTLVTVSS    120
ASTKGPSVFP LAPSSKSTSG GTAALGCLVK DYFPEPVTVS WNSGALTSGV HTFPAVLQSS    180
```

```
GLYSLSSVVT  VPSSSLGTQT  YICNVNHKPS  NTKVDKRVEP  KSCDKTHTCP  PCPAPELLGG   240
PSVFLFPPKP  KDTLMISRTP  EVTCVVVDVS  HEDPEVKFNW  YVDGVEVHNA  KTKPREEQYN   300
STYRVVSVLT  VLHQDWLNGK  EYKCKVSNKA  LPAPIEKTIS  KAKGQPREPQ  VYTLPPSREE   360
MTKNQVSLTC  LVKGFYPSDI  AVEWESNGQP  ENNYKTTPPV  LDSDGSFFLY  SKLTVDKSRW   420
QQGNVFSCSV  MHEALHNHYT  QKSLSLSPGK                                      450

SEQ ID NO: 179           moltype = DNA   length = 1350
FEATURE                  Location/Qualifiers
misc_feature             1..1350
                         note = Description of Artificial Sequence: Synthetic
                         polynucleotide
source                   1..1350
                         mol_type = other DNA
                         organism = synthetic construct
SEQUENCE: 179
caagtccagc ttgtccagtc gggagcggaa gtgaagaaac cggggtcgtc ggtcaaagta   60
tcgtgtaaag cgtcgggata tacgtttacg gactataaca tggattgggt acgacaggct  120
ccgggaaaat cattggaatg gattggacag attaatcgga ataatggggg tatcttcttt  180
aatcaaaagt ttaaagggag ggcgacgttg acggtggaca aatcgacaaa tacggcgtat  240
atggaattgt cgtcgcttcg gtcggaggac acggcggtgt attactcgc gagggaggcg   300
atcacgacgg tcgggcgat ggattattgg ggacaggga cgcttgtgac ggtatcgtcg   360
gcctcaacaa aaggaccaag tgtgttccca ctcgcccccta gcagcaagag tacatccggg  420
ggcactgcag cactcggctg cctcgtcaag gattattttc cagagccagt aaccgtgagc  480
tggaacagtg gagcactcac ttctggtgtc catacttttc ctgctgtcct gcaaagctct  540
ggcctgtact cactcagctc cgtcgtgacc gtgccatctt catctctggg cactcagacc  600
tacatctgta atgtaaacca caagcctagc aatactaagg tcgataagcg ggtggaaccc  660
aagagctgcg acaagactca cacttgtccc ccatgccctg ccctgaact tctgggcggt   720
cccagcgtct ttttgttccc accaaagcct aaagatactc tgatgataag tagaacaccc  780
gaggtgacat gtgttgttgt agacgtttcc cacgaggacc cagaggttaa gttcaactgg  840
tacgttgatg gagtcgaagt acataatgct aagaccaagc ctagagagga gcagtataat  900
agtacatacc gtgtagtcag tgttctcaca gtgctgcacc aagactggct caacggcaaa  960
gaatacaaat gcaaagtgtc caacaaagca ctcccagccc ctatcgagaa gactattgt  1020
aaggcaaagg gcagcctcg tgaaccacag gtgtacactc tgccacccag tagagaggaa  1080
atgacaaaga accaagtctc attgacctgc ctggtgaaga gcttctaccc cagcgacatc  1140
gccgttgagt gggagagtaa cggtcagcct gagaacaatt acaagacaac cccccagtg  1200
ctggatagtg acgggtcttt ctttctgtac agtaagctga ctgtggacaa gtcccgctgg  1260
cagcagggta acgtcttcag ctgttccgtg atgcacgagg cattgcacaa ccactacacc  1320
cagaagtcac tgagcctgag cccagggaag                                   1350

SEQ ID NO: 180           moltype = AA   length = 450
FEATURE                  Location/Qualifiers
REGION                   1..450
                         note = Description of Artificial Sequence: Synthetic
                         polypeptide
source                   1..450
                         mol_type = protein
                         organism = synthetic construct
SEQUENCE: 180
QVQLVQSGAE  VKKPGSSVKV  SCKASGYTFT  DYNMDWVRQA  PGKSLEWIGQ  INPNNGGIFF    60
NQKFKGRATL  TVDKSTNTAY  MELSSLRSED  TAVYYCAREA  ITTVGAMDYW  GQGTLVTVSS   120
ASTKGPSVFP  LAPSSKSTSG  GTAALGCLVK  DYFPEPVTVS  WNSGALTSGV  HTFPAVLQSS   180
GLYSLSSVVT  VPSSSLGTQT  YICNVNHKPS  NTKVDKRVEP  KSCDKTHTCP  PCPAPELLGG   240
PSVFLFPPKP  KDTLMISRTP  EVTCVVVDVS  HEDPEVKFNW  YVDGVEVHNA  KTKPREEQYN   300
STYRVVSVLT  VLHQDWLNGK  EYKCKVSNKA  LPAPIEKTIS  KAKGQPREPQ  VYTLPPSREE   360
MTKNQVSLTC  LVKGFYPSDI  AVEWESNGQP  ENNYKTTPPV  LDSDGSFFLY  SKLTVDKSRW   420
QQGNVFSCSV  MHEALHNHYT  QKSLSLSPGK                                      450

SEQ ID NO: 181           moltype = DNA   length = 1350
FEATURE                  Location/Qualifiers
misc_feature             1..1350
                         note = Description of Artificial Sequence: Synthetic
                         polynucleotide
source                   1..1350
                         mol_type = other DNA
                         organism = synthetic construct
SEQUENCE: 181
caggtccagc ttgtgcaatc gggagcggaa gtgaagaaac cggggagcgtc ggtaaaagtc   60
tcgtgcaaag cgtcgggta tacgtttacg gactataaca tggattgggt gcgccaagcg  120
cctggacagt gtcttgaatg gatgggcag attaatccga ataatggagg gatcttcttt  180
aatcagaat tcaaaggaag ggtaacgctg acgacagaca cgtcaacatc gacggcctat  240
atggaattgc ggtcgttgcg atcagatgat acggcggtct actattgtgc gagggaggcg  300
attacgacgg tgggagcgat ggattattgg ggacagggga cgttggtaac ggtatcgtcg  360
gcctcaacaa aaggaccaag tgtgttccca ctcgccccta gcagcaagag tacatccggg   420
ggcactgcag cactcggctg cctcgtcaag gattattttc cagagccagt aaccgtgagc   480
tggaacagtg gagcactcac ttctggtgtc catacttttc ctgctgtcct gcaaagctct  540
ggcctgtact cactcagctc cgtcgtgacc gtgccatctt catctctggg cactcagacc  600
tacatctgta atgtaaacca caagcctagc aatactaagg tcgataagcg ggtggaaccc  660
aagagctgcg acaagactca cacttgtccc ccatgccctg ccctgaact tctgggcggt   720
cccagcgtct ttttgttccc accaaagcct aaagatactc tgatgataag tagaacaccc  780
```

```
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt cttttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

```
SEQ ID NO: 182          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 182
QVQLVQSGAE VKKPGASVKV SCKASGYTFT DYNMDWVRQA PGQGLEWMGQ INPNNGGIFF     60
NQKFKGRVTL TTDTSTSTAY MELRSLRSDD TAVYYCAREA ITTVGAMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKRVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 183          moltype = DNA  length = 1350
FEATURE                 Location/Qualifiers
misc_feature            1..1350
                        note = Description of Artificial Sequence: Synthetic
                         polynucleotide
source                  1..1350
                        mol_type = other DNA
                        organism = synthetic construct
SEQUENCE: 183
caggtccagc ttgtgcaatc gggagcggaa gtgaagaaac cgggagcgtc ggtaaaagtc     60
tcgtgcaaag cgtcgggta tacgtttacg gactataaca tggactgggt gcgccaagcg    120
cctggacaga gccttgaatg gatggggcag attaatccga ataatggagg gatcttcttt    180
aatcagaaat tccaggaag gtaacgctg acgacagaca cgtcaacatc gacggcctat    240
atggaattgc ggtcgttgcg atcagatgat acggcggtct actattgtgc gagggaggcg    300
attacgacgg tgggagcgat ggattattgg ggacaggggga cgttggtaac ggtatcgtcg    360
gcctcaacaa aaggaccaag tgtgttccca ctcgccccta gcagcaagag tacatccggg    420
ggcactgcag cactcggctg cctcgtcaag gattactttc cagagccagt aaccgtgagc    480
tggaacagtg gagcactcac ttctggtgtc cacttttttc ctgctgtcct gcaaagtctc    540
ggcctgtact cactcagctc cgtcgtgacc gtgccatctt catctctggg cactcagacc    600
tacatctgta atgtaaacca caagcctagc aatactaagg tcgataagcg ggtgaaaccc    660
aagagctgcg acaagactca cacttgtccc ccatgccctg ccctgaact tctgggcggt    720
cccagcgtct ttttgttccc accaaagcct aaagatactc tgatgataag tagaaccact    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt cttttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350

SEQ ID NO: 184          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 184
QVQLVQSGAE VKKPGASVKV SCKASGYTFT DYNMDWVRQA PGQSLEWMGQ INPNNGGIFF     60
NQKFQGRVTL TTDTSTSTAY MELRSLRSDD TAVYYCAREA ITTVGAMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKRVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450
```

-continued

```
SEQ ID NO: 185          moltype = DNA  length = 1350
FEATURE                 Location/Qualifiers
misc_feature            1..1350
                        note = Description of Artificial Sequence: Synthetic
                         polynucleotide
source                  1..1350
                        mol_type = other DNA
                        organism = synthetic construct
SEQUENCE: 185
caggtccagc ttgtgcaatc gggagcggaa gtgaagaaac cgggagcgtc ggtaaaagtc    60
tcgtgcaaag cgtcgggtta tacgtttacg gactataaca tggactgggt gcgccaagcg   120
cctggacagg gtcttgaatg gatggggcag attaatccga ataatggagg gatcttcttt   180
aatcagaaat tccagggaag ggtaacgctg acgacagaca cgtcaacatc gacgacctat   240
atggaattgc ggtcgttgcg atcagatgat acgcggtct  actattgtgc gagggaggcg   300
attacgacgg tgggagcgat ggattattgg ggacagggga cgttggtaac ggtatcgtcg   360
gcctcaacaa aaggaccaag tgtgttccca ctcgccccta gcagcaagag tacatccggg   420
ggcactgcag cactcggctg cctcgtcaag gattattttc cagagccagt aaccgtgagc   480
tggaacagtg gagcactcac ttctggtgtc catactttc  ctgctgtcct gcaaagctct   540
ggcctgtact cactcagctc cgtcgtgacc gtgccatctt catctctggg cactcagacc   600
tacatctgta atgtaaacca caagcctagc aatactaagg tcgataagcg ggtggaaccc   660
aagagctgcg acaagactca cacttgtccc ccatgccctg cccctgaact tctgggcggt   720
cccagcgtct tttgttccc  accaaagcct aaagatactc tgatgataag tagaacaccc   780
gaggtgacat gtgttgttgt agacgtttcc cacgaggacc cagaggttaa gttcaactgg   840
tacgttgatg gagtcgaagt acataatgct aagaccaagc ctagagagga gcagtataat   900
agtacatacc gtgtagtcag tgttctcaca gtgctgcacc aagactggct caacggcaaa   960
gaatacaaat gcaaagtgtc caacaaagca ctcccagccc ctatcgagaa gactattagt  1020
aaggcaaagg ggcagcctcg tgaaccacag gtgtacactc tgccacccag tagagaggaa  1080
atgacaaaga accaagtctc attgacctgc ctggtgaaag gcttctaccc cagcgacatc  1140
gccgttgagt gggagagtaa cggtcagcct gagaacaatt acaagacaac cccccagtg   1200
ctggatagta acgggtcttt cttttctgtac agtaagctga ctgtggacaa gtccgctgtg  1260
cagcagggta acgtcttcag ctgttccgtg atgcacgagg cattgcacaa ccactacacc  1320
cagaagtcac tgagcctgag cccagggaag                                    1350

SEQ ID NO: 186          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 186
QVQLVQSGAE VKKPGASVKV SCKASGYTFT DYNMDWVRQA PGQGLEWMGQ INPNNGGIFF     60
NQKFQGRVTL TTDTSTSTAY MELRSLRSDD TAVYYCAREA ITTVGAMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKRVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 187          moltype = DNA  length = 1350
FEATURE                 Location/Qualifiers
misc_feature            1..1350
                        note = Description of Artificial Sequence: Synthetic
                         polynucleotide
source                  1..1350
                        mol_type = other DNA
                        organism = synthetic construct
SEQUENCE: 187
caagtacagc ttgtacagtc gggagcggaa gtcaagaaac cgggatcgtc ggtcaaagtg    60
tcgtgtaaag cgtcgggata tacgtttagc gactataaca tggattgggt gcgacaagcg   120
cctgggcagg gacttgaatg gatgggtcag atcaatccga ataatggggg aatctttttc   180
aatcagaagt ttaaagggag ggtaacgctg acgcggata aaagcacgtc aacggcgtat   240
atggagttgt cgtcgttgcg gtcggaggac acggcgtct  attactgcgc gagggaagcg   300
attacgacgg tgggagcgat ggattattgg ggcagggaa cgcttgtaac ggtgtcatcg   360
gcctcaacaa aaggaccaag tgtgttccca ctcgccccta gcagcaagag tacatccggg   420
ggcactgcag cactcggctg cctcgtcaag gattattttc cagagccagt aaccgtgagc   480
tggaacagtg gagcactcac ttctggtgtc catactttc  ctgctgtcct gcaaagctct   540
ggcctgtact cactcagctc cgtcgtgacc gtgccatctt catctctggg cactcagacc   600
tacatctgta atgtaaacca caagcctagc aatactaagg tcgataagcg ggtggaaccc   660
aagagctgcg acaagactca cacttgtccc ccatgccctg cccctgaact tctgggcggt   720
cccagcgtct tttgttccc  accaaagcct aaagatactc tgatgataag tagaacaccc   780
gaggtgacat gtgttgttgt agacgtttcc cacgaggacc cagaggttaa gttcaactgg   840
tacgttgatg gagtcgaagt acataatgct aagaccaagc ctagagagga gcagtataat   900
agtacatacc gtgtagtcag tgttctcaca gtgctgcacc aagactggct caacggcaaa   960
gaatacaaat gcaaagtgtc caacaaagca ctcccagccc ctatcgagaa gactattagt  1020
aaggcaaagg ggcagcctcg tgaaccacag gtgtacactc tgccacccag tagagaggaa  1080
```

```
atgacaaaga accaagtctc attgacctgc ctggtgaaag gcttctaccc cagcgacatc  1140
gccgttgagt gggagagtaa cggtcagcct gagaacaatt acaagacaac ccccccagtg  1200
ctggatagtg acgggtcttt cttcctgtac agtaagctga ctgtggacaa gtcccgctgg  1260
cagcagggta acgtcttcag ctgttccgtg atgcacgagg cattgcacaa ccactacacc  1320
cagaagtcac tgagcctgag cccagggaag                                   1350
```

| | |
|---|---|
| SEQ ID NO: 188 | moltype = AA  length = 450 |
| FEATURE | Location/Qualifiers |
| REGION | 1..450 |
| | note = Description of Artificial Sequence: Synthetic polypeptide |
| source | 1..450 |
| | mol_type = protein |
| | organism = synthetic construct |

SEQUENCE: 188

```
QVQLVQSGAE VKKPGSSVKV SCKASGYTFS DYNMDWVRQA PGQGLEWMGQ INPNNGGIFF   60
NQKFKGRVTL TADKSTSTAY MELSSLRSED TAVYYCAREA ITTVGAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450
```

| | |
|---|---|
| SEQ ID NO: 189 | moltype = DNA  length = 1350 |
| FEATURE | Location/Qualifiers |
| misc_feature | 1..1350 |
| | note = Description of Artificial Sequence: Synthetic polynucleotide |
| source | 1..1350 |
| | mol_type = other DNA |
| | organism = synthetic construct |

SEQUENCE: 189

```
caagtacagc ttgtacagtc gggagcggaa gtcaagaaac cgggatcgtc ggtcaaagtg   60
tcgtgtaaag cgtcgggata tacgtttagc gactataaca tggattgggt gcgacaagcg  120
cctgggcagg gacttgaatg gatgggtcag atcaatccga ataatggggg aatcttttc   180
aatcagaagt tcaggggag ggtaacgctg acggcggata aaagcacgtc aacggcgtat   240
atggagttgt cgtcgttgcg gtcggaggac acggcggtct attactgcgc gagggaagcg   300
attacgacgg tgggagcgat ggattattgg gggcagggaa cgcttgtaac ggtgtcatcg   360
gcctcaacaa aaggaccaag tgtgttccca ctcgccccta gcagcaagag tacatccgg   420
ggcactgcag cactcggctg cctcgtcaag gattatttc cagagccagt aaccgtgagc   480
tggaacagtg agcactcac ttctggtgtc catactttc ctgctgtcct gcaaagctct   540
ggcctgtact cactcagctc cgtcgtgacc gtgccatctc catctctggg cactcagacc   600
tacatctgta atgtaaacca caagcctagc aatactaagg tcgataagcg ggtgaaaccc   660
aagagctgcg acaagactca cacttgtccc ccatgccctg cccctgaact tctgggcggt   720
cccagcgtct ttttgttccc accaaagcct aaagatactc tgatgataag tagaacaccc   780
gaggtgacat gtgttgttgt agacgtttcc cacgaggacc cagaggttaa gttcaactgg   840
tacgttgatg gagtcgaagt acataatgct aagaccaagc ctagagagga gcagtataat   900
agtacatacc gtgtagtcag tgttctcaca gtgctgcacc aagactggct caacggcaaa   960
gaatacaaat gcaaagtgtc caacaaagca ctcccagccc tatcgagaa gactattagt  1020
aaggcaaagg ggcagcctcg tgaaccacag gtgtacactc tgccacccag tagagagaa  1080
atgacaaaga accaagtctc attgacctgc ctggtgaaag gcttctaccc cagcgacatc  1140
gccgttgagt gggagagtaa cggtcagcct gagaacaatt acaagacaac ccccccagtg  1200
ctggatagtg acgggtcttt cttcctgtac agtaagctga ctgtggacaa gtcccgctgg  1260
cagcagggta acgtcttcag ctgttccgtg atgcacgagg cattgcacaa ccactacacc  1320
cagaagtcac tgagcctgag cccagggaag                                   1350
```

| | |
|---|---|
| SEQ ID NO: 190 | moltype = AA  length = 450 |
| FEATURE | Location/Qualifiers |
| REGION | 1..450 |
| | note = Description of Artificial Sequence: Synthetic polypeptide |
| source | 1..450 |
| | mol_type = protein |
| | organism = synthetic construct |

SEQUENCE: 190

```
QVQLVQSGAE VKKPGSSVKV SCKASGYTFS DYNMDWVRQA PGQGLEWMGQ INPNNGGIFF   60
NQKFKGRVTL TADKSTSTAY MELSSLRSED TAVYYCAREA ITTVGAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450
```

| | |
|---|---|
| SEQ ID NO: 191 | moltype = DNA  length = 1347 |
| FEATURE | Location/Qualifiers |
| misc_feature | 1..1347 |
| | note = Description of Artificial Sequence: Synthetic |

```
                       polynucleotide
source                 1..1347
                       mol_type = other DNA
                       organism = synthetic construct
SEQUENCE: 191
caggtgacac tcaaagaatc aggacccgga atccttcagc ccagccagac cttgtcgctg    60
acttgttcgt tctccggttt cagcctgaat acttatggga tgggtgtgtc atggatcagg   120
caaccgtccg ggaaaggatt ggagtggctc gcgcacatct actgggacga tgacaaacgc   180
tacaatcctt cgctgaagag ccgattgacg atttccaagg atgcctcgaa caaccgggta   240
tttcttaaga tcacgtcggt cgatacggca gacacggcga cctattactg cgcccaaaga   300
gggtacgatg actattgggg atattggggc caggggacac tcgtcacaat ttcagctgcc   360
tcaacaaaag gaccaagtgt gttcccactc gcccctagca gcaagagtac atccgggggc   420
actgcagcac tcggctgcct cgtcaaggat tattttccag agccagtaac cgtgagctgg   480
aacagtggag cactcacttc tggtgtccat acttttcctg ctgtcctgca aagctctggc   540
ctgtactcac tcagctccgt cgtgaccgtg ccatcttcat ctctgggcac tcagacctac   600
atctgtaatg taaaccacaa gcctagcaat actaaggtcg ataagcgggt ggaacccaag   660
agctgcgaca agactcacac ttgtccccca tgccctgccc ctgaacttct gggcggtccc   720
agcgtctttt tgttcccacc aaagcctaaa gatactctga tgataagtag aacacccgag   780
gtgacatgtg ttgttgtaga cgtttcccac gaggacccag aggttaagtt caactggtac   840
gttgatggag tcgaagtaca taatgctaag accaagccta gagaggagca gtataatagt   900
acataccgtg tagtcagtgt tctcacagtg ctgcaccaag actggctcaa cggcaaagaa   960
tacaaatgca aagtgtccaa caaagcactc ccagccccta tcgagaagac tattagtaag  1020
gcaaagggc agcctcgtga accacaggtg tacactctgc cacccagtag agaggaaatg  1080
acaaagaacc aagtctcatt gacctgcctg gtgaaaggct tctacccag cgacatcgcc  1140
gttgagtggg agagtaacgg tcagcctgag aacaattaca gacaacccc ccagtgctg   1200
gatagtgacg ggtctttctt tctgtacagt aagctgactg tggacaagtc ccgctggcag  1260
cagggtaacg tcttcagctg ttccgtgatg cacgaggcat gcacaacca ctacacccag  1320
aagtcactga gcctgagccc agggaag                                      1347

SEQ ID NO: 192         moltype = AA    length = 449
FEATURE                Location/Qualifiers
REGION                 1..449
                       note = Description of Artificial Sequence: Synthetic
                       polypeptide
source                 1..449
                       mol_type = protein
                       organism = synthetic construct
SEQUENCE: 192
QVTLKESGPG ILQPSQTLSL TCSFSGFSLN TYGMGVSWIR QPSGKGLEWL AHIYWDDDKR    60
YNPSLKSRLT ISKDASNNRV FLKITSVDTA DTATYYCAQR GYDDYWGYWG QGTLVTISAA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 193         moltype = DNA   length = 1347
FEATURE                Location/Qualifiers
misc_feature           1..1347
                       note = Description of Artificial Sequence: Synthetic
                       polynucleotide
source                 1..1347
                       mol_type = other DNA
                       organism = synthetic construct
SEQUENCE: 193
caggtgactt tgaaagaatc cggtcccgca ttggtaaagc caacccagac acttacgctc    60
acatgtacat tttccggatt cagcttgaac acttacggga tgggagtgtc gtggattcgg   120
caacctccgg ggaaggctct ggagtggctg gcgcacatct actgggatga tgacaaaagg   180
tataacccct cacttaaaac gagactacg atctcgaagg acacaagcaa gaatcaggtc   240
gtcctcacga ttacgaatgt agacccggtg gatactgccg tctattactg cgcgcaacgc   300
gggtatgatg actactgggg atattggggt cagggcaccc tcgtgaccat ctcgtcagcc   360
tcaacaaaag gaccaagtgt gttcccactc gcccctagca gcaagagtac atccgggggc   420
actgcagcac tcggctgcct cgtcaaggat tattttccag agccagtaac cgtgagctgg   480
aacagtggag cactcacttc tggtgtccat acttttcctg ctgtcctgca aagctctggc   540
ctgtactcac tcagctccgt cgtgaccgtg ccatcttcat ctctgggcac tcagacctac   600
atctgtaatg taaaccacaa gcctagcaat actaaggtcg ataagcgggt ggaacccaag   660
agctgcgaca agactcacac ttgtccccca tgccctgccc ctgaacttct gggcggtccc   720
agcgtctttt tgttcccacc aaagcctaaa gatactctga tgataagtag aacacccgag   780
gtgacatgtg ttgttgtaga cgtttcccac gaggacccag aggttaagtt caactggtac   840
gttgatggag tcgaagtaca taatgctaag accaagccta gagaggagca gtataatagt   900
acataccgtg tagtcagtgt tctcacagtg ctgcaccaag actggctcaa cggcaaagaa   960
tacaaatgca aagtgtccaa caaagcactc ccagccccta tcgagaagac tattagtaag  1020
gcaaagggc agcctcgtga accacaggtg tacactctgc cacccagtag agaggaaatg  1080
acaaagaacc aagtctcatt gacctgcctg gtgaaaggct tctacccag cgacatcgcc  1140
gttgagtggg agagtaacgg tcagcctgag aacaattaca gacaacccc ccagtgctg   1200
gatagtgacg ggtctttctt tctgtacagt aagctgactg tggacaagtc ccgctggcag  1260
cagggtaacg tcttcagctg ttccgtgatg cacgaggcat gcacaacca ctacacccag  1320
aagtcactga gcctgagccc agggaag                                      1347
```

```
SEQ ID NO: 194          moltype = AA   length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 194
QVTLKESGPA LVKPTQTLTL TCTFSGFSLN TYGMGVSWIR QPPGKALEWL AHIYWDDDKR    60
YNPSLKTRLT ISKDTSKNQV VLTITNVDPV DTAVYYCAQR GYDDYWGYWG QGTLVTISSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 195          moltype = DNA   length = 1347
FEATURE                 Location/Qualifiers
misc_feature            1..1347
                        note = Description of Artificial Sequence: Synthetic
                         polynucleotide
source                  1..1347
                        mol_type = other DNA
                        organism = synthetic construct
SEQUENCE: 195
caagtaacgc tcaaggagtc cggacccacc ttggtgaagc cgacgcagac cttgactctt    60
acgtgcactt tctcgggggtt ttcactgaat acgtacgagg tgggtgtctc atggatcagg   120
caacctccgg ggaaaggatt ggaatggctg gcgcacatct actgggatga cgataagaga   180
tataacccaa gcctcaagtc gcggctcacc attacaaaag atacatcgaa aaatcaggtc   240
gtacttacta tcacgaacat ggaccccgtg acacagcaa catattactg tgcccagcgc    300
ggctatgacg attattgggg ttactgggga cagggaacac tggtcacggt gtccagcgcc   360
tcaacaaaag gaccaagtgt gttcccactc gccccctagca gcaagagtac atccggggcg   420
actcagcac tcggctgcct cgtcaaggat tattttccag agccagtaac cgtgagctgg    480
aacagtggag cactcacttc tggtgtccat acttttcctg ctgtcctgca aagctctggc   540
ctgtactcac tcagctccgt cgtgaccgtg ccatcttcat ctctgggcac tcagacctac   600
atctgtaatg taaaccacaa gcctagcaat actaaggtcg ataagcgggt ggaaccaag    660
agctgcgaca agactcacac ttgtccccca tgccctgccc ctgaacttct gggcggtccc   720
agcgtctttt tgttcccacc aaagcctaaa gatactctga tgataagtag aacacccgag   780
gtgacatgtg ttgttgtaga cgtttcccac gaggacccag aggttaagtt caactggtac   840
gttgatggag tcgaagtaca taatgctaag accaagccta gagaggagca gtataatagt   900
acataccgtg tagtcagtgt tctcacagtg ctgcaccaag actggctcaa cggcaaagaa   960
tacaaatgca aagtgtccaa caaagcactc cagcccccta tcgagaagac tattagtaag   1020
gcaaaggggc agcctcgtga accacaggtg tacactctgc cacccagtag agaggaaatg   1080
acaaagaacc aagtctcatt gacctgcctg gtgaaaggct tctaccccag cgacatcgcc   1140
gttgagtggg agagtaacgg tcagcctgag aacaattaca agacaacccc ccagtgctg    1200
gatagtgacg ggtcttttctt tctgtacagt aagctgactg tggacaagtc ccgctggcag   1260
cagggtaacg tcttcagctg ttccgtgatg cacgaggcat tgcacaacca ctacacccag   1320
aagtcactga gcctgagccc agggaag                                      1347

SEQ ID NO: 196          moltype = AA   length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 196
QVTLKESGPT LVKPTQTLTL TCTFSGFSLN TYGMGVSWIR QPPGKGLEWL AHIYWDDDKR    60
YNPSLKSRLT ITKDTSKNQV VLTITNMDPV DTATYYCAQR GYDDYWGYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 197          moltype = DNA   length = 1347
FEATURE                 Location/Qualifiers
misc_feature            1..1347
                        note = Description of Artificial Sequence: Synthetic
                         polynucleotide
source                  1..1347
                        mol_type = other DNA
                        organism = synthetic construct
SEQUENCE: 197
```

```
caggtcacgc tgaaagagtc aggtcccgga atccttcaac cttcgcagac attgtcactc    60
acatgttcct tctccgggtt ctcgctctcg acttatggca tgggtgtagg atggattcgg   120
cagcccagcg ggaaggggct tgagtggttg gcggatatct ggtgggacga cgacaaatac   180
tacaatccga gcctgaagtc ccgcctcacc atttcgaaag atacgtcatc aaacgaagtc   240
tttttgaaga tcgccatcgt ggacacggcg gatacagcga cgtattactg cgccagaagg   300
ggacactaca gcgcaatgga ttattgggga caggggacct cggtgactgt gtcgtccgcc   360
tcaacaaaag gaccaagtgt gttcccactc gcccctagca gcaagagtac atccgggggc   420
actgcagcac tcggctgcct cgtcaaggat tattttccag agccagtaac cgtgagctgg   480
aacagtggag cactcacttc tggtgtccat acttttcctg ctgtcctgca aagctctggc   540
ctgtactcac tcagctccgt cgtgaccgtg ccatcttcat ctctgggcac tcagacctac   600
atctgtaatg taaaccacaa gcctagcaat actaaggtcg ataagcgggt ggaacccaag   660
agctgcgaca agactcacac ttgtccccca tgccctgccc ctgaacttct gggcggtccc   720
agcgtctttt tgttcccacc aaagcctaaa gatactctga tgataagtag aacacccgag   780
gtgacatgtg ttgttgtaga cgtttcccac gaggacccag aggttaagtt caactggtac   840
gttgatggag tcgaagtaca taatgctaag accaagccta gagaggagca gtataatagt   900
acataccgtg tagtcagtgt tctcacagtg ctgcaccaag actggctcaa cggcaaagaa   960
tacaaatgca aagtgtccaa caaagcactc ccagccccta tcgagaagac tattagtaag  1020
gcaaaggggc agcctcgtga accacaggtg tacactctgc cacccagtag agaggaaatg  1080
acaaagaacc aagtctcatt gacctgcctg gtgaaaggct tctacccag cgacatcgcc   1140
gttgagtggg agagtaacgg tcagcctgag aacaattaca agacaacccc ccagtgctg   1200
gatagtgacg ggtcttttctt tctgtacagt aagctgactg tggacaagtc ccgctggcag  1260
cagggtaacg tcttcagctg ttccgtgatg cacgaggcat tgcacaacca ctacacccag  1320
aagtcactga gcctgagccc agggaag                                      1347

SEQ ID NO: 198           moltype = AA  length = 449
FEATURE                  Location/Qualifiers
REGION                   1..449
                         note = Description of Artificial Sequence: Synthetic
                         polypeptide
source                   1..449
                         mol_type = protein
                         organism = synthetic construct
SEQUENCE: 198
QVTLKESGPG ILQPSQTLSL TCSFSGFSLS TYGMGVGWIR QPSGKGLEWL ADIWWDDDKY    60
YNPSLKSRLT ISKDTSSNEV FLKIAIVDTA DTATYYCARR GHYSAMDYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 199           moltype = DNA  length = 1347
FEATURE                  Location/Qualifiers
misc_feature             1..1347
                         note = Description of Artificial Sequence: Synthetic
                         polynucleotide
source                   1..1347
                         mol_type = other DNA
                         organism = synthetic construct
SEQUENCE: 199
cagatcactt tgaaagaaag cggaccgacc ttggtcaagc ccacacaaac cctcacgctc    60
acgtgtacat tttcggggtt ctcgctttca acttacggga tgggagtagg gtggattcgc   120
cagccgcctg gtaaagcgtt ggagtggctt gcagacatct ggtgggacga cgataagtac   180
tataatcct cgctcaagtc cagactgacc atcacgaaag atagagcaa gaaccaggtc   240
gtgctgacaa tgactaacat ggacccagtg gatacggcta catattactg cgccaggcgg   300
ggtcactact cagcgatgga ttattggggc cagggaacac tggtaacggt gtcgtccgcc   360
tcaacaaaag gaccaagtgt gttcccactc gcccctagca gcaagagtac atccgggggc   420
actgcagcac tcggctgcct cgtcaaggat tattttccag agccagtaac cgtgagctgg   480
aacagtggag cactcacttc tggtgtccat acttttcctg ctgtcctgca aagctctggc   540
ctgtactcac tcagctccgt cgtgaccgtg ccatcttcat ctctgggcac tcagacctac   600
atctgtaatg taaaccacaa gcctagcaat actaaggtcg ataagcgggt ggaacccaag   660
agctgcgaca agactcacac ttgtccccca tgccctgccc ctgaacttct gggcggtccc   720
agcgtctttt tgttcccacc aaagcctaaa gatactctga tgataagtag aacacccgag   780
gtgacatgtg ttgttgtaga cgtttcccac gaggacccag aggttaagtt caactggtac   840
gttgatggag tcgaagtaca taatgctaag accaagccta gagaggagca gtataatagt   900
acataccgtg tagtcagtgt tctcacagtg ctgcaccaag actggctcaa cggcaaagaa   960
tacaaatgca aagtgtccaa caaagcactc ccagccccta tcgagaagac tattagtaag  1020
gcaaaggggc agcctcgtga accacaggtg tacactctgc cacccagtag agaggaaatg  1080
acaaagaacc aagtctcatt gacctgcctg gtgaaaggct tctacccag cgacatcgcc   1140
gttgagtggg agagtaacgg tcagcctgag aacaattaca agacaacccc ccagtgctg   1200
gatagtgacg ggtcttttctt tctgtacagt aagctgactg tggacaagtc ccgctggcag  1260
cagggtaacg tcttcagctg ttccgtgatg cacgaggcat tgcacaacca ctacacccag  1320
aagtcactga gcctgagccc agggaag                                      1347

SEQ ID NO: 200           moltype = AA  length = 449
FEATURE                  Location/Qualifiers
REGION                   1..449
                         note = Description of Artificial Sequence: Synthetic
```

```
                            polypeptide
source                      1..449
                            mol_type = protein
                            organism = synthetic construct
SEQUENCE: 200
QITLKESGPT LVKPTQTLTL TCTFSGFSLS TYGMGVGWIR QPPGKALEWL ADIWWDDDKY    60
YNPSLKSRLT ITKDTSKNQV VLTMTNMDPV DTATYYCARR GHYSAMDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 201              moltype = DNA   length = 1347
FEATURE                     Location/Qualifiers
misc_feature                1..1347
                            note = Description of Artificial Sequence: Synthetic
                             polynucleotide
source                      1..1347
                            mol_type = other DNA
                            organism = synthetic construct
SEQUENCE: 201
caagtgactc tcaaggagtc cggacccgcc ctggtcaaac caacgcagac actgacgctc    60
acatgcacct tcagcggatt ttcgttgtca acgtacggga tgggtgtggg gtggattcgc   120
cagcctccgg ggaaagccct tgaatggttg gcggacatct ggtgggatga tgacaagtac   180
tataatccct cacttaagtc acggttgacg atctcgaaag acaccagcaa gaaccaggta   240
gtgctgacaa tgactaacat ggacccggtc gatacagcgg tctactattg tgctagaagg   300
ggacactact ccgcaatgga ttattggggt caggggacgc tcgtaaccgt gtcgtcggcc   360
tcaacaaaag gaccaagtgt gttcccactc gcccctagca gcaagagtac atccgggagc   420
actgcagcac tcggctgcct cgtcaaggat tattttccag agccagtaac cgtgagctgg   480
aacagtggag cactcacttc tggtgtccat acttttcctg ctgtcctgca aagctctggc   540
ctgtactcac tcagctccgt cgtgaccgtg ccatcttcat ctctgggcac tcagacctac   600
atctgtaatg taaaccacaa gcctagcaat actaaggtcg ataagcgggt ggaaccgaag   660
agctgcgaca agactcacac ttgtcccccc atgccctgcc ctgaacttct gggcggtccc   720
agcgtctttt tgttcccacc aaagcctaaa gatactctga tgataagtag aacacccgag   780
gtgacatgtg ttgttgtaga cgtttcccac gaggacccag aggttaagtt caactggtac   840
gttgatggag tcgaagtaca taatgctaag accaagccta gagaggagca gtataatagt   900
acatccgtta gtcagtgt tctcacagtg ctgcaccaag actggctcaa cggcaaagaa   960
tacaaatgca aagtgtccaa caaagcactc ccagccccta tcgagaagac tattagtaag  1020
gcaaaggggc agcctcgtga accacaggtg tacactctgc cacccagtag agaggaaatg  1080
acaaagaacc aagtctcatt gacctgcctg gtgaaaggct ctacccag cgacatcgcc  1140
gttgagtggg agagtaacgg tcagcctgag aacaattaca actccagtgctg  1200
gatagtgacg ggtctttctt tctgtacagt aagctgactg tggacaagtc ccgctggcag  1260
cagggtaacg tcttcagctg ttccgtgatg cacgaggcat tgcacaacca ctacacccag  1320
aagtcactga gcctgagccc agggaag                                     1347

SEQ ID NO: 202              moltype = AA   length = 449
FEATURE                     Location/Qualifiers
REGION                      1..449
                            note = Description of Artificial Sequence: Synthetic
                             polypeptide
source                      1..449
                            mol_type = protein
                            organism = synthetic construct
SEQUENCE: 202
QVTLKESGPA LVKPTQTLTL TCTFSGFSLS TYGMGVGWIR QPPGKALEWL ADIWWDDDKY    60
YNPSLKSRLT ISKDTSKNQV VLTMTNMDPV DTAVYYCARR GHYSAMDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 203              moltype = DNA   length = 642
FEATURE                     Location/Qualifiers
misc_feature                1..642
                            note = Description of Artificial Sequence: Synthetic
                             polynucleotide
source                      1..642
                            mol_type = other DNA
                            organism = synthetic construct
SEQUENCE: 203
gacatccaaa tgacccagtc acccgcgagc ctttcggcgt cggtcggaga acggtcacg    60
atcacgtgcc ggacatcaga gaatctccat aactaccctcg cgtggtatca acagaagcag   120
gggaagtcgc cccagttgct tgtatacgat gcgaaaacgt tggcggatgg ggtgccgtcc   180
agattctcgg gatcgggctc ggggacgcag tactcgctca gatcaattc gctgcagccg   240
gaggactttg ggtcgtacta ttgtcagcat ttttggtcat caccgtatac atttggaggt   300
```

```
ggaacgaaac ttgagattaa gcgcacagtt gctgccccca gcgtgttcat tttcccacct    360
agcgatgagc agctgaaaag cggtactgcc tctgtcgtat gcttgctcaa caacttttac    420
ccacgtgagg ctaaggtgca gtggaaagtg gataatgcac ttcaatctgg aaacagtcaa    480
gagtccgtga cagaacagga cagcaaagac tcaacttatt cactctcttc caccctgact    540
ctgtccaagg cagactatga aaaacacaag gtatacgcct gcgaggttac acaccagggt    600
ttgtctagtc ctgtcaccaa gtccttcaat agggcgaat gt                        642

SEQ ID NO: 204           moltype = AA  length = 214
FEATURE                  Location/Qualifiers
REGION                   1..214
                         note = Description of Artificial Sequence: Synthetic
                         polypeptide
source                   1..214
                         mol_type = protein
                         organism = synthetic construct
SEQUENCE: 204
DIQMTQSPAS LSASVGETVT ITCRTSENLH NYLAWYQQKQ GKSPQLLVYD AKTLADGVPS     60
RFSGSGSGTQ YSLKINSLQP EDFGSYYCQH FWSSPYTFGG GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 205           moltype = DNA  length = 642
FEATURE                  Location/Qualifiers
misc_feature             1..642
                         note = Description of Artificial Sequence: Synthetic
                         polynucleotide
source                   1..642
                         mol_type = other DNA
                         organism = synthetic construct
SEQUENCE: 205
gacatccaaa tgacccagtc gccgtcgtcg ctttcagcgt cggtagggga tcgggtcaca     60
attacgtgcc gaacgtcaga gaatttgcat aactaccctcg cgtggtatca gcagaagccc   120
gggaagtcac cgaaactcct tgtctacgat gcgaaaacgc tggcggatgg agtgccgtcg   180
agattctcgg gaagcggatc cggtacggac tatacgctta cgatctcatc gctccagccc   240
gaggactttg cgacgtacta ttgtcagcat ttttggtcgt cgccctacac atttgggcag   300
gggaccaagt tggaaatcaa agcgcacagtt gctgccccca gcgtgttcat tttcccacct    360
agcgatgagc agctgaaaag cggtactgcc tctgtcgtat gcttgctcaa caacttttac    420
ccacgtgagg ctaaggtgca gtggaaagtg gataatgcac ttcaatctgg aaacagtcaa    480
gagtccgtga cagaacagga cagcaaagac tcaacttatt cactctcttc caccctgact    540
ctgtccaagg cagactatga aaaacacaag gtatacgcct gcgaggttac acaccagggt    600
ttgtctagtc ctgtcaccaa gtccttcaat agggcgaat gt                        642

SEQ ID NO: 206           moltype = AA  length = 214
FEATURE                  Location/Qualifiers
REGION                   1..214
                         note = Description of Artificial Sequence: Synthetic
                         polypeptide
source                   1..214
                         mol_type = protein
                         organism = synthetic construct
SEQUENCE: 206
DIQMTQSPSS LSASVGDRVT ITCRTSENLH NYLAWYQQKP GKSPKLLVYD AKTLADGVPS     60
RFSGSGSGTD YTLTISSLQP EDFATYYCQH FWSSPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 207           moltype = DNA  length = 642
FEATURE                  Location/Qualifiers
misc_feature             1..642
                         note = Description of Artificial Sequence: Synthetic
                         polynucleotide
source                   1..642
                         mol_type = other DNA
                         organism = synthetic construct
SEQUENCE: 207
gacatccaaa tgacccagtc gccgtcgtcg ctttcagcgt cggtagggga tcgggtcaca     60
attacgtgcc gaacgtcaga gaatttgcat aactaccctcg cgtggtatca gcagaagccc   120
gggaaggccc cgaaactcct tatctacgat gcgaaaacgc tggcggatgg agtgccgtcg   180
agattctcgg gaagcggatc cggtacggac tatacgctta cgatctcatc gctccagccc   240
gaggactttg cgacgtacta ttgtcagcat ttttggtcgt cgccctacac atttgggcag   300
gggaccaagt tggaaatcaa agcgcacagtt gctgccccca gcgtgttcat tttcccacct    360
agcgatgagc agctgaaaag cggtactgcc tctgtcgtat gcttgctcaa caacttttac    420
ccacgtgagg ctaaggtgca gtggaaagtg gataatgcac ttcaatctgg aaacagtcaa    480
gagtccgtga cagaacagga cagcaaagac tcaacttatt cactctcttc caccctgact    540
ctgtccaagg cagactatga aaaacacaag gtatacgcct gcgaggttac acaccagggt    600
ttgtctagtc ctgtcaccaa gtccttcaat agggcgaat gt                        642

SEQ ID NO: 208           moltype = AA  length = 214
FEATURE                  Location/Qualifiers
```

```
                                       REGION             1..214
                                                          note = Description of Artificial Sequence: Synthetic
                                                             polypeptide
                                       source            1..214
                                                          mol_type = protein
                                                          organism = synthetic construct
SEQUENCE: 208
DIQMTQSPSS  LSASVGDRVT  ITCRTSENLH  NYLAWYQQKP  GKAPKLLIYD  AKTLADGVPS    60
RFSGSGSGTD  YTLTISSLQP  EDFATYYCQH  FWSSPYTFGQ  GTKLEIKRTV  AAPSVFIFPP   120
SDEQLKSGTA  SVVCLLNNFY  PREAKVQWKV  DNALQSGNSQ  ESVTEQDSKD  STYSLSSTLT   180
LSKADYEKHK  VYACEVTHQG  LSSPVTKSFN  RGEC                                 214

SEQ ID NO: 209          moltype = DNA   length = 642
FEATURE                 Location/Qualifiers
misc_feature            1..642
                        note = Description of Artificial Sequence: Synthetic
                           polynucleotide
source                  1..642
                        mol_type = other DNA
                        organism = synthetic construct
SEQUENCE: 209
gacatccaaa tgacccagtc gccgtcgtcg ctttcagcgt cggtagggga tcgggtcaca  60
attacgtgcc gaacgtcaga gaatttgcat aactacctcg cgtggtatca gcagaagccc 120
gggaagtcac cgaaactcct tatctacgat gcgaaaacgc tggcggatgg agtgccgtcg 180
agattctcgg gaagcggatc cggtacggac tatacgctta cgatctcatc gctccagccc 240
gaggactttg cgacgtacta ttgtcagcat cgcccctacac atttgggcag 300
gggaccaagt tggaaatcaa gcgcacagtt gctgccccca gcgtgttcat ttttcccacct 360
agcgatgagc agctgaaaag cggtactgcc tctgtcgtat gcttgctcaa caacttttac 420
ccacgtgagg ctaaggtgca gtggaaagtg gataatgcac ttcaatctgg aaacagtcaa 480
gagtccgtga cagaacagga cagcaaagac tcaacttatt cactctcttc caccctgact 540
ctgtccaagg cagactatga aaaacacaag gtatacgcct gcgaggttac acaccagggt 600
ttgtctagtc ctgtcaccaa gtccttcaat aggggcgaat gt                   642

SEQ ID NO: 210          moltype = AA    length = 214
FEATURE                 Location/Qualifiers
REGION                  1..214
                        note = Description of Artificial Sequence: Synthetic
                           polypeptide
source                  1..214
                        mol_type = protein
                        organism = synthetic construct
SEQUENCE: 210
DIQMTQSPSS  LSASVGDRVT  ITCRTSENLH  NYLAWYQQKP  GKSPKLLIYD  AKTLADGVPS    60
RFSGSGSGTD  YTLTISSLQP  EDFATYYCQH  FWSSPYTFGQ  GTKLEIKRTV  AAPSVFIFPP   120
SDEQLKSGTA  SVVCLLNNFY  PREAKVQWKV  DNALQSGNSQ  ESVTEQDSKD  STYSLSSTLT   180
LSKADYEKHK  VYACEVTHQG  LSSPVTKSFN  RGEC                                 214

SEQ ID NO: 211          moltype = DNA   length = 642
FEATURE                 Location/Qualifiers
misc_feature            1..642
                        note = Description of Artificial Sequence: Synthetic
                           polynucleotide
source                  1..642
                        mol_type = other DNA
                        organism = synthetic construct
SEQUENCE: 211
gatatcgtca tgacccagtc ccagaagttc atgtcaactt cagtgggaga cagagtgtcc  60
gtcacatgta aagcctcgca aaatgtggga accaacgtag cgtggttcca gcagaaacct 120
ggccaatcac cgaaggcact gatctactcg gccagctata ggtactccgg agtaccagat 180
cggtttacgg ggtcggggag cgggacggac tttatcctca ctatttccaa tgtccagtcg 240
gaggaccttg cggaatactt ctgccagcag tataacaact atcccctcac gtttggtgct 300
ggtacaaaat tggagttgaa gcgcacagtt gctgccccca gcgtgttcat ttttcccacct 360
agcgatgagc agctgaaaag cggtactgcc tctgtcgtat gcttgctcaa caacttttac 420
ccacgtgagg ctaaggtgca gtggaaagtg gataatgcac ttcaatctgg aaacagtcaa 480
gagtccgtga cagaacagga cagcaaagac tcaacttatt cactctcttc caccctgact 540
ctgtccaagg cagactatga aaaacacaag gtatacgcct gcgaggttac acaccagggt 600
ttgtctagtc ctgtcaccaa gtccttcaat aggggcgaat gt                   642

SEQ ID NO: 212          moltype = AA    length = 214
FEATURE                 Location/Qualifiers
REGION                  1..214
                        note = Description of Artificial Sequence: Synthetic
                           polypeptide
source                  1..214
                        mol_type = protein
                        organism = synthetic construct
SEQUENCE: 212
DIVMTQSQKF  MSTSVGDRVS  VTCKASQNVG  TNVAWFQQKP  GQSPKALIYS  ASYRYSGVPD    60
RFTGSGSGTD  FILTISNVQS  EDLAEYFCQQ  YNNYPLTFGA  GTKLELKRTV  AAPSVFIFPP   120
```

```
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 213          moltype = DNA   length = 642
FEATURE                 Location/Qualifiers
misc_feature            1..642
                        note = Description of Artificial Sequence: Synthetic
                        polynucleotide
source                  1..642
                        mol_type = other DNA
                        organism = synthetic construct
SEQUENCE: 213
gacatccaaa tgacccaatc gccctcctcc ctctccgcat cagtagggga ccgcgtcaca      60
attacttgca aagcgtcgca gaacgtcgga acgaatgtgg cgtggtttca gcagaagccc    120
ggaaaagctc cgaagagctt gatctactcg gcctcatata ggtattcggg tgtgccgagc    180
cggtttagcg ggtcggggtc aggtactgat ttcacgctca caatttcatc gttgcagcca    240
gaagatttcg ccacatatta ctgtcagcag tacaacaatt accctctgac gttcggccag    300
ggaaccaaac ttgagatcaa gcgcacagtt gctgcccca gcgtgttcat tttcccacct    360
agcgatgagc agctgaaaag cggtactgcc tctgtcgtat gcttgctcaa caactttac    420
ccacgtgagg ctaaggtgca gtggaaagtg gataatgcac ttcaatctgg aaacagtcaa    480
gagtccgtga cagaacagga cagcaaagac tcaacttatt cactctcttc cacccctgact  540
ctgtccaagg cagactatga aaaacacaag gtatacgcct gcgaggttac acaccagggt    600
ttgtctagtc ctgtcaccaa gtccttcaat agggccgaat gt                      642

SEQ ID NO: 214          moltype = AA   length = 214
FEATURE                 Location/Qualifiers
REGION                  1..214
                        note = Description of Artificial Sequence: Synthetic
                        polypeptide
source                  1..214
                        mol_type = protein
                        organism = synthetic construct
SEQUENCE: 214
DIQMTQSPSS LSASVGDRVT ITCKASQNVG TNVAWFQQKP GKAPKSLIYS ASYRYSGVPS     60
RFSGSGSGTD FTLTISSLQP EDFATYYCQQ YNNYPLTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 215          moltype = DNA   length = 642
FEATURE                 Location/Qualifiers
misc_feature            1..642
                        note = Description of Artificial Sequence: Synthetic
                        polynucleotide
source                  1..642
                        mol_type = other DNA
                        organism = synthetic construct
SEQUENCE: 215
gacatcgtga tgacacagtc acagaaattc atgtccacat ccgtcggtga tagagtatcc     60
gtcacgtgta aggcctcgca aaacgtagga actaatgtgg cgtggtatca acagaagcca    120
ggacagtcac ccaaagcact catctacagc ccctcatatc ggtacagcgg ggtgccggac    180
aggttcacgg gatcggggag cgggaccgat tttacactga ccatttcgaa tgtccagtcg    240
gaggaccttg cggaatactt ctgccagcag tataactcgt accctcacac gtttggaggt    300
ggcactaagt tggagatgaa acgcacagtt gctgcccca gcgtgttcat tttcccacct    360
agcgatgagc agctgaaaag cggtactgcc tctgtcgtat gcttgctcaa caactttac    420
ccacgtgagg ctaaggtgca gtggaaagtg gataatgcac ttcaatctgg aaacagtcaa    480
gagtccgtga cagaacagga cagcaaagac tcaacttatt cactctcttc cacccctgact  540
ctgtccaagg cagactatga aaaacacaag gtatacgcct gcgaggttac acaccagggt    600
ttgtctagtc ctgtcaccaa gtccttcaat agggccgaat gt                      642

SEQ ID NO: 216          moltype = AA   length = 214
FEATURE                 Location/Qualifiers
REGION                  1..214
                        note = Description of Artificial Sequence: Synthetic
                        polypeptide
source                  1..214
                        mol_type = protein
                        organism = synthetic construct
SEQUENCE: 216
DIVMTQSQKF MSTSVGDRVS VTCKASQNVG TNVAWYQQKP GQSPKALIYS PSYRYSGVPD     60
RFTGSGSGTD FTLTISNVQS EDLAEYFCQQ YNSYPHTFGG GTKLEMKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 217          moltype = DNA   length = 642
FEATURE                 Location/Qualifiers
misc_feature            1..642
                        note = Description of Artificial Sequence: Synthetic
                        polynucleotide
source                  1..642
```

```
                    mol_type = other DNA
                    organism = synthetic construct
SEQUENCE: 217
gatatccaga tgacacagtc accctcgtcg ctctcagctt ccgtaggcga cagggtcact    60
attacgtgta aagcatcaca gaacgtcgga acgaatgtgg cgtggtttca gcagaagccc   120
gggaagagcc ccaaagcgct tatctactcc ccgtcgtatc ggtattccgg tgtgccaagc   180
agattttcgg ggtcaggttc gggaactgac tttaccctga ccatctcgtc cctccaaccg   240
gaagatttcg ccacgtactt ctgccagcag tacaacagct atcctcacac attcggacaa   300
gggacaaagt tggagattaa acgcacagtt gctgccccca gcgtgttcat tttcccacct   360
agcgatgagc agctgaaaag cggtactgcc tctgtcgtat gcttgctcaa caacttttac   420
ccacgtgagg ctaaggtgca gtggaaagtg gataatgcac ttcaatctgg aaacagtcaa   480
gagtccgtga cagaacagga cagcaaagac tcaacttatt cactctcttc caccctgact   540
ctgtccaagg cagactatga aaaacacaag gtatacgcct gcgaggttac acaccagggt   600
ttgtctagtc ctgtcaccaa gtccttcaat aggggcgaat gt                      642

SEQ ID NO: 218      moltype = AA   length = 214
FEATURE             Location/Qualifiers
REGION              1..214
                    note = Description of Artificial Sequence: Synthetic
                    polypeptide
source              1..214
                    mol_type = protein
                    organism = synthetic construct
SEQUENCE: 218
DIQMTQSPSS LSASVGDRVT ITCKASQNVG TNVAWFQQKP GKSPKALIYS PSYRYSGVPS    60
RFSGSGSGTD FTLTISSLQP EDFATYFCQQ YNSYPHTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 219      moltype = DNA   length = 1035
FEATURE             Location/Qualifiers
misc_feature        1..1035
                    note = Description of Artificial Sequence: Synthetic
                    polynucleotide
source              1..1035
                    mol_type = other DNA
                    organism = synthetic construct
SEQUENCE: 219
gggtgtaaac cctgcatctg cacggtgccg gaggtgtcct ccgtctttat cttccctccc    60
aaacccaagg atgtgctgac aatcactttg actccaaaag tcacatgcgt agtcgtggac   120
atctcgaaaa acgacccgga agtgcagttc gtgtggtttg ttgatgatgt agaagtgcat   180
accgctcaaa cccagccgag ggaagaacag tttaacagca cgtttaggag tgtgtcggaa   240
ctgccccatta tgcaccagga ttggcttaat gggaaggagt tcaaatgtcg cgtgaatagt   300
gcggcgttcc cagcccctat tgaaaagact atttccaaaa cgaagggtcg gcccaaagct   360
ccccaagtat acacaatccc tccgccgaaa gaacaaatgg caaaagacaa agtgagtttg   420
acgtgcatga tcacggactt ttttccggag gatatcaccg tcgaatggca atggaatggg   480
caacctgccg aaaactacaa gaatacacaa cccattatgg ataccgatgg atcgtatttc   540
gtctactcaa agttgaacgt acagaagtca aattgggagg cagggaatac gttcacttgc   600
agtgttttgc acgaaggcct cataaccac atacgaaa agtcactgtc gcactcccg    660
ggaaaaatcg agggcagaat ggatggtgga ggagggtcgg cgcgcaacgg ggaccactgt   720
ccgctcggcc ccgggcgttg ctgccgtctg cacacgggtg gcgcgtcgct ggaagacctg   780
ggctgggccg attgggtgct gtcgccacgg gaggtgcaag tgaccatgtg catcggcgcg   840
tgcccgagcc agttccgggc ggcaaacatg cacgcgcaga tcaagacgag cctgcaccgc   900
ctgaagcccg acacggtgcc agcgccctgc tgcgtgcccg ccagctacaa tcccatggtg   960
ctcattcaaa agaccgacac cggggtgtcg ctccagacct atgatgactt gttagccaaa  1020
gactgccact gcata                                                   1035

SEQ ID NO: 220      moltype = AA   length = 345
FEATURE             Location/Qualifiers
REGION              1..345
                    note = Description of Artificial Sequence: Synthetic
                    polypeptide
source              1..345
                    mol_type = protein
                    organism = synthetic construct
SEQUENCE: 220
GCKPCICTVP EVSSVFIFPP KPKDVLTITL TPKVTCVVVD ISKDDPEVQF SWFVDDVEVH    60
TAQTQPREEQ FNSTFRSVSE LPIMHQDWLN GKEFKCRVNS AAFPAPIEKT ISKTKGRPKA   120
PQVYTIPPPK EQMAKDKVSL TCMITDFFPE DITVEWQWNG QPAENYKNTQ PIMDTDGSYF   180
VYSKLNVQKS NWEAGNTFTC SVLHEGLHNH HTEKSLSHSP GKIEGRMDGG GGSARNGDHC   240
PLGPGRCCRL HTVRASLEDL GWADWVLSPR EVQVTMCIGA CPSQFRAANM HAQIKTSLHR   300
LKPDTVPAPC CVPASYNPMV LIQKTDTGVS LQTYDDLLAK DCHCI                   345

SEQ ID NO: 221      moltype = DNA   length = 1026
FEATURE             Location/Qualifiers
misc_feature        1..1026
                    note = Description of Artificial Sequence: Synthetic
                    polynucleotide
source              1..1026
```

```
                            mol_type = other DNA
                            organism = synthetic construct
SEQUENCE: 221
tcgaaaccca cttgccctcc tccggagctg ttgggcggac cctccgtgtt tatctttccc    60
ccgagccga aagataccct tatgatctca cggacgccgg aggtcacttg cgtagtagtg   120
gatgtgtcgg aggatgaccc cgaagtccga ttcacctggt atatcaataa cgagcaagtg   180
aggacagcga ggccccccact tagggagcag cagttcaact ccacaattcg ggtcgtcagc   240
actttgccca tcgctcatga ggactggctc cgcggaaaag agttcaagtg taaggtgcat   300
aacaaggcat tgccagcgcc tattgaaaag acaatctcga aagcgcgagg gcagccgctc   360
gagcccaaag tgtatacgat gggaccccccg agggaagaat tgtcgtcgcg ctcagtaagc   420
cttacgtgca tgattaacgg tttctaccct agcgacatca gcgtagagtg ggaaaagaat   480
ggaaaggcgg aggataacta caagacgact cccgcggtgc tggattcgga tgggtcgtac   540
tttctgtata gcaaattgtc agtcccgacc tcagaatggc agagggtgga cgtgttcacg   600
tgctccgtga tgcacgaagc acttcacaat cactacaccc agaaatcaat ctcgcggtcc   660
ccaggcaaag gtggaggagg gtcggctcac gcccaccctc gcgattcgtg tccgctgggg   720
cctggtagat gctgtcatct cgagacagtc caggccacgc tggaggacct cgggtggtca   780
gactgggtcc tgtccccacg acaactgcag ctttcgatgt gcgtggggga atgtccgcac   840
ttgtacagat cggcgaatac ccacgctcag attaaggcac gactccatgg tttgcagcca   900
gataaagtcc ccgcacccttg ctgtgtcccc agctcatata ctcctgtcgt actcatgcat   960
cggacagaca gcggcgtgtc gcttcaaacg tatgacgacc tcgtagcgag aggatgtcat  1020
tgcgcc                                                             1026

SEQ ID NO: 222         moltype = AA   length = 342
FEATURE                Location/Qualifiers
REGION                 1..342
                       note = Description of Artificial Sequence: Synthetic
                        polypeptide
source                 1..342
                       mol_type = protein
                       organism = synthetic construct
SEQUENCE: 222
SKPTCPPPEL LGGPSVFIFP PKPKDTLMIS RTPEVTCVVV DVSEDDPEVQ FTWYINNEQV    60
RTARPPLREQ QFNSTIRVVS TLPIAHEDWL RGKEFKCKVH NKALPAPIEK TISKARGQPL   120
EPKVYTMGPP REELSSRSVS LTCMINGFYP SDISVEWEKN GKAEDNYKTT PAVLDSDGSY   180
FLYSKLSVPT SEWQRGDVFT CSVMHEALHN HYTQKSISRS PGKGGGGSAH AHPRDSCPLG   240
PGRCCHLETV QATLEDLGWS DWVLSPRQLQ LSMCVGECPH LYRSANTHAQ IKARLHGLQP   300
DKVPAPCCVP SSYTPVVLMH RTDSGVSLQT YDDLVARGCH CA                      342

SEQ ID NO: 223         moltype = AA   length = 350
FEATURE                Location/Qualifiers
REGION                 1..350
                       note = Description of Artificial Sequence: Synthetic
                        polypeptide
source                 1..350
                       mol_type = protein
                       organism = synthetic construct
SEQUENCE: 223
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKIEG RMDGGGGSAR   240
NGDHCPLGPG RCCRLHTVRA SLEDLGWADW VLSPREVQVT MCIGACPSQF RAANMHAQIK   300
TSLHRLKPDT VPAPCCVPAS YNPMVLIQKT DTGVSLQTYD DLLAKDCHCI               350

SEQ ID NO: 224         moltype = AA   length = 344
FEATURE                Location/Qualifiers
REGION                 1..344
                       note = Description of Artificial Sequence: Synthetic
                        polypeptide
source                 1..344
                       mol_type = protein
                       organism = synthetic construct
SEQUENCE: 224
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGG GSARNGDHCP   240
LGPGRCCRLH TVRASLEDLG WADWVLSPRE VQVTMCIGAC PSQFRAANMH AQIKTSLHRL   300
KPDTVPAPCC VPASYNPMVL IQKTDTGVSL QTYDDLLAKD CHCI                    344

SEQ ID NO: 225         moltype = DNA   length = 22
FEATURE                Location/Qualifiers
misc_feature           1..22
                       note = Description of Artificial Sequence: Synthetic primer
source                 1..22
                       mol_type = other DNA
                       organism = synthetic construct
SEQUENCE: 225
ctaatacgac tcactatagg gc                                             22
```

```
SEQ ID NO: 226          moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 226
tatgcaaggc ttacaaccac a                                              21

SEQ ID NO: 227          moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 227
aggacagggg ttgattgttg a                                              21

SEQ ID NO: 228          moltype = DNA   length = 27
FEATURE                 Location/Qualifiers
misc_feature            1..27
                        note = Description of Artificial Sequence: Synthetic primer
source                  1..27
                        mol_type = other DNA
                        organism = synthetic construct
SEQUENCE: 228
ctcattcctg ttgaagctct tgacaat                                        27

SEQ ID NO: 229          moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 229
aagcagtggt atcaacgcag agt                                            23

SEQ ID NO: 230          moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 230
cgactgaggc acctccagat gtt                                            23

SEQ ID NO: 231          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 231
gtaaaacgac ggccagt                                                   17

SEQ ID NO: 232          moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 232
caggaaacag ctatgacc                                                  18

SEQ ID NO: 233          moltype = DNA   length = 45
FEATURE                 Location/Qualifiers
misc_feature            1..45
                        note = Description of Artificial Sequence: Synthetic primer
source                  1..45
                        mol_type = other DNA
                        organism = synthetic construct
SEQUENCE: 233
```

```
ctaatacgac tcactatagg gcaagcagtg gtatcaacgc agagt            45

SEQ ID NO: 234          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 234
GYTFSDY                                                       7

SEQ ID NO: 235          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 235
GYTFSDYN                                                      8

SEQ ID NO: 236          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 236
QINPYNHLIF FNQKFQG                                           17

SEQ ID NO: 237          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 237
QINPNNGLIF FNQKFQG                                           17

SEQ ID NO: 238          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 238
QINPNNGLIF FNQKFKG                                           17

SEQ ID NO: 239          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 239
QINPYNHLIF FNQKFKG                                           17

SEQ ID NO: 240          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 240
NPYNHL                                                        6

SEQ ID NO: 241          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
```

```
SEQUENCE: 241
NPNNGL                                                                        6

SEQ ID NO: 242          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 242
INPYNHLI                                                                      8

SEQ ID NO: 243          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 243
INPNNGLI                                                                      8

SEQ ID NO: 244          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 244
QHFWSDPYT                                                                     9

SEQ ID NO: 245          moltype = DNA   length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 245
caggtccagc ttgtgcaatc gggagcggaa gtgaagaaac cgggagcgtc ggtaaaagtc    60
tcgtgcaaag cgtcggggta tacgtttacg gactataaca tggactgggt gcgccaagcg   120
cctggacaga gccttgaatg gatggggcag attaatccgt acaatcacct gatcttcttt   180
aatcagaaat tccagggaag ggtaacgctg acgacagaca cgtcaacatc gacggcctat   240
atggaattgc ggtcgttgcg atcagatgat acggcggtct actattgtgc gagggaggcg   300
attacgacgg tgggagcgat ggattattgg ggacagggga cgttggtaac ggtatcgtcg   360

SEQ ID NO: 246          moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 246
QVQLVQSGAE VKKPGASVKV SCKASGYTFT DYNMDWVRQA PGQSLEWMGQ INPYNHLIFF    60
NQKFQGRVTL TTDTSTSTAY MELRSLRSDD TAVYYCAREA ITTVGAMDYW GQGTLVTVSS   120

SEQ ID NO: 247          moltype = DNA   length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 247
caggtccagc ttgtgcaatc gggagcggaa gtgaagaaac cgggagcgtc ggtaaaagtc    60
tcgtgcaaag cgtcggggta tacgtttacg gactataaca tggactgggt gcgccaagcg   120
cctggacaga gccttgaatg gatggggcag attaatccga ataatggact gatcttcttt   180
aatcagaaat tccagggaag ggtaacgctg acgacagaca cgtcaacatc gacggcctat   240
atggaattgc ggtcgttgcg atcagatgat acggcggtct actattgtgc gagggaggcg   300
attacgacgg tgggagcgat ggattattgg ggacagggga cgttggtaac ggtatcgtcg   360

SEQ ID NO: 248          moltype = AA   length = 120
FEATURE                 Location/Qualifiers
```

```
REGION                          1..120
                                note = Description of Artificial Sequence: Synthetic
                                 polypeptide
source                          1..120
                                mol_type = protein
                                organism = synthetic construct
SEQUENCE: 248
QVQLVQSGAE VKKPGASVKV SCKASGYTFT DYNMDWVRQA PGQSLEWMGQ INPNNGLIFF    60
NQKFQGRVTL TTDTSTSTAY MELRSLRSDD TAVYYCAREA ITTVGAMDYW GQGTLVTVSS   120

SEQ ID NO: 249                  moltype = DNA   length = 360
FEATURE                         Location/Qualifiers
misc_feature                    1..360
                                note = Description of Artificial Sequence: Synthetic
                                 polynucleotide
source                          1..360
                                mol_type = other DNA
                                organism = synthetic construct
SEQUENCE: 249
caagtacagc ttgtacagtc gggagcggaa gtcaagaaac cgggatcgtc ggtcaaagtg    60
tcgtgtaaag cgtcgggata tacgtttagc gactataaca tggattgggt gcgacaagcg   120
cctgggcagg gacttgaatg gatgggtcag atcaatgggc ataatgggct gatcttttc   180
aatcagaagt ttaagggag ggtaacgctg acggcggata aaagcacgtc aacggcgtat   240
atggagttgt cgtcgttgcg gtcggaggac acggcggtct attactgcgc gagggaagcg   300
attacgacgg tgggagcgat ggattattgg gggcaggaa cgcttgtaac ggtgtcatcg   360

SEQ ID NO: 250                  moltype = AA   length = 120
FEATURE                         Location/Qualifiers
REGION                          1..120
                                note = Description of Artificial Sequence: Synthetic
                                 polypeptide
source                          1..120
                                mol_type = protein
                                organism = synthetic construct
SEQUENCE: 250
QVQLVQSGAE VKKPGSSVKV SCKASGYTFS DYNMDWVRQA PGQGLEWMGQ INPNNGLIFF    60
NQKFKGRVTL TADKSTSTAY MELSSLRSED TAVYYCAREA ITTVGAMDYW GQGTLVTVSS   120

SEQ ID NO: 251                  moltype = DNA   length = 360
FEATURE                         Location/Qualifiers
misc_feature                    1..360
                                note = Description of Artificial Sequence: Synthetic
                                 polynucleotide
source                          1..360
                                mol_type = other DNA
                                organism = synthetic construct
SEQUENCE: 251
caagtacagc ttgtacagtc gggagcggaa gtcaagaaac cgggatcgtc ggtcaaagtg    60
tcgtgtaaag cgtcgggata tacgtttagc gactataaca tggattgggt gcgacaagcg   120
cctgggcagg gacttgaatg gatgggtcag atcaatccgt acaatcacct gatcttttc   180
aatcagaagt ttaagggag ggtaacgctg acggcggata aaagcacgtc aacggcgtat   240
atggagttgt cgtcgttgcg gtcggaggac acggcggtct attactgcgc gagggaagcg   300
attacgacgg tgggagcgat ggattattgg gggcaggaa cgcttgtaac ggtgtcatcg   360

SEQ ID NO: 252                  moltype = AA   length = 120
FEATURE                         Location/Qualifiers
REGION                          1..120
                                note = Description of Artificial Sequence: Synthetic
                                 polypeptide
source                          1..120
                                mol_type = protein
                                organism = synthetic construct
SEQUENCE: 252
QVQLVQSGAE VKKPGSSVKV SCKASGYTFS DYNMDWVRQA PGQGLEWMGQ INPYNHLIFF    60
NQKFKGRVTL TADKSTSTAY MELSSLRSED TAVYYCAREA ITTVGAMDYW GQGTLVTVSS   120

SEQ ID NO: 253                  moltype = DNA   length = 321
FEATURE                         Location/Qualifiers
misc_feature                    1..321
                                note = Description of Artificial Sequence: Synthetic
                                 polynucleotide
source                          1..321
                                mol_type = other DNA
                                organism = synthetic construct
SEQUENCE: 253
gacatccaaa tgacccagtc gccgtcgtcg ctttcagcgt cggtagggga tcgggtcaca    60
attacgtgcc gaacgtcaga gaatttgcat aactacctcg cgtggtatca gcagaagccc   120
gggaagtcac cgaaactcct tatctacgat gcgaaacgc tggcggatgg agtgccgtcg   180
agattctcgg gaagcggatc cggtacggac tatacgctta cgatctcatc gctccagccc   240
```

```
gaggactttg cgacgtacta ttgtcagcat ttttggtcgg accccctacac atttgggcag    300
gggaccaagt tggaaatcaa g                                               321
```

SEQ ID NO: 254         moltype = AA   length = 107
FEATURE                Location/Qualifiers
REGION                 1..107
                       note = Description of Artificial Sequence: Synthetic
                         polypeptide
source                 1..107
                       mol_type = protein
                       organism = synthetic construct
SEQUENCE: 254
```
DIQMTQSPSS LSASVGDRVT ITCRTSENLH NYLAWYQQKP GKSPKLLIYD AKTLADGVPS    60
RFSGSGSGTD YTLTISSLQP EDFATYYCQH FWSDPYTFGQ GTKLEIK                  107
```

SEQ ID NO: 255         moltype = DNA   length = 1350
FEATURE                Location/Qualifiers
misc_feature           1..1350
                       note = Description of Artificial Sequence: Synthetic
                         polynucleotide
source                 1..1350
                       mol_type = other DNA
                       organism = synthetic construct
SEQUENCE: 255
```
caggtccagc ttgtgcaatc gggagcggaa gtgaagaaac cgggagcgtc ggtaaaagtc    60
tcgtgcaaag cgtcggggta tacgtttacg gactataaca tggactgggt gcgccaagcg   120
cctggacaga gccttgaatg gatggggcag attaatccgt acaatcaccct gatcttcttt   180
aatcagaaat tccagggaag ggtaacgctg acgacagaca cgtcaacatc gacggcctat   240
atggaattgc ggtcgttgcg atcagatgat acggcggtct actattgtgc gagggaggcg   300
attacgacgg tgggagcgat ggattattgg ggacagggga cgttggtaac ggtatcgtcg   360
gcctcaacaa aaggaccaag tgtgttccca ctcgcccccta gcagcaagag tacatccgga   420
ggcactgcag cactcggctg cctcgtcaag gattattttc cagagccagt aaccgtgagc   480
tggaacagtg gagcactcac ttctggtgtc catacttttc ctgctgtcct gcaaagctct   540
ggcctgtact cactcagctc cgtcgtgacc gtgccatctt catctctggg cactcagacc   600
tacatctgta atgtaaacca caagcctagc aatactaagg tcgataagcg ggtgaaccc    660
aagagctgcg acaagactca cacttgtccc ccatgccctg cccctgaact tctgggcggt   720
cccagcgtct ttctgttccc accaaagcct aaagatactc tgatgataag tagaacaccc   780
gaggtgacat gtgttgttgt agacgtttcc cacgaggacc cagaggttaa gttcaactgg   840
tacgttgatg gagtcgaagt acataatgct aagaccaagc ctagagagga gcagtataat   900
agtacatacc gtgtagtcag tgttctcaca gtgctgcacc aagactggct caacggcaaa   960
gaatacaaat gcaaagtgtc caacaaagca ctcccagccc ctatcgagaa gactattagt  1020
aaggcaaagg ggcagcctcg tgaaccacag gtgtacactc tgccacccag tagagaggaa  1080
atgacaaaga accaagtctc attgacctgc tggtgaagg gcttctaccc cagcgacatc  1140
gccgttgagt gggagagtaa cggtcagcct gagaacaatt acaagacaac ccccccagtg  1200
ctggatagtg acgggtcttt cttctgtac agtaagctga ctgtggacaa gtcccgctgg  1260
cagcagggta acgtcttcag ctgttccgtg atgcacgagg cattgcacaa ccactacacc  1320
cagaagtcac tgagcctgag cccagggaag                                  1350
```

SEQ ID NO: 256         moltype = AA   length = 450
FEATURE                Location/Qualifiers
REGION                 1..450
                       note = Description of Artificial Sequence: Synthetic
                         polypeptide
source                 1..450
                       mol_type = protein
                       organism = synthetic construct
SEQUENCE: 256
```
QVQLVQSGAE VKKPGASVKV SCKASGYTFT DYNMDWVRQA PGQSLEWMGQ INPYNHLIFF    60
NQKFQGRVTL TTDTSTSTAY MELRSLRSDD TAVYYCAREA ITTVGAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450
```

SEQ ID NO: 257         moltype = DNA   length = 1350
FEATURE                Location/Qualifiers
misc_feature           1..1350
                       note = Description of Artificial Sequence: Synthetic
                         polynucleotide
source                 1..1350
                       mol_type = other DNA
                       organism = synthetic construct
SEQUENCE: 257
```
caggtccagc ttgtgcaatc gggagcggaa gtgaagaaac cgggagcgtc ggtaaaagtc    60
tcgtgcaaag cgtcggggta tacgtttacg gactataaca tggactgggt gcgccaagcg   120
cctggacaga gccttgaatg gatggggcag attaatccga ataatggact gatcttcttt   180
aatcagaaat tccagggaag ggtaacgctg acgacagaca cgtcaacatc gacggcctat   240
```

```
atggaattgc ggtcgttgcg atcagatgat acggcggtct actattgtgc gaggaggcg    300
attacgacgg tgggagcgat ggattattgg ggacaggga cgttggtaac ggtatcgtcg    360
gcctcaacaa aaggaccaag tgtgttccca ctcgcccta gcagcaagag tacatccggg    420
ggcactgcag cactcggctg cctcgtcaag gattattttc cagagccagt aaccgtgagc    480
tggaacagtg gagcactcac ttctggtgtc catactttc ctgctgtcct gcaaagctct     540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg ccctgaact tctgggcggt     720
cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag tgtacactc tgccacccag tagagaggaa    1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagta acgggtcttt ctttctgtac agtaagctga ctgtggacaa gtcccgctgg   1260
cagcaggta acgtcttcag ctgttccgtg atgcacgagg cattgcacaa ccactacacc    1320
cagaagtcac tgagcctgag cccagggaag                                    1350

SEQ ID NO: 258         moltype = AA  length = 450
FEATURE                Location/Qualifiers
REGION                 1..450
                       note = Description of Artificial Sequence: Synthetic
                       polypeptide
source                 1..450
                       mol_type = protein
                       organism = synthetic construct
SEQUENCE: 258
QVQLVQSGAE VKKPGASVKV SCKASGYTFT DYNMDWVRQA PGQSLEWMGQ INPNNGLIFF     60
NQKFQGRVTL TTDTSTSTAY MELRSLRSDD TAVYYCAREA ITTVGAMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKRVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 259         moltype = DNA  length = 1350
FEATURE                Location/Qualifiers
misc_feature           1..1350
                       note = Description of Artificial Sequence: Synthetic
                       polynucleotide
source                 1..1350
                       mol_type = other DNA
                       organism = synthetic construct
SEQUENCE: 259
caagtacagc ttgtacagtc gggagcggaa gtcaagaaac cgggatcgtc ggtcaaagtg     60
tcgtgtaaag cgtcgggata tacgtttagc gactataaca tggattgggt gcgacaagcg    120
cctgggcagg gacttgaatg gatgggtcag atcaatccga ataatgggct gatcttttc    180
aatcagaagt ttaaagggag ggtaacgctg acggcggata aagcacgtc aacggctat     240
atggagttgt cgtcgttgcg gtcggaggac acggcggtct attactgcgc gagggaagcg    300
attacgacgg tgggagcgat ggattattgg ggacaggaa cgcttgtaac ggtgtcatcg    360
gcctcaacaa aaggaccaag tgtgttccca ctcgcccta gcagcaagag tacatccggg    420
ggcactgcag cactcggctg cctcgtcaag gattattttc cagagccagt aaccgtgagc    480
tggaacagtg gagcactcac ttctggtgtc catactttc ctgctgtcct gcaaagctct     540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg ccctgaact tctgggcggt     720
cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag tgtacactc tgccacccag tagagaggaa    1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagta acgggtcttt ctttctgtac agtaagctga ctgtggacaa gtcccgctgg   1260
cagcaggta acgtcttcag ctgttccgtg atgcacgagg cattgcacaa ccactacacc    1320
cagaagtcac tgagcctgag cccagggaag                                    1350

SEQ ID NO: 260         moltype = AA  length = 450
FEATURE                Location/Qualifiers
REGION                 1..450
                       note = Description of Artificial Sequence: Synthetic
                       polypeptide
source                 1..450
                       mol_type = protein
                       organism = synthetic construct
```

SEQUENCE: 260
QVQLVQSGAE VKKPGSSVKV SCKASGYTFS DYNMDWVRQA PGQGLEWMGQ INPNNGLIFF  60
NQKFKGRVTL TADKSTSTAY MELSSLRSED TAVYYCAREA ITTVGAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 261          moltype = DNA   length = 1350
FEATURE                 Location/Qualifiers
misc_feature            1..1350
                        note = Description of Artificial Sequence: Synthetic
                         polynucleotide
source                  1..1350
                        mol_type = other DNA
                        organism = synthetic construct
SEQUENCE: 261
caagtacagc ttgtacagtc gggagcggaa gtcaagaaac cgggatcgtc ggtcaaagtg   60
tcgtgtaaag cgtcgggata tacgtttagc gactataaca tggattgggt gcgacaagcg  120
cctgggcagg gacttgaatg gatgggtcag atcaatccgt acaatcacct gatcttttc   180
aatcagaagt ttaaagggag ggtaacgctg acgcggata aaagcacgtc aacggcgtat   240
atggagttgt cgtcgttgcg gtcggaggac acggcggtct attactgcgc gagggaagcg  300
attacgacgg tgggagcgat ggattattgg ggcagggaa cgcttgtaac ggtgtcatcg   360
gcctcaacaa aaggaccaag tgtgttccca ctcgcccta gcagcaagag tacatcggga  420
ggcactgcag cactcggctg cctcgtcaag gattattttc cagagccagt aaccgtgagc  480
tggaacagtg gagcactcac ttctggtgtc catactttc ctgctgtcct gcaaagctct   540
ggcctgtact cactcagctc cgtcgtgacc gtgccatctt catctctggg cactcagacc  600
tacatctgta atgtaaacca caagcctagc aatactaagg tcgataagcg ggtgaaccc   660
aagagctgcg acaagactca cacttgtccc ccatgccctg ccctgaact tctgggcggt  720
cccagcgtct ttttgttccc accaaagcct aaagatactc tgatgataag tagaacaccc  780
gaggtgacat gtgttgttgt agacgttttcc acgaggacc cagaggttaa gttcaactgg   840
tacgttgatg gagtcgaagt acataatgct aagacgaaga ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt  1020
aaggcaaagg gcagcctcg tgaaccacag gtgtacactc tgccacccag tagagaggaa  1080
atgacaaaga accaagtctc attgacctgc ctggtgaaag gcttctaccc cagcgacatc  1140
gccgttgagt gggagagtaa cggtcagcct gagaacaact acaagacaac cccccagtg  1200
ctggatagtg acgggtcttt cttctctac agtaagctga ctgtggacaa gtccgctgtg  1260
cagcagggta acgtcttcag ctgttccgtg atgcacgagg cattgcacaa ccactacacc  1320
cagaagtcac tgagcctgag cccagggaag                                  1350

SEQ ID NO: 262          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 262
QVQLVQSGAE VKKPGSSVKV SCKASGYTFS DYNMDWVRQA PGQGLEWMGQ INPYNHLIFF  60
NQKFKGRVTL TADKSTSTAY MELSSLRSED TAVYYCAREA ITTVGAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 263          moltype = DNA   length = 642
FEATURE                 Location/Qualifiers
misc_feature            1..642
                        note = Description of Artificial Sequence: Synthetic
                         polynucleotide
source                  1..642
                        mol_type = other DNA
                        organism = synthetic construct
SEQUENCE: 263
gacatccaaa tgacccagtc gccgtcgtcg ctttcagcgt cggtagggga tcgggtcaca   60
attacgtgcc aacgtcaga gaatttgcat aactaccctcg cgtggtatca gcagaagccc  120
gggaagtcac cgaaactcct tatctacgat gcgaaaacgc tggcggatgg agtgccgtcg  180
agattctcgg gaagcggatc cggtacggac tatacgctta cgatctcatc gctccagcc  240
gaggactttg cgacgtacta ttgtcagcat ttttggtcgg acccctacac atttgggcag  300
gggaccaagt tggaaatcaa agcgcacagtt gctgcccca gcgtgttcat tttcccacct  360
agcgatgagc agctgaaaag cggtactgcc tctgtcgtat gcttgctcaa caacttttac   420
ccacgtgagg ctaaggtgca gtggaaagtg gataatgcac ttcaatctgg aacagtcaa  480
gagtccgtga cagaacagga cagcaaagac tcaacttatt cactctcttc caccctgact  540

```
ctgtccaagg cagactatga aaaacacaag gtatacgcct gcgaggttac acaccagggt    600
ttgtctagtc ctgtcaccaa gtccttcaat aggggcgaat gt                      642

SEQ ID NO: 264         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 264
DIQMTQSPSS LSASVGDRVT ITCRTSENLH NYLAWYQQKP GKSPKLLIYD AKTLADGVPS    60
RFSGSGSGTD YTLTISSLQP EDFATYYCQH FWSDPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 265         moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 265
GGGG                                                                 4

SEQ ID NO: 266         moltype = AA  length = 6
FEATURE                Location/Qualifiers
REGION                 1..6
                       note = Description of Artificial Sequence: Synthetic 6xHis
                        tag
source                 1..6
                       mol_type = protein
                       organism = synthetic construct
SEQUENCE: 266
HHHHHH                                                               6
```

What is claimed is:

1. A method of treating cachexia in a mammal comprising administering to the mammal an effective amount of an anti-GDF15 antibody or antigen-binding fragment thereof comprising a CDR H1, a CDR H2, a CDR H3, a CDR L1, a CDR L2, and a CDR L3, wherein the CDR H1, CDR H2, and CDR H3 are found in the amino acid sequence of SEQ ID NO: 250, and wherein the CDR L1, CDR L2, and CDR L3 are found in the amino acid sequence of SEQ ID NO: 92.

2. The method of claim 1, wherein the CDR H1 comprises the amino acid sequence of SEQ ID NO: 1, the CDR H2 comprises the amino acid sequence of SEQ ID NO: 238, the CDR H3 comprises the amino acid sequence of SEQ ID NO: 15, the CDR L1 comprises the amino acid sequence of SEQ ID NO: 21, the CDR L2 comprises the amino acid sequence of SEQ ID NO: 26, and the CDR L3 comprises the amino acid sequence of SEQ ID NO: 32.

3. The method of claim 1, wherein the anti-GDF15 antibody comprises an immunoglobulin heavy chain variable region and an immunoglobulin light chain variable region, wherein the immunoglobulin heavy chain variable region comprises an amino acid sequence having at least 95% identity to that of SEQ ID NO: 250, and the immunoglobulin light chain variable region comprises an amino acid sequence having at least 95% identity to that of SEQ ID NO: 92.

4. The method of claim 1, wherein loss of muscle mass associated with cachexia is inhibited.

5. The method of claim 1, wherein involuntary weight loss associated with cachexia is inhibited or reduced.

6. The method of claim 1, wherein loss of organ mass associated with cachexia is inhibited.

7. The method of claim 6, wherein the cachexia is associated with an underlying disease selected from the group consisting of cancer, chronic heart failure, chronic kidney disease, COPD, AIDS, multiple sclerosis, rheumatoid arthritis, sepsis, and tuberculosis.

8. The method of claim 6, wherein the organ is kidney, liver, heart or spleen.

9. The method of claim 6, wherein the loss of organ mass is accompanied by a loss of muscle mass, a loss of fat mass or involuntary weight loss.

10. The method of claim 1 further comprising administering a second agent to the mammal in need thereof, wherein the second agent is selected from the group consisting of an inhibitor of Activin-A, an inhibitor of ActRIIB, an inhibitor of IL-6, an inhibitor of IL-6R, a melanocortin peptide inhibitor, a melanocortin receptor inhibitor, a ghrelin, a ghrelin mimetic, a GHS-R1a agonist, a SARM, a TNFα inhibitor, an IL-1α inhibitor, a myostatin inhibitor, a beta-blocker and an anti-cancer agent.

11. The method of claim 1, wherein sarcopenia associated with cachexia is treated.

12. The method of claim 1, wherein the incidence and/or severity of cachexia is decreased, thereby increasing the maximum tolerated dose of an anti-cancer agent capable of causing cachexia.

13. The method of claim 10, wherein the antibody or antigen-binding fragment thereof is administered in combination with the anti-cancer agent.

14. The method of claim 1, wherein the anti-GDF15 antibody or antigen-binding fragment thereof comprises an immunoglobulin heavy chain variable region and an immunoglobulin light chain variable region, wherein the immunoglobulin heavy chain variable region comprises the amino acid sequence of SEQ ID NO:250, and the immunoglobulin light chain variable region comprises the amino acid sequence of SEQ ID NO:92.

15. The method of claim 1, wherein the cachexia is associated with an underlying disease selected from the group consisting of cancer, chronic heart failure, chronic kidney disease, COPD, AIDS, multiple sclerosis, rheumatoid arthritis, sepsis, and tuberculosis.

16. The method of claim 1, wherein appetite in a mammal suffering from cachexia is increased.

17. The method of claim 4, wherein the cachexia is associated with an underlying disease selected from the group consisting of cancer, chronic heart failure, chronic kidney disease, COPD, AIDS, multiple sclerosis, rheumatoid arthritis, sepsis, and tuberculosis.

18. The method of claim 4, wherein the loss of muscle mass is accompanied by a loss of fat mass.

* * * * *